United States Patent
Protter et al.

(10) Patent No.: US 11,485,725 B2
(45) Date of Patent: Nov. 1, 2022

(54) DERIVATIVES OF PIPERLONGUMINE AND USES THEREOF

(71) Applicant: Auransa Inc., Palo Alto, CA (US)

(72) Inventors: Andrew Asher Protter, Palo Alto, CA (US); Michael John Green, Half Moon Bay, CA (US); Hak Jin Chang, Harvard, MA (US); Son Minh Pham, San Francisco, CA (US); Sarvajit Chakravarty, Edmond, OK (US); Gregory R. Luedtke, Salinas, CA (US); Pek Yee Lum, Palo Alto, CA (US)

(73) Assignee: Auransa Inc., Palo Alto, CA (US)

(*) Notice: Subject to any disclaimer, the term of this patent is extended or adjusted under 35 U.S.C. 154(b) by 0 days.

(21) Appl. No.: 16/766,538

(22) PCT Filed: Nov. 14, 2018

(86) PCT No.: PCT/US2018/061112
§ 371 (c)(1),
(2) Date: May 22, 2020

(87) PCT Pub. No.: WO2019/103897
PCT Pub. Date: May 31, 2019

(65) Prior Publication Data
US 2021/0198235 A1 Jul. 1, 2021

Related U.S. Application Data

(60) Provisional application No. 62/599,522, filed on Dec. 15, 2017, provisional application No. 62/654,523, filed on Apr. 8, 2018.

(51) Int. Cl.
| | |
|---|---|
| *C07D 401/06* | (2006.01) |
| *C07D 401/14* | (2006.01) |
| *C07D 211/86* | (2006.01) |
| *C07D 211/96* | (2006.01) |
| *C07D 413/06* | (2006.01) |
| *C07D 491/056* | (2006.01) |
| *C07D 405/06* | (2006.01) |
| *C07D 405/14* | (2006.01) |
| *C07D 401/12* | (2006.01) |
| *C07D 401/04* | (2006.01) |
| *C07D 403/06* | (2006.01) |
| *C07D 223/10* | (2006.01) |

(52) U.S. Cl.
CPC .......... *C07D 401/06* (2013.01); *C07D 211/86* (2013.01); *C07D 211/96* (2013.01); *C07D 223/10* (2013.01); *C07D 401/04* (2013.01); *C07D 401/12* (2013.01); *C07D 401/14* (2013.01); *C07D 403/06* (2013.01); *C07D 405/06* (2013.01); *C07D 405/14* (2013.01); *C07D 413/06* (2013.01); *C07D 491/056* (2013.01)

(58) Field of Classification Search
CPC .. C07D 401/06; C07D 401/14; C07D 211/86; C07D 211/96; C07D 413/06; C07D 491/056; C07D 405/06; C07D 405/14; C07D 223/10
See application file for complete search history.

(56) References Cited

U.S. PATENT DOCUMENTS

| | | |
|---|---|---|
| 5,602,145 A | 2/1997 | Samanen |
| 6,534,535 B1 | 3/2003 | Zhu et al. |
| 7,723,384 B2 | 5/2010 | Lubisch et al. |
| 8,318,737 B2 | 11/2012 | Foley et al. |
| 8,471,026 B2 | 6/2013 | Blackburn et al. |
| 9,108,923 B2 | 8/2015 | Adams et al. |
| 2009/0312373 A1 | 12/2009 | Lee et al. |
| 2011/0086860 A1 | 4/2011 | Kimura et al. |
| 2012/0059004 A1 | 3/2012 | Elliott et al. |
| 2014/0024639 A1 | 1/2014 | Adams et al. |
| 2014/0094465 A1 | 4/2014 | Sun et al. |
| 2020/0377510 A1 | 12/2020 | Protter et al. |

FOREIGN PATENT DOCUMENTS

| | | |
|---|---|---|
| AU | 2002303620 A1 | 11/2002 |
| AU | 2011331301 A1 | 5/2013 |
| AU | 2011270701 B2 | 5/2015 |
| AU | 2015231413 A1 | 10/2016 |
| CA | 2443835 A1 | 11/2002 |
| CA | 2623026 A1 | 4/2007 |
| CA | 2589013 C | 12/2016 |
| CN | 101245059 A | 8/2008 |
| CN | 101401850 A | 4/2009 |
| CN | 100493498 C | 6/2009 |

(Continued)

OTHER PUBLICATIONS

Rao et al., European Journal of Medicinal Chemistry (2012), 57, pp. 344-361. (Year: 2012).*
PubChem CID 102060706, National Center for Biotechnology Information. PubChem Compound Summary for CID 102060706. https://pubchem.ncbi.nlm.nih.gov/compound/102060706. Accessed Jan. 27, 2022, create date Dec. 24, 2015. (Year: 2015).*
Han, L.C. et al. (Jul. 22, 2016). "Horner-Wadsworth-Emmons Approach to Piperlongumine Analogues With Potent Anti-Cancer Activity," Organic & Biomolecular Chemistry 14(31):7585-7593.
International Preliminary Report on Patentability dated May 26, 2020, for International Application No. PCT/US2018/061112, filed Nov. 14, 2018, five pages.

(Continued)

*Primary Examiner* — Laura L Stockton
(74) *Attorney, Agent, or Firm* — Morrison & Foerster LLP

(57) ABSTRACT

The present invention relates to a group of 1-[(E)-3-(3,4,5-trimethoxyphenyl)prop-2-enoyl]-2,3-dihydropyridin-6-one (piperlongumine) derivatives, analogs and pharmaceutically acceptable salts thereof. The present invention also relates to processes for preparing the same; a pharmaceutical composition and formulation containing a derivative of piperlongumine; and use of the derivatives and analogs for treating cancer.

23 Claims, 1 Drawing Sheet

(56) References Cited

FOREIGN PATENT DOCUMENTS

| | | | |
|---|---|---|---|
| CN | 101774875 | A | 7/2010 |
| CN | 101352487 | B | 4/2011 |
| CN | 102125552 | A | 7/2011 |
| CN | 102146054 | A | 8/2011 |
| CN | 101554409 | B | 11/2011 |
| CN | 102228270 | A | 11/2011 |
| CN | 101810612 | B | 4/2012 |
| CN | 102649784 | A | 8/2012 |
| CN | 101863872 | B | 6/2013 |
| CN | 102288712 | B | 6/2013 |
| CN | 103230548 | A | 8/2013 |
| CN | 103340934 | A | 10/2013 |
| CN | 103393765 | A | 11/2013 |
| CN | 103601670 | A | 2/2014 |
| CN | 103969385 | A | 8/2014 |
| CN | 102007106 | B | 9/2014 |
| CN | 104910174 | A | 9/2015 |
| CN | 105367495 | A | 3/2016 |
| CN | 107382966 | A | 11/2017 |
| EP | 1633751 | A1 | 3/2006 |
| EP | 3288941 | A1 | 3/2018 |
| IN | 2013KN01466 | A | 10/2013 |
| JP | 2003096330 | A | 4/2003 |
| JP | 2016525093 | A | 8/2016 |
| KR | 20150077974 | A | 7/2015 |
| WO | 2009125809 | A1 | 10/2009 |
| WO | 2012065963 | A2 | 5/2012 |
| WO | 2016014625 | A1 | 1/2016 |
| WO | 2019103897 | A1 | 5/2019 |

OTHER PUBLICATIONS

International Search Report and Written Opinion of the Searching Authority dated Feb. 27, 2019, for Patent Application No. PCT/US2018/061112, eight pages.

Lad, N. P. et al. (Dec. 9, 2016). "Piperiongumine Derived Cyclic Sulfonamides (Sultams): Synthesis and in Vitro Exploration for Therapeutic Potential Against Hela Cancer Cell Lines," European Journal of Medicinal Chemistry 126:870-878.

Meegan, M.J. et al. (Jan. 5, 2017, e-pub. Sep. 16, 2016). "Piperlongumine (Piplartine) and Analogues: Antiproliferative Microtubule-Destabilising Agents," European J. Med. Chem. 125:453-463.

Rao, V. R. et al. (Nov. 1, 2012). "Synthesis and Biological Evaluation of New Piplartine Analogues as Potent Aldose Reductase Inhibitors (Aris)," European Journal of Medicinal Chemistry 57:344-361.

Sun, L. D. et al. (Jun. 1, 2015). "Development and Mechanism Investigation of a New Piperlongumine Derivative as a Potent Anti-Inflammatory Agent," Biochemical Pharmacology 95(3): 156-169.

Wu, Y., et al. (Jul. 23, 2014). "Design, Synthesis and Biological Activity of Piperlongumine Derivatives as Selective Anticancer Agents," European Journal of Medicinal Chemistry 82:545-551.

Xu, X. et al. (Mar. 1, 2017). "Identification of Novel ROS Inducer by Merging the Fragments of Piperlongumine and Dicoumarol," Bioorganic & Medicinal Chemistry Letters 27(5):1325-1328.

Zhang, Y. et al. (Apr. 13, 2017). "Novel Non-Trimethoxylphenyl Piperlongumine Derivatives Selectively Kill Cancer Cells," Bioorganic & Medicinal Chemistry Letters 27(11):2308-2312.

Zou, Y. et al. (Feb. 9, 2018). "Novel Ligustrazine-Based Analogs of Piperlongumine Potently Suppress Proliferation and Metastasis of Colorectal Cancer Cells in Vitro and in Vivo," Journal of Medicinal Chemistry 61(5):1821-1832.

Zou, Y. et al. (Sep. 29, 2017). "Synthesis and Evaluation of N-Heteroaromatic Ring-Based Analogs of Piperlongumine as Potent Anticancer Agents," European Journal of Medicinal Chemistry 138:313-319.

* cited by examiner

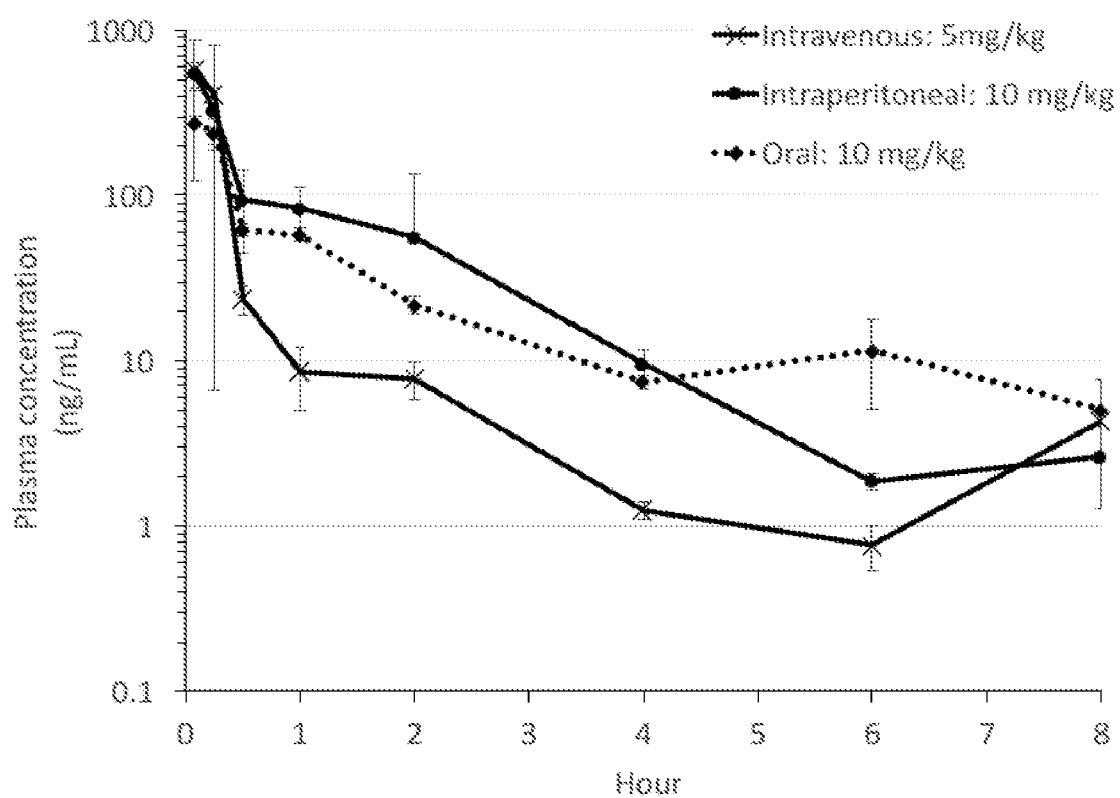

DERIVATIVES OF PIPERLONGUMINE AND USES THEREOF

CROSS REFERENCE TO RELATED APPLICATIONS

This application is a national stage application under 35 U.S.C. § 371 of International Application No. PCT/US2018/061112 filed Nov. 14, 2018, which claims the priority of U.S. provisional application Ser. No. 62/590,522, filed Nov. 24, 2017, and U.S. provisional application Ser. No. 62/654,523, filed Apr. 8, 2018, each of which is incorporated herein by reference in its entirety for all purposes.

FIELD OF THE INVENTION

The present invention relates to novel organic compounds useful for therapy or prophylaxis in a mammal, and in particular to the treatment of various types of cancer.

BACKGROUND OF THE INVENTION

Piperlongumine is a small molecule alkaloid isolated from a number of *Piper* plant species, including the long pepper plant *Piper longum* L. This molecule has gained increasing attention for its antitumor properties and has been reported to be selectively toxic by increasing the level of reactive oxygen species (ROS) in tumor cells and inducing downstream apoptotic cell death. However, the precise mechanism of piperlongumine's antitumor effects remains largely unknown.

Piperlongumine is a chalcone-type compound, consisting of two ring systems linked by an α-β-unsaturated carbonyl chain. One of the two rings of piperlongumine is an aromatic phenyl substituted with three methoxy groups, while the second is a 2-piperidinone-type ring containing a conjugated alkene.

Various analogues of piperlongumine having substitutions around the two ring structures as well as in the linker have been described (U.S. Pat. Nos. 9,108,923; 8,318,737; US2009/0312373; US 2012/0059004; WO2016014625; Lad et al., *European J. Med. Chem.* (2017) 126:870-878; Meegan et al., *European* J. Med. Chem. (2017) 125:453-463; Wu et al., *European J. Med. Chem.* (2014) 82:545-551; and Han et al., *Org. Biomol. Chem.* (2016) 14:7585-7593). Furthermore, several analogues of piperlongumine containing modifications in the aromatic ring were described by Zou et al., *European J. Med. Chem.* (2017) 138:313-319. Although these analogues of piperlongumine were reported to exhibit increased cytotoxicity levels in vitro, none of these compounds has demonstrated any improvement in vivo over the naturally occurring piperlongumine, particularly their efficacy and other pharmacological properties that are desirable as an anticancer drug.

Therefore, there exists a need for derivatives and analogues of piperlongumine that exhibit pharmacological properties superior to piperlongumine.

BRIEF DESCRIPTION OF THE DRAWINGS

FIG. 1 illustrates plasma pharmacokinetics of Compound 1 ((E)-1-(3-(8-methoxy-2,3-dihydrobenzo[b][1,4]dioxin-6-yl)acryloyl)-5,6-dihydropyridin-2(1H)-one) in mice dosed intravenously (5 mg/kg), intraperitoneally (10 mg/kg) and orally (10 mg/kg) (n=5 per each dosing category).

BRIEF SUMMARY

The present disclosure provides compositions of piperlongumine derivatives and methods of use therefor. The present invention is based on a discovery that novel derivatives of piperlongumine are useful for treating cancer as they demonstrate increased cytotoxicity or other beneficial pharmacological effect, inter alias, bioavailability and metabolic stability to overcome the shortcomings of piperlongumine as a therapeutic compound. The compounds and compositions described herein are to be administered to a subject in need of treatment for a cell proliferation disorder such as cancer. Non-limiting examples of cancer include leukemia, lymphoma, lung cancer, liver cancer, gastric cancer, colon cancer, CNS cancer, melanoma, ovarian cancer, renal cancer, prostate cancer, breast cancer, head and neck cancers, brain cancer and pancreatic cancer. The subject is typically a mammal diagnosed as being in need of treatment for one or more of such proliferative disorders, and frequently the subject is a human. The methods comprise administering an effective amount of at least one compound of the invention; optionally the compound may be administered in combination with one or more additional therapeutic agents, particularly therapeutic agents known to be useful for treating the cancer or proliferative disorder afflicting the particular subject.

The present disclosure provides compounds of Formula (I), and pharmaceutically acceptable salts thereof.

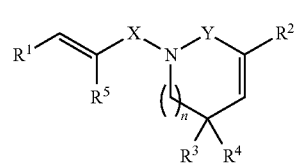

Formula (I)

When n is an integer of 1 according to Formula (I), then
X or Y is independently C(O) or S(O)$_2$;
R$^1$ is selected from the group consisting of:
i) a 3-9 member saturated or partially unsaturated cycloalkyl group having 0-5 heteroatom(s);
ii) a 5 member monocyclic heteroaryl group having 2-3 heteroatoms;
iii) a 6 member monocyclic heteroaryl group having 1-3 heteroatom(s), wherein said 6 member monocyclic heteroaryl group has:
   a) 1-3 heteroatom(s) when X or Y is S(O)$_2$ or when at least one of R$^2$, R$^3$ or R$^4$ is substituted;
   b) two heteroatoms when said 6 member monocyclic heteroaryl group is pyridazinyl or pyrimidyl; or
   c) three heteroatoms when at least one of X and Y is independently C(O);
iv) a 7-9 member monocyclic unsaturated cycloheteroalkyl group having 1-3 heteroatom(s);
v) a 7-13 member polycyclic heteroaryl group having 1-5 heteroatom(s), wherein said 7-13 member heteroaryl group has:
   a) 1-5 heteroatom(s) when at least one of X or Y is S(O)$_2$ and at least one of R$^2$, R$^3$ or R$^4$ is substituted; or
   b) 2-5 heteroatoms when X and Y are C(O); and
vi) a C$_1$-C$_3$ alkyl group,
   wherein said heteroatom(s) contained in each cyclic group is independently selected from the group consisting of N, O, and S; and wherein each cyclic group is optionally substituted with halo, alkyl, alkenyl, alkynyl, alkoxy, acyl, acyloxy, carboxylic acid, ester, amine, amide, carbonate, carbamate, carbonyl, cyano, nitro, thioether, thioester, cycloalkyl, cycloheteroalkyl, heterocyclyl, aryl, or heteroaryl, any of which is unsubstituted or substituted with halo, hydroxyl, sulfhydryl, nitro, nitroso, cyano, azido, alkyl, alkenyl, cycloalkyl, cycloheteroalkyl, heterocyclyl, aryl or heteroaryl;

$R^2$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl;

each of $R^3$ and $R^4$ is independently selected from the group consisting of hydrogen, halo, hydroxyl, alkyl, alkenyl, and alkynyl, any of which is optionally substituted with halo, hydroxyl, alkyl, or cycloalkyl, or $R^3$ taken together with one or more atoms of $R^4$ forms a cycloalkyl or cycloheteroalkyl; and $R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl; or when n is an integer of 0 or 2 according to Formula (I), then X or Y is independently C(O) or $S(O)_2$;

$R^1$ is selected from the group consisting of:
a) branched $C_1$-$C_3$ alkyl,
b) saturated or partially unsaturated $C_3$-$C_9$ cycloalkyl having no heteroatom, and
c) saturated, partially unsaturated or unsaturated 3-13 membered heterocyclyl having 1-5 heteroatom(s) independently selected from the group consisting of N, O, and S,
wherein each group is optionally substituted with halo, alkyl, alkenyl, alkynyl, alkoxy, acyl, acyloxy, carboxylic acid, ester, amine, amide, carbonate, carbamate, carbonyl, cyano, nitro, thioether, thioester, cycloalkyl, cycloheteroalkyl, aryl, heteroaryl, or heterocyclyl, any of which is unsubstituted or substituted with halo, hydroxyl, sulfhydryl, nitro, nitroso, cyano, azido, alkyl, alkenyl, cycloalkyl, cycloheteroalkyl, aryl, heteroaryl, or heterocyclyl;

$R^2$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl;

each of $R^3$ and $R^4$ is independently selected from the group consisting of hydrogen, halo, hydroxyl, alkyl, alkenyl, alkynyl, alkoxy, cycloalkyl, and cycloheteroalkyl, any of which is optionally substituted with halo, hydroxyl, alkyl, or cycloalkyl; or $R^3$ taken together with one or more atoms of $R^4$ forms a cycloalkyl or cycloheteroalkyl, each of which is optionally substituted with halo, hydroxyl, alkyl, alkenyl, alkynyl, or alkoxy; and $R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In some aspects, each of X and Y is independently C(O) or $S(O)_2$ according to the provisos that govern the integer n.

In one aspect, $R^1$ can be a 3-9 member saturated cycloalkyl group having no heteroatom.

In another aspect, $R^1$ can be a 3-9 member saturated cycloheteroalkyl group having 1-5 heteroatom(s) is selected from the group consisting of aziridinyl, diaziridinyl, oxiranyl, dioxiranyl, oxaziridinyl, thiiranyl, azetidinyl, diazetidinyl, oxetanyl, dioxetanyl, thietanyl, dithietanyl, pyrrolidinyl, imidazolidinyl, pyrazolidinyl, tetrahydropyranyl, tetrahydrofuranyl, oxolanyl, oxazolidinyl, thiolanyl, thiazolidinyl, piperidinyl, piperazinyl, morpholinyl, thiomorpholinyl, oxanyl, dioxanyl, thianyl, dithianyl, hexahydro-1,3,5-triazinyl, trioxanyl, trithianyl, azepanyl, diazepanyl, oxepanyl, thiepanyl, azocanyl, oxocanyl, thiocanyl, azonanyl, oxonanyl, quinolizinyl, and thionanyl.

In one embodiment, $R^1$ can be piperidinyl, piperazinyl, morpholinyl, thiomorpholinyl, dioxanyl, tetrahydropyranyl, tetrahydrofuranyl, oxanyl, oxolanyl, or oxazolidinyl.

In one aspect, $R^1$ can be a 3-9 member partially unsaturated cycloalkyl group selected from the group consisting of pyranyl, pyrrolinyl, pyrazolinyl, imidazolinyl, pyridonyl, dihydropyranyl, dihydropyrrolyl, dihydroimidazolyl, dihydropyrimidinyl, dihydropyrazinyl, dihydrotriazinyl, dihydropyridinyl, dihydrooxadiazolyl, thiazolinyl, dioxinyl, oxazinyl, and oxazolyl. In a preferred embodiment, $R^1$ is pyridonyl, optionally substituted with an alkyl.

In one aspect, $R^1$ can be a 5 member unsaturated monocyclic heteroaryl group selected from the group consisting of pyrazolyl, imidazolyl, triazolyl, tetrazolyl, thiazolyl, dithiazolyl, isothiazolyl, thiadiazolyl, furazanyl, oxazolyl, isoxazolyl, and oxadiazolyl, with the proviso that $R^1$ is not furanyl or thiophenyl particularly when Y is $S(O)_2$. In one embodiment, the 5 member unsaturated monocyclic heteroaryl group is furazanyl. In another embodiment, the 5 member unsaturated monocyclic heteroaryl group is pyrazolyl. In another embodiment, the 5 member unsaturated monocyclic heteroaryl group is triazolyl. In another embodiment, the 5 member unsaturated monocyclic heteroaryl group is imidazolyl. In a preferred embodiment, the 5 member unsaturated monocyclic heteroaryl group is oxadiazolyl, for example, 1,2,3-oxadiazolyl, 1,2,4-oxadiazolyl, and 1,3,4-oxadiazolyl.

In one aspect, $R^1$ can be a 6 member monocyclic heteroaryl group selected from the group consisting of pyridinyl, diazinyl (e.g., pyrazinyl, pyrimidinyl, or pyridazinyl), triazinyl (e.g., 1,2,3-triazinyl, 1,2,4-triazinyl, or 1,3,5-triazinyl), pyranyl, oxazinyl (e.g., 1,2-oxazinyl; 1,3-oxazinyl, or 1,4-oxazinyl), thiazinyl, dioxinyl, dithiinyl, and triazinyl, with the proviso that $R^1$ is not pyridinyl or parazinyl when both X and Y are independently C(O).

In one aspect, $R^1$ can be a 7-9 member unsaturated monocyclic cycloheteroalkyl group having 1-3 heteroatom(s) selected from azepinyl, diazepinyl, oxepinyl, thiepinyl, thiazepinyl, azocinyl, oxocinyl, thiocinyl, azoninyl, oxoninyl, or thioninyl.

In one aspect, $R^1$ can be a polycyclic heteroaryl group is selected from the group consisting of dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, benzodioxinyl, purinyl, isoindolyl, isoquinolinyl, quinoxalinyl, quinazolinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzooxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, and fluorenyl, with the proviso that $R^1$ is not indolyl or imidazopyridinyl when Y is $S(O)_2$ or that $R^1$ is not quinolinyl when both X and Y are C(O). In one aspect, the polycyclic heteroaryl is a 7-13 member polycyclic heteroaryl group formed by covalently bonding a heteroaryl group to a cycloheteroalkyl group, for example, fusing pyridinyl, pyridazinyl, pyrimidinyl, or pyrazinyl with dioxanyl. In one embodiment, $R^1$ is dihydrobenzodioxinyl. In one embodiment, $R^1$ is dihydrodioxinopyridinyl. In one embodiment, $R^1$ is dihydrodioxinopyridazinyl. In one embodiment, $R^1$ is dihydrodioxinopyrimidinyl. In one embodiment, $R^1$ is dihydrodioxinopyrazinyl. In one embodiment, $R^1$ is dihydropyrrolopyridinyl. In one embodiment, $R^1$ is tetrahydronaphthyridinyl. In one embodiment, $R^1$ is tetrahydropyridopyridazinyl. In one embodiment, $R^1$ is tetrahydropyridopyrazinyl. In one embodiment, $R^1$ is tetrahydropyridopyrimidinyl. In one embodiment, $R^1$ is benzodioxinyl.

In one aspect, $R^1$ can be $C_1$-$C_3$ alkyl. In one embodiment, $R^1$ is a branched $C_1$-$C_3$ alkyl group, optionally substituted with halo, hydroxyl, alkyl, alkenyl, alkynyl, alkoxy, cycloalkyl, cycloheteroalkyl, aryl, heteroaryl, or heterocyclyl.

In one aspect, $R^2$ can be hydrogen, halo, cyano, or alkynyl.

In one aspect, $R^3$ can be hydrogen, halo, hydroxyl, alkyl, alkenyl, or alkynyl.

In one aspect, $R^4$ can be hydrogen, halo, hydroxyl, alkyl, alkenyl, or alkynyl.

In another aspect, $R^3$ taken together with one or more atoms of $R^4$ forms a cycloalkyl or cycloheteroalkyl.

In yet another aspect, $R^2$, $R^3$, or $R^4$ is optionally and independently substituted with halo, cyano, hydroxyl, alkyl, alkenyl, alkynyl, alkoxy, cycloalkyl, cycloheteroalkyl, aryl, heteroaryl, or heterocyclyl.

In one aspect, $R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In one embodiment, $R^5$ is hydrogen.

In one embodiment, $R^5$ is cyano.

In another embodiment, $R^5$ is alkyl optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one particular embodiment, $R^5$ is methyl. In another particular embodiment, $R^5$ is methyl substituted with phenyl. In another embodiment, $R^5$ is ethyl.

In one embodiment, $R^5$ can be in geometric isomerism. For example, $R^5$ can be attached in a cis or trans conformation with respect to $R^1$.

In some other aspects, n can be any integer of 1, 2, or 3 with the proviso that at least one of X or Y is $S(O)_2$ and at least one of $R^2$, $R^3$ or $R^4$ is substituted. In one aspect, $R^1$ can be a 3-13 member substituted or unsubstituted heterocyclyl group having 1-5 heteroatom(s) independently selected from the group consisting of N, O, and S.

In one aspect, $R^1$ can be a 3-9 member saturated cycloheteroalkyl group having 1-5 heteroatom(s) selected from the group consisting of aziridinyl, diaziridinyl, oxiranyl, dioxiranyl, oxaziridinyl, thiiranyl, azetidinyl, diazetidinyl, oxetanyl, dioxetanyl, thietanyl, dithietanyl, pyrrolidinyl, imidazolidinyl, pyrazolidinyl, tetrahydropyranyl, tetrahydrofuranyl, oxolanyl, oxazolidinyl, thiolanyl, thiazolidinyl, piperidinyl, piperazinyl, morpholinyl, thiomorpholinyl, oxanyl, dioxanyl, thianyl, dithianyl, hexahydro-1,3,5-triazinyl, trioxanyl, trithianyl, azepanyl, diazepanyl, oxepanyl, thiepanyl, azocanyl, oxocanyl, thiocanyl, azonanyl, oxonanyl, quinolizinyl, and thionanyl. In one embodiment, $R^1$ can be piperidinyl, piperazinyl, morpholinyl, thiomorpholinyl, dioxanyl, tetrahydropyranyl, tetrahydrofuranyl, oxanyl, oxolanyl, or oxazolidinyl.

In another aspect, $R^1$ can be a 3-9 member partially unsaturated cycloheteroalkyl group selected from the group consisting of pyranyl, pyrrolinyl, pyrazolinyl, imidazolinyl, pyridonyl, dihydropyranyl, dihydropyrrolyl, dihydroimidazolyl, dihydropyrimidinyl, dihydropyrazinyl, dihydrotriazinyl, dihydropyridinyl, dihydrooxadiazolyl, thiazolinyl, dioxinyl, oxazinyl, and oxazolyl. In a preferred embodiment, $R^1$ is pyridonyl, optionally substituted with an alkyl.

In another aspect, $R^1$ can be an unsaturated 3-4 member monocyclic heterocyclyl group having 1-3 heteroatom(s), including, for example, azirinyl, oxirenyl, thiirenyl, diazirinyl, azetyl, diazetyl, oxetyl, dioxetyl, thietyl, and dithietyl.

In another aspect, $R^1$ can be a 5 member unsaturated monocyclic heteroaryl group having 2-3 heteroatoms. In one embodiment, the 5 member monocyclic heteroaryl group is selected from the group consisting of pyrrolyl, pyrrolinyl, pyrazolyl, pyrazolinyl, imidazolyl, imidazolinyl, triazolyl (e.g., 1,2,3-triazolyl and 1,2,4-triazolyl), tetrazolyl, thiophenyl, thiazolyl, dithiazolyl, thiazolinyl, isothiazolyl, thiadiazolyl, furanyl, furazanyl, oxazolyl, isoxazolyl, and oxadiazolyl (e.g., 1,2,5-oxidiazolyl, 1,2,3-oxidiazolyl, and 1,2,4-oxidiazolyl), optionally substituted. In one embodiment, the 5 member unsaturated monocyclic heteroaryl group is furazanyl. In one embodiment, the 5 member unsaturated monocyclic heteroaryl group is oxadiazolyl, for example, 1,2,3-oxadiazolyl, 1,2,4-oxadiazolyl, and 1,3,4-oxadiazolyl. In one preferred embodiment, the 5 member unsaturated monocyclic heteroaryl group is 1,2,4-oxadiazolyl which is optionally substituted. In another embodiment, the 5 member unsaturated monocyclic heteroaryl group is triazolyl. In one preferred embodiment, the triazolyl is 1,2,3-triazolyl or 1,2,4-triazolyl, each of which is optionally substituted. In yet another embodiment, $R^1$ is tetrazolyl. In yet another embodiment, $R^1$ is imidazolyl optionally substituted. In yet another preferred embodiment, $R^1$ is pyrazonyl optionally substituted. The 5 member monocyclic heteroaryl group may be optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In another aspect, the 3-13 member heterocyclyl group of $R^1$ can be a 6 member unsaturated monocyclic heteroaryl group selected from the group consisting of pyridyl, pyridinyl, diazinyl (e.g., pyrazinyl, pyrimidinyl, or pyridazinyl), and triazinyl (e.g., 1,2,3-triazinyl, 1,2,4-triazinyl, or 1,3,5-triazinyl).

In another aspect, the 3-13 member heterocyclyl group of $R^1$ can be a 7-9 member unsaturated monocyclic cycloheteroalkyl having 1-3 heteroatom(s) selected from azepinyl, diazepinyl, oxepinyl, thiepinyl, thiazepinyl, azocinyl, oxocinyl, thiocinyl, azoninyl, oxoninyl, or thioninyl.

In another aspect, the 3-13 member heterocyclyl group of $R^1$ is a 7-13 member polycyclic heterocycle group having 1-5 heteroatom(s). In one embodiment, the 7-13 member polycyclic heterocycle group can be a polycyclic heteroaryl is selected from the group consisting of dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, benzodioxinyl, purinyl, isoindolyl, isoquinolinyl, quinoxalinyl, quinazolinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzooxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, and fluorenyl. In another embodiment, the polycyclic heteroaryl is a 7-13 member polycyclic heteroaryl group formed by covalently bonding a heteroaryl to a dioxanyl, for example, fusing a pyridinyl, pyridazinyl, pyrimidinyl, or pyrazinyl with a dioxanyl. In one particular embodiment, $R^1$ is dihydrobenzodioxinyl. In another particular embodiment, $R^1$ is dihydrodioxinopyridinyl. In yet another particular embodiment, $R^1$ is dihydrodioxinopyridazinyl. In yet another particular embodiment, $R^1$ is dihydrodioxinopyrimidinyl. In yet another particular embodiment, $R^1$ is dihydrodioxinopyrazinyl. In yet another embodiment, $R^1$ is dihydropyrrolopyridinyl. In still another embodiment, $R^1$ is tetrahydronaphthyridinyl. In still another embodiment, $R^1$ is tetrahydropyridopyridazinyl. In still another embodiment, $R^1$ is tetrahydropyridopyrazinyl. In still another embodiment, $R^1$ is tetrahydropyridopyrimidinyl. In still another embodiment, $R^1$ is benzodioxinyl.

In one aspect, $R^2$ can be selected from hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, aryl, heteroaryl, or heterocyclyl, each of which is optionally substituted with halo, hydroxyl, sulfhydryl, nitro, nitroso, cyano, azido, alkyl, alkenyl, cycloalkyl, cycloheteroalkyl, aryl, heteroaryl or heterocyclyl. In one embodiment, $R^2$ can be hydrogen, halo, cyano, or alkynyl.

In one aspect, each of $R^3$ and $R^4$ is independently selected from the group consisting of hydrogen, halo, hydroxyl, alkyl, alkenyl, alkynyl, alkoxy, cycloalkyl, and cycloheteroalkyl, any of which is optionally substituted with halo, hydroxyl, alkyl, or cycloalkyl.

In another aspect, $R^3$ taken together with one or more atoms of $R^4$ forms a cycloalkyl or cycloheteroalkyl, each of which is optionally substituted with halo, hydroxyl, alkyl, alkenyl, alkynyl, or alkoxy.

In one aspect, $R^5$ is selected from the group consisting of halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In one embodiment, $R^5$ is hydrogen.

In one embodiment, $R^5$ is cyano.

In another embodiment, $R^5$ is alkyl optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one particular embodiment, $R^5$ is methyl. In another particular embodiment, $R^5$ is methyl substituted with phenyl. In another embodiment, $R^5$ is ethyl.

In one embodiment, $R^5$ can be in geometric isomerism. For example, $R^5$ can be attached in a cis or trans conformation with respect to R'.

The present invention contemplates pharmaceutical compositions comprising a compound of Formula (I) and a pharmaceutically acceptable carrier. In certain embodiments, such pharmaceutical compositions are formulated for intravenous administration, subcutaneous administration, inhalation, oral administration, rectal administration, parenteral, intravitreal administration, intramuscular administration, intranasal administration, dermal administration, topical administration, otic administration, ophthalmic administration, buccal administration, tracheal administration, bronchial administration, or sublingual administration. In other embodiments, such pharmaceutical compositions are formulated as tablets, pills, solution, capsules, liquid, an inhalant, nasal spray solution, suppository, gel, emulsion, or ointment.

The present invention also contemplates methods for treating a cell-proliferative disease or condition, such as cancer, comprising administering to a subject in need of such treatment a therapeutically effective amount of a compound of Formula (I), a pharmaceutically acceptable salt thereof, pharmaceutical compositions or medicaments thereof, wherein the cell proliferative disease or condition include, for example, leukemia, lymphoma, osteosarcoma, melanoma, breast cancer, renal cancer, prostate cancer, gastric cancer, colorectal cancer, liver cancer, thyroid cancer, head and neck cancer, ovarian cancer, pancreatic cancer, neuronal cancer, lung cancer, or uterine cancer. In one aspect, the present invention provides methods of inhibiting growth of cancer cells with the compound of Formula (I) or a pharmaceutically acceptable salt thereof.

DETAILED DESCRIPTION

The present disclosure provides a group of 1-[(E)-3-(3,4,5-trimethoxyphenyl)prop-2-enoyl]-2,3-dihydropyridin-6-one (piperlongumine) derivatives and pharmaceutically acceptable salts thereof that are useful in treating a preliferative disease such as cancer. Disclosed herein are novel composition of piperlongumine derivatives and methods of synthesizing and administering such derivatives. The present disclosure also provides pharmaceutical formulations comprising at least one of the compounds described herein with a pharmaceutically acceptable carrier, diluent or excipient therefor.

Definitions

As used herein, "a" or "an" means "at least one" or "one or more."

As used herein, "or" means "and/or."

As used herein, the term "alkyl" refers to saturated hydrocarbon groups in a straight, branched, or cyclic configuration or any combination thereof, and particularly contemplated alkyl groups include those having ten or less carbon atoms, especially 1-6 carbon atoms and lower alkyl groups having 1-4 carbon atoms. Exemplary alkyl groups are methyl, ethyl, propyl, isopropyl, butyl, sec-butyl, tert-butyl, pentyl, isopentyl, hexyl, cyclopropylmethyl, and the like. Alkyl groups can be unsubstituted, or they can be substituted to the extent that such substitution is chemically feasible. Typical substituents include, but are not limited to, halo, =O, =N—CN, =N—OR$^a$, =NR$^a$, —OR$^a$, —NR$^a{}_2$, —SR$^a$, —SO$_2$R$^a$, —SO$_2$NR$^a{}_2$, —NR$^a$SO$_2$R$^a$, —NR$^a$CONR$^a{}_2$, —NR$^a$COOR$^a$, —NR$^a$COR$^a$, —NO$_2$, —CN, —COOR$^a$, —CONR$^a{}_2$, —OOCR$^a$, —COR$^a$, and —R$^a$, wherein each R$^a$ is independently H, C$_1$-C$_8$ alkyl, C$_2$-C$_8$ heteroalkyl, C$_3$-C$_8$ heterocyclyl, C$_4$-C$_{10}$ heterocycloalkyl, C$_1$-C$_8$ acyl, C$_2$-C$_8$ heteroacyl, C$_2$-C$_8$ alkenyl, C$_2$-C$_8$ heteroalkenyl, C$_2$-C$_8$ alkynyl, C$_2$-C$_8$ heteroalkynyl, C$_6$-C$_{10}$ aryl, or C$_5$-C$_{10}$ heteroaryl, and each R$^a$ is optionally substituted with halo, =O, =N—CN, =N—OR$^b$, =NR$^b$, —OR$^b$, —NR$^b{}_2$, —SR$^b$, —SO$_2$R$^b$, —SO$_2$NR$^b{}_2$, —NR$^b$SO$_2$R$^b$, —NR$^b$CONR$^b{}_2$, —NR$^b$COOR$^b$, —NR$^b$COR$^b$, —NO$_2$, —CN, —COOR$^b$, —CONR$^b{}_2$, —OOCR$^b$, —COR$^b$, and —R$^b$, wherein each R$^b$ is independently H, C$_1$-C$_8$ alkyl, C$_2$-C$_8$ heteroalkyl, C$_3$-C$_8$ heterocyclyl, C$_4$-C$_{10}$ heterocycloalkyl, C$_1$-C$_8$ acyl, C$_2$-C$_8$ heteroacyl, C$_2$-C$_8$ alkenyl, C$_2$-C$_8$ heteroalkenyl, C$_2$-C$_8$ alkynyl, C$_2$-C$_8$ heteroalkynyl, C$_6$-C$_{10}$ aryl, or C$_5$-C$_{10}$ heteroaryl. Alkyl, alkenyl and alkynyl groups can also be substituted by C$_1$-C$_8$ acyl, C$_2$-C$_8$ heteroacyl, C$_6$-C$_{10}$ aryl or C$_5$-C$_{10}$ heteroaryl, each of which can be substituted by the substituents that are appropriate for the particular group. Where a substituent group contains two R$^a$ or R$^b$ groups on the same or adjacent atoms (e.g., —NR$^b{}_2$, or —NR$^b$—C(O)R$^b$), the two R$^a$ or R$^b$ groups can optionally be taken together with the atoms in the substituent group to which are attached to form a ring having 5-8 ring members, which can be substituted as allowed for the R$^a$ or R$^b$ itself, and can contain an additional heteroatom (N, O or S) as a ring member.

As used herein, the term "alkenyl" refers to hydrocarbon chain having at least two carbon atoms and at least one carbon-carbon double bond and includes straight, branched, or cyclic alkenyl groups having two to ten carbon atoms. Non-limiting examples of "alkenyl" include ethenyl, propenyl, butenyl, pentenyl, and cyclic alkenyl groups. An alkenyl can be unsubstituted or substituted with one or more suitable substituents.

As used herein, the term "alkynyl" refers to unbranched and branched hydrocarbon moieties having at least two (preferably three) carbon atoms and at least one carbon-carbon triple bond and includes ethynyl, propynyl, butynyl, cyclopropylethynyl, and the like. An alkynyl can be unsubstituted or substituted with one or more suitable substituents.

As used herein, the term "alkoxy" refers to the alkyl groups above bound through oxygen, examples of which include methoxy, ethoxy, propyloxy, isopropoxy, tert-butoxy, methoxyethoxy, benzyloxy, allyloxy, and the like. In addition, alkoxy also refers to polyethers such as —O—(CH$_2$)$_2$—O—CH$_3$, and the like. An alkoxy can be any hydrocarbon group connected through an oxygen atom wherein the hydrocarbon portion may have any number of carbon atoms, typically 1-10 carbon atoms, may further include a double or triple bond and may include one or two oxygen, sulfur or nitrogen atoms in the alkyl chains. An alkoxy can be unsubstituted or substituted with one or more suitable substituents, e.g., aryl, heteroaryl, cycloalkyl, and/or heterocyclyl.

As used herein, the term "cycloalkyl" refers to cyclic alkane in which a chain of carbon atoms of a hydrocarbon forms a ring, and includes a monocyclic or polycyclic hydrocarbon ring group, for example, cyclopropyl, cyclobutyl, cyclopentyl, cyclohexyl, cycloheptyl, cyclooctyl, cyclodecyl, adamantyl, norpinanyl, decalinyl, norbornyl, housanyl, and the like. Further, a cycloalkyl can also include one or two double bonds, which form the "cycloalkenyl" groups (e.g., cyclopropenyl, cyclobutenyl, cyclopentenyl, cyclohexenyl, cycloheptenyl, cyclooctenyl, norbornenyl, norbornadienyl, and the like). A cycloalkyl can also comprise one or more heteroatoms and referred to as "cycloheteroalkyl" and can include, for example, piperazinyl piperidinyl, morpholinyl, thiomorpholinyl, oxanyl, dioxanyl (e.g., 1,4-dioxanyl), thianyl, dithianyl, hexahydro-1,3,5-triazinyl, trioxanyl, trithianyl, pyrrolidinyl, imidazolidinyl, pyranyl, tetrahydropyranyl, pyrazolidinyl, oxolanyl, oxazolidinyl, thiolanyl, thiazolidinyl, pyrrolinyl, pyrazolinyl, imidazolinyl, tetrahydrofuranyl, and the like. A cycloalkyl or cycloheteroalkyl group can be unsubstituted or substituted with one or more suitable substituents.

As used herein, the term "hetero" refers to an atom of any element other than carbon or hydrogen. As used herein, the term "heteroatom" means nitrogen (N), oxygen (O), or sulfur (S).

As used herein, the term "heterocycle" or "heterocyclyl" encompasses all limitations of "cycloheteroalkyl" and "heteroaryl" groups in so far as chemically feasible. The term "heterocycle" or "heterocyclyl" refers to any compound in which a plurality of atoms forms a ring via a plurality of covalent bonds, wherein the ring includes at least one atom other than a carbon atom as a ring member. A heterocycle can be saturated, unsaturated, or partially unsaturated. An unsaturated heterocycle can be aromatic aryl. Non-limiting examples of a heterocyclic ring include 3-, 4-, 5-, 6-, 7-, 8- and 9-membered monocyclic rings containing one or more N, O, or S as the non-carbon member(s) and are as follows: (1) a saturated 3 atom heterocyclic ring can be, for example, aziridinyl, diaziridinyl, oxiranyl, dioxiranyl, oxaziridinyl, thiiranyl, or the like, and an unsaturated 3 atom heterocyclic ring can be, for example, azirinyl, oxirenyl, thiirenyl, diazirinyl, or the like; (2) a saturated 4 atom heterocyclic ring can be, for example, azetidinyl, diazetidinyl, oxetanyl, dioxetanyl, thietanyl, dithietanyl, or the like, and an unsaturated 4 atom heterocyclic ring can be, for example, azetyl, diazetyl, oxetyl, dioxetyl, thietyl, dithietyl, or the like; (3) a saturated 5 atom heterocyclic ring can be, for example, pyrrolidinyl, imidazolidinyl, pyrazolidinyl, oxolanyl, oxazolidinyl, thiolanyl, thiazolidinyl, or the like, and an unsaturated and partially unsaturated 5 atom heterocyclic ring can be, for example, pyrrolyl, pyrrolinyl, pyrazolyl, pyrazolinyl, imidazolyl, imidazolinyl, triazolyl, tetrazolyl, thiophenyl, thiazolyl, dithiazolyl, thiazolinyl, isothiazolyl, thiadiazolyl, furanyl, furazanyl, oxazolyl, isoxazolyl, oxadiazolyl, or the like; (4) a saturated 6 atom heterocyclic ring can be, for example, piperidinyl, piperazinyl, morpholinyl, thiomorpholinyl, oxanyl, dioxanyl (e.g., 1,4-dioxacyclohexane), thianyl, dithianyl, hexahydro-1,3,5-triazinyl, trioxanyl, trithianyl, or the like, and an unsaturated 6 atom heterocyclic ring can be, for example, pyridinyl, diazinyl (e.g., pyrimidinyl, or pyridazinyl), pyranyl, oxazinyl (e.g., 1,2-oxazinyl; 1,3-oxazinyl, or 1,4-oxazinyl), thiazinyl, 1,4-dioxinyl, dithiinyl, triazinyl (e.g., 1,2,3-triazinyl, 1,2,4-triazinyl, or 1,3,5-triazinyl), tetrazinyl, pentazinyl, thiopyranyl, or the like; (5)

a saturated 7 atom heterocyclic ring can be, for example, azepanyl, diazepanyl, oxepanyl, thiepanyl, or the like, and an unsaturated 7 atom heterocyclic ring can be, for example, azepinyl, diazepinyl, oxepinyl, thiepinyl, thiazepinyl, or the like; (6) a saturated 8 atom heterocyclic ring can be, for example, azocanyl, oxocanyl, thiocanyl, or the like, and an unsaturated 8 atom heterocyclic ring can be, for example, azocinyl, oxocinyl, thiocinyl, or the like; and (7) a saturated 9 atom heterocyclic ring can be, for example, azonanyl, oxonanyl, thionanyl, or the like, and an unsaturated 9 atom heterocyclic ring can be, for example, azoninyl, oxoninyl, thioninyl, or the like. Further contemplated heterocycles may be fused, for example, covalently bound with two atoms on the first non-heterocyclic group (e.g., phenyl) to one or two heterocycles (e.g., 1,4-dioxanyl, 1,4-dioxinyl, and tetrahydropyranyl), or covalently bound with two atoms on the first heterocyclic ring (e.g., pyrrolyl, imidazolyl, thiazolyl, pyrimidinyl, and pyridinyl) to one or two nonheterocyclic or heterocyclic group (e.g., 1,4-dioxanyl, 1,4-dioxinyl, and morpholinyl), and taken together are thus termed "fused heterocycle" or "fused heterocyclic moieties" or "heteroaryl-fused-cycloheteroalkyl" as used herein. The fused heterocycle can be, for example, a saturated or unsaturated (e.g., aromatic) bicyclic or tricyclic compound. Non-limiting examples of fused heterocycle include dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinolinyl, isoquinolinyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, fluorenyl, and the like. Where the heterocyclic ring is aromatic, it can be also referred to herein as "heteroaryl" or "heteroaromatic" as described further below. A heterocyclic ring that is not aromatic can be substituted with any group suitable for alkyl group substituents described above.

As used herein, the term "aryl" refers to unsubstituted or substituted aromatic monocyclic or polycyclic groups, which may further include one or more non-carbon atoms. The term "aryl" also includes aromatic rings fused to non-aromatic carbocyclic ring, or to a heterocyclyl group having 1-7 heteroatoms. The term "aryl" may be interchangeably used with "aryl ring," "aromatic group," and "aromatic ring." An aryl group may contain 1-9 heteroatom(s) that are generally referred to as "heteroaryl." Heteroaryl groups typically have 4 to 14 atoms, 1 to 9 of which are independently selected from the group consisting of N, O, and S. In a 5-8 membered aromatic group, for example, a heteroaryl group can contain 1-4 heteroatoms. An aryl or heteroaryl can be unsubstituted or substituted with one or more suitable substituents.

An aryl or heteroaryl can be a mono- or polycyclic (e.g., bicyclic) aromatic group. Typical aryl groups include, for example, phenyl and naphthalenyl and the like. Typical heteroaryl groups include, for example, quinolinyl, pyrrolyl, pyrazolyl, imidazolyl, triazolyl, tetrazolyl, thiophenyl, thiazolyl, dithiazolyl, thiazolinyl, isothiazolyl, thiadiazolyl, furanyl, furazanyl, oxazolyl, isoxazolyl, oxadiazolyl, pyridinyl, diazinyl (e.g., pyrazinyl, pyrimidinyl, or pyridazinyl), triazinyl (e.g., 1,2,3-triazinyl, 1,2,4-triazinyl, or 1,3,5-triazinyl), pyranyl, oxazinyl (e.g., 1,2-oxazinyl; 1,3-oxazinyl, or 1,4-oxazinyl), thiazinyl, dioxinyl, dithiinyl, triazinyl, tetrazinyl, pentazinyl, thiopyranyl, azepinyl, diazepinyl, oxepinyl, thiepinyl, thiazepinyl, azocinyl, oxocinyl, thiocinyl, azoninyl, oxoninyl, thioninyl, indolyl, indazolyl, purinyl, isoindolyl, quinolinyl, isoquinolinyl, quinoxalinyl, acridinyl, quinazolinyl, cinnolinyl, phthalazinyl, benzimidazolyl, benzofuranyl, isobenzofuranyl, benzoxazolyl, benzisoxazolyl, benzothiazolyl, or the like. Polycyclic aryl or polycyclic heteroaryl groups can be formed by fusing (i.e., covalently bonding) 2 atoms on the first aryl or heteroaryl ring with at least one carbocyclic or heterocyclic group, and are thus termed "fused aryl" or "heteroaryl-fused-cycloheteroalkyl."

As used herein, the term "heteroaryl-fused-cycloheteroalkyl" refers to a heterocyclyl moiety consisting of a monocyclic heteroaryl group, such as pyridyl or furanyl, fused to a cycloheteroalkyl group, in which the heteroaryl and cycloheteroalkyl parts are as defined herein. Exemplary heteroaryl-fused-heterocycloalkyl groups include dihydrodioxinopyridinyl, dihydrodioxinopyridazinyl, dihydrodioxinopyrimidinyl, dihydrodioxinopyrazinyl, dihydrodioxinotriazinyl, dihydropyrrolopyridinyl, dihydrofuranopyridinyl and dioxolopyridinyl. The heteroaryl-fused-heterocycloalkyl group may be attached to the remainder of the molecule by any available carbon or nitrogen atom.

Typical heteroaryl groups include 5 or 6 member monocyclic aromatic groups such as pyridyl, pyrimidyl, pyrazinyl, pyridazinyl, thienyl, furanyl, pyrrolyl, pyrazolyl, thiazolyl, oxazolyl, isothiazolyl, isoxazolyl, thiophenyl, triazolyl (1,2,4-triazolyl and 1,2,3-triazolyl), tetrazolyl, furazanyl, oxadiazolyl (1,2,5-oxadiazolyl and 1,2,3-oxadiazolyl), and imidazolyl and the fused bicyclic moieties formed by fusing one of heterocyclic groups with a phenyl ring or with any of the heteroaromatic monocyclic groups include indolyl, benzimidazolyl, indazolyl, benzotriazolyl, isoquinolyl, quinolyl, benzothiazolyl, benzofuranyl, pyrazolopyridyl, pyrazolopyrimidyl, quinazolinyl, quinoxalinyl, cinnolinyl, imidazopyrimidinyl, and the like.

As used herein, the term "monocyclic" refers to an unsubstituted or substituted single ring structure. As used herein, the terms "polycyclic" and "bicyclic" refer to an unsubstituted or substituted poly-ring structure that comprises at least two ring structures fused by any two adjacent atoms. A bicyclic ring can be an aryl or heteroaryl ring fused to an aromatic ring or a non-aromatic carbocyclic ring such as cycloalkyl or cycloheteroalkyl. A bicyclic ring can be also non-aromatic carbocyclic ring fused to another non-aromatic carbocyclic ring such as cycloalkyl or cycloheteroalkyl. Non-limiting examples of bicyclic rings include dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, decalinyl, purinyl, indolyl, isoindolyl, quinolyl, quinazolinyl, benzimidazolyl, imidazopyridyl, cinnolinyl, phthalazinyl, imidazopyrimidinyl, and the like. Any monocyclic or fused bicyclic system which has the characteristics of aromaticity in terms of electron distribution throughout the ring system is included in this definition. It also includes bicyclic groups where at least the ring which is directly attached to the remainder of the molecule has the characteristics of aromaticity.

Aryl and heteroaryl groups can be substituted where permitted. Suitable substituents include, but are not limited to, halo, $R^a$, $-OR^a$, $-NR^a_2$, $-SR^a$, $-SO_2R^a$, $-SO_2NR^a_2$, $-NR^aSO_2R^a$, $-NR^aCONR^a_2$, $-NR^aCOOR^a$, $-NR^aCOR^a$, $-CN$, $-COOR^a$, $-CONR^a_2$, $-OOCR^a$, $-COR^a$, and $-NO_2$, wherein each $R^a$ is independently H, $C_1$-$C_8$ alkyl, $C_2$-$C_8$ heteroalkyl, $C_3$-$C_8$ heterocyclyl, $C_4$-$C_{10}$ heterocycloalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl, and each $R^a$ is optionally substituted with halo, =O, =N—CN, =N—$OR^b$, $-NR^b$, $-OR^b$, $-NR^b_2$, $-SR^b$, $-SO_2R^b$, $-SO_2NR^b_2$, $-NR^bSO_2R^b$, $-NR^bCONR^b_2$, $-NR^bCOOR^b$, $-NR^bCOR^b$, $-CN$, $-COOR^b$, $-CONR^b_2$, $-OOCR^b$, $-COR^b$, and $-NO_2$, wherein each $R^b$ is independently H, $C_1$-$C_8$ alkyl, $C_2$-$C_5$ heteroalkyl, $C_3$-$C_5$ heterocyclyl, $C_4$-$C_{10}$ heterocycloalkyl, $C_1$-$C_8$ acyl, $C_2$-$C_8$ heteroacyl, $C_2$-$C_8$ alkenyl, $C_2$-$C_8$ heteroalkenyl, $C_2$-$C_8$ alkynyl, $C_2$-$C_8$ heteroalkynyl, $C_6$-$C_{10}$ aryl, or $C_5$-$C_{10}$ heteroaryl. Alkyl, alkenyl and alkynyl groups can also be substituted by $C_1$-$C_8$ acyl, $C_2$-$C_8$ heteroacyl, $C_6$-$C_{10}$ aryl or $C_5$-$C_{10}$ heteroaryl, each of which can be substituted by the substituents that are appropriate for the particular group. Where a substituent group contains two $R^a$ or $R^b$ groups on the same or adjacent atoms (e.g., $-NR^b_2$, or $-NR^b$—$C(O)R^b$), the two $R^a$ or $R^b$ groups can optionally be taken together with the atoms in the substituent group to which are attached to form a ring having 5-8 ring members, which can be substituted as allowed for the $R^a$ or $R^b$ itself, and can contain an additional heteroatom (N, O or S) as a ring member.

The term "sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cycloalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein each alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

As used herein, the term "acyl" when used without the "substituted" modifier refers to the group —C(O)R, in which R is a hydrogen, alkyl, aryl, halides, aralkyl or heteroaryl, as those terms are defined herein.

As used herein, the term "acyloxy" refers a straight-chain or branched alkanoyl group having 1 to 6 carbon atoms, such as formyl, acetyl, propanoyl, butyryl, valeryl, pivaloyl and hexanoyl, and arylcarbonyl group described below, or a heteroarylcarbonyl group described below. The aryl moiety of the arylcarbonyl group means a group having 6 to 16 carbon atoms such as phenyl, biphenyl, naphthyl, or pyrenyl. The heteroaryl moiety of the heteroarylcarbonyl group contains at least one hetero atom from 0, N, and S, such as pyridyl, pyrimidyl, pyrroleyl, furyl, benzofuryl, thienyl, benzothienyl, imidazolyl, triazolyl, quinolyl, iso-quinolyl, benzoimidazolyl, thiazolyl, benzothiazolyl, oxazolyl, and indolyl.

As used herein, the term "carboxylic acid" refers to a group —C(O)OH.

As used herein, the term "ester," as used herein, refers to a group —C(O)O—.

As used herein, the term "nitro" means —$NO_2$.

As used herein, the term "cyano" means —CN.

As used herein, the term "azido" means relating to a monovalent group containing —$N_3$.

As used herein, the term "sulfhydryl" means thiol, —SH.

As used herein, the term "amine" means primary, secondary and tertiary amines, $NH_2$, —R—NH—R', and —R—N—(R")R', respectively.

As used herein, the term "amide" means primary, secondary and tertiary amides, —R—C(O)$NH_2$, —R—C(O)NH—R', and —R—C(O)NR'R", respectively.

As used herein, the term "carbonate" means ester of carbonic acid, a group containing C(=O)(O—)$_2$.

As used herein, the term "carbamate" means a group containing $NH_2$COOH.

As used herein, the term "hydroxyl" means —OH.

As used herein, the terms "halo," "halogen," and "halide" mean fluoro (—F), chloro (—Cl), bromo (—Br), and iodo (—I).

As used herein, the term "haloalkyl" refers to any alkyl having one or more hydrogen atoms replaced by one or more halogen atoms. Non-limiting examples of haloalkyl include —$CF_3$, —CFH, and the like.

As used herein, the term "arylalkyl" refers to any alkyl in which one or more hydrogen atoms are replaced by an aryl or heteroaryl group. Examples of arylalkyl include benzyl ($C_6H_5CH_2$—) and the like.

As used herein, the term "hydroxyalkyl" refers to any hydroxy derivative of alkyl and includes any alkyl having one or more hydrogen atoms replaced by a —OH group.

The term "haloalkyl" refers to an alkyl group as described above with one or more hydrogen atoms on the alkyl group substituted with a halo group. Examples of such groups include, without limitation, fluoroalkyl groups, such as fluoroethyl, difluoromethyl, trifluoromethyl, trifluoroethyl and the like.

The term "haloalkoxy" refers to the group alkyl-O— with one or more hydrogen atoms on the alkyl group substituted with a halo group (e.g., —F, —Cl, —Br, and —I) and include, for example, groups such as trifluoromethoxy and the like.

The term "substituted" as used herein refers to a replacement of a hydrogen atom of the unsubstituted group with a functional group, and particularly contemplated functional groups include nucleophilic groups (e.g., —$NH_2$, —OH, —SH, —CN, etc.), electrophilic groups (e.g., C(O)OR, C(X)OH, etc.), polar groups (e.g., —OH), non-polar groups (e.g., heterocycle, aryl, alkyl, alkenyl, alkynyl, etc.), ionic groups (e.g., —$NH_3^+$), and halogens (e.g., —F, —Cl), NHCOR, NHCONH_2, OCH_2COOH, OCH_2CONH_2, OCH_2CONHR, NHCH_2COOH, NHCH_2CONH_2, NHSO_2R, OCH_2-heterocycles, PO_3H, SO_3H, amino acids, and all chemically reasonable combinations thereof. Moreover, the term "substituted" also includes multiple degrees of substitution, and where multiple substituents are disclosed or claimed, the substituted compound can be independently substituted by one or more of the disclosed or claimed substituent moieties.

Unless indicated otherwise, the nomenclature of substituents that are not explicitly defined herein are arrived at by naming the terminal portion of the functionality followed by the adjacent functionality toward the point of attachment. For example, the substituent "alkylaryloxycarbonyl" refers to the group (alkyl)-(aryl)-O—C(O)—.

As to any of the groups disclosed herein which contain one or more substituents, it is understood that such groups do not contain any substitution or substitution patterns which are sterically impractical and/or synthetically non-feasible. In addition, the subject compounds include all stereochemical isomers arising from the substitution of these compounds. In addition to the disclosure herein, in a certain embodiment, a group that is substituted has 1 substituent, 1 or 2 substituents, 1, 2, or 3 substituents, or 1, 2, 3, or 4 substituents.

As used herein, the term "administration" or "administering" of the subject compound refers to providing a compound of the invention to a subject in need of treatment.

As used herein, the term "acceptable" with respect to a formulation, composition or ingredient, as used herein, means having no persistent detrimental effect on the general health of the subject being treated.

The term "about" when referring to a number or a numerical range means that the number or numerical range referred to is an approximation within experimental variability (or within statistical experimental error), and thus the number or numerical range may vary from, for example, between 1% and 10% of the stated number or numerical range.

As used herein, the term "carrier" refers to chemical compounds or agents that facilitate the incorporation of a compound described herein into cells or tissues.

As used herein, the terms "comprise," "have," and "include" are open-ended linking verbs. Any forms or tenses of one or more of these verbs, such as "comprises," "comprising," "has," "having," "includes," and "including" are open-ended. For example, any method that "comprises," "has," or "includes" one or more moieties is not limited to possessing only those one or more moieties and also covers other unlisted moieties.

Derivatives of Piperlongumine

Disclosed herein is a novel class of compounds having Formula (I), pharmaceutical acceptable salts, protected derivatives, individual isomers and mixture of isomers thereof.

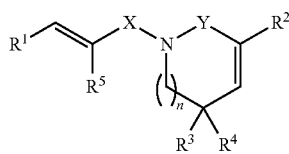

Formula (I)

When n is an integer of 1 according to Formula (I), then
X or Y is independently C(O) or $S(O)_2$;
$R^1$ is selected from the group consisting of:
  i) a 3-9 member saturated or partially unsaturated cycloalkyl group having 0-5 heteroatom(s);
  ii) a 5 member monocyclic heteroaryl group having 2-3 heteroatoms;
  iii) a 6 member monocyclic heteroaryl group having 1-3 heteroatom(s), wherein said 6 member monocyclic heteroaryl group has:
    a) 1-3 heteroatom(s) when X or Y is $S(O)_2$ or when at least one of $R^2$, $R^3$ or $R^4$ is substituted;
    b) two heteroatoms when said 6 member monocyclic heteroaryl group is pyridazinyl or pyrimidyl; or
    c) three heteroatoms when X or Y is independently C(O);
  iv) a 7-9 member monocyclic unsaturated cycloheteroalkyl group having 1-3 heteroatom(s);
  v) a 7-13 member polycyclic heteroaryl group having 1-5 heteroatom(s), wherein said 7-13 member heteroaryl group has:
    a) 1-5 heteroatom(s) when at least one of X or Y is $S(O)_2$ and at least one of $R^2$, $R^3$ or $R^4$ is substituted; or
    b) 2-5 heteroatoms when X and Y are C(O); and
  vi) a $C_1$-$C_3$ alkyl group,
  wherein said heteroatom(s) contained in each cyclic group is independently selected from the group consisting of N, O, and S; and wherein each cyclic group is optionally substituted with halo, alkyl, alkenyl, alkynyl, alkoxy, acyl, acyloxy, carboxylic acid, ester, amine, amide, carbonate, carbamate, carbonyl, cyano, nitro, thioether, thioester, cycloalkyl, cycloheteroalkyl, heterocyclyl, aryl, or heteroaryl, any of which is unsubstituted or substituted with halo, hydroxyl, sulfhydryl, nitro, nitroso, cyano, azido, alkyl, alkenyl, cycloalkyl, cycloheteroalkyl, heterocyclyl, aryl, or heteroaryl,
$R^2$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl;
each of $R^3$ and $R^4$ is independently selected from the group consisting of hydrogen, halo, hydroxyl, alkyl, alkenyl, and alkynyl, any of which is optionally substituted with halo, hydroxyl, alkyl, or cycloalkyl, or $R^3$ taken together with one or more atoms of $R^4$ forms a cycloalkyl or cycloheteroalkyl; and
$R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In some aspects, X is C(O) and Y is $S(O)_2$.
In some aspects, X is $S(O)_2$ and Y is C(O).
In some aspects, X is $S(O)_2$ and Y is $S(O)_2$.
In some aspects when X or Y is $S(O)_2$, $R^1$ can be a 3-9 member cycloalkyl group.

Particularly, $R^1$ can be a 3-9 member saturated or partially unsaturated cycloalkyl group having 0-5 heteroatom(s). For example, $R^1$ can be a 3-9 member saturated cycloalkyl group having no heteroatom selected from cyclopropyl, cyclobutyl, cyclopentyl, cyclohexyl, cycloheptyl, cyclooctyl, cyclodecyl, adamantyl, norpinanyl, decalinyl, norbornyl, or housanyl. In one particular embodiment, $R^1$ is cyclopropyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl. In another embodiment, $R^1$ is cyclohexyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl. In another embodiment, the 3-9 member cycloalkyl group can be a cycloalkenyl selected from the group consisting of cyclopropenyl, cyclobutenyl, cyclopentenyl, cyclohexenyl, cycloheptenyl, cyclooctenyl, norbornenyl, and norbornadienyl.

In one aspect, $R^1$ can be a 3-9 member cycloheteroalkyl group containing one or more heteroatoms, each heteroatom independently selected from N, O, or S. For example, $R^1$ can be a 3-9 member saturated cycloalkyl group having 1-5 heteroatom(s) such as aziridinyl, diaziridinyl, oxiranyl, dioxiranyl, oxaziridinyl, thiiranyl, azetidinyl, diazetidinyl, oxetanyl, dioxetanyl, thietanyl, dithietanyl, pyrrolidinyl, imidazolidinyl, pyrazolidinyl, tetrahydropyranyl, tetrahydrofuranyl, oxolanyl, oxazolidinyl, thiolanyl, thiazolidinyl, piperidinyl, piperazinyl, morpholinyl, thiomorpholinyl, oxanyl, dioxanyl, thianyl, dithianyl, hexahydro-1,3,5-triazinyl, trioxanyl, trithianyl, azepanyl, diazepanyl, oxepanyl, thiepanyl, azocanyl, oxocanyl, thiocanyl, azonanyl, oxonanyl, quinolizinyl, and thionanyl. In one embodiment, $R^1$ is piperidinyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl.

In one aspect, $R^1$ can be a 3-9 member partially unsaturated cycloalkyl group having 1-5 heteroatom(s), e.g., pyranyl, pyrrolinyl, pyrazolinyl, imidazolinyl, pyridonyl, dihydropyranyl, dihydropyrrolyl, dihydroimidazolyl, dihydropyrimidinyl, dihydropyrazinyl, dihydrotriazinyl, dihydropyridinyl, dihydrooxadiazolyl, thiazolinyl, dioxinyl, oxazinyl, and oxazolyl. In a preferred embodiment, $R^1$ is pyridonyl optionally substituted with alkyl.

In one embodiment, the cycloalkyl or cycloheteroalkyl is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In some embodiments when X or Y is $S(O)_2$, $R^1$ can be a 3-5 member monocyclic heterocyclyl group having 1-3 heteroatom(s), each heteroatom independently selected from N, O, or S. In one embodiment, the 3-5 member monocyclic heterocyclyl group can be an unsaturated 3-4 member monocyclic heterocyclyl group having 1-3 heteroatom(s), e.g., azirinyl, oxirenyl, thiirenyl, diazirinyl, azetyl, diazetyl, oxetyl, dioxetyl, thietyl, or dithietyl. In one embodiment, $R^1$ is a 5 member unsaturated monocyclic heteroaryl group having 2-3 heteroatoms. In a preferred embodiment, the 5 member monocyclic heteroaryl group is selected from the group consisting of pyrazolyl, imidazolyl, triazolyl (e.g., 1,2,3-triazolyl and 1,2,4-triazolyl), tetrazolyl, thiophenyl, thiazolyl, dithiazolyl, isothiazolyl, thiadiazolyl, furanyl, furazanyl, oxazolyl, isoxazolyl, and oxadiazolyl (e.g., 1,2,5-oxidiazolyl, 1,2,3-oxidiazolyl, and 1,2,4-oxidiazolyl), with the proviso that $R^1$ is not furanyl or thiophenyl when Y is $S(O)_2$. In one particular embodiment, $R^1$ is furazanyl. In yet another preferred embodiment, $R^1$ is 1,2,4-oxadiazolyl which is optionally substituted. In yet another preferred embodiment, $R^1$ is 1,2,3-triazolyl or 1,2,4-triazolyl, each of which is optionally substituted. In yet another preferred embodiment, $R^1$ is tetrazolyl. In yet another preferred embodiment, $R^1$ is imidazolyl optionally substituted. In yet another preferred embodiment, $R^1$ is pyrazonyl optionally substituted. The 5 member unsaturated monocyclic heteroaryl group can be substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect, $R^1$ can be a 6 member unsaturated monocyclic heteroaryl group having 1-3 heteroatom(s) with the proviso that $R^1$ is not pyridinyl or parazinyl when both X and Y are C(O). In one embodiment, the $R^1$ is a 6 member monocyclic heteroaryl group selected from the group consisting of pyridinyl, diazinyl (e.g., pyrazinyl, pyrimidinyl, and pyridazinyl), pyranyl, oxazinyl (e.g., 1,2-oxazinyl, 1,3-oxazinyl, and 1,4-oxazinyl), thiazinyl, dioxinyl, dithiinyl, triazinyl (e.g., 1,2,3-triazinyl, 1,2,4-triazinyl, and 1,3,5-triazinyl), tetrazinyl, pentazinyl, or thiopyranyl. In a preferred embodiment, the 6 member monocyclic heteroaryl group is pyrazinyl, pyridazinyl or pyrimidyl. In another preferred embodiment, the 6 member monocyclic heteroaryl group is triazinyl (e.g., 1,2,3-triazinyl, 1,2,4-triazinyl, and 1,3,5-triazinyl). The 6 member monocyclic heteroaryl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when X or Y is $S(O)_2$, $R^1$ can be a 7-9 member unsaturated monocyclic heterocyclyl group having 1-4 heteroatom(s). In one embodiment, the 7-9 member monocyclic unsaturated heterocyclyl group is selected from the group consisting of azepinyl, diazepinyl, oxepinyl, thiepinyl, thiazepinyl, azocinyl, oxocinyl, thiocinyl, azoninyl, oxoninyl, and thioninyl. The 7-9 member monocyclic unsaturated heterocyclyl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when X or Y is $S(O)_2$, $R^1$ is a 7-13 member polycyclic aryl group having 0-5 heteroatom(s). In one particular aspect, $R^1$ is a 7-13 member polycyclic aryl group having no heteroatom. In another particular aspect, $R^1$ is a 7-13 member polycyclic heteroaryl group having 1-5 heteroatom(s). In another particular aspect, the 7-13 member polycyclic heteroaryl group is formed by covalently bonding an aryl or a heteroaryl group to a heterocyclyl group. For example, dihydrobenzodioxinyl can be formed by covalently bonding a phenyl group to a heterocyclyl a group, e.g., dioxanyl. Similarly, a 7-13 member polycyclic heteroaryl group can be formed by covalently bonding a pyridinyl, pyridazinyl, pyrimidinyl, or pyrazinyl to a dioxanyl, leading to dihydrodioxinopyridinyl, dihydrodioxinopyridazinyl, dihydrodioxinopyrimidinyl, or dihydrodioxinopyrazinyl, respectively. The 7-13 member polycyclic aryl group having 1-5 heteroatom(s) is selected from the group consisting of dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinolinyl, isoquinolinyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, and fluorenyl, with the proviso that $R^1$ is not indolyl or imidazopyridinyl when Y is $S(O)_2$ or that $R^1$ is not quinolinyl when both X and Y are C(O). In one embodiment, the polycyclic heteroaryl is a 7-13 member polycyclic heteroaryl group formed by covalently bonding a heteroaryl group to a cycloheteroalkyl group, for example, fusing pyridinyl, pyridazinyl, pyrimidinyl, or pyrazinyl with dioxanyl. In one embodiment, $R^1$ is dihydrobenzodioxinyl. In one embodiment, $R^1$ is dihydrodioxinopyridinyl. In one embodiment, $R^1$ is dihydrodioxinopyridazinyl. In one embodiment, $R^1$ is dihydrodioxinopyrimidinyl. In one embodiment, $R^1$ is dihydrodioxinopyrazinyl. In one embodiment, $R^1$ is dihydropyrrolopyridinyl. In one embodiment, $R^1$ is tetrahydronaphthyridinyl. In one embodiment, $R^1$ is tetrahydropyridopyridazinyl. In one embodiment, $R^1$ is tetrahydropyridopyrazinyl. In one embodiment, $R^1$ is tetrahydropyridopyrimidinyl. In one embodiment, $R^1$ is benzodioxinyl. The 7-9 member polycyclic unsaturated heteroaryl group is optionally substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect, $R^2$ is selected from hydrogen, halo, hydroxyl, alkyl, alkenyl, alkynyl, alkoxy, acyl, acyloxy, carobxylic acid, ester, amine, amide, carbonate, carbamate, cyano, nitro, thioether, thioester, cycloalkyl, cycloheteroalkyl, heterocyclyl, aryl, or heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one embodiment, $R^2$ can be hydrogen, halo, cyano, or alkynyl. In one particular embodiment, $R^2$ is hydrogen. In another particular embodiment, $R^2$ is halo (—F, —Cl, —Br, or —I). In another particular embodiment, $R^2$ is cyano. In another particular embodiment, $R^2$ is alkynyl, optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In a preferred embodiment, $R^2$ is alkynyl substituted with halo, cycloalkyl, aryl or heteroaryl.

In one aspect, $R^3$ is selected from hydrogen, halo, hydroxyl, alkyl, alkenyl, or alkynyl, any of which is optionally substituted with halo, hydroxyl, alkyl, or cycloalkyl.

In one aspect, $R^4$ is hydrogen, halo, hydroxyl, alkyl, alkenyl, or alkynyl, any of which is optionally substituted with halo, hydroxyl, alkyl, or cycloalkyl.

In one aspect, $R^3$ is taken together with one or more atoms of $R^4$ forms a cycloalkyl or cycloheteroalkyl, each of which are optionally and independently substituted with halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, aryl, heteroaryl, or heterocyclyl.

In one aspect, $R^5$ is selected from the group consisting of halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In one embodiment, $R^5$ is hydrogen.

In one embodiment, $R^5$ is cyano.

In another embodiment, $R^5$ is alkyl optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one particular embodiment, $R^5$ is methyl. In another particular embodiment, $R^5$ is methyl substituted with phenyl. In another embodiment, $R^5$ is ethyl.

In one embodiment, $R^5$ can be in geometric isomerism. For example, $R^5$ can be attached in a cis or trans conformation with respect to R'.

In some aspects when X and Y are C(O) and n is an integer of 1 according to Formula (I), le can be a saturated or partially unsaturated 3-9 member cycloalkyl group having 0-5 heteroatom(s). For example, in one aspect, $R^1$ can be a 3-9 member saturated cycloalkyl group having no heteroatom selected from cyclopropyl, cyclobutyl, cyclopentyl, cyclohexyl, cycloheptyl, cyclooctyl, cyclodecyl, adamantyl, norpinanyl, decalinyl, norbornyl, or housanyl. In another embodiment, the 3-9 member cycloalkyl is a cycloalkenyl group selected from the group consisting of cyclopropenyl, cyclobutenyl, cyclopentenyl, cyclohexenyl, cycloheptenyl, cyclooctenyl, norbornenyl, and norbornadienyl. In one embodiment, $R^1$ is cyclopropyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl. In another embodiment, $R^1$ is cyclohexyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl.

In another aspect when X and Y are C(O) and n is an integer of 1 according to Formula (I), $R^1$ can be a 3-9 member cycloheteroalkyl group containing one or more heteroatoms, each heteroatom independently selected from N, O, or S. For example, $R^1$ can be a 3-9 member saturated cycloalkyl group having 1-5 heteroatom(s) such as aziridinyl, diazirdinyl, oxiranyl, dioxiranyl, oxaziridinyl, thiiranyl, azetidinyl, diazetidinyl, oxetanyl, dioxetanyl, thietanyl, dithietanyl, pyrrolidinyl, imidazolidinyl, pyrazolidinyl, tetrahydropyranyl, tetrahydrofuranyl, oxolanyl, oxazolidinyl, thiolanyl, thiazolidinyl, piperidinyl, piperazinyl, morpholinyl, thiomorpholinyl, oxanyl, dioxanyl, thianyl, dithianyl, hexahydro-1,3,5-triazinyl, trioxanyl, trithianyl, azepanyl, diazepanyl, oxepanyl, thiepanyl, azocanyl, oxocanyl, thiocanyl, azonanyl, oxonanyl, quinolizinyl, and thionanyl. In one embodiment, $R^1$ is piperidinyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl.

In another aspect when X and Y are C(O) and n is an integer of 1 according to Formula (I), $R^1$ can be a 3-9 member partially unsaturated cycloalkyl group having 1-5 heteroatom(s), e.g., pyranyl, pyrrolinyl, pyrazolinyl, imidazolinyl, pyridonyl, dihydropyranyl, dihydropyrrolyl, dihydroimidazolyl, dihydropyrimidinyl, dihydropyrazinyl, dihydrotriazinyl, dihydropyridinyl, dihydrooxadiazolyl, thiazolinyl, dioxinyl, oxazinyl, and oxazolyl. In a preferred embodiment, $R^1$ is pyridonyl optionally substituted with alkyl.

In another aspect when X and Y are C(O) and n is an integer of 1 according to Formula (I), the cycloalkyl or cycloheteroalkyl is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In another aspect when X and Y are C(O) and n is an integer of 1 according to Formula (I), $R^1$ can be a 3-5 member monocyclic heterocyclyl group having 1-3 heteroatom(s), each heteroatom independently selected from N, O, or S. In one embodiment, the 3-5 member monocyclic heterocyclyl group can be an unsaturated 3-4 member monocyclic heterocyclyl group having 1-3 heteroatom(s), e.g., azirinyl, oxirenyl, thiirenyl, diazirinyl, azetyl, diazetyl, oxetyl, dioxetyl, thietyl, or dithietyl. In one embodiment, $R^1$ is a 5 member unsaturated monocyclic heteroaryl group having 2-3 heteroatoms. In one embodiment, $R^1$ is a 5 member unsaturated monocyclic heteroaryl group having 3 heteroatoms. In a preferred embodiment, the 5 member monocyclic heteroaryl group is selected from the group consisting of pyrazolyl, imidazolyl, triazolyl (e.g., 1,2,3-triazolyl and 1,2,4-triazolyl), tetrazolyl, thiophenyl, thiazolyl, dithiazolyl, isothiazolyl, thiadiazolyl, furanyl, furazanyl, oxazolyl, isoxazolyl, and oxadiazolyl (e.g., 1,2,5-oxidiazolyl, 1,2,3-oxidiazolyl, and 1,2,4-oxidiazolyl), with the proviso that $R^1$ is not furanyl or thiophenyl. In one particular embodiment, $R^1$ is furazanyl. In yet another preferred embodiment, $R^1$ is 1,2,4-oxadiazolyl which is optionally substituted. In yet another preferred embodiment, $R^1$ is 1,2,3-triazolyl or 1,2,4-triazolyl, each of which is optionally substituted. In yet another preferred embodiment, $R^1$ is tetrazolyl. In yet another preferred embodiment, $R^1$ is imidazolyl optionally substituted. In yet another preferred embodiment, $R^1$ is pyrazonyl optionally substituted. The 5 member unsaturated monocyclic heteroaryl group can be substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In another aspect when X and Y are C(O) and n is an integer of 1 according to Formula (I), $R^1$ is a 6 member monocyclic heteroaryl group having 1-3 heteroatom(s) with the proviso that $R^1$ is not pyridinyl or parazinyl. In one embodiment, the $R^1$ is a 6 member monocyclic heteroaryl group selected from the group consisting of pyrimidinyl, pyridazinyl, pyranyl, oxazinyl (e.g., 1,2-oxazinyl, 1,3-oxazinyl, and 1,4-oxazinyl), thiazinyl, dioxinyl, dithiinyl, triazinyl (e.g., 1,2,3-triazinyl, 1,2,4-triazinyl, and 1,3,5-triazinyl), tetrazinyl, pentazinyl, or thiopyranyl. In a preferred embodiment, the 6 member monocyclic heteroaryl group is pyridazinyl or pyrimidyl. In another preferred embodiment, the 6 member monocyclic heteroaryl group is triazinyl (e.g., 1,2,3-triazinyl, 1,2,4-triazinyl, and 1,3,5-triazinyl). The 6 member monocyclic heteroaryl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In another aspect when X and Y are C(O) and n is an integer of 1 according to Formula (I), $R^1$ can be a 7-9 member unsaturated monocyclic heterocyclyl group having 1-4 heteroatom(s). In one embodiment, the 7-9 member monocyclic unsaturated heterocyclyl group is selected from the group consisting of azepinyl, diazepinyl, oxepinyl, thiepinyl, thiazepinyl, azocinyl, oxocinyl, thiocinyl, azoninyl, oxoninyl, and thioninyl. The 7-9 member monocyclic unsaturated heterocyclyl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In another aspect when X and Y are C(O) and n is an integer of 1 according to Formula (I), $R^1$ is a 7-13 member polycyclic aryl group having 0-5 heteroatom(s). In one embodiment, $R^1$ is a 7-13 member polycyclic aryl group having no heteroatom. In another embodiment, $R^1$ is a 7-13 member polycyclic heteroaryl group having 1-5 heteroatom(s). In one particular embodiment, the 7-13 member polycyclic heteroaryl group is formed by covalently bonding an aryl or a heteroaryl group to a heterocyclyl group. For example, dihydrobenzodioxinyl can be formed by covalently bonding a phenyl group to a heterocyclyl a group, e.g., dioxanyl. Similarly, a 7-13 member polycyclic heteroaryl group can be formed by covalently bonding a pyridinyl, pyridazinyl, pyrimidinyl, or pyrazinyl to a dioxanyl, leading to dihydrodioxinopyridinyl, dihydrodioxinopyridazinyl, dihydrodioxinopyrimidinyl, or dihydrodioxinopyrazinyl, respectively. The 7-13 member polycyclic aryl group having 1-5 heteroatom(s) is selected from the group consisting of dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, and fluorenyl, with the proviso that $R^1$ is not quinolinyl. In one embodiment, the polycyclic heteroaryl is a 7-13 member polycyclic heteroaryl group formed by covalently bonding a heteroaryl group to a cycloheteroalkyl group, for example, fusing pyridinyl, pyridazinyl, pyrimidinyl, or pyrazinyl with dioxanyl. In one embodiment, $R^1$ is dihydrobenzodioxinyl. In one embodiment, $R^1$ is dihydrodioxinopyridinyl. In one embodiment, $R^1$ is dihydrodioxinopyridazinyl. In one embodiment, $R^1$ is dihydrodioxinopyrimidinyl. In one embodiment, $R^1$ is dihydrodioxinopyrazinyl. In one embodiment, $R^1$ is dihydropyrrolopyridinyl. In one embodiment, $R^1$ is tetrahydronaphthyridinyl. In one embodiment, $R^1$ is tetrahydropyridopyridazinyl. In one embodiment, $R^1$ is tetrahydropyridopyrazinyl. In one embodiment, $R^1$ is tetrahydropyridopyrimidinyl. In one embodiment, $R^1$ is benzodioxinyl. The 7-9 member polycyclic unsaturated heteroaryl group is optionally substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In another aspect when X and Y are C(O) and n is an integer of 1 according to Formula (I), $R^1$ can be a a $C_1$-$C_3$ alkyl group. In one embodiment, $R^1$ is a branched alkyl group (e.g., tert-butyl).

In one aspect when X and Y are C(O) and n is an integer of 1 according to Formula (I), $R^2$ is selected from hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, or heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one embodiment, $R^2$ is hydrogen. In another embodiment, $R^2$ is halo (—F, —Cl, —Br, or —I). In another embodiment, $R^2$ is cyano. In one embodiment, $R^e$ is alkynyl, optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In a preferred embodiment, $R^2$ is alkynyl substituted with halo, cycloalkyl, aryl or heteroaryl.

In one aspect when X and Y are C(O) and n is an integer of 1 according to Formula (I), $R^3$ is selected from hydrogen, halo, hydroxyl, alkyl, alkenyl, or alkynyl, any of which is optionally substituted with halo, hydroxyl, alkyl, or cycloalkyl.

In one aspect when X and Y are C(O) and n is an integer of 1 according to Formula (I), $R^4$ is hydrogen, halo, hydroxyl, alkyl, alkenyl, or alkynyl, any of which is optionally substituted with halo, hydroxyl, alkyl, or cycloalkyl.

In one aspect when X and Y are C(O) and n is an integer of 1 according to Formula (I), $R^3$ is taken together with one or more atoms of $R^4$ forms a cycloalkyl or cycloheteroalkyl, each of which are optionally and independently substituted with halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl.

In one aspect when X and Y are C(O) and n is an integer of 1 according to Formula (I), $R^5$ is selected from the group consisting of halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In one embodiment, $R^5$ is hydrogen.

In one embodiment, $R^5$ is cyano.

In another embodiment, $R^5$ is alkyl optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one particular embodiment, $R^5$ is methyl. In another particular embodiment, $R^5$ is methyl substituted with phenyl. In another embodiment, $R^5$ is ethyl.

In one embodiment, $R^5$ can be in geometric isomerism. For example, $R^5$ can be attached in a cis or trans conformation with respect to R'.

The heteroatom(s) contained in each cyclic group described above is independently selected from the group consisting of N, O, and S; and each cyclic group is optionally substituted with halo, alkyl, alkenyl, alkynyl, alkoxy, acyl, acyloxy, carboxylic acid, ester, amine, amide, carbonate, carbamate, carbonyl, cyano, nitro, thioether, thioester, cycloalkyl, cycloheteroalkyl, heterocyclyl, aryl, or heteroaryl, any of which is unsubstituted or substituted with halo, hydroxyl, sulfhydryl, nitro, nitroso, cyano, azido, alkyl, alkenyl, cycloalkyl, cycloheteroalkyl, aryl, heteroaryl, or heterocyclyl.

The present disclosure also contemplates compounds of Formula (I) having n that is an integer of 0 or 2. When n is an integer of 0 or 2, X or Y can be independently C(O) or $S(O)_2$.

In some aspects, X is C(O) and Y is C(O).
In other aspects, X is C(O) and Y is $S(O)_2$.
In other aspects, X is $S(O)_2$ and Y is C(O).
In yet other aspects, X is $S(O)_2$ and Y is $S(O)_2$.

In some aspects when n is an integer of 0 or 2, and X or Y is independently C(O) or $S(O)_2$, $R^1$ can be selected from the group consisting of branched $C_1$-$C_3$ alkyl (e.g., tert-butyl), $C_3$-$C_9$ cycloalkyl, $C_3$-$C_9$ cycloheteroalkyl, and $C_3$-$C_{13}$ heterocyclyl having 1-5 heteroatom(s), each of the heteroatom independently selected from N, O, or S. The $R^1$ group can be optionally substituted with halo, alkyl, alkenyl, alkynyl, alkoxy, acyl, acyloxy, carboxylic acid, ester, amine, amide, carbonate, carbamate, carbonyl, cyano, nitro, thioether, thioester, cycloalkyl, cycloheteroalkyl, heterocyclyl, aryl, or heteroaryl, any of which can be unsubstituted or further substituted with halo, hydroxyl, sulfhydryl, nitro, nitroso, cyano, azido, alkyl, alkenyl, cycloalkyl, cycloheteroalkyl, heterocyclyl, aryl or heteroaryl. In one embodiment when n is an integer of 0 or 2 and X or Y is independently C(O) or $S(O)_2$, $R^1$ can be a branched $C_1$-$C_3$ alkyl. In one particular embodiment when n is an integer of 0 or 2 and X or Y is independently C(O) or $S(O)_2$, $R^1$ is tert-butyl.

In one aspect when n is an integer of 0 or 2 and X or Y is independently C(O) or $S(O)_2$, le can be a 3-9 member cycloalkyl group. Particularly, $R^1$ can be a 3-9 member saturated or partially unsaturated cycloalkyl group having 0-5 heteroatom(s).

For example, $R^1$ can be a 3-9 member saturated cycloalkyl group having no heteroatom selected from cyclopropyl, cyclobutyl, cyclopentyl, cyclohexyl, cycloheptyl, cyclooctyl, cyclodecyl, adamantyl, norpinanyl, decalinyl, norbornyl, or housanyl. In one another embodiment, $R^1$ is cyclopropyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl. In another embodiment, $R^1$ is cyclohexyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl. In another embodiment, the 3-9 member cycloalkyl group can be a cycloalkenyl selected from the group consisting of cyclopropenyl, cyclobutenyl, cyclopentenyl, cyclohexenyl, cycloheptenyl, cyclooctenyl, norbornenyl, and norbornadienyl.

In another aspect when n is an integer of 0 or 2 and X or Y is independently C(O) or $S(O)_2$, $R^1$ can be a 3-9 member cycloheteroalkyl group containing one or more heteroatoms, each heteroatom independently selected from N, O, or S. For example, $R^1$ can be a 3-9 member saturated cycloheteroalkyl group having 1-5 heteroatom(s) such as aziridinyl, diaziridinyl, oxiranyl, dioxiranyl, oxaziridinyl, thiiranyl, azetidinyl, diazetidinyl, oxetanyl, dioxetanyl, thietanyl, dithietanyl, pyrrolidinyl, imidazolidinyl, pyrazolidinyl, tetrahydropyranyl, tetrahydrofuranyl, oxolanyl, oxazolidinyl, thiolanyl, thiazolidinyl, piperidinyl, piperazinyl, morpholinyl, thiomorpholinyl, oxanyl, dioxanyl, thianyl, dithianyl, hexahydro-1,3,5-triazinyl, trioxanyl, trithianyl, azepanyl, diazepanyl, oxepanyl, thiepanyl, azocanyl, oxocanyl, thiocanyl, azonanyl, oxonanyl, quinolizinyl, and thionanyl. In one embodiment, $R^1$ is piperidinyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl.

In one aspect when n is an integer of 0 or 2 and X or Y is independently $C(O)$ or $S(O)_2$, le can be a 3-9 member partially unsaturated cycloalkyl group having 1-5 heteroatom(s), e.g., pyranyl, pyrrolinyl, pyrazolinyl, imidazolinyl, pyridonyl, dihydropyranyl, dihydropyrrolyl, dihydroimidazolyl, dihydropyrimidinyl, dihydropyrazinyl, dihydrotriazinyl, dihydropyridinyl, dihydrooxadiazolyl, thiazolinyl, dioxinyl, oxazinyl, and oxazolyl. In a preferred embodiment, le is pyridonyl optionally substituted with alkyl.

In one aspect when n is an integer of 0 or 2 and X or Y is independently $C(O)$ or $S(O)_2$, the cycloalkyl or cycloheteroalkyl is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when n is an integer of 0 or 2 and X or Y is independently $C(O)$ or $S(O)_2$, R1 can be a 3-5 member monocyclic heterocyclyl group having 1-3 heteroatom(s), each heteroatom independently selected from N, O, or S. In one embodiment, the 3-5 member monocyclic heterocyclyl group can be an unsaturated 3-4 member monocyclic heterocyclyl group having 1-3 heteroatom(s), e.g., azirinyl, oxirenyl, thiirenyl, diazirinyl, azetyl, diazetyl, oxetyl, dioxetyl, thietyl, or dithietyl. In one embodiment, $R^1$ is a 5 member unsaturated monocyclic heteroaryl group having 2-3 heteroatoms. In a preferred embodiment, the 5 member monocyclic heteroaryl group is selected from the group consisting of pyrazolyl, imidazolyl, triazolyl (e.g., 1,2,3-triazolyl and 1,2,4-triazolyl), tetrazolyl, thiophenyl, thiazolyl, dithiazolyl, isothiazolyl, thiadiazolyl, furanyl, furazanyl, oxazolyl, isoxazolyl, and oxadiazolyl (e.g., 1,2,5-oxidiazolyl, 1,2,3-oxidiazolyl, and 1,2,4-oxidiazolyl), with the proviso that $R^1$ is not furanyl or thiophenyl when Y is $S(O)_2$. In one particular embodiment, $R^1$ is furazanyl. In yet another preferred embodiment, $R^1$ is 1,2,4-oxadiazolyl which is optionally substituted. In yet another preferred embodiment, $R^1$ is 1,2,3-triazolyl or 1,2,4-triazolyl, each of which is optionally substituted. In yet another preferred embodiment, $R^1$ is tetrazolyl. In yet another preferred embodiment, $R^1$ is imidazolyl optionally substituted. In yet another preferred embodiment, $R^1$ is pyrazonyl optionally substituted. The 5 member unsaturated monocyclic heteroaryl group can be substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when n is an integer of 0 or 2 and X or Y is independently $C(O)$ or $S(O)_2$, $R^1$ can be a 6 member unsaturated monocyclic heteroaryl group having 1-3 heteroatom(s) with the proviso that $R^1$ is not pyridinyl or parazinyl when both X and Y are $C(O)$. In one embodiment, the $R^1$ is a 6 member monocyclic heteroaryl group selected from the group consisting of pyridinyl, diazinyl (e.g., pyrazinyl, pyrimidinyl, and pyridazinyl), pyranyl, oxazinyl (e.g., 1,2-oxazinyl, 1,3-oxazinyl, and 1,4-oxazinyl), thiazinyl, dioxinyl, dithiinyl, triazinyl (e.g., 1,2,3-triazinyl, 1,2,4-triazinyl, and 1,3,5-triazinyl), tetrazinyl, pentazinyl, or thiopyranyl. In a preferred embodiment, the 6 member monocyclic heteroaryl group is pyrazinyl, pyridazinyl or pyrimidyl. In another preferred embodiment, the 6 member monocyclic heteroaryl group is triazinyl (e.g., 1,2,3-triazinyl, 1,2,4-triazinyl, and 1,3,5-triazinyl). The 6 member monocyclic heteroaryl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when n is an integer of 0 or 2 and X or Y is independently $C(O)$ or $S(O)_2$, $R^1$ can be a 7-9 member unsaturated monocyclic heterocyclyl group having 1-4 heteroatom(s). In one embodiment, the 7-9 member monocyclic unsaturated heterocyclyl group is selected from the group consisting of azepinyl, diazepinyl, oxepinyl, thiepinyl, thiazepinyl, azocinyl, oxocinyl, thiocinyl, azoninyl, oxoninyl, and thioninyl. The 7-9 member monocyclic unsaturated heterocyclyl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when n is an integer of 0 or 2 and X or Y is independently $C(O)$ or $S(O)_2$, $R^1$ is a 7-13 member polycyclic aryl group having 0-5 heteroatom(s). In one embodiment, $R^1$ is a 7-13 member polycyclic aryl group having no heteroatom. In another embodiment, $R^1$ is a 7-13 member polycyclic heteroaryl group having 1-5 heteroatom(s). In another embodiment, the 7-13 member polycyclic heteroaryl group is formed by covalently bonding an aryl or a heteroaryl group to a heterocyclyl group. For example, dihydrobenzodioxinyl can be formed by covalently bonding a phenyl group to a heterocyclyl a group, e.g., dioxanyl. Similarly, a 7-13 member polycyclic heteroaryl group can be formed by covalently bonding a pyridinyl, pyridazinyl, pyrimidinyl, or pyrazinyl to a dioxanyl, leading to dihydrodioxinopyridinyl, dihydrodioxinopyridazinyl, dihydrodioxinopyrimidinyl, or dihydrodioxinopyrazinyl, respectively. The 7-13 member polycyclic aryl group having 1-5 heteroatom(s) is selected from the group consisting of dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinolinyl, isoquinolinyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, and fluorenyl. In one embodiment, the polycyclic heteroaryl is a 7-13 member polycyclic heteroaryl group formed by covalently bonding a heteroaryl group to a cycloheteroalkyl group, for example, fusing pyridinyl, pyridazinyl, pyrimidinyl, or pyrazinyl with dioxanyl. In one particular embodiment, $R^1$ is dihydrobenzodioxinyl. In one particular embodiment, $R^1$ is dihydrodioxinopyridinyl. In one particular embodiment, $R^1$ is dihydrodioxinopyridazinyl. In one particular embodiment, $R^1$ is dihydrodioxinopyrimidinyl. In one particular embodiment, $R^1$ is dihydrodioxinopyrazinyl. In one particular embodiment, $R^1$ is dihydropyrrolopyridinyl. In one particular embodiment, $R^1$ is tetrahydronaphthyridinyl. In one particular embodiment, $R^1$ is tetrahydropyridopyridazinyl. In one particular embodiment, $R^1$ is tetrahydropyridopyrazinyl. In one particular embodiment, $R^1$ is tetrahydropyridopyrimidinyl. In one particular embodiment, $R^1$ is benzodioxinyl. The 7-9 member polycyclic unsaturated heteroaryl group is optionally substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In some aspects when n is an integer of 0 or 2 and X or Y is independently C(O) or $S(O)_2$, $R^2$ can be selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which may optionally be substituted with halo, hydroxyl, sulfhydryl, nitro, nitroso, cyano, azido, alkyl, alkenyl, cycloalkyl, cycloheteroalkyl, heterocyclyl, aryl or heteroaryl; and In some aspects when n is an integer of 0 or 2 and X or Y is independently C(O) or $S(O)_2$, each of $R^3$ and $R^4$ is independently selected from the group consisting of hydrogen, halo, hydroxyl, alkyl, alkenyl, alkynyl, alkoxy, cycloalkyl, and cycloheteroalkyl, any of which can optionally be substituted with halo, hydroxyl, alkyl, or cycloalkyl.

In some aspects when n is an integer of 0 or 2 and X or Y is independently C(O) or $S(O)_2$, $R_3$ taken together with one or more atoms of $R^4$ forms a cycloalkyl or cycloheteroalkyl, each of which is optionally substituted with halo, hydroxyl, alkyl, alkenyl, alkynyl, or alkoxy.

In one aspect when n is an integer of 0 or 2 and X or Y is independently C(O) or $S(O)_2$, $R^5$ is selected from the group consisting of halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In one embodiment, $R^5$ is hydrogen.

In another embodiment, $R^5$ is cyano.

In yet another embodiment, $R^5$ is alkyl optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one particular embodiment, $R^5$ is methyl. In another particular embodiment, $R^5$ is methyl substituted with phenyl. In another embodiment, $R^5$ is ethyl.

In one embodiment, $R^5$ can be in geometric isomerism. For example, $R^5$ can be attached in a cis or trans conformation with respect to R'.

The present invention also contemplates at least one of X or Y is $S(O)_2$ and at least one of $R^2$, $R^3$ or $R^4$ is substituted according to Formula (I), wherein n can be any integer of 1, 2, or 3.

In some aspects, at least one of X or Y is $S(O)_2$ and at least one of $R^2$, $R^3$ or $R^4$ is substituted. In some aspects, X are Y are independently $S(O)_2$ and at least one of $R^2$, $R^3$ or $R^4$ is substituted, In one aspect when at least one of X or Y is $S(O)_2$ and at least one of $R^2$, $R^3$ or $R^4$ is substituted, $R^1$ can be selected from the group consisting of branched $C_1$-$C_3$ alkyl (e.g., tert-butyl), $C_3$-$C_9$ cycloalkyl, $C_3$-$C_9$ cycloheteroalkyl, and $C_3$-$C_{13}$ heterocyclyl having 1-5 heteroatom(s), each of the $R^1$ heteroatom independently selected from N, O, or S. The $R^1$ group can be optionally substituted with halo, alkyl, alkenyl, alkynyl, alkoxy, acyl, acyloxy, carboxylic acid, ester, amine, amide, carbonate, carbamate, carbonyl, cyano, nitro, thioether, thioester, cycloalkyl, cycloheteroalkyl, heterocyclyl, aryl, or heteroaryl, any of which can be unsubstituted or further substituted with halo, hydroxyl, sulfhydryl, nitro, nitroso, cyano, azido, alkyl, alkenyl, cycloalkyl, cycloheteroalkyl, heterocyclyl, aryl or heteroaryl. In one embodiment when n is an integer of 0 or 2 and X or Y is independently C(O) or $S(O)_2$, $R^1$ can be a branched $C_1$-$C_3$ alkyl. In one particular embodiment when n is an integer of 0 or 2 and X or Y is independently C(O) or $S(O)_2$, $R^1$ is tert-butyl.

In one aspect when at least one of X or Y is $S(O)_2$ and at least one of $R^2$, $R^3$ or $R^4$ is substituted, $R^1$ can be a 3-9 member cycloalkyl group. Particularly, $R^1$ can be a 3-9 member saturated or partially unsaturated cycloalkyl group having 0-5 heteroatom(s).

For example, $R^1$ can be a 3-9 member saturated cycloalkyl group having no heteroatom selected from cyclopropyl, cyclobutyl, cyclopentyl, cyclohexyl, cycloheptyl, cyclooctyl, cyclodecyl, adamantyl, norpinanyl, decalinyl, norbornyl, or housanyl. In one another embodiment, $R^1$ is cyclopropyl optionally substituted with halo, alkyl, alkenyl, alkynyl, alkoxy, acyl, acyloxy, carbocylic acid, ester, amine, amide, carbonate, carbamoyl, carbonyl, cyano, nitro, thioether, thioester, cycloalkyl, cycloheteroalkyl, aryl, heteroaryl, or heterocyclyl. In another embodiment, $R^1$ is cyclohexyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl. In another embodiment, the 3-9 member cycloalkyl group can be a cycloalkenyl selected from the group consisting of cyclopropenyl, cyclobutenyl, cyclopentenyl, cyclohexenyl, cycloheptenyl, cyclooctenyl, norbornenyl, and norbornadienyl.

In one aspect when at least one of X or Y is $S(O)_2$ and at least one of $R^2$, $R^3$ or $R^4$ is substituted, $R^1$ can be a 3-9 member cycloheteroalkyl group containing one or more heteroatoms, each heteroatom independently selected from N, O, or S. For example, $R^1$ can be a 3-9 member saturated cycloheteroalkyl group having 1-5 heteroatom(s) such as aziridinyl, diaziridinyl, oxiranyl, dioxiranyl, oxaziridinyl, thiiranyl, azetidinyl, diazetidinyl, oxetanyl, dioxetanyl, thietanyl, dithietanyl, pyrrolidinyl, imidazolidinyl, pyrazolidinyl, tetrahydropyranyl, tetrahydrofuranyl, oxolanyl, oxazolidinyl, thiolanyl, thiazolidinyl, piperidinyl, piperazinyl, morpholinyl, thiomorpholinyl, oxanyl, dioxanyl, thianyl, dithianyl, hexahydro-1,3,5-triazinyl, trioxanyl, trithianyl, azepanyl, diazepanyl, oxepanyl, thiepanyl, azocanyl, oxocanyl, thiocanyl, azonanyl, oxonanyl, quinolizinyl, and thionanyl. In one embodiment, $R^1$ is piperidinyl optionally substituted with halo, alkyl, alkenyl, alkynyl, alkoxy, acyl, acyloxy, carbocylic acid, ester, amine, amide, carbonate, carbamate, carbonyl, cyano, nitro, thioether, thioester, cycloalkyl, cycloheteroalkyl, aryl, heteroaryl, or heterocyclyl.

In one aspect when at least one of X or Y is $S(O)_2$ and at least one of $R^2$, $R^3$ or $R^4$ is substituted, $R^1$ can be a 3-9 member partially unsaturated cycloalkyl group having 1-5 heteroatom(s), e.g., pyranyl, pyrrolinyl, pyrazolinyl, imidazolinyl, pyridonyl, dihydropyranyl, dihydropyrrolyl, dihydroimidazolyl, dihydropyrimidinyl, dihydropyrazinyl, dihydrotriazinyl, dihydropyridinyl, dihydrooxadiazolyl, thiazolinyl, dioxinyl, oxazinyl, and oxazolyl. In a preferred embodiment, $R^1$ is pyridonyl optionally substituted with alkyl.

In one aspect when at least one of X or Y is $S(O)_2$ and at least one of $R^2$, $R^3$ or $R^4$ is substituted, the cycloalkyl or cycloheteroalkyl is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when at least one of X or Y is $S(O)_2$ and at least one of $R^2$, $R^3$ or $R^4$ is substituted, $R^1$ can be a 3-5 member monocyclic heterocyclyl group having 1-3 heteroatom(s), each heteroatom independently selected from N, O, or S. In one embodiment, the 3-5 member monocyclic heterocyclyl group can be an unsaturated 3-4 member monocyclic heterocyclyl group having 1-3 heteroatom(s), e.g., azirinyl, oxirenyl, thiirenyl, diazirinyl, azetyl, diazetyl, oxetyl, dioxetyl, thietyl, or dithietyl. In one embodiment, $R^1$ is a 5 member unsaturated monocyclic heteroaryl group having 2-3 heteroatoms. In a preferred embodiment, the 5 member monocyclic heteroaryl group is selected from the group consisting of pyrazolyl, imidazolyl, triazolyl (e.g., 1,2,3-triazolyl and 1,2,4-triazolyl), tetrazolyl, thiophenyl, thiazolyl, dithiazolyl, isothiazolyl, thiadiazolyl, furanyl, furazanyl, oxazolyl, isoxazolyl, and oxadiazolyl (e.g., 1,2,5-oxidiazolyl, 1,2,3-oxidiazolyl, and 1,2,4-oxidiazolyl). In one particular embodiment, $R^1$ is furazanyl. In yet another preferred embodiment, $R^1$ is 1,2,4-oxadiazolyl which is optionally substituted. In yet another preferred embodiment, $R^1$ is 1,2,3-triazolyl or 1,2,4-triazolyl, each of which is optionally substituted. In yet another preferred embodiment, $R^1$ is tetrazolyl. In yet another preferred embodiment, $R^1$ is imidazolyl optionally substituted. In yet another preferred embodiment, $R^1$ is pyrazonyl optionally substituted. The 5 member unsaturated monocyclic heteroaryl group can be substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when at least one of X or Y is $S(O)_2$ and at least one of $R^2$, $R^3$ or $R^4$ is substituted, $R^1$ can be a 6 member unsaturated monocyclic heteroaryl group having 1-3 heteroatom(s). In one embodiment, the $R^1$ is a 6 member monocyclic heteroaryl group selected from the group consisting of pyridinyl, diazinyl (e.g., pyrazinyl, pyrimidinyl, and pyridazinyl), pyranyl, oxazinyl (e.g., 1,2-oxazinyl, 1,3-oxazinyl, and 1,4-oxazinyl), thiazinyl, dioxinyl, dithiinyl, triazinyl (e.g., 1,2,3-triazinyl, 1,2,4-triazinyl, and 1,3,5-triazinyl), tetrazinyl, pentazinyl, or thiopyranyl. In a preferred embodiment, the 6 member monocyclic heteroaryl group is pyrazinyl, pyridazinyl or pyrimidyl. In another preferred embodiment, the 6 member monocyclic heteroaryl group is triazinyl (e.g., 1,2,3-triazinyl, 1,2,4-triazinyl, and 1,3,5-triazinyl). The 6 member monocyclic heteroaryl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, aryl, heteroaryl, or heterocyclyl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when at least one of X or Y is $S(O)_2$ and at least one of $R^2$, $R^3$ or $R^4$ is substituted, $R^1$ can be a 7-9 member unsaturated monocyclic heterocyclyl group having 1-4 heteroatom(s). In one embodiment, the 7-9 member monocyclic unsaturated heterocyclyl group is selected from the group consisting of azepinyl, diazepinyl, oxepinyl, thiepinyl, thiazepinyl, azocinyl, oxocinyl, thiocinyl, azoninyl, oxoninyl, and thioninyl. The 7-9 member monocyclic unsaturated heterocyclyl group is optionally and independently substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In one aspect when at least one of X or Y is $S(O)_2$ and at least one of $R^2$, $R^3$ or $R^4$ is substituted, $R^1$ is a 7-13 member polycyclic aryl group having 0-5 heteroatom(s). In one embodiment, $R^1$ is a 7-13 member polycyclic aryl group having no heteroatom. In another embodiment, $R^1$ is a 7-13 member polycyclic heteroaryl group having 1-5 heteroatom(s). In another embodiment, the 7-13 member polycyclic heteroaryl group is formed by covalently bonding an aryl or a heteroaryl group to a heterocyclyl group. For example, dihydrobenzodioxinyl can be formed by covalently bonding a phenyl group to a heterocyclyl a group, e.g., dioxanyl. Similarly, a 7-13 member polycyclic heteroaryl group can be formed by covalently bonding a pyridinyl, pyridazinyl, pyrimidinyl, or pyrazinyl to a dioxanyl, leading to dihydrodioxinopyridinyl, dihydrodioxinopyridazinyl, dihydrodioxinopyrimidinyl, or dihydrodioxinopyrazinyl, respectively. The 7-13 member polycyclic aryl group having 1-5 heteroatom(s) is selected from the group consisting of dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinolinyl, isoquinolinyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, and fluorenyl. In one embodiment, the polycyclic heteroaryl is a 7-13 member polycyclic heteroaryl group formed by covalently bonding a heteroaryl group to a cycloheteroalkyl group, for example, fusing pyridinyl, pyridazinyl, pyrimidinyl, or pyrazinyl with dioxanyl. In one particular embodiment, $R^1$ is dihydrobenzodioxinyl. In one particular embodiment, $R^1$ is dihydrodioxinopyridinyl. In one particular embodiment, $R^1$ is dihydrodioxinopyridazinyl. In one particular embodiment, $R^1$ is dihydrodioxinopyrimidinyl. In one particular embodiment, $R^1$ is dihydrodioxinopyrazinyl. In one particular embodiment, $R^1$ is dihydropyrrolopyridinyl. In one particular embodiment, $R^1$ is tetrahydronaphthyridinyl. In one particular embodiment, $R^1$ is tetrahydropyridopyridazinyl. In one particular embodiment, $R^1$ is tetrahydropyridopyrazinyl. In one particular embodiment, $R^1$ is tetrahydropyridopyrimidinyl. In one particular embodiment, $R^1$ is benzodioxinyl. The 7-9 member polycyclic unsaturated heteroaryl group is optionally substituted with halo, alkyl, alkenyl, alkynyl, alkoxy, acyl, acyloxy, carboxylic acid, ester, amine, amide, carbonate, carbamate, carbonyl, cyano, nitro, cycloalkyl, cycloheteroalkyl, heterocyclyl, aryl, or heteroaryl, any of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl.

In another aspect, $R^1$ can be a 3-13 member substituted or unsubstituted heterocyclyl group having 1-5 heteroatom(s) independently selected from the group consisting of N, O, and S, such as: a) a 3-9 member monocyclic heterocycle group selected from pyridyl, pyrimidyl, pyrazinyl, pyridazinyl, thienyl, furanyl, pyrrolyl, pyrazolyl, thiazolyl, oxazolyl, isothiazolyl, isoxazolyl, thiophenyl, triazolyl (1,2,4-triazolyl and 1,2,3-triazolyl), tetrazolyl, oxadiazolyl (1,2,5-oxadiazolyl and 1,2,3-oxadiazolyl), and imidazolyl; and b) a 7-13 member polycyclic heterocycle group selected from dihydrobenzodioxinyl, dihydrodioxinopyridinyl, dihydrodioxinopyridazinyl, dihydrodioxinopyrimidinyl, dihydrodioxinopyrazinyl, dihydropyrrolopyridinyl, tetrahydronaphthyridinyl, tetrahydropyridopyridazinyl, tetrahydropyridopyrazinyl, tetrahydropyridopyrimidinyl, chromanyl, indolyl, purinyl, isoindolyl, quinolinyl, isoquinolinyl, quinoxalinyl, quinazolinyl, quinolizinyl, 1,8-naphthyridinyl, pyrido[3,2-d]pyrimidinyl, pyrido[4,3-d]pyrimidinyl, pyrido[3,4-b]pyrazinyl, pyrido[2,3-b]pyrazinyl, pteridinyl, acridinyl, cinnolinyl, phthalazinyl, benzimidazolyl, phenazinyl, phenoxazinyl, phenothiazinyl, phenoxathiinyl, benzazepinyl, benzodiazepinyl, benzofuranyl, dibenzofuranyl, isobenzofuranyl, benzothiophenyl, benzoxazinyl, quinolin-2(1H)-onyl, isoquinolin-1(2H)-onyl, indazolyl, benzoxazolyl, benzisoxazolyl, benzothiazolyl, dibenzazepinyl, dibenzoxepinyl, dibenzothiazepinyl, dibenzothiepinyl, carbazolyl, or fluorenyl.

In one aspect when X or Y is independently $S(O)_2$ and at least one of $R^2$, $R^3$ or $R^4$ is substituted, $R^2$ can be selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which may optionally be substituted with halo, hydroxyl, sulfhydryl, nitro, nitroso, cyano, azido, alkyl, alkenyl, cycloalkyl, cycloheteroalkyl, heterocyclyl, aryl or heteroaryl; each of $R^3$ and $R^4$ is independently selected from the group consisting of hydrogen, halo, hydroxyl, alkyl, alkenyl, alkynyl, alkoxy, cycloalkyl, and cycloheteroalkyl, any of which can optionally be substituted with halo, hydroxyl, alkyl, or cycloalkyl, or $R^3$ taken together with one or more atoms of $R^4$ forms a cycloalkyl or cycloheteroalkyl, each of which is optionally substituted with halo, hydroxyl, alkyl, alkenyl, alkynyl, or alkoxy.

In one aspect when X or Y is independently $S(O)_2$ and at least one of $R^2$, $R^3$ or $R^4$ is substituted, $R^5$ is selected from the group consisting of halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

In one embodiment, $R^5$ is hydrogen.

In another embodiment, $R^5$ is cyano.

In yet another embodiment, $R^5$ is alkyl optionally substituted with halo, hydroxyl, sulfhydryl, nitro, nitroso, cyano, azido, alkyl, alkenyl, cycloalkyl, cycloheteroalkyl, heterocyclyl, aryl or heteroaryl. In one particular embodiment, $R^5$ is methyl. In another particular embodiment, $R^5$ is methyl substituted with phenyl. In another embodiment, $R^5$ is ethyl.

In one embodiment, $R^5$ can be in geometric isomerism. For example, $R^5$ can be attached in a cis or trans conformation with respect to R'.

The compounds of the current disclosure, or their pharmaceutically acceptable salts may contain one or more asymmetric centers and may thus give rise to enantiomers, diastereomers, and other stereoisomeric forms that are defined, in terms of absolute stereochemistry, as (R)- or (5)- or, as (D)- or (L)- for amino acids. The present invention is meant to include all such possible isomers, as well as their racemic and optically pure forms. A "stereoisomer" refers to a compound made up of the same atoms bonded by the same bonds but having different three-dimensional structures, which are not interchangeable. The present disclosure contemplates various stereoisomers and mixtures thereof and includes "enantiomers", which refers to two stereoisomers whose molecules are nonsuperimposeable mirror images of one another. Optically active (+) and (−), (R)- and (S)-, or (D)- and (L)-isomers may be prepared using chiral synthons or chiral reagents, or resolved using conventional techniques, for example, chromatography and fractional crystallization. Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). When the compounds described herein contain olefinic double bonds or other centers of geometric asymmetry, and unless specified otherwise, it is intended that the compounds include both E and Z geometric isomers.

When desired, the (R)- and (S)-isomers of the compounds of the present disclosure, if present, may be resolved by methods known to those skilled in the art, for example by formation of diastereoisomeric salts or complexes which may be separated, for example, by crystallization; via formation of diastereoisomeric derivatives which may be separated, for example, by crystallization, gas-liquid or liquid chromatography; selective reaction of one enantiomer with an enantiomer-specific reagent, for example enzymatic oxidation or reduction, followed by separation of the modified and unmodified enantiomers; or gas-liquid or liquid chromatography in a chiral environment, for example on a chiral support, such as silica with a bound chiral ligand or in the presence of a chiral solvent. Alternatively, a specific enantiomer may be synthesized by asymmetric synthesis using optically active reagents, substrates, catalysts or solvents, or by converting one enantiomer to the other by asymmetric transformation.

Compounds may be dosed in their enantiomerically pure form. In some examples, the compound has an enantiomeric excess greater than about 50%, 60%, 70%, 80%, 90%, 95%, 96%, 97%, 98%, or 99%. Compounds may be dosed in their diasteriomerically pure form. In some examples, the compound has a diasteriomeric excess greater than about 50%, 60%, 70%, 80%, 90%, 95%, 96%, 97%, 98%, or 99%.

Compounds may have stereocenters in the R-configuration. Compounds may have stereocenters in the S-configuration.

Some compounds may exhibit polymorphism. It is to be understood that the present disclosure encompasses any racemic, optically-active, polymorphic, or stereoisomeric form, or mixtures thereof, of a compound of the disclosure, which possesses the useful properties described herein, it being well known in the art how to prepare optically active forms (for example, by resolution of the racemic form by recrystallization techniques, by synthesis from optically-active starting materials, by chiral synthesis, or by chromatographic separation using a chiral stationary phase).

The present invention provided herein contemplates pharmaceutical compositions comprising a compound of Formula (I). A pharmaceutical composition (e.g., for oral administration or for injection, infusion, subcutaneous delivery, intramuscular delivery, intraperitoneal delivery, sublingual delivery, or other method) may be in the form of a liquid. A liquid pharmaceutical composition may include, for example, one or more of the following: a sterile diluent such as water, saline solution, preferably physiological saline, Ringer's solution, isotonic sodium chloride, fixed oils that may serve as the solvent or suspending medium, polyethylene glycols, glycerin, propylene glycol or other solvents; antibacterial agents; antioxidants; chelating agents; buffers and agents for the adjustment of tonicity such as sodium chloride or dextrose. A parenteral composition can be enclosed in ampoules, disposable syringes or multiple dose vials made of glass or plastic. The use of physiological saline is preferred, and an injectable pharmaceutical composition is preferably sterile. A liquid pharmaceutical composition may be delivered orally.

For oral formulations, at least one of the compounds or agents described herein can be used alone or in combination with appropriate additives to make tablets, powders, granules or capsules, and if desired, with diluents, buffering agents, moistening agents, preservatives, coloring agents, and flavoring agents. The compounds may be formulated with a buffering agent to provide for protection of the compound from low pH of the gastric environment and/or an enteric coating. A compound included in a pharmaceutical composition may be formulated for oral delivery with a flavoring agent, e.g., in a liquid, solid or semi-solid formulation and/or with an enteric coating. In some cases, the compounds of this disclosure may be solubilized and encapsulated (e.g., in a liposome or a biodegradable polymer), or used in the form of microcrystals coated with an appropriate nontoxic lipid.

A pharmaceutical composition comprising any one of the compounds or agents described herein may be formulated for sustained or slow release (also called timed release or controlled release). Such compositions may generally be prepared using well known technology and administered by, for example, oral, rectal, intradermal, or subcutaneous implantation, or by implantation at the desired target site. Sustained-release formulations may contain the compound dispersed in a carrier matrix and/or contained within a reservoir surrounded by a rate controlling membrane. Excipients for use within such formulations are biocompatible, and may also be biodegradable; preferably the formulation provides a relatively constant level of active component release. Non-limiting examples of excipients include water, alcohol, glycerol, chitosan, alginate, chondroitin, Vitamin E, mineral oil, and dimethyl sulfoxide (DMSO). The amount of compound contained within a sustained release formulation depends upon the site of implantation, the rate and expected duration of release, and the nature of the condition, disease or disorder to be treated or prevented.

The present disclosure further provides salts of any compound described herein. The term "salt" refers to salts derived from a variety of organic and inorganic counter ions well known in the art. Salts include, for example, acid-addition salts and base-addition salts. The acid that is added to a compound to form an acid-addition salt can be an organic acid or an inorganic acid. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. A base that is added to a compound to form a base-addition salt can be an organic base or an inorganic base. In some cases, a salt can be a metal salt. In some cases, a salt can be an ammonium salt. Inorganic bases from which salts can be derived include, for example, sodium, potassium, lithium, ammonium, calcium, magnesium, iron, zinc, copper, manganese, aluminum, and the like. Organic bases from which salts can be derived include, for example, primary, secondary, and tertiary amines, substituted amines including naturally occurring substituted amines, cyclic amines, basic ion exchange resins, and the like.

Acid addition salts can arise from the addition of an acid to a compound described herein. In some cases, the acid can be organic. In some cases, the acid can be inorganic. Non-limiting examples of suitable acids include hydrochloric acid, hydrobromic acid, hydroiodic acid, nitric acid, nitrous acid, sulfuric acid, sulfurous acid, a phosphoric acid, nicotinic acid, isonicotinic acid, lactic acid, salicylic acid, 4-aminosalicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, citric acid, oxalic acid, maleic acid, hydroxymaleic acid, methylmaleic acid, glycolic acid, malic acid, cinnamic acid, mandelic acid, 2-phenoxybenzoic acid, 2-acetoxybenzoic acid, embonic acid, phenylacetic acid, N-cyclohexylsulfamic acid, methanesulfonic acid, ethanesulfonic acid, benzenesulfonic acid, p-toluenesulfonic acid, 2-hydroxyethanesulfonic acid, ethane-1,2-disulfonic acid, 4-methylbenzenesulfonic acid, naphthalene-2-sulfonic acid, naphthalene-1,5-disulfonic acid, 2-phosphoglyceric acid, 3-phosphoglyceric acid, glucose-6-phosphoric acid, and an amino acid.

Non-limiting examples of suitable acid addition salts include a hydrochloride salt, a hydrobromide salt, a hydroiodide salt, a nitrate salt, a nitrite salt, a sulfate salt, a sulfite salt, a phosphate salt, a hydrogen phosphate salt, a dihydrogen phosphate salt, a carbonate salt, a bicarbonate salt, a nicotinate salt, an isonicotinate salt, a lactate salt, a salicylate salt, a 4-aminosalicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a citrate salt, an oxalate salt, a maleate salt, a hydroxymaleate salt, a methylmaleate salt, a glycolate salt, a malate salt, a cinnamate salt, a mandelate salt, a 2-phenoxybenzoate salt, a 2-acetoxybenzoate salt, an embonate salt, a phenylacetate salt, an N-cyclohexylsulfamate salt, a methanesulfonate salt, an ethanesulfonate salt, a benzenesulfonate salt, a p-toluenesulfonate salt, a 2-hydroxyethanesulfonate salt, an ethane-1,2-disulfonate salt, a 4-methylbenzenesulfonate salt, a naphthalene-2-sulfonate salt, a naphthalene-1,5-disulfonate salt, a 2-phosphoglycerate salt, a 3-phosphoglycerate salt, a glucose-6-phosphate salt, and an amino acid salt.

Metal salts can arise from the addition of an inorganic base to a compound described herein. The inorganic base consists of a metal cation paired with a basic counterion, such as, for example, hydroxide, carbonate, bicarbonate, or phosphate. The metal can be an alkali metal, alkaline earth metal, transition metal, or main group metal. Non-limiting examples of suitable metals include lithium, sodium, potassium, caesium, cerium, magnesium, manganese, iron, calcium, strontium, cobalt, titanium, aluminium, copper, cadmium, and zinc.

Non-limiting examples of suitable metal salts include a lithium salt, a sodium salt, a potassium salt, a caesium salt, a cerium salt, a magnesium salt, a manganese salt, an iron salt, a calcium salt, a strontium salt, a cobalt salt, a titanium salt, an aluminium salt, a copper salt, a cadmium salt, and a zinc salt.

Ammonium salts can arise from the addition of ammonia or an organic amine to a compound described herein. Non-limiting examples of suitable organic amines include triethyl amine, diisopropyl amine, ethanol amine, diethanol amine, triethanol amine, morpholine, N-methylmorpholine, piperidine, N-methylpiperidine, N-ethylpiperidine, dibenzyl amine, piperazine, pyridine, pyrrazole, pipyrrazole, imidazole, pyrazine, pipyrazine, ethylenediamine, N,N'-dibenzylethylene diamine, procaine, chloroprocaine, choline, dicyclohexyl amine, and N-methylglucamine. Non-limiting examples of suitable ammonium salts can be a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzyl amine salt, a piperazine salt, a pyridine salt, a pyrrazole salt, a pipyrrazole salt, an imidazole salt, a pyrazine salt, a pipyrazine salt, an ethylene diamine salt, an N,N'-dibenzylethylene diamine salt, a procaine salt, a chloroprocaine salt, a choline salt, a dicyclohexyl amine salt, and a N-methylglucamine salt.

The present disclosure further provides a pharmaceutically acceptable carrier or a pharmaceutically acceptable excipient of any compound described herein. A pharmaceutically acceptable carrier or excipient may include any and all solvents, dispersion media, coatings, emulsions, isotonic and absorption delaying agents and the like. The use of such media and agents for pharmaceutically active substances is well known in the art. Except insofar as any conventional media or agent is incompatible with an active compound of Formula (I), its use in the therapeutic compositions of the disclosure is contemplated. Supplementary active ingredients can also be incorporated into the compositions. The pharmaceutically acceptable excipient can also include vehicles and carriers capable of being co-administered with a compound to facilitate the performance of its intended function. Any other conventional carrier suitable for use with the multi-binding compounds also falls within the scope of the present disclosure.

In making the compositions of this disclosure, the active ingredient can be diluted by an excipient. Some examples of suitable excipients include lactose, dextrose, sucrose, sorbitol, mannitol, starches, gum acacia, calcium phosphate, alginates, tragacanth, gelatin, calcium silicate, microcrystalline cellulose, polyethylene glycol (PEG), polyvinylpyrrolidone, cellulose, water, sterile saline, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the disclosure can be formulated so as to provide quick, sustained or delayed release of the active ingredient after administration to the patient by employing procedures known in the art.

In some cases, the pharmaceutical compositions described herein may comprise an excipient that can provide long term preservation, bulk up a formulation that contains potent active ingredients, facilitate drug absorption, reduce viscosity, add flavoring, or enhance the solubility of the pharmaceutical composition. Non-limiting examples of excipients can include anti-adherents, binders (e.g., sucrose, lactose, starches, cellulose, gelatin, or PEG), coatings (e.g., hydroxypropyl methylcellulose or gelatin), disintegrants, dyes, flavors (e.g., mint, peach, raspberry, or vanilla), glidants, lubricants, preservatives (e.g., acids, esters, phenols, mercurial compounds, or ammonium compounds), sorbents, or vehicles (e.g., petroleum or mineral oil).

Methods of Treatment

The compounds and compositions described herein can be administered to a subject in need of treatment for a cell proliferation disorder such as cancer, particularly cancers selected from leukemia, lymphoma, osteosarcoma, melanoma, breast cancer, renal cancer, prostate cancer, gastric cancer, colorectal cancer, liver cancer, thyroid cancer, head and neck cancer, ovarian cancer, pancreatic cancer, neuronal cancer, lung cancer, or uterine cancer. The subject is typically a mammal diagnosed as being in need of treatment for one or more of such proliferative disorders, and frequently the subject is a human. The methods comprise administering an effective amount of at least one compound of the invention; optionally the compound may be administered in combination with one or more additional therapeutic agents, particularly the therapeutic agents known to be useful for treating the cancer or proliferative disorder afflicting the particular subject.

The compounds of the present disclosure or their pharmaceutically acceptable salts are generally administered in a therapeutically effective amount. The term "therapeutically effective amount" may refer to the amount (or dose) of a compound or other therapy that is necessary and sufficient to prevent, reduce, ameliorate, treat or eliminate a condition, or risk thereof, when administered to a subject in need of such compound or other therapy. The amount of the compound actually administered to a subject may be determined by a physician or caregiver, in the light of the relevant circumstances, including the condition to be treated, the chosen route of administration, the compound administered and its relative activity, the age, weight, the response of the individual patient, the severity of the patient's symptoms, and the like. Thus, the therapeutically effective amount may vary, for example, it may vary depending upon the subject's condition, the weight and age of the subject, the severity of the disease condition, the manner of administration and the like.

The compounds of the current disclosure may be administered by any of the accepted modes of administration of agents having similar utilities, for example, by cutaneous, oral, topical, intradermal, intrathecal, intravenous, subcutaneous, intramuscular, intra-articular, intraspinal or spinal, nasal, epidural, rectal, vaginal, or transdermal/transmucosal routes. The most suitable route will depend on the nature and severity of the condition being treated. Intravenous administration may be a route of administration for compounds of this disclosure. Oral administration may be a route of administration for compounds of this disclosure. Subcutaneous, intradermal and percutaneous injections can be routes for the compounds of this disclosure. Sublingual administration may be a route of administration for compounds of this disclosure. In a particular example, the pharmaceutical composition provided herein may be administered to a human patient orally. In another particular example, the pharmaceutical composition provided herein may be administered to a human patient intravenously.

A subject of this disclosure may have any type of cancer. Examples of cancer can include, but are not limited to, adrenal cancer, anal cancer, bile duct cancer, bladder cancer, cancer of the blood, bone cancer, a brain tumor, breast cancer, cancer of the cardiovascular system, cervical cancer, colon cancer, cancer of the digestive system, cancer of the endocrine system, endometrial cancer, esophageal cancer, eye cancer, gallbladder cancer, a gastrointestinal tumor, kidney cancer, laryngeal cancer, leukemia, liver cancer, lung cancer, lymphoma, mesothelioma, cancer of the muscular system, myelodysplastic syndrome, myeloma, nasal cavity cancer, nasopharyngeal cancer, cancer of the nervous system, cancer of the lymphatic system, oral cancer, oropharyngeal cancer, ovarian cancer, pancreatic cancer, penile cancer, pituitary tumors, prostate cancer, cancer of the reproductive system, cancer of the respiratory system, a sarcoma, salivary gland cancer, skeletal system cancer, skin cancer, small intestine cancer, stomach cancer, testicular cancer, thymus cancer, thyroid cancer, bladder cancer, or vaginal cancer. The term 'lymphoma' may refer to any type of lymphoma including B-cell lymphoma (e.g., diffuse large B-cell lymphoma, follicular lymphoma, small lymphocytic lymphoma, mantle cell lymphoma, marginal zone B-cell lymphoma, Burkitt lymphoma, lymphoplasmacytic lymphoma, hairy cell leukemia, or primary central nervous system lymphoma) or a T-cell lymphoma (e.g., precursor T-lymphoblastic lymphoma, or peripheral T-cell lymphoma). The term "leukemia" may refer to any type of leukemia including acute leukemia or chronic leukemia. Types of leukemia include acute myeloid leukemia, chronic myeloid leukemia, acute lymphocytic leukemia, acute undifferentiated leukemia, or chronic lymphocytic leukemia.

Examples of cancer include cancers that cause solid tumors as well as cancers that do not cause solid tumors.

Furthermore, any of the cancers mentioned herein may be a primary cancer (e.g., a cancer that is named after the part of the body where it first started to grow) or a secondary or metastatic cancer (e.g., a cancer that has originated from another part of the body).

A patient at risk of cancer may be at risk because of a particular condition such as a pre-cancerous condition. Pre-cancerous conditions include but are not limited to actinic keratosis, Barrett's esophagus, atrophic gastritis, ductal carcinoma in situ, dyskeratosis congenita, sideropenic dysphagia, lichen planus, oral submucous fibrosis, solar elastosis, cervical dysplasia, leukoplakia, and erythroplakia). In some cases, a patient may be at risk of cancer because of cell or tissue dysplasia (e.g., an abnormal change in cell number, abnormal change in cell shape, abnormal change in cell size, or abnormal change in cell pigmentation).

Compounds of the present disclosure or a pharmaceutically acceptable salt thereof can be administered, e.g., intravenously, orally, subcutaneously, at a dose of, for example, about 0.05 mg per kg, 0.06 mg per kg, about 0.07 mg per kg, about 0.08 mg per kg, about 0.09 mg per kg, about 0.1 mg per kg, about 0.2 mg per kg, about 0.3 mg per kg, about 0.4 mg per kg, about 0.5 mg per kg, about 0.6 mg per kg, about 0.7 mg per kg, about 0.8 mg per kg, about 0.9 mg per kg, about 1.0 mg per kg, about 1.5 mg per kg, about 2.0, mg per kg about 3.0 mg per kg, about 4.0 mg per kg, about 5.0 mg per kg, about 6.0 mg per kg, about 7.0 mg per kg, about 8.0 mg per kg, about 9.0 mg per kg, about 10 mg per kg, about 11 mg per kg, about 12 mg per kg, about 13 mg per kg, about 14 mg per kg, about 15 mg per kg, about 16 mg per kg, about 17 mg per kg, about 18 mg per kg, about 19 mg per kg, about 20 mg per kg, about 21 mg per kg, about 22 mg per kg, about 23 mg per kg, about 24 mg per kg, about 25 mg per kg, about 26 mg per kg, about 27, mg per kg about 28 mg per kg, about 29 mg per kg, or 30 mg per kg.

In one embodiment, compounds of the present disclosure or a pharmaceutically acceptable salt thereof can be administered intravenously at a dose of, for example, 0.05 mg per kg, 0.06 mg per kg, about 0.07 mg per kg, about 0.08 mg per kg, about 0.09 mg per kg, about 0.1 mg per kg, about 0.2 mg per kg, about 0.3 mg per kg, about 0.4 mg per kg, about 0.5 mg per kg, 0.6 mg per kg, about 0.7 mg per kg, about 0.8 mg per kg, about 0.9 mg per kg, about 1.0 mg per kg, about 1.5 mg per kg, about 2.0 mg per kg, about 5 mg per kg, about 6 mg per kg, about 7 mg per kg, about 8 mg per kg, about 9 mg per kg, about 10 mg per kg, about 11 mg per kg, about 12 mg per kg, about 13 mg per kg, about 14 mg per kg, about 15 mg per kg, about 16 mg per kg, about 17 mg per kg, about 18 mg per kg, about 19 mg per kg, about 20 mg per kg, about 21 mg per kg, about 22 mg per kg, about 23 mg per kg, about 24 mg per kg, about 25 mg per kg, about 26 mg per kg, about 27 mg per kg, about 28 mg per kg, about 29 mg per kg, or about 30 mg per kg of patient.

In one embodiment, compounds of the present disclosure or a pharmaceutically acceptable salt thereof can be administered orally at a dose of, for example, 0.05 mg per kg, 0.06 mg per kg, about 0.07 mg per kg, about 0.08 mg per kg, about 0.09 mg per kg, about 0.1 mg per kg, about 0.2 mg per kg, about 0.3 mg per kg, about 0.4 mg per kg, about 0.5 mg per kg, 0.6 mg per kg, about 0.7 mg per kg, about 0.8 mg per kg, about 0.9 mg per kg, about 1.0 mg per kg, about 1.5 mg per kg, about 2.0 mg per kg, about 5 mg per kg, about 6 mg per kg, about 7 mg per kg, about 8 mg per kg, about 9 mg per kg, about 10 mg per kg, about 11 mg per kg, about 12 mg per kg, about 13 mg per kg, about 14 mg per kg, about 15 mg per kg, about 16 mg per kg, about 17 mg per kg, about 18 mg per kg, about 19 mg per kg, about 20 mg per kg, about 21 mg per kg, about 22 mg per kg, about 23 mg per kg, about 24 mg per kg, about 25 mg per kg, about 26 mg per kg, about 27 mg per kg, about 28 mg per kg, about 29 mg per kg, or about 30 mg per kg of patient.

In one embodiment, compounds of the present disclosure or a pharmaceutically acceptable salt thereof can be administered subcutaneously at a dose of, for example, 0.05 mg per kg, 0.06 mg per kg, about 0.07 mg per kg, about 0.08 mg per kg, about 0.09 mg per kg, about 0.1 mg per kg, about 0.2 mg per kg, about 0.3 mg per kg, about 0.4 mg per kg, about 0.5 mg per kg, 0.6 mg per kg, about 0.7 mg per kg, about 0.8 mg per kg, about 0.9 mg per kg, about 1.0 mg per kg, about 1.5 mg per kg, about 2.0 mg per kg, about 5 mg per kg, about 6 mg per kg, about 7 mg per kg, about 8 mg per kg, about 9 mg per kg, about 10 mg per kg, about 11 mg per kg, about 12 mg per kg, about 13 mg per kg, about 14 mg per kg, about 15 mg per kg, about 16 mg per kg, about 17 mg per kg, about 18 mg per kg, about 19 mg per kg, about 20 mg per kg, about 21 mg per kg, about 22 mg per kg, about 23 mg per kg, about 24 mg per kg, about 25 mg per kg, about 26 mg per kg, about 27 mg per kg, about 28 mg per kg, about 29 mg per kg, or about 30 mg per kg of patient.

Combination Therapy

The disclosure provided herein describes methods to treat cancer in a subject by administering to the subject at least one compound of the present disclosure. The methods disclosed herein can further comprise administering to the subject a combination of a compound of Formula (I) or a salt thereof and at least one additional anticancer agent wherein the combined composition may be administered as a co-formulation or separately.

In certain particular embodiments, more than one compound of the current disclosure may be administered at a time to the subject. In some embodiments, two compounds of the current disclosure in combination may act synergistically or additively, and either compound may be used in a lesser amount than if administered alone.

In certain embodiments, compounds disclosed herein and/or pharmaceutical compositions thereof can be used with additional therapeutic agent(s) in combination therapy. The compounds disclosed herein and/or pharmaceutical compositions thereof and the therapeutic agent can act additively or, more preferably, synergistically. In some embodiments, compounds disclosed herein and/or pharmaceutical compositions thereof are administered concurrently with the administration of another therapeutic agent. For example, compounds disclosed herein and/or pharmaceutical compositions thereof may be administered together with another therapeutic agent. In other embodiments, compounds disclosed herein and/or pharmaceutical compositions thereof are administered prior or subsequent to administration of other therapeutic agents. The additional therapeutic agent(s) used in combination therapy can be an anticancer agent such as etoposide, cisplatin, oxaliplatin, gemcitabine, irinotecan, anthracycline, and taxol.

The present invention is further illustrated by the following examples which should not be construed as further limiting. The contents of all references, patents and published patent applications cited throughout this application, as well as the Figures and the Appendix of sequences provided herein, are expressly incorporated herein by reference in their entirety.

EXAMPLES

Derivatives of piperlongumine were designed and synthesized (see Table 1) using the synthesis methods described further below.

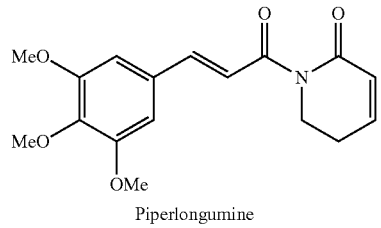 [SMILES: COc1cc(/C=C/C(=O)N2CCC=CC2=O)cc(OC)c1OC]

Piperlongumine

General Information $^1$H NMR spectra and $^{13}$C NMR spectra were recorded on a Varian 400 MHz or Bruker Avance III 500 MHz spectrometers. Spectra are referenced to residual chloroform (δ 7.26, $^1$H), DMSO (δ 2.54, $^1$H) or methanol (δ 3.34, $^1$H) unless otherwise noted. Chemical shifts are reported in ppm (δ); multiplicities are indicated by s (singlet), d (doublet), t (triplet), q (quartet), quint (quintet), sext (sextet), m (multiplet) and br (broad). Coupling constants, J, are reported in Hertz. Silica gel chromatography was performed using a Teledyne Isco CombiFlash® Rf+ instrument using Hi-Purit Silica Flash Cartridges (National Chromatography Inco) or Redi Sep Rf Gold C18 Cartridges (Teledyne Isco). Analytical HPLC was performed on a Waters ACQUITY UPLC with a photodiode array detector using and a Waters ACQUITY BEH Shield RPC18 (2.1×50 mm, 1.7 µm) column. Analytical LCMS was performed on a Waters ACQUITY UPLC with a Waters 3100 mass detector. Chiral HPLC was performed on a Waters Alliance e2695 with a photodiode array detector using Daicel Chiralpak® AD-H, Chiralpak® IA, Chiralpak® IB, Chiralpak® IC, Chiralcel® OD-H or Chiralcel® OJ-H columns. Optical rotations were obtained on a Jasco P-2000 digital polarimeter and are reported as $[α]_D^T$ temperature (T), concentration (c=g/100 mL) and solvent. Commercially available reagents and solvents were used as received unless otherwise indicated.

TABLE 1

| No. | Structure | Name | MOLP-8 IC$_{50}$ (µM) | DU4475 IC$_{50}$ (µM) | HCT 116 IC$_{50}$ (µM) |
|---|---|---|---|---|---|
| 1 | 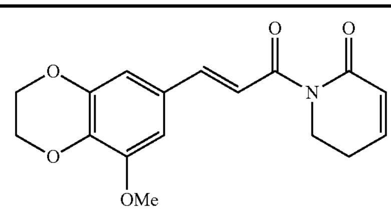 | (E)-1-(3-(8-methoxy-2,3-dihydrobenzo[b][1,4]dioxin-6-yl)acryloyl)-5,6-dihydropyridin-2(1H)-one | 0.74 | 0.83 | 1.9 |

TABLE 1-continued

| No. | Structure | Name | MOLP-8 IC$_{50}$ (μM) | DU4475 IC$_{50}$ (μM) | HCT 116 IC$_{50}$ (μM) |
| --- | --- | --- | --- | --- | --- |
| 2 | 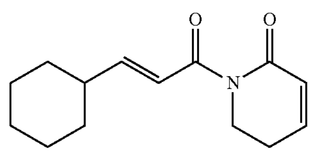 [SMILES: O=C1C=CCCN1C(=O)/C=C/C1CCCCC1] | (E)-1-(3-cyclohexylacryloyl)-5,6-dihydropyridin-2(1H)-one | 1.05 | 0.95 | 2.6 |
| 3 | 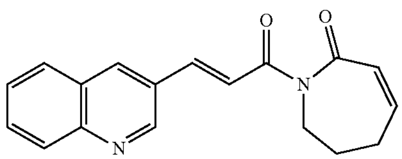 [SMILES: O=C1C=CCCCN1C(=O)/C=C/c1cnc2ccccc2c1] | (E)-1-(3-(quinolin-3-yl)acryloyl)-1,5,6,7-tetrahydro-2H-azepin-2-one | 0.36 | 0.76 | 1.7 |
| 4 | 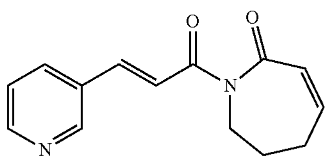 [SMILES: O=C1C=CCCCN1C(=O)/C=C/c1cccnc1] | (E)-1-(3-(pyridin-3-yl)acryloyl)-1,5,6,7-tetrahydro-2H-azepin-2-one | 0.52 | 0.59 | 1.9 |
| 5 | 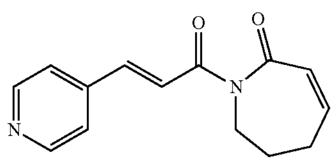 [SMILES: O=C1C=CCCCN1C(=O)/C=C/c1ccncc1] | (E)-1-(3-(pyridin-4-yl)acryloyl)-1,5,6,7-tetrahydro-2H-azepin-2-one | 0.49 | 0.57 | 2.0 |
| 6 | 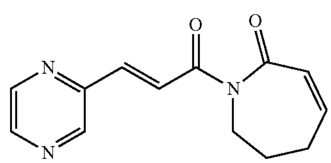 [SMILES: O=C1C=CCCCN1C(=O)/C=C/c1cnccn1] | (E)-1-(3-(pyrazin-2-yl)acryloyl)-1,5,6,7-tetrahydro-2H-azepin-2-one | 0.44 | 0.56 | 2.4 |
| 7 | 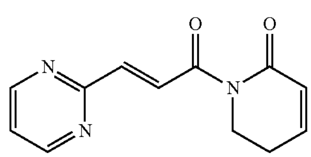 [SMILES: O=C1C=CCCN1C(=O)/C=C/c1ncccn1] | (E)-1-(3-(pyrimidin-2-yl)acryloyl)-5,6-dihydropyridin-2(1H)-one | 0.57 | 0.49 | 1.5 |
| 8 | 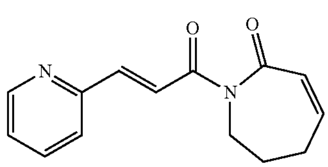 [SMILES: O=C1C=CCCCN1C(=O)/C=C/c1ccccn1] | (E)-1-(3-(pyridin-2-yl)acryloyl)-1,5,6,7-tetrahydro-2H-azepin-2-one | 0.41 | 0.50 | 1.5 |
| 9 | 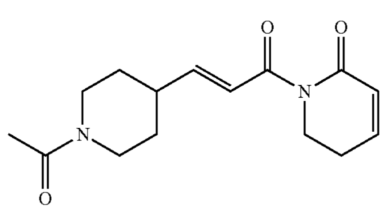 [SMILES: CC(=O)N1CCC(/C=C/C(=O)N2CCC=CC2=O)CC1] | (E)-1-(3-(1-acetylpiperidin-4-yl)acryloyl)-5,6-dihydropyridin-2(1H)-one | 0.97 | 0.92 | 5.7 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 10 | 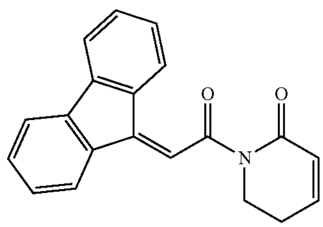 [SMILES: O=C1C=CCCN1C(=O)C=C1c2ccccc2-c2ccccc21] | 1-(2-(9H-fluoren-9-ylidene)acetyl)-5,6-dihydropyridin-2(1H)-one | 2.12 | 0.95 | 1.9 |
| 11 | 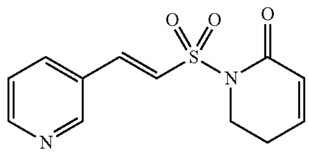 [SMILES: O=C1C=CCCN1S(=O)(=O)/C=C/c1cccnc1] | (E)-1-((2-(pyridin-3-yl)vinyl)sulfonyl)-5,6-dihydropyridin-2(1H)-one | 0.50 | 0.58 | 1.9 |
| 12 | 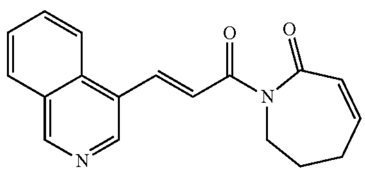 [SMILES: O=C1C=CCCCN1C(=O)/C=C/c1cncc2ccccc12] | (E)-1-(3-(isoquinolin-4-yl)acryloyl)-1,5,6,7-tetrahydro-2H-azepin-2-one | 0.89 | 0.60 | 0.96 |
| 13 | 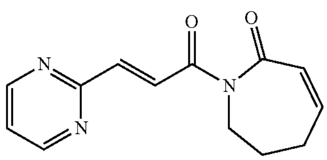 | (E)-1-(3-(pyrimidin-2-yl)acryloyl)-1,5,6,7-tetrahydro-2H-azepin-2-one | 0.51 | 0.67 | 1.3 |
| 14 | 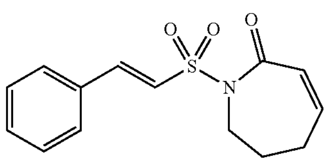 [SMILES: O=C1C=CCCCN1S(=O)(=O)/C=C/c1ccccc1] | (E)-1-(styrylsulfonyl)-1,5,6,7-tetrahydro-2H-azepin-2-one | 3.51 | 3.04 | 7.0 |
| 15 | 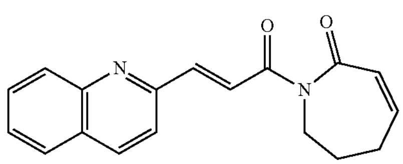 [SMILES: O=C1C=CCCCN1C(=O)/C=C/c1ccc2ccccc2n1] | (E)-1-(3-(quinolin-2-yl)acryloyl)-1,5,6,7-tetrahydro-2H-azepin-2-one | 0.5 | 0.5 | 0.88 |
| 16 | 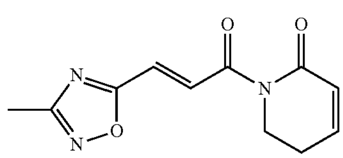 [SMILES: Cc1noc(/C=C/C(=O)N2CCC=CC2=O)n1] | (E)-1-(3-(3-methyl-1,2,4-oxadiazol-5-yl)acryloyl)-5,6-dihydropyridin-2(1H)-one | 0.66 | 0.75 | 0.96 |
| 17 | 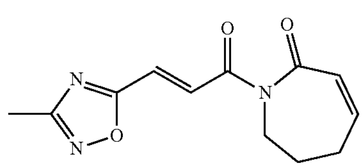 [SMILES: Cc1noc(/C=C/C(=O)N2CCCC=CC2=O)n1] | (E)-1-(3-(3-methyl-1,2,4-oxadiazol-5-yl)acryloyl)-1,5,6,7-tetrahydro-2H-azepin-2-one | 0.33 | 1.16 | 5.93 |
| 18 | 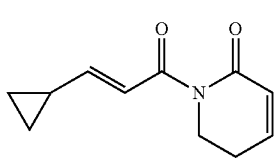 [SMILES: O=C1C=CCCN1C(=O)/C=C/C1CC1] | (E)-1-(3-cyclopropylacryloyl)-5,6-dihydropyridin-2(1H)-one | 0.68 | 2.05 | 14.2 |

TABLE 1-continued

| No. | Structure | Name | MOLP-8 IC$_{50}$ (μM) | DU4475 IC$_{50}$ (μM) | HCT 116 IC$_{50}$ (μM) |
| --- | --- | --- | --- | --- | --- |
| 19 | 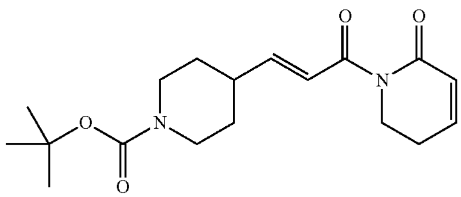 [SMILES: CC(C)(C)OC(=O)N1CCC(/C=C/C(=O)N2CCC=CC2=O)CC1] | tert-butyl (E)-4-(3-oxo-3-(6-oxo-3,6-dihydropyridin-1(2H)-yl)prop-1-en-1-yl)piperidine-1-carboxylate | 0.41 | 0.82 | 1.97 |
| 20 | 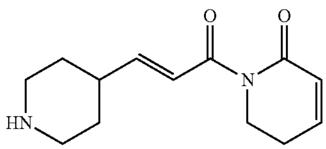 [SMILES: O=C1C=CCCN1C(=O)/C=C/C1CCNCC1] | (E)-1-(3-(piperidin-4-yl)acryloyl)-5,6-dihydropyridin-2(1H)-one | 0.69 | 1.32 | 2.13 |
| 21 | 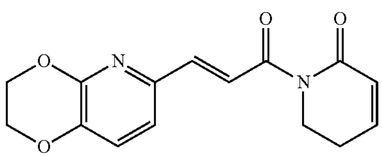 [SMILES: O=C1C=CCCN1C(=O)/C=C/c1ccc2c(n1)OCCO2] | (E)-1-(3-(2,3-dihydro-[1,4]dioxino[2,3-b]pyridin-6-yl)acryloyl)-5,6-dihydropyridin-2(1H)-one | 0.68 | 0.53 | 3.16 |
| 22 | 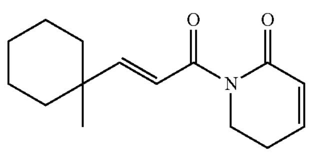 [SMILES: CC1(/C=C/C(=O)N2CCC=CC2=O)CCCCC1] | (E)-1-(3-(1-methylcyclohexyl)acryloyl)-5,6-dihydropyridin-2(1H)-one | 2.21 | 1.84 | 3.85 |
| 23 | 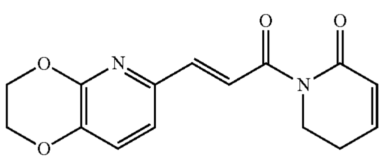 [SMILES: O=C1C=CCCN1C(=O)/C=C/c1ccc2c(n1)OCCO2] | (E)-1-(3-(2,3-dihydro-[1,4]dioxino[2,3-b]pyridin-6-yl)acryloyl)-5,6-dihydropyridin-2(1H)-one | 0.7 | 0.5 | 3.16 |
| 24 | 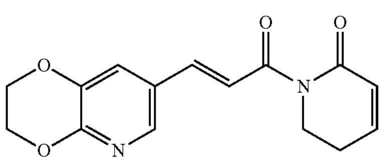 [SMILES: O=C1C=CCCN1C(=O)/C=C/c1cnc2c(c1)OCCO2] | (E)-1-(3-(2,3-dihydro-[1,4]dioxino[2,3-b]pyridin-7-yl)acryloyl)-5,6-dihydropyridin-2(1H)-one | 0.32 | 0.68 | 1.9 |
| 25 | 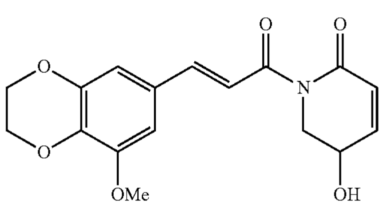 [SMILES: COc1cc(/C=C/C(=O)N2CC(O)C=CC2=O)cc2c1OCCO2] | 5-hydroxy-1-[(2E)-3-(8-methoxy-2,3-dihydro-1,4-benzodioxin-6-yl)prop-2-enoyl]-5,6-dihydropyridin-2(1H)-one | 0.37 | 1.77 | 4.61 |
| 26 | 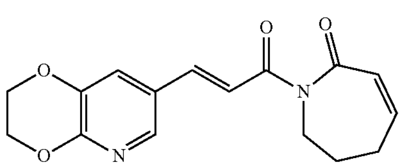 [SMILES: O=C1C=CCCCN1C(=O)/C=C/c1cnc2c(c1)OCCO2] | (E)-1-(3-(2,3-dihydro-[1,4]dioxino[2,3-b]pyridin-7-yl)acryloyl)-6,7-dihydro-1H-azepin-2(5H)-one | 0.17 | 0.63 | 3.42 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 27 | 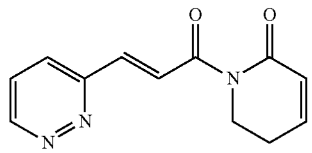 [SMILES: O=C1C=CCCN1C(=O)/C=C/c1cccnn1] | (E)-1-(3-(pyridazin-3-yl)acryloyl)-5,6-dihydropyridin-2(1H)-one | 0.76 | 0.95 | 1.9 |
| 28 | 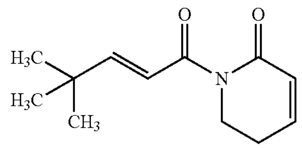 | (E)-1-(4,4-dimethylpent-2-enoyl)-5,6-dihydropyridin-2(1H)-one | 0.49 | 1.38 | 3.53 |
| 29 | 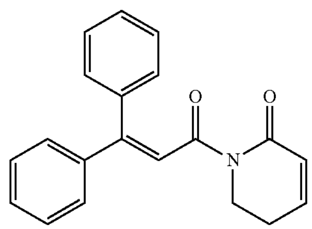 [SMILES: O=C1C=CCCN1C(=O)C=C(c1ccccc1)c1ccccc1] | 1-(3,3-diphenylacryloyl)-5,6-dihydropyridin-2(1H)-one | 2.7 | 1.72 | 6.4 |
| 30 | 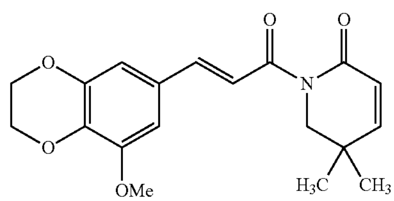 [SMILES: COc1cc(/C=C/C(=O)N2CC(C)(C)C=CC2=O)cc2c1OCCO2] | (E)-1-(3-(8-methoxy-2,3-dihydrobenzo[b][1,4]dioxin-6-yl)acryloyl)-5,5-dimethyl-5,6-dihydropyridin-2(1H)-one | 2.8 | 5.5 | 9.9 |
| 31 | 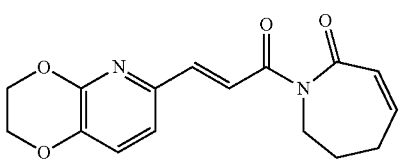 [SMILES: O=C1C=CCCCN1C(=O)/C=C/c1ccc2c(n1)OCCO2] | (E)-1-(3-(2,3-dihydro-[1,4]dioxino[2,3-b]pyridin-6-yl)acryloyl)-1,5,6,7-tetrahydroazepin-2-one | 0.27 | 0.56 | 1.55 |
| 32 | 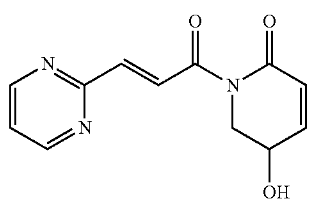 [SMILES: O=C1C=CC(O)CN1C(=O)/C=C/c1ncccn1] | 5-hydroxy-1-[(2E)-3-(pyrimidin-2-yl)prop-2-enoyl]-5,6-dihydropyridin-2(1H)-one | 0.38 | 1.49 | 7.2 |
| 33 | 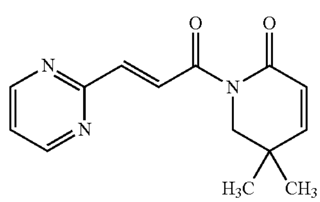 [SMILES: CC1(C)C=CC(=O)N(C(=O)/C=C/c2ncccn2)C1] | (E)-5,5-dimethyl-1-(3-(pyrimidin-2-yl)acryloyl)-5,6-dihydropyridin-2(1H)-one | 0.56 | 1.3 | 4.07 |
| 34 | 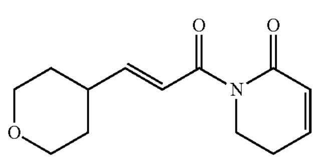 [SMILES: O=C1C=CCCN1C(=O)/C=C/C1CCOCC1] | 1-[(2E)-3-(tetrahydro-2H-pyran-4-yl)prop-2-enoyl]-5,6-dihydropyridin-2(1H)-one | 0.51 | 1.43 | 3.8 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 35 | 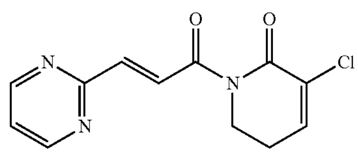 [SMILES: O=C(/C=C/c1ncccn1)N1CCC=C(Cl)C1=O] | (E)-3-chloro-1-(3-(pyrimidin-2-yl)acryloyl)-5,6-dihydropyridin-2(1H)-one | 0.08 | 0.21 | 0.38 |
| 36 | 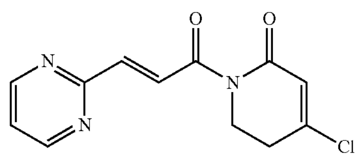 [SMILES: O=C1C=C(Cl)CCN1C(=O)/C=C/c1ncccn1] | (E)-4-chloro-1-(3-(pyrimidin-2-yl)acryloyl)-5,6-dihydropyridin-2(1H)-one | N/A | N/A | 2.97 |
| 37 | 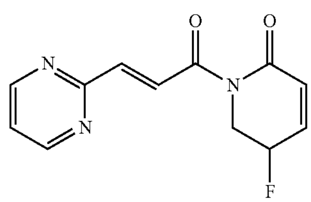 [SMILES: O=C1C=CC(F)CN1C(=O)/C=C/c1ncccn1] | (E)-5-fluoro-1-(3-(pyrimidin-2-yl)acryloyl)-5,6-dihydropyridin-2(1H)-one | 0.11 | 0.42 | 0.87 |
| 38 | 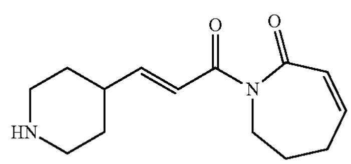 [SMILES: O=C1C=CCCCN1C(=O)/C=C/C1CCNCC1] | (E)-1-(3-(piperidin-4-yl)acryloyl)-6,7-dihydro-1H-azepin-2(5H)-one | 0.23 | 1.03 | 0.92 |
| 39 | 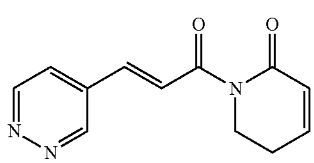 [SMILES: O=C1C=CCCN1C(=O)/C=C/c1ccnnc1] | (E)-1-(3-(pyridazin-4-yl)acryloyl)-5,6-dihydropyridin-2(1H)-one | 0.3 | 0.65 | N/A |
| 40 | 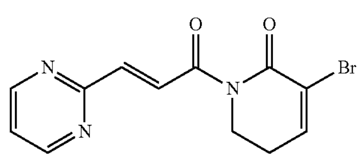 [SMILES: O=C(/C=C/c1ncccn1)N1CCC=C(Br)C1=O] | 3-bromo-1-[(2E)-3-(pyrimidin-2-yl)prop-2-enoyl]-5,6-dihydropyridin-2(1H)-one | 0.04 | 0.1 | 0.36 |
| 41 | 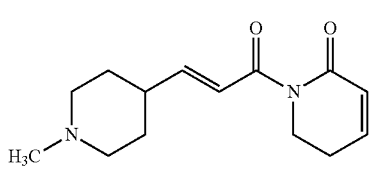 [SMILES: CN1CCC(/C=C/C(=O)N2CCC=CC2=O)CC1] | (E)-1-(3-(1-methylpiperidin-4-yl)acryloyl)-5,6-dihydropyridin-2(1H)-one | N/A | N/A | 1.24 |
| 42 | 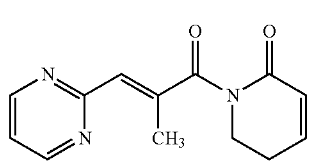 [SMILES: C/C(=C\c1ncccn1)C(=O)N1CCC=CC1=O] | (E)-1-(2-methyl-3-(pyrimidin-2-yl)acryloyl)-5,6-dihydropyridin-2(1H)-one | N/A | N/A | 2.2 |
| 43 | 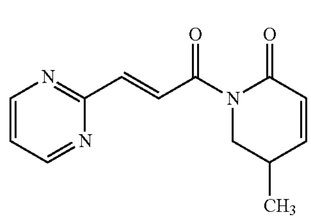 [SMILES: CC1C=CC(=O)N(C(=O)/C=C/c2ncccn2)C1] | (E)-5-methyl-1-(3-(pyrimidin-2-yl)acryloyl)-5,6-dihydropyridin-2(1H)-one | 0.28 | 0.53 | 1.27 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 44 | 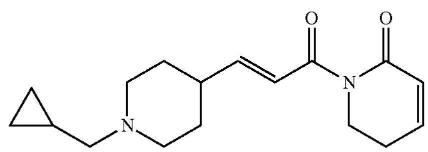 [SMILES: O=C1C=CCCN1C(=O)/C=C/C1CCN(CC2CC2)CC1] | (E)-1-(3-(1-(cyclopropylmethyl)piperidin-4-yl)acryloyl)-5,6-dihydropyridin-2(1H)-one | 0.49 | 1.05 | 1.35 |
| 45 | 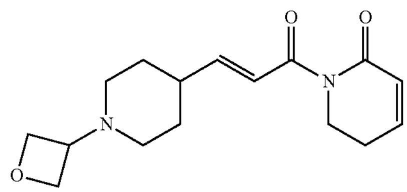 [SMILES: O=C1C=CCCN1C(=O)/C=C/C1CCN(C2COC2)CC1] | (E)-1-(3-(1-(oxetan-3-yl)piperidin-4-yl)acryloyl)-5,6-dihydropyridin-2(1H)-one | 0.72 | 1.35 | 3.24 |
| 46 | 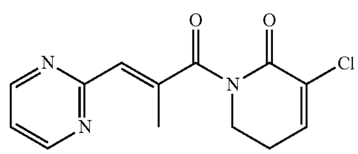 [SMILES: C/C(=C\c1ncccn1)C(=O)N1CCC=C(Cl)C1=O] | (E)-3-chloro-1-(2-methyl-3-(pyrimidin-2-yl)acryloyl)-5,6-dihydropyridin-2(1H)-one | N/A | N/A | 0.97 |
| 47 | 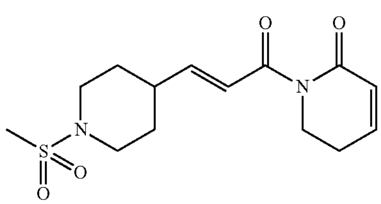 [SMILES: CS(=O)(=O)N1CCC(/C=C/C(=O)N2CCC=CC2=O)CC1] | 1-{(2E)-3-[1-(methylsulfonyl)piperidin-4-yl]prop-2-enoyl}-5,6-dihydropyridin-2(1H)-one | N/A | N/A | 3.14 |
| 48 | 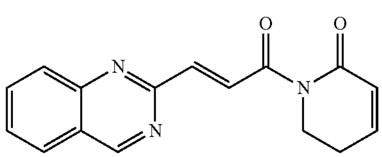 [SMILES: O=C1C=CCCN1C(=O)/C=C/c1ncc2ccccc2n1] | (E)-1-(3-(quinazolin-2-yl)acryloyl)-5,6-dihydropyridin-2(1H)-one | 0.29 | 0.35 | N/A |
| 49 | 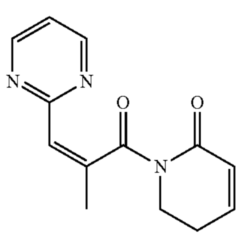 [SMILES: C/C(=C/c1ncccn1)C(=O)N1CCC=CC1=O] | 1-[(2E)-3-(4,5-dihydropyrimidin-2-yl)-2-methylprop-2-enoyl]-5,6-dihydropyridin-2(1H)-one | 6.11 | 5.06 | N/A |
| 50 | 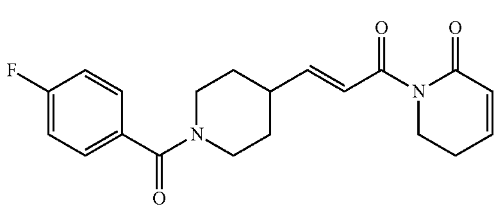 [SMILES: O=C(c1ccc(F)cc1)N1CCC(/C=C/C(=O)N2CCC=CC2=O)CC1] | (E)-1-(3-(1-(4-fluorobenzoyl)piperidin-4-yl)acryloyl)-5,6-dihydropyridin-2(1H)-one | 0.41 | 0.5 | N/A |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 51 | 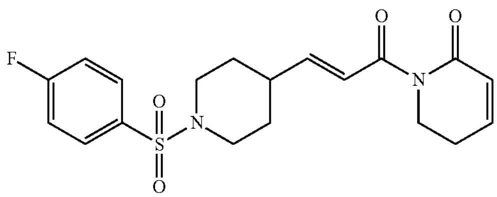 [SMILES: O=C1C=CCCN1C(=O)/C=C/C1CCN(S(=O)(=O)c2ccc(F)cc2)CC1] | (E)-1-(3-(1-(4-fluorophenylsulfonyl)piperidin-4-yl)acryloyl)-5,6-dihydropyridin-2(1H)-one | 0.56 | 0.57 | N/A |
| 52 | 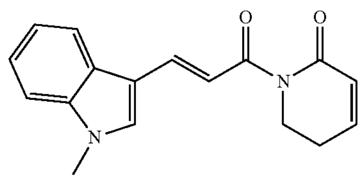 [SMILES: Cn1cc(/C=C/C(=O)N2CCC=CC2=O)c2ccccc21] | 1-[(2E)-3-(1-methyl-1H-indol-3-yl)prop-2-enoyl]-5,6-dihydropyridin-2(1H)-one | 1.00 | 1.52 | N/A |
| 53 | 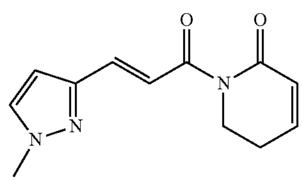 [SMILES: Cn1ccc(/C=C/C(=O)N2CCC=CC2=O)n1] | 1-[(2E)-3-(1-methyl-1H-pyrazol-3-yl)prop-2-enoyl]-5,6-dihydropyridin-2(1H)-one | 0.56 | 0.73 | 2.12 |
| 54 | 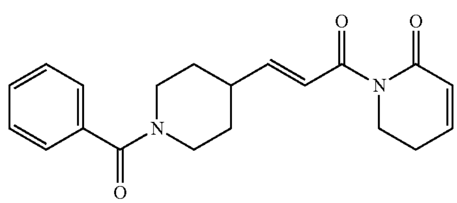 [SMILES: O=C(c1ccccc1)N1CCC(/C=C/C(=O)N2CCC=CC2=O)CC1] | 1-[(2E)-3-(1-benzoylpiperidin-4-yl)prop-2-enoyl]-5,6-dihydropyridin-2(1H)-one | N/A | N/A | 1.4 |
| 55 | 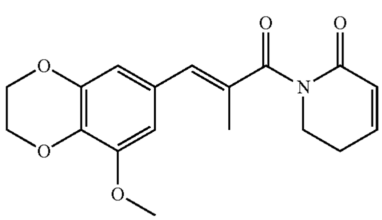 [SMILES: COc1cc(/C=C(\C)C(=O)N2CCC=CC2=O)cc2c1OCCO2] | 1-[(2E)-3-(8-methoxy-2,3-dihydro-1,4-benzodioxin-6-yl)-2-methylprop-2-enoyl]-5,6-dihydropyridin-2(1H)-one | 0.58 | 0.83 | 1.96 |
| 56 | 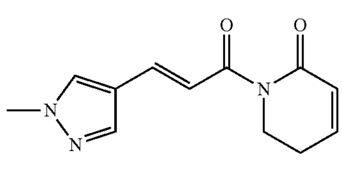 [SMILES: Cn1cc(/C=C/C(=O)N2CCC=CC2=O)cn1] | (E)-1-(3-(1-methyl-1H-pyrazol-4-yl)acryloyl)-5,6-dihydropyridin-2(1H)-one | 0.60 | 1.38 | 3.6 |
| 57 | 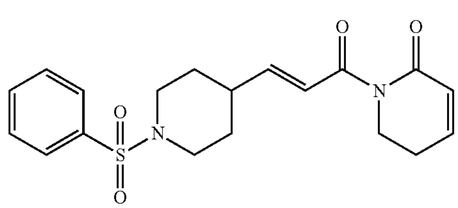 [SMILES: O=C1C=CCCN1C(=O)/C=C/C1CCN(S(=O)(=O)c2ccccc2)CC1] | (E)-1-(3-(1-(phenylsulfonyl)piperidin-4-yl)acryloyl)-5,6-dihydropyridin-2(1H)-one | 0.68 | 0.53 | 1.36 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 58 | 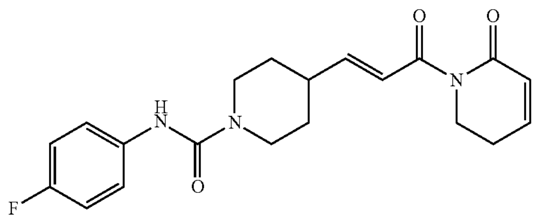 [SMILES: O=C(Nc1ccc(F)cc1)N1CCC(/C=C/C(=O)N2CCC=CC2=O)CC1] | N-(4-fluorophenyl)-4-[(1E)-3-oxo-3-(6-oxo-3,6-dihydropyridin-1(2H)-yl)prop-1-en-1-yl]piperidine-1-carboxamide | 0.38 | 0.44 | 1.1 |
| 59 | 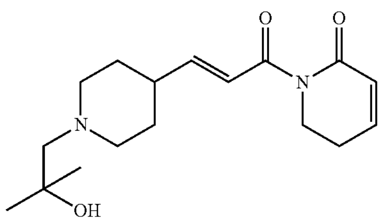 [SMILES: CC(C)(O)CN1CCC(/C=C/C(=O)N2CCC=CC2=O)CC1] | 1-{(2E)-3-[1-(2-hydroxy-2-methylpropyl)piperidin-4-yl]prop-2-enoyl}-5,6-dihydropyridin-2(1H)-one | 0.39 | 0.84 | N/A |
| 60 | 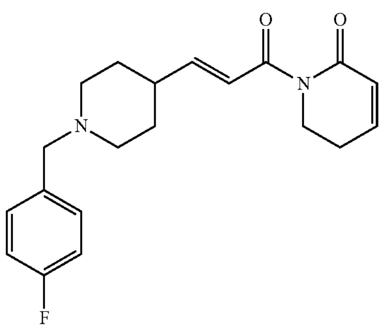 [SMILES: O=C1C=CCCN1C(=O)/C=C/C1CCN(Cc2ccc(F)cc2)CC1] | 1-{3-[1-(4-fluorobenzyl)piperidin-4-yl]prop-2-enoyl}-5,6-dihydropyridin-2(1H)-one | 0.34 | 0.59 | N/A |
| 61 | 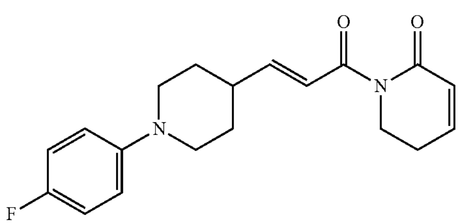 [SMILES: O=C1C=CCCN1C(=O)/C=C/C1CCN(c2ccc(F)cc2)CC1] | 1-{3-[1-(4-fluorophenyl)piperidin-4-yl]prop-2-enoyl}-5,6-dihydropyridin-2(1H)-one | 0.68 | 0.95 | N/A |
| 62 | 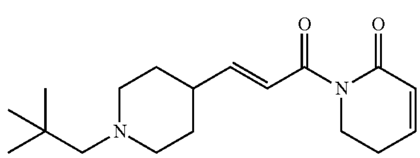 [SMILES: CC(C)(C)CN1CCC(/C=C/C(=O)N2CCC=CC2=O)CC1] | (E)-1-(3-(1-neopentylpiperidin-4-yl)acryloyl)-5,6-dihydropyridin-2(1H)-one | 0.31 | 0.58 | 1.73 |
| 63 | 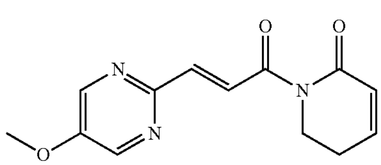 [SMILES: COc1cnc(/C=C/C(=O)N2CCC=CC2=O)nc1] | (E)-1-(3-(5-methoxypyrimidin-2-yl)acryloyl)-5,6-dihydropyridin-2(1H)-one | 0.29 | 0.48 | 2.11 |
| 64 | 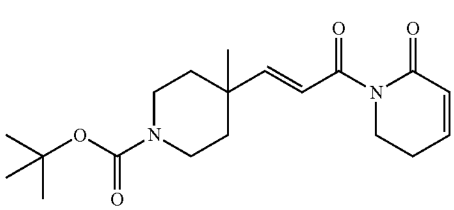 [SMILES: CC1(/C=C/C(=O)N2CCC=CC2=O)CCN(C(=O)OC(C)(C)C)CC1] | tert-butyl (E)-4-methyl-4-(3-oxo-3-(6-oxo-3,6-dihydropyridin-1(2H)-yl)prop-1-en-1-yl)piperidine-1-carboxylate | N/A | N/A | 4.32 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 65 | 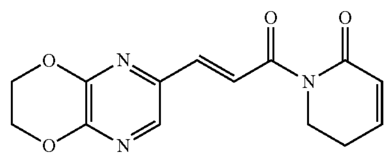 [SMILES: O=C1C=CCCN1C(=O)/C=C/c1cnc2c(n1)OCCO2] | (E)-1-(3-(2,3-dihydro-[1,4]dioxino[2,3-b]pyrazin-6-yl)acryloyl)-5,6-dihydropyridin-2(1H)-one | N/A | N/A | 2.25 |
| 66 | 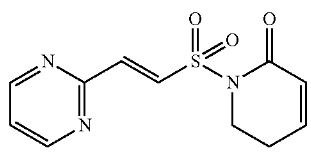 [SMILES: O=C1C=CCCN1S(=O)(=O)/C=C/c1ncccn1] | 1-{[(E)-2-(pyrimidin-2-yl)ethenyl]sulfonyl}-5,6-dihydropyridin-2(1H)-one | 0.21 | 0.95 | 3.11 |
| 67 | 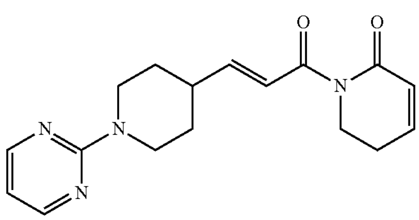 [SMILES: O=C1C=CCCN1C(=O)/C=C/C1CCN(c2ncccn2)CC1] | 1-{(2E)-3-[1-(pyrimidin-2-yl)piperidin-4-yl]prop-2-enoyl}-5,6-dihydropyridin-2(1H)-one | 0.76 | 0.96 | 3.4 |
| 68 | 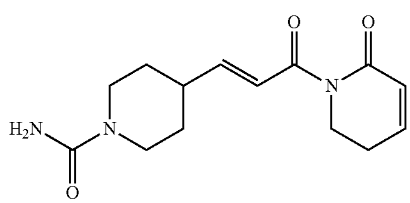 [SMILES: NC(=O)N1CCC(/C=C/C(=O)N2CCC=CC2=O)CC1] | (E)-4-(3-oxo-3-(6-oxo-3,6-dihydropyridin-1(2H)-yl)prop-1-en-1-yl)piperidine-1-carboxamide | 0.67 | 1.55 | 7.38 |
| 69 | 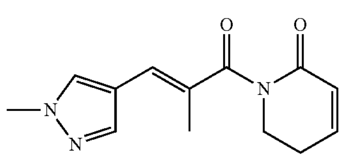 [SMILES: C/C(=C\c1cnn(C)c1)C(=O)N1CCC=CC1=O] | 1-[(2E)-2-methyl-3-(1-methyl-1H-pyrazol-4-yl)prop-2-enoyl]-5,6-dihydropyridin-2(1H)-one | 1.98 | 4.01 | 14 |
| 70 | 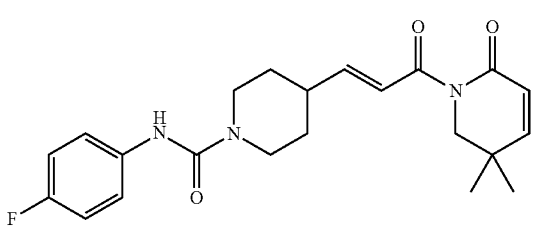 [SMILES: CC1(C)C=CC(=O)N(C(=O)/C=C/C2CCN(C(=O)Nc3ccc(F)cc3)CC2)C1] | (E)-4-(3-(3,3-dimethyl-6-oxo-3,6-dihydropyridin-1(2H)-yl)-3-oxoprop-1-en-1-yl)-N-(4-fluorophenyl)piperidine-1-carboxamide | 1.35 | 1.75 | 7.06 |
| 71 | 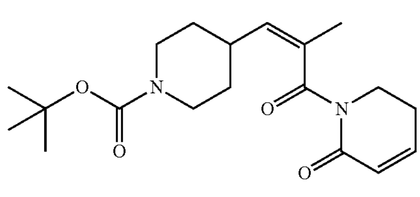 [SMILES: C/C(=C/C1CCN(C(=O)OC(C)(C)C)CC1)C(=O)N1CCC=CC1=O] | (Z)-tert-butyl 4-(2-methyl-3-oxo-3-(2-oxo-5,6-dihydropyridin-1(2H)-yl)prop-1-enyl)piperidine-1-carboxylate | 3.91 | 4.67 | 13.6 |
| 72 | 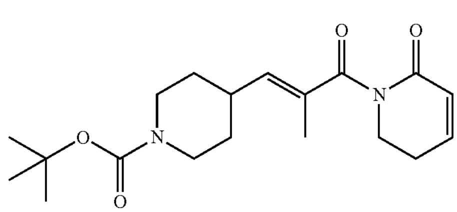 [SMILES: C/C(=C\C1CCN(C(=O)OC(C)(C)C)CC1)C(=O)N1CCC=CC1=O] | tert-butyl (E)-4-(2-methyl-3-oxo-3-(6-oxo-3,6-dihydropyridin-1(2H)-yl)prop-1-en-1-yl)piperidine-1-carboxylate | 2.67 | 4.43 | 10.3 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 73 | 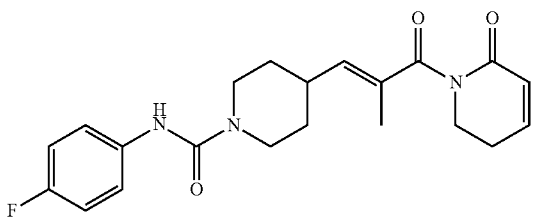 [SMILES: C/C(=C\C1CCN(C(=O)Nc2ccc(F)cc2)CC1)C(=O)N1CCC=CC1=O] | (E)-N-(4-fluorophenyl)-4-(2-methyl-3-oxo-3-(6-oxo-3,6-dihydropyridin-1(2H)-yl)prop-1-en-1-yl)piperidine-1-carboxamide | 0.95 | 1.62 | 4.28 |
| 74 | 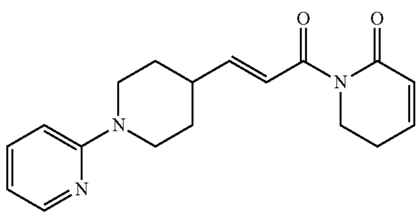 [SMILES: O=C1C=CCCN1C(=O)/C=C/C1CCN(c2ccccn2)CC1] | (E)-1-(3-(1-(pyridin-2-yl)piperidin-4-yl)acryloyl)-5,6-dihydropyridin-2(1H)-one | 0.66 | 1 | 2.58 |
| 75 | 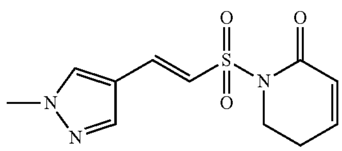 [SMILES: Cn1cc(/C=C/S(=O)(=O)N2CCC=CC2=O)cn1] | 1-{[(E)-2-(1-methyl-1H-pyrazol-4-yl)ethenyl]sulfonyl}-5,6-dihydropyridin-2(1H)-one | 0.86 | 1.6 | 4.62 |
| 76 | 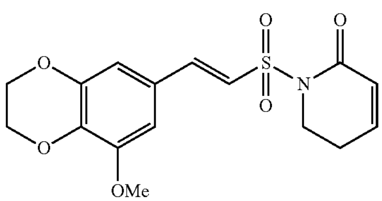 [SMILES: COc1cc(/C=C/S(=O)(=O)N2CCC=CC2=O)cc2c1OCCO2] | 1-{[(E)-2-(8-methoxy-2,3-dihydro-1,4-benzodioxin-6-yl)ethenyl]sulfonyl}-5,6-dihydropyridin-2(1H)-one | 0.563 | 1 | 1.85 |
| 77 | 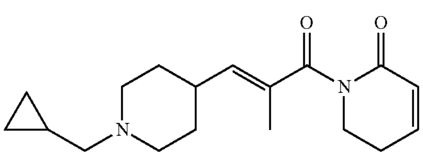 [SMILES: C/C(=C\C1CCN(CC2CC2)CC1)C(=O)N1CCC=CC1=O] | (E)-1-(3-(1-(cyclopropylmethyl)piperidin-4-yl)-2-methylacryloyl)-5,6-dihydropyridin-2(1H)-one | 3.34 | 5.44 | 7.5 |
| 78 | 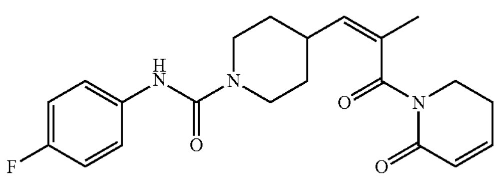 [SMILES: C/C(=C/C1CCN(C(=O)Nc2ccc(F)cc2)CC1)C(=O)N1CCC=CC1=O] | (Z)-1-(3-(1-(4-fluorophenyl)piperidin-4-yl)-2-methylacryloyl)-5,6-dihydropyridin-2(1H)-one | 0.95 | 1.53 | 4.85 |
| 79 | 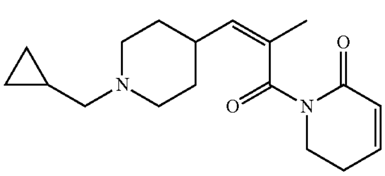 [SMILES: C/C(=C/C1CCN(CC2CC2)CC1)C(=O)N1CCC=CC1=O] | (Z)-1-(3-(1-(cyclopropylmethyl)piperidin-4-yl)-2-methylacryloyl)-5,6-dihydropyridin-2(1H)-one | 1.03 | 1.91 | 2.69 |
| 80 | 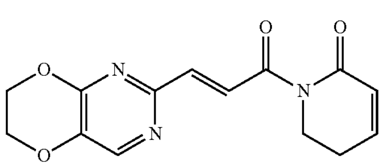 [SMILES: O=C1C=CCCN1C(=O)/C=C/c1ncc2c(n1)OCCO2] | (E)-1-(3-(6,7-dihydro-[1,4]dioxino[2,3-d]pyrimidin-2-yl)acryloyl)-5,6-dihydropyridin-2(1H)-one | 1.15 | 1.8 | 3.21 |

TABLE 1-continued

| No. | Structure | Name | MOLP-8 IC$_{50}$ (μM) | DU4475 IC$_{50}$ (μM) | HCT 116 IC$_{50}$ (μM) |
| --- | --- | --- | --- | --- | --- |
| 81 | 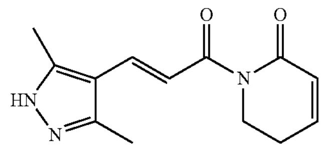 [SMILES: Cc1n[nH]c(C)c1/C=C/C(=O)N1CCC=CC1=O] | (E)-1-(3-(3,5-dimethyl-1H-pyrazol-4-yl)acryloyl)-5,6-dihydropyridin-2(1H)-one | 1.49 | 2.7 | 5.1 |
| 82 | 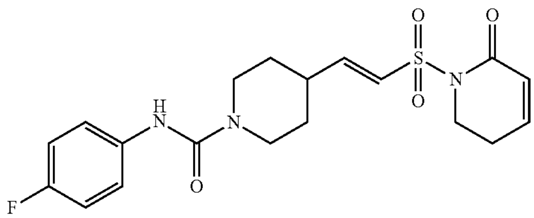 [SMILES: O=C(Nc1ccc(F)cc1)N1CCC(/C=C/S(=O)(=O)N2CCC=CC2=O)CC1] | (E)-N-(4-fluorophenyl)-4-(2-((6-oxo-3,6-dihydropyridin-1(2H)-yl)sulfonyl)vinyl)piperidine-1-carboxamide | 0.36 | 0.8 | 2.25 |
| 83 | 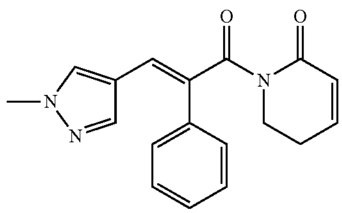 [SMILES: Cn1cc(/C=C(/C(=O)N2CCC=CC2=O)c2ccccc2)cn1] | 1-[(2E)-3-(1-methyl-1H-pyrazol-4-yl)-2-phenylprop-2-enoyl]-5,6-dihydropyridin-2(1H)-one | 2.75 | 4.84 | 11.1 |
| 84 | 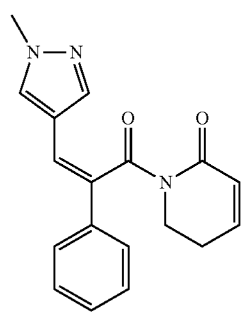 [SMILES: Cn1cc(/C=C(\C(=O)N2CCC=CC2=O)c2ccccc2)cn1] | (Z)-1-(3-(1-methyl-1H-pyrazol-4-yl)-2-phenylacryloyl)-5,6-dihydropyridin-2(1H)-one | 1.55 | 1.63 | 3.71 |
| 85 | 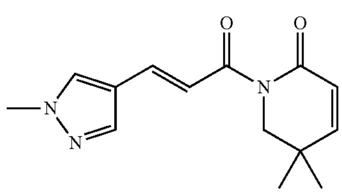 [SMILES: Cn1cc(/C=C/C(=O)N2CC(C)(C)C=CC2=O)cn1] | (E)-5,5-dimethyl-1-(3-(1-methyl-1H-pyrazol-4-yl)acryloyl)-5,6-dihydropyridin-2(1H)-one | 4.6 | 6.79 | 31 |
| 86 | 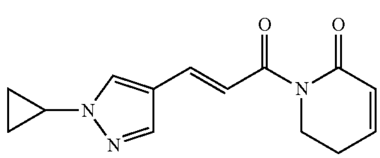 [SMILES: O=C1C=CCCN1C(=O)/C=C/c1cnn(C2CC2)c1] | (E)-1-(3-(1-cyclopropyl-1H-pyrazol-4-yl)acryloyl)-5,6-dihydropyridin-2(1H)-one | 0.85 | 1.67 | 3.83 |
| 87 | 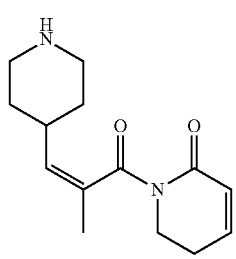 [SMILES: C/C(=C/C1CCNCC1)C(=O)N1CCC=CC1=O] | (Z)-1-(2-methyl-3-(piperidin-4-yl)acryloyl)-5,6-dihydropyridin-2(1H)-one 2,2,2-trifluoroacetate | 3.66 | 5.53 | 10.1 |

TABLE 1-continued

| No. | Structure | Name | MOLP-8 IC$_{50}$ (μM) | DU4475 IC$_{50}$ (μM) | HCT 116 IC$_{50}$ (μM) |
|---|---|---|---|---|---|
| 88 | 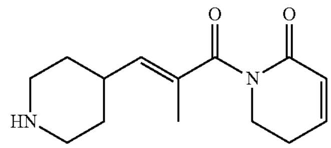 [SMILES: C/C(=C\C1CCNCC1)C(=O)N1CCC=CC1=O] | (E)-1-(2-methyl-3-(piperidin-4-yl)acryloyl)-5,6-dihydropyridin-2(1H)-one 2,2,2-trifluoroacetate | 3.78 | 6.56 | 7.06 |
| 89 | 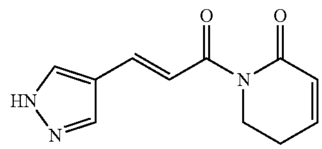 [SMILES: O=C1C=CCCN1C(=O)/C=C/c1cn[nH]c1] | (E)-1-(3-(1H-pyrazol-4-yl)acryloyl)-5,6-dihydropyridin-2(1H)-one | 3.58 | 8.41 | 2.7 |
| 90 | 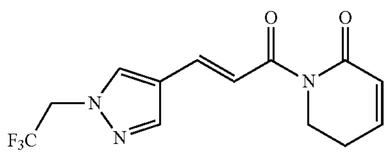 [SMILES: O=C1C=CCCN1C(=O)/C=C/c1cnn(CC(F)(F)F)c1] | 1 11-{(2E)-3-[1-(2,2,2-trifluoroethyl)-1H-pyrazol-4-yl]prop-2-enoyl}-5,6-dihydropyridin-2(1H)-one | 0.44 | 1.47 | 7.07 |
| 91 | 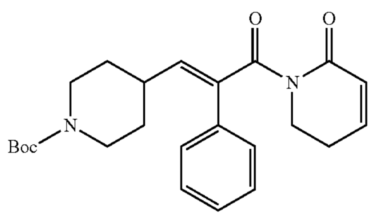 [SMILES: CC(C)(C)OC(=O)N1CCC(/C=C(/C(=O)N2CCC=CC2=O)c2ccccc2)CC1] | (E)-tert-butyl 4-(3-oxo-3-(2-oxo-5,6-dihydropyridin-1(2H)-yl)-2-phenylprop-1-enyl)piperidine-1-carboxylate | 3.2 | 4.14 | 9.16 |
| 92 | 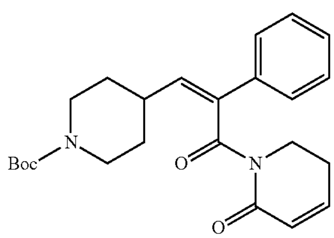 [SMILES: CC(C)(C)OC(=O)N1CCC(/C=C(\C(=O)N2CCC=CC2=O)c2ccccc2)CC1] | (Z)-tert-butyl 4-(3-oxo-3-(2-oxo-5,6-dihydropyridin-1(2H)-yl)-2-phenylprop-1-enyl)piperidine-1-carboxylate | 4.32 | 4.75 | 9.72 |
| 93 | 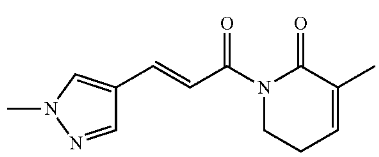 | (E)-3-methyl-1-(3-(1-methyl-1H-pyrazol-4-yl)acryloyl)-5,6-dihydropyridin-2(1H)-one | N/A | N/A | 88.3 |
| 94 | 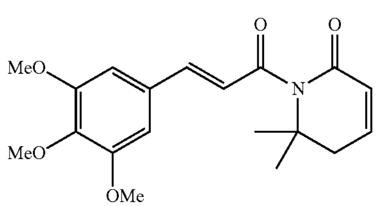 [SMILES: COc1cc(/C=C/C(=O)N2C(=O)C=CCC2(C)C)cc(OC)c1OC] | (E)-6,6-dimethyl-1-(3-(3,4,5-trimethoxyphenyl)acryloyl)-5,6-dihydropyridin-2(1H)-one | N/A | N/A | 3.15 |
| 95 | 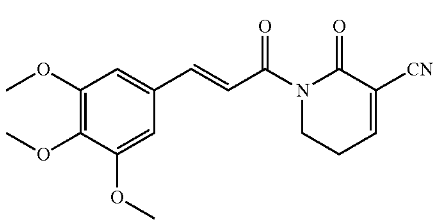 [SMILES: COc1cc(/C=C/C(=O)N2CCC=C(C#N)C2=O)cc(OC)c1OC] | (E)-2-oxo-1-(3-(3,4,5-trimethoxyphenyl)acryloyl)-1,2,5,6-tetrahydropyridine-3-carbonitrile | N/A | N/A | N/A |

TABLE 1-continued

| No. | Structure | Name | MOLP-8 IC$_{50}$ (μM) | DU4475 IC$_{50}$ (μM) | HCT 116 IC$_{50}$ (μM) |
| --- | --- | --- | --- | --- | --- |
| 96 | 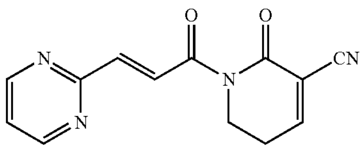 [SMILES: N#CC1=CCCN(C(=O)/C=C/c2ncccn2)C1=O] | (E)-2-oxo-1-(3-(pyrimidin-2-yl)acryloyl)-1,2,5,6-tetrahydropyridine-3-carbonitrile | N/A | N/A | N/A |
| 97 | 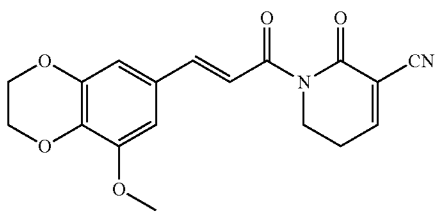 [SMILES: COc1cc(/C=C/C(=O)N2CCC=C(C#N)C2=O)cc2c1OCCO2] | (E)-1-(3-(8-methoxy-2,3-dihydrobenzo[b][1,4]dioxin-6-yl)acryloyl)-2-oxo-1,2,5,6-tetrahydropyridine-3-carbonitrile | N/A | N/A | N/A |
| 98 | 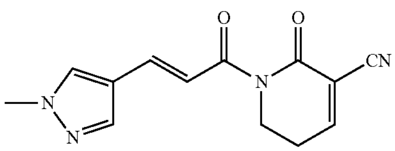 [SMILES: Cn1cc(/C=C/C(=O)N2CCC=C(C#N)C2=O)cn1] | (E)-1-(3-(1-methyl-1H-pyrazol-4-yl)acryloyl)-2-oxo-1,2,5,6-tetrahydropyridine-3-carbonitrile | N/A | N/A | N/A |

* N/A: not determined

Example 1

Preparation of (E)-1-(3-(8-methoxy-2,3-dihydrobenzo[b][1,4]dioxin-6-yl)acryloyl)-5,6-dihydropyridin-2(1H)-one

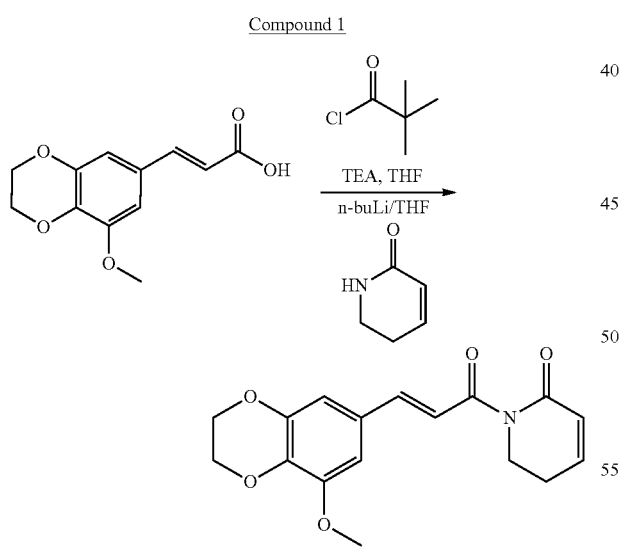

Compound 1

To a solution of (E)-3-(8-methoxy-2,3-dihydrobenzo[b][1,4]dioxin-6-yl)acrylic acid (0.2 g, 0.847 mmol) in dry THF was added triethylamine (0.12 mL, 0.932 mmol, 1.1 eq) and pivaloyl chloride (0.11 mL, 0.932 mmol, 1.1 eq) the reaction mixture was stirred at 0° C. for 45 min. Progress was monitored by TLC. After completion, the mixture was filtered and the filtrate was used directly for the next step. To a stirred solution of 5,6-dihydropyridin-2(1H)-one (0.1 g, 1.03 mmol, 1.0 eq) in dry THF at −78° C. was added n-BuLi (2.5 M in hexane, 0.45 mL, 1.13 mmol, 1.1 eq) and the mixture was allowed to stir at the same temperature for 30 min. To this solution was added a solution of (E)-3-(8-methoxy-2,3-dihydrobenzo[b][1,4]dioxin-6-yl)acrylic pivalic anhydride (0.29 g, 0.927 mmol, 0.9 eq). The mixture was allowed to stir at −78° C. for 1 h. Progress was monitored by TLC and LCMS. After 1 h, the reaction mixture was brought to 0° C., diluted with water (30 mL) and extracted with ethyl acetate (3×30 mL). The combined organic layers were washed with brine, dried over anhydrous Na$_2$SO$_4$, filtered and evaporated to dryness under vacuum. The crude material was purified by reversed phase HPLC to afford the title compound (58 mg, 21.8%).

LCMS: 316 [M+1]$^+$ $^1$H NMR: (400 MHz, CDCl$_3$) δ 7.62 (d, 1H), 7.39 (d, 1H), 6.90-6.95 (m, 1H), 6.75 (d, 2H), 6.02 (d, 1H), 4.35 (t, 2H), 4.25 (t, 2H), 4.01 (t, 2H), 3.88 (s, 3H), 2.41-2.46 (m, 2H).

Example 2

Preparation of (E)-1-(3-cyclohexylacryloyl)-5,6-dihydropyridin-2(1H)-one

Compound 2

Step-1

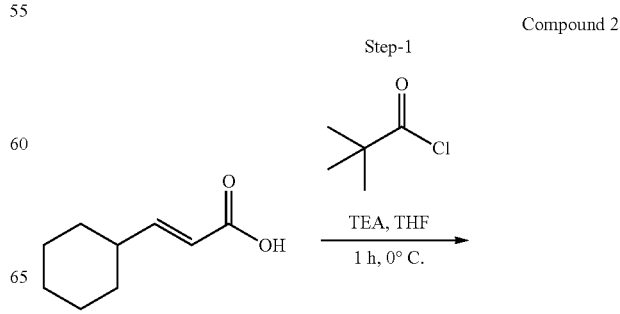

Step-1

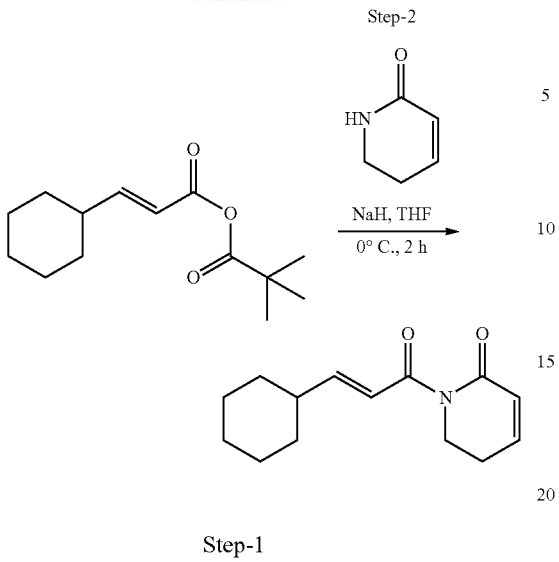

To a stirred solution of (E)-3-cyclohexylacrylic acid (400 mg, 2.59 mmol) in THF (5 mL) at 0° C. was added triethylamine (0.55 mL, 3.89 mmol, 1.5 eq.) and pivaloyl chloride (0.35 mL, 2.85 mmol, 1.1 eq.) and the reaction mixture was allowed to stir at 0° C. for 1 h. Progress was monitored by TLC. After completion, the reaction mixture was filtered and the filtrate was carried to the next step without further purification.

LCMS: 239 [M+1]+

Step-2

To the stirred solution of 5,6-dihydropyridin-2(1H)-one (200 mg, 2.06 mmol) in THF (5 mL) at 0° C. was added NaH (174 mg, 3.08 mmol, 1.5 eq) and the mixture was stirred at 0° C. for 30 mins. To this was added (E)-3-cyclohexylacrylic pivalic anhydride (540 mg, 2.27 mmol, 1.1 eq) and the resulting mixture was allowed to stir at 0° C. for 2 h. Progress was monitored by TLC. After completion, the reaction mixture was diluted with water (20 mL) and extracted with EtOAc (2×100 mL). The combined organic layers were washed with brine, dried over Na₂SO₄, filtered and concentrated under reduced pressure. The crude product was purified by reversed phase HPLC to afford the title compound (43 mg, 9.0%) as a white solid.

LCMS: 234 [M+1]+

¹H NMR: (400 MHz, CDCl₃) δ 6.98 (m, 1H), 6.82 (m, 1H), 6.78 (d, 1H), 6.0 (d, 1H), 3.98 (t, 2H), 2.42 (d, 2H), 2.19 (m, 1H), 1.78 (t, 4H), 1.67 (d, 1H), 1.36-1.10 (m, 5H).

Example 3

Preparation of (E)-1-(3-(quinolin-3-yl)acryloyl)-1,5,6,7-tetrahydro-2H-azepin-2-one Compound 3

Step-1

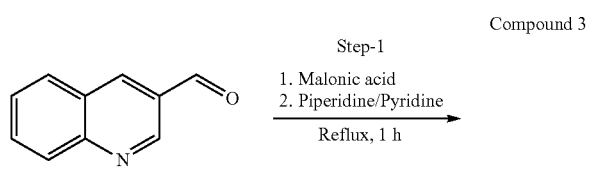

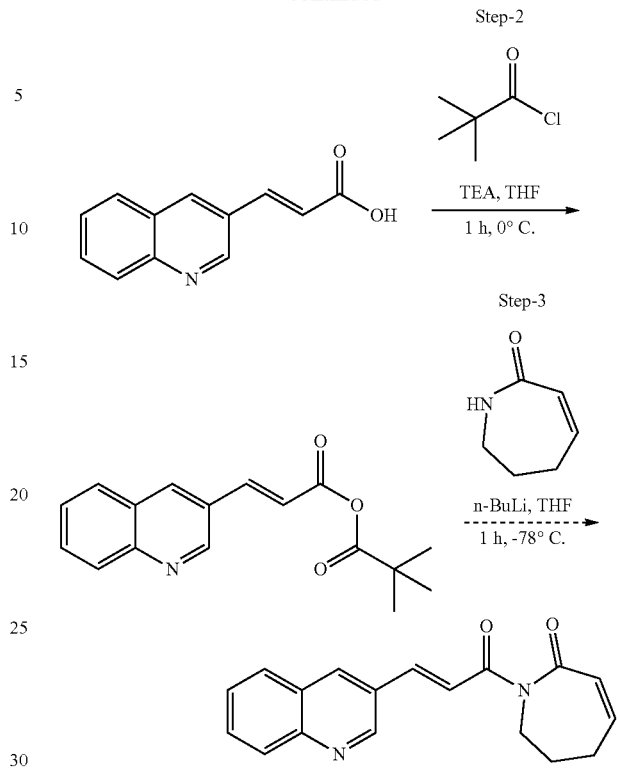

To the stirred solution of quinoline-3-carbaldehyde (350 mg, 2.23 mmol) in pyridine (10 mL) and piperidine (2 mL) at room temperature was added malonic acid (487 mg, 4.68 mmol, 2.1 eq). The reaction mixture was heated to 110° C. and allowed to proceed for 1 h. Progress of the reaction was monitored by TLC. After completion, the reaction mixture was diluted with 1N HCl (20 mL) and extracted with EtOAc (2×100 mL). The combined organic layers were washed with water, dried over Na₂SO₄, filtered and concentrated under reduced pressure to obtain (E)-3-(quinolin-3-yl)acrylic acid (210 mg, 47%) which was used without further purification.

LCMS: 200 [M+1]+

Step-2

To a stirred solution of (E)-3-(quinolin-3-yl)acrylic acid (150 mg, 0.75 mmol, 1.0 eq) in THF (5 mL) at 0° C. was added triethylamine (0.16 mL, 1.13 mmol, 1.5 eq) and pivaloyl chloride (0.1 mL, 0.83 mmol, 1.1 eq) and the reaction mixture was allowed to stir at 0° C. for 1 h. Progress was monitored by TLC. After completion, the reaction mixture was filtered and the filtrate was carried to the next step without further purification.

LCMS: 284 [M+1]+

Step-3

To the stirred solution of 1,5,6,7-tetrahydro-2H-azepin-2-one (75 mg, 0.67 mmol) in THF (5 mL) at −78° C. was added n-BuLi (2.5 M in hexane, 0.35 mL, 0.88 mmol, 1.3 eq) and the resulting mixture was stirred at −78° C. for 30 min. To this was added pivalic (E)-3-(quinolin-3-yl)acrylic anhydride (210 mg, 0.74 mmol, 1.1 eq) and the mixture was stirred at −70° C. for 2 h. Progress was monitored by TLC. After completion, the reaction mixture was diluted with water (20 mL) and extracted with EtOAc (2×100 mL). The combined organic layers were washed with brine, dried over $Na_2SO_4$, filtered and concentrated under reduced pressure. The crude product was purified by reversed phase HPLC to afford the title compound (10 mg, 5.1%) as a white solid.

LCMS: 293 [M+1]$^+$ $^1$H NMR: (400 MHz, CDCl$_3$) δ 9.10 (s, 1H), 8.32 (s, 1H), 8.11 (d, 1H), 7.87 (m, 2H), 7.75 (t, 1H), 7.66 (d, 1H), 7.58 (t, 1H), 6.6-6.54 (m, 1H), 6.15-6.12 (d, 1H), 4.05 (t, 2H), 2.45 (q, 2H), 2.04 (m, 2H).

Example 4

Preparation of (E)-1-(3-(pyridin-3-yl)acryloyl)-1,5,6,7-tetrahydro-2H-azepin-2-one

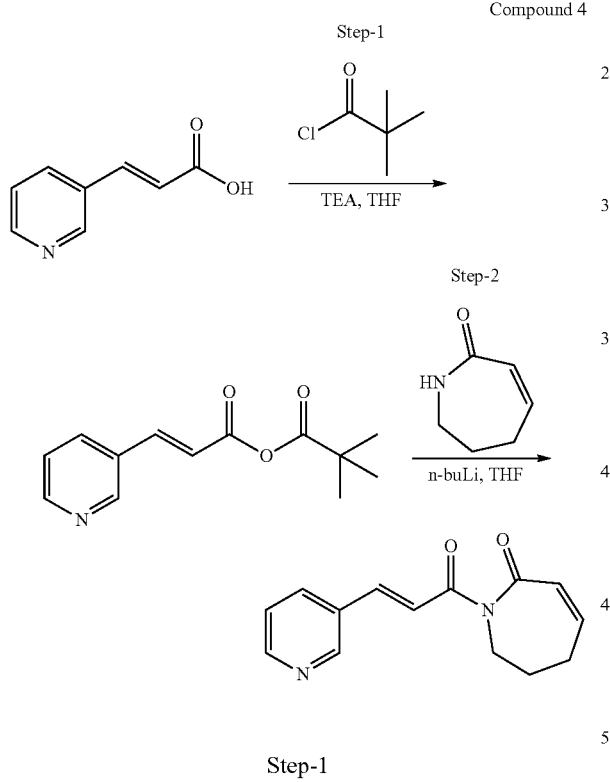

Compound 4

Step-1

To a solution of (E)-3-(pyridin-3-yl)acrylic acid (0.2 g, 1.34 mmol) in dry THF (10 mL) was added triethylamine (0.18 mL, 1.47 mmol, 1.1 eq) followed by pivaloyl chloride 2 (0.18 mL, 1.47 mmol, 1.1 eq) and the mixture was stirred at 0° C. for 45 min. Progress was monitored by TLC. After completion, reaction mixture was filtered and the filtrate was carried to the next step without further purification.

Step-2

To a stirred solution of 1,5,6,7-tetrahydro-2H-azepin-2-one (0.1 g, 0.89 mmol) in dry THF at −78° C. was added n-BuLi (2.5 M in hexane, 0.45 mL, 0.98 mmol, 1.1 eq) and the mixture was allowed to stir at the same temperature for 30 min. To this mixture was added a solution of pivalic (E)-3-(pyridin-3-yl)acrylic anhydride (0.187 g, 0.80 mmol, 0.9 eq) in THF (10 mL) and the resulting mixture was allowed to stir at −78° C. for 1 h. Progress was monitored by TLC and LCMS. After completion, the reaction mixture was warmed to 0° C., diluted with water (30 mL) and extracted with EtOAc (3×30 mL). The combined organic layers were washed with brine (30 mL), dried over anhydrous $Na_2SO_4$, filtered and concentrated. The crude material was purified by reversed phase HPLC to afford the title compound (60 mg, 18.8%).

LCMS: 243 [M+1]$^+$ $^1$H NMR: (500 MHz, CDCl$_3$) δ 8.82-8.74 (m, 1H), 8.61-8.56 (m, 1H), 7.90 (dt, 1H), 7.72 (d, 1H), 7.51 (d, 1H), 7.31 (dd, 1H), 6.56 (dt, 1H), 6.11 (dd, 1H), 4.06-3.92 (m, 2H), 2.49-2.33 (m, 2H), 2.07-1.92 (m, 2H).

Example 5

Preparation of (E)-1-(3-(pyridin-4-yl)acryloyl)-1,5,6,7-tetrahydro-2H-azepin-2-one

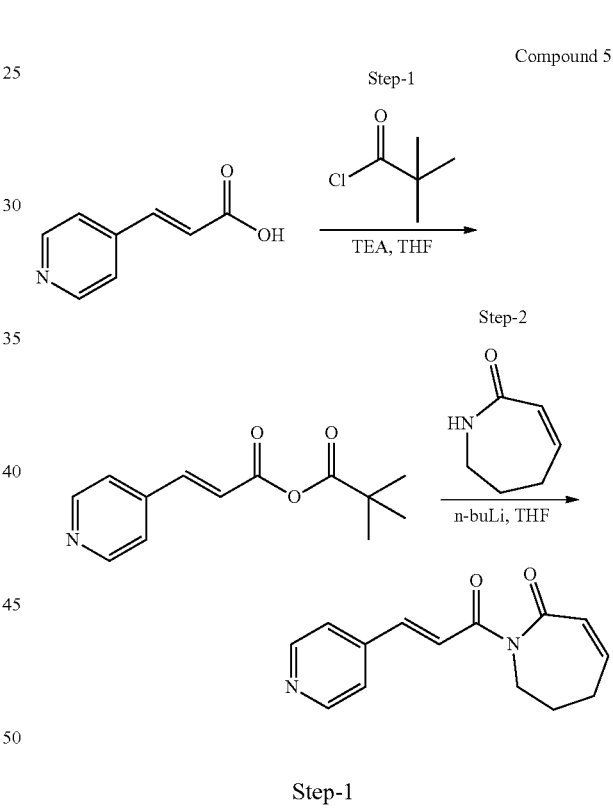

Compound 5

Step-1

To a solution of (E)-3-(pyridin-4-yl)acrylic acid (0.2 g, 1.34 mmol) in dry THF (10 mL) was added triethylamine (0.18 mL, 1.47 mmol, 1.1 eq) followed by pivaloyl chloride (0.18 mL, 1.47 mmol, 1.1 eq.) and the reaction mixture was stirred at 0° C. for 45 min. Progress was monitored by TLC. After completion, the reaction mixture was filtered and the filtrate was used directly for the next step.

Step-2

To a stirred solution of 1,5,6,7-tetrahydro-2H-azepin-2-one (0.1 g, 0.89 mmol) in dry THF (10 mL) at −78° C. was added n-BuLi (2.5 M in hexane, 0.45 mL, 0.98 mmol, 1.1 eq) and the mixture was allowed to stir at the same temperature for 30 min. To this mixture was added a solution of pivalic (E)-3-(pyridin-4-yl)acrylic anhydride (0.187 g, 0.80 mmol, 0.9 eq.) in THF (10 mL) and the resulting mixture was allowed to stir at −78° C. for 1 h. Progress was monitored by TLC and LCMS. After completion, the reaction mixture was warmed to 0° C., diluted with water (30 mL) and extracted with EtOAc (3×30 mL). The combined organic layers were washed with brine, dried over anhydrous Na$_2$SO$_4$, filtered and concentrated. The crude material was purified by reversed phase HPLC to afford the title compound (80 mg, 25.1%).

LCMS: 243 [M+1]$^+$ $^1$H NMR: (500 MHz, CDCl$_3$) δ 8.63 (d, 2H), 7.65-7.53 (m, 2H), 7.43-7.38 (m, 2H), 6.57 (dt, 1H), 6.12 (dt, 1H), 4.03-3.97 (m, 2H), 2.47-2.39 (m, 2H), 2.06-1.97 (m, 2H).

Example 6

Preparation of (E)-1-(3-(pyrazin-2-yl)acryloyl)-1,5,6,7-tetrahydro-2H-azepin-2-one Step-2

To the stirred solution of 1,5,6,7-tetrahydro-2H-azepin-2-one (100 mg, 0.90 mmol) in THF (5 mL) at −78° C. was added n-BuLi (0.47 mL, 1.17 mmol, 1.3 eq) and the reaction mixture was stirred at −78° C. for 30 min. To this mixture was added a solution of pivalic (E)-3-(pyrazin-2-yl)acrylic anhydride (211 mg, 0.90 mmol, 1.1 eq.) in THF (5 mL) and the resulting mixture was stirred at −78° C. for 2 h. Progress was monitored by TLC. After completion, the reaction mixture was diluted with water (20 mL) and extracted with EtOAc (2×100 mL). The combined organic layers were washed with brine, dried over Na$_2$SO$_4$, filtered and concentrated under reduced pressure. The crude material was purified by reversed phase HPLC to afford the title compound (21 mg, 9.6%) as white solid.

LCMS: 244 [M+1]$^+$ $^1$H NMR: (500 MHz, CDCl$_3$) δ 8.69 (d, 1H), 8.60 (t, 1H), 8.51 (d, 1H), 7.89 (d, 1H), 7.69 (d, 1H), 6.57 (d, 1H), 6.12 (d, 1H), 4.01 (t, 2H), 2.43 (q, 2H), 2.06-1.96 (m, 2H).

Example 7

Preparation of (E)-1-(3-(pyrimidin-2-yl)acryloyl)-5,6-dihydropyridin-2(1H)-one

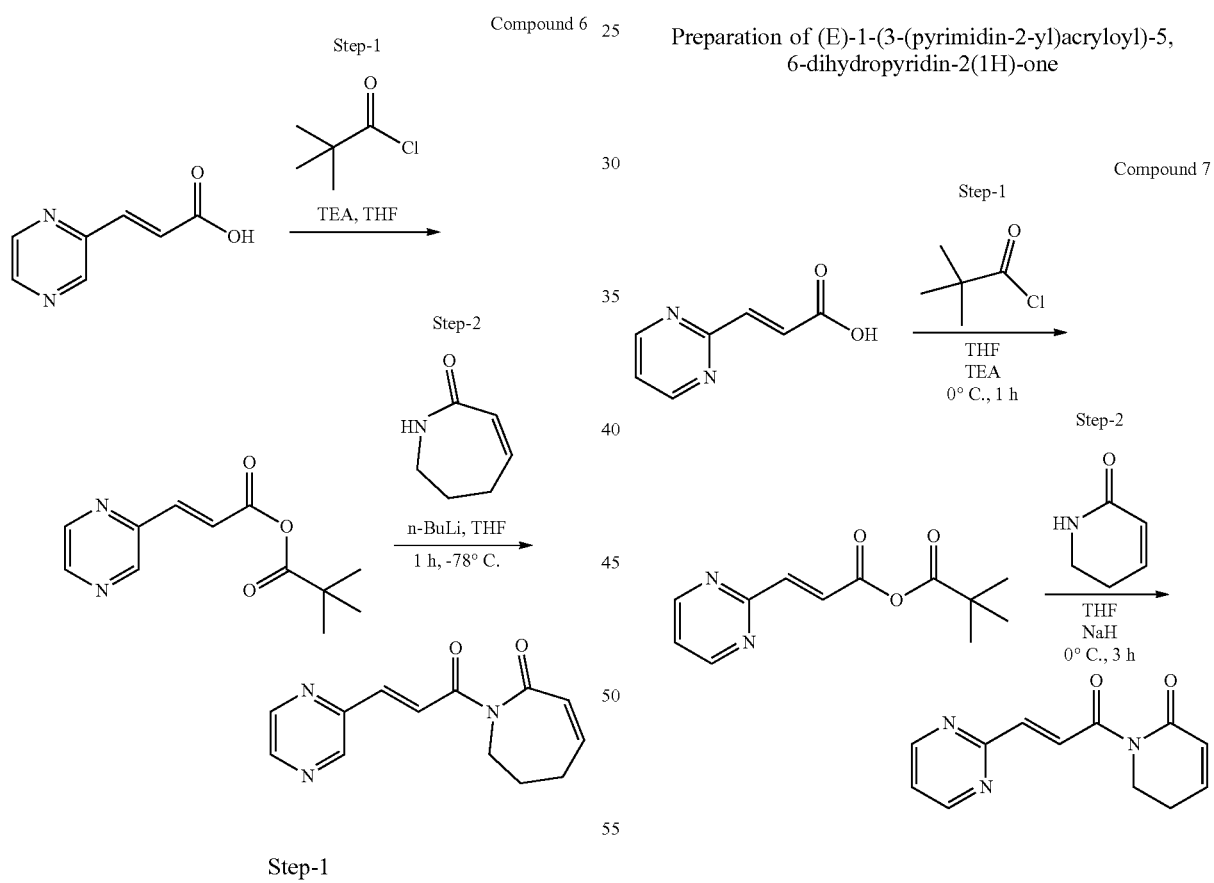

Step-1

To a stirred solution of (E)-3-(pyrazin-2-yl)acrylic acid (150 mg, 0.99 mmol) in THF (5 mL) at 0° C. was added triethylamine (0.2 mL, 1.50 mmol, 1.5 eq) followed by pivaloyl chloride (0.13 mL, 1.10 mmol, 1.1 eq.) and the reaction mixture was allowed to stir at 0° C. for 1 h. Progress was monitored by TLC. After completion, the reaction mixture was filtered and the filtrate was carried to next step without any further purification.

LCMS: 235 [M+1]$^+$

Step-1

To a stirred solution of (E)-3-(pyrimidin-2-yl)prop-2-enoic acid (150 mg, 1.0 mmol) in THF (8 mL) at 0° C. was added triethylamine (0.1 mL, 1.1 mmol) followed by pivaloyl chloride (0.1 mL, 1.1 mmol) and the resulting mixture was stirred at the same temperature for 1 h. Progress was monitored by TLC. After completion, the reaction mixture was filtered and the filtrate was carried to next step without any further purification.

Step-2

To a stirred solution of 5,6-dihydropyridin-2(1H)-one (80 mg, 0.82 mmol) in THF (5 mL) was added NaH (39 mg, 0.98 mmol, 1.2 eq) at 0° C. and the resulting mixture was allowed to stir at the same temperature for 30 min. To this mixture was added a solution of 2,2-dimethylpropanoic (E)-3-(pyrimidin-2-yl)prop-2-enoic anhydride (200 mg, 1.1 mmol, 1.3 eq) in THF (8 mL) and the resulting mixture was allowed to stir at the same temperature for 3 h. Progress was monitored by TLC and LCMS. After completion, the reaction mixture was diluted with ice cold water (20 mL) and extracted with EtOAc (3×50 mL). The combined organic layers were washed with water (2×25 mL), dried over anhydrous $Na_2SO_4$ and filtered. Removal of solvent under reduce pressure afforded an oily residue which was purified by reversed phase HPLC to afford the title compound (30 mg, 13%).

LCMS: 230 $[M+1]^+$ $^1$H NMR: (500 MHz, $CDCl_3$) δ 8.76 (d, 2H), 8.07 (d, 1H), 7.65 (d, 1H), 7.19 (t, 1H), 6.96 (dt, 1H), 6.05 (d, 1H), 4.05 (t, 2H), 2.50 (tdd, 2H).

Example 8

Preparation of (E)-1-(3-(pyridin-2-yl)acryloyl)-1,5,6,7-tetrahydro-2H-azepin-2-one Compound 8

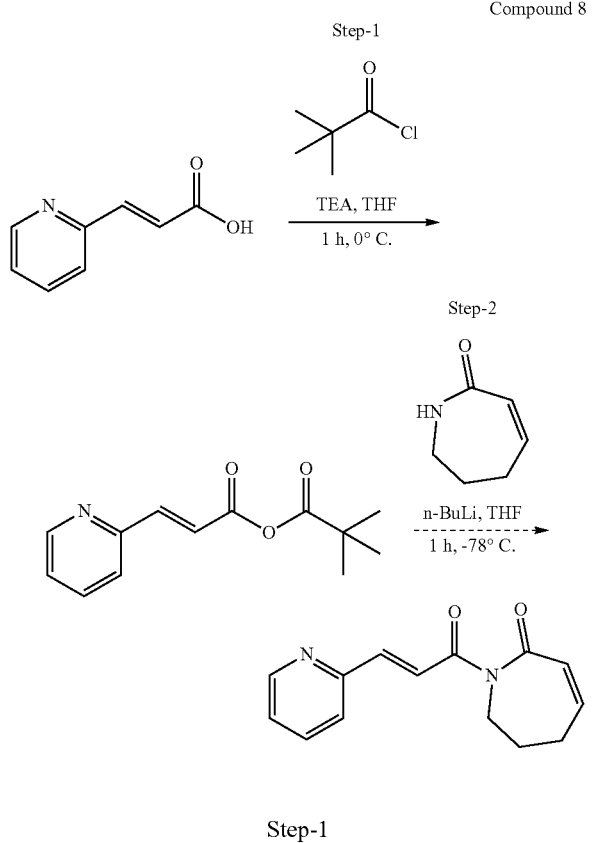

Step-1

To a stirred solution of (E)-3-(pyridin-2-yl)acrylic acid (150 mg, 1.01 mmol) in THF (5 mL) at 0° C. was added triethylamine (0.21 mL, 1.51 mmol, 1.5 eq) followed by pivaloyl chloride (0.13 mL, 1.11 mmol, 1.1 eq) and the reaction mixture was allowed to stir at 0° C. for 1 h. Progress was monitored by TLC. After completion, the reaction mixture was filtered and the filtrate was carried to next step without any further purification.

LCMS: 234 $[M+1]^+$

Step-2

To a stirred solution of 1,5,6,7-tetrahydro-2H-azepin-2-one (100 mg, 0.90 mmol) in THF (5 mL) at −78° C. was added n-BuLi (2.5 M in hexane, 0.47 mL, 1.17 mmol, 1.3 eq) and the reaction mixture was stirred at −78° C. for 30 min. To this reaction mixture was added pivalic (E)-3-(pyridin-2-yl)acrylic anhydride (210 mg, 0.90 mmol, 1.1 eq) and stirred at −78° C. for 2 h. Progress was monitored by TLC. After completion, the reaction mixture was diluted with water (20 mL) and extracted with EtOAc (2×100 mL). The combined organic layers were washed with brine, dried over $Na_2SO_4$, filtered and concentrated. The crude material was purified by reversed phase HPLC to afford the title compound (28 mg, 12.8%) as a white solid.

LCMS: 243 $[M+1]^+$ $^1$H NMR: (500 MHz, $CDCl_3$) δ 8.64 (d, 1H), 7.82-7.66 (m, 3H), 7.46 (d, 1H), 7.25-7.21 (m, 1H), 6.55 (d, 1H), 6.11 (d, 1H), 4.00 (t, 2H), 2.41 (q, 2H), 2.04-1.92 (m, 2H).

Example 9

Preparation of (E)-1-(3-(1-acetylpiperidin-4-yl)acryloyl)-5,6-dihydropyridin-2(1H)-one Compound 9

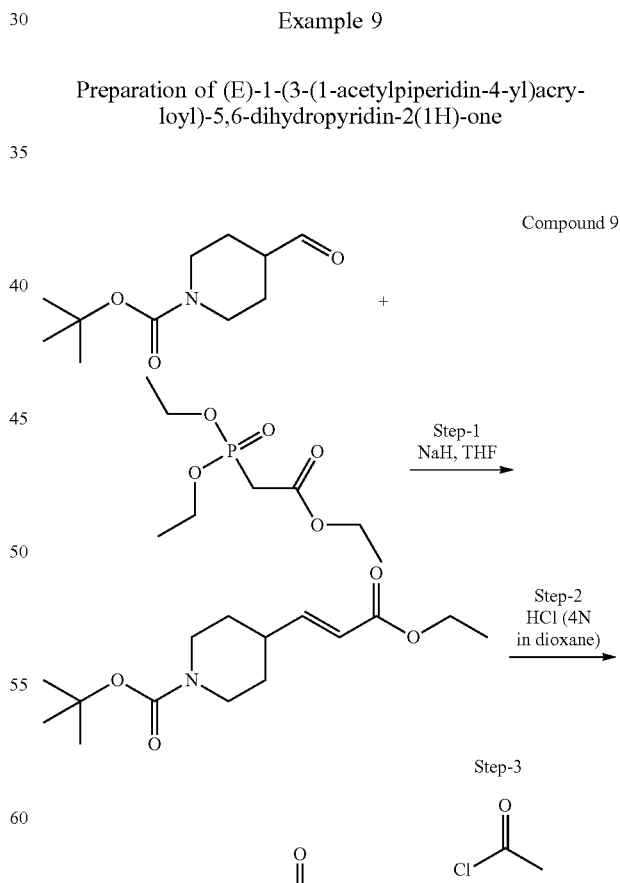

75

-continued

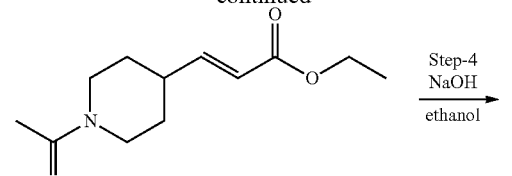

Step-4
NaOH
ethanol

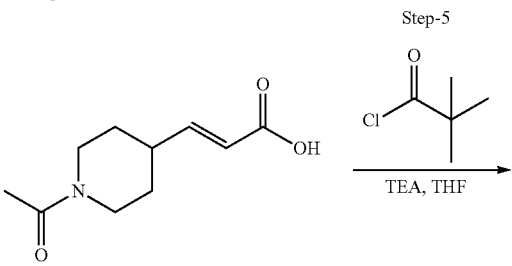

Step-5

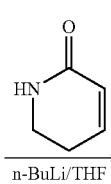

TEA, THF

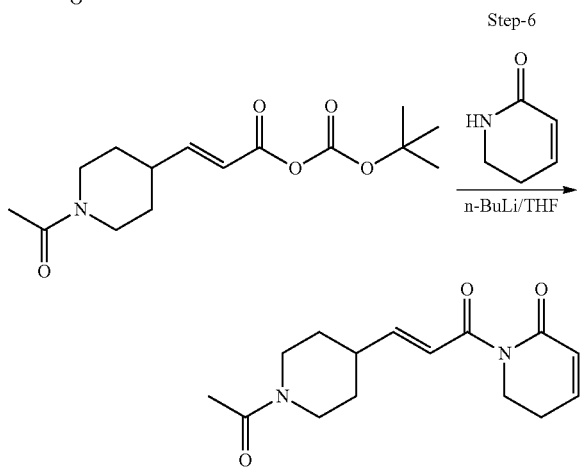

n-BuLi/THF

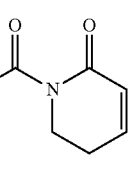

Step-6

Step-1

To a suspension of sodium hydride (60% in mineral oil, 1.03 g, 25.8 mmol, 1.1 eq) in THF (50 mL) was added ethyl 2-(diethoxyphosphoryl)acetate (10.51 g, 46.9 mmol, 2.0 eq) dropwise at 0° C. and the mixture was allowed to stir at the same temperature for 30 min. To this mixture was added a solution of tert-butyl 4-formylpiperidine-1-carboxylate (5.0 g, 23.5 mmol) in THF (5 mL) and the resulting mixture was allowed to stir at room temperature for 1 h. Progress was monitored by TLC. After completion, the mixture was diluted with saturated aqueous NH$_4$Cl (100 mL) and extracted with EtOAc (3×50 mL). The combined organic layers were washed with brine, dried over anhydrous Na$_2$SO$_4$, filtered and evaporated to dryness under vacuum. The crude product was purified by CombiFlash to afford tert-butyl (E)-4-(3-ethoxy-3-oxoprop-1-en-1-yl)piperidine-1-carboxylate (3.5 g, 52.7%).

LCMS: 284 [M+1]$^+$

Step-2

A solution of tert-butyl (E)-4-(3-ethoxy-3-oxoprop-1-en-1-yl)piperidine-1-carboxylate (1.50 g, 7.18 mmol) in 4N HCl in dioxane (30 mL) was stirred at room temperature for 4 h. Progress was monitored by TLC. After completion, the reaction mixture was evaporated under reduce pressure, triturated with Et$_2$O to afford ethyl (E)-3-(piperidin-4-yl) acrylate hydrochloride (0.85 g, 88%).

LCMS: 184 [M+1]$^+$

76

Step-3

To a stirred solution of ethyl (E)-3-(piperidin-4-yl)acrylate hydrochloride (0.85 g, 4.37 mmol) and triethylamine (1.22 mL, 8.74 mmol, 2.0 eq) in CH$_2$Cl$_2$ at 0° C. was added acetyl chloride (0.37 mL, 5.24 mmol, 1.2 eq) dropwise. The ice bath was removed and the mixture was stirred at room temperature for 4 h. Progress was monitored by TLC and LCMS. After completion, the reaction mixture was diluted with saturated aqueous NH$_4$Cl (30 mL) and extracted with EtOAc (3×30 mL). The combined organic layers were washed with brine, dried over anhydrous Na$_2$SO$_4$, filtered and evaporated under vacuum. The crude product was purified by CombiFlash to afford ethyl (E)-3-(1-acetylpiperidin-4-yl)acrylate (0.56 g, 57%) as a pale yellow oil.

LCMS: 226 [M+1]$^+$

Step-4

To a solution of ethyl (E)-3-(1-acetylpiperidin-4-yl)acrylate (0.56 g, 2.48 mmol) in EtOH (200 mL) was added a solution of NaOH (0.298 g, 7.44 mmol) in water (20 mL) and the reaction mixture was stirred at 70° C. for 4 h. The mixture was concentrated under vacuum and then acidified with 2N HCl to pH 3. The mixture was then diluted saturated aqueous NH$_4$Cl (30 mL) and extracted with CH$_2$Cl$_2$ (3×30 mL). The combined organic layers were washed with brine (50 mL), dried over anhydrous Na$_2$SO$_4$ and filtered. The solvent was removed under reduced pressure to obtain (E)-3-(1-acetylpiperidin-4-yl)acrylic acid (0.32 g, 65%) as crystalline solid.

LCMS: 198 [M+1]$^+$

Step-5

To a solution of (E)-3-(1-acetylpiperidin-4-yl)acrylic acid (0.3 g, 1.52 mmol) in dry THF was added triethylamine (0.21 mL, 1.67 mmol, 1.1 eq) followed by pivaloyl chloride (0.2 mL, 1.67 mmol, 1.1 eq) and the reaction mixture was stirred at 0° C. for 45 min. Progress was monitored by TLC. After completion, the reaction mixture was filtered used directly for the next step.

Step-6

To a stirred solution of 5,6-dihydropyridin-2(1H)-one (0.1 g, 1.03 mmol) in dry THF at −78° C. was added n-BuLi (2.5 M in hexane, 0.45 mL, 1.13 mmol, 1.1 eq) and the mixture was allowed to stir at the same temperature for 30 min. To this solution was added a solution of (E)-3-(1-acetylpiperidin-4-yl)acrylic (tert-butyl carbonic) anhydride (0.275 g, 0.92 mmol, 0.9 eq) in THF and the reaction mixture was allowed to stir at −78° C. for 1 h. Progress was monitored by TLC and LCMS. After completion, the reaction mixture was brought to 0° C., diluted with water (30 mL) and extracted with EtOAc (3×30 mL). The combined organic layers were washed with brine, dried over anhydrous Na$_2$SO$_4$, filtered and evaporated to dryness under vacuum. The crude material which was purified by reversed phase HPLC to afford the title compound (0.014 g, 15%).

LCMS: 277 [M+1]$^+$ $^1$H NMR: (400 MHz, CDCl$_3$) δ 6.88-6.97 (m, 2H), 6.85 (d, 1H), 6.00 (d, 1H), 4.50-4.45 (m, 1H), 4.45-4.02 (m, 2H), 3.90-3.80 (m, 1H), 3.18-3.08 (m, 1H), 2.50-2.35 (m, 2H), 2.10 (s, 3H), 190-1.25 (m, 6H).

Example 10

Preparation of 1-(2-(9H-fluoren-9-ylidene)acetyl)-5,6-dihydropyridin-2(1H)-one

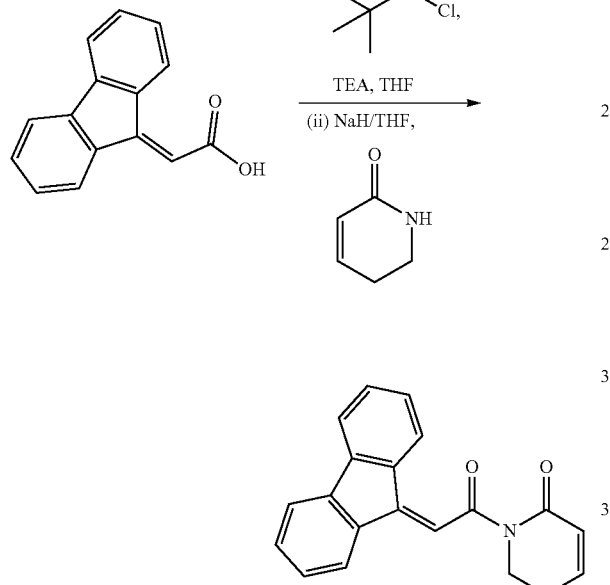

Compound 10

To a stirred solution of 9H-fluoren-9-ylideneacetic acid (180 mg, 0.80 mmol) in THF (5 mL) at 0° C. was triethylamine (0.1 mL, 0.96 mmol, 1.2 eq) dropwise followed by the addition of pivaloyl chloride (115 mg, 1.2 mmol, 1.2 eq) and the reaction mixture was allowed to stir at same temperature for 1 h. Progress was monitored by TLC and the reaction mixture was used directly in the next step. To a solution of 5,6-dihydropyridin-2(1H)-one (100 mg, 1.030 mmol) in THF (5 mL) at 0° C. was added NaH (49 mg, 1.23 mmol, 1.2 eq) and the reaction mixture was allowed to stir at the same temperature for 30 min. To this solution at 0° C. was added the mixed anhydride solution through a syringe filter and the resulting mixture was allowed to stir as 0° C. for 1 h. Progress was monitored by TLC and LCMS. After completion, the reaction mixture was diluted with water (50 mL) and extracted with EtOAc (2×40 mL). The combined organic layers were washed with water (3×20 mL), dried over anhydrous Na$_2$SO$_4$ and filtered. The solvent was removed under reduced pressure and the crude product was purified by reversed phase HPLC to afford the title compound (28 mg, 9%).

LCMS: 302 [M+1]$^+$ $^1$H NMR: (400 MHz, CDCl$_3$) δ 8.34 (d, 1H), 7.70 (d, 2H), 7.63 (dd, 1H), 7.44 (d, 2H), 7.37 (dt, 1H), 7.27 (d, 1H), 7.24 (d, 1H), 6.98 (d, 1H), 6.05 (d, 1H), 4.18-4.08 (m, 2H), 2.50-2.25 (m, 2H).

Example 11

Preparation of (E)-1-((2-(pyridin-3-yl)vinyl)sulfonyl)-5,6-dihydropyridin-2(1H)-one

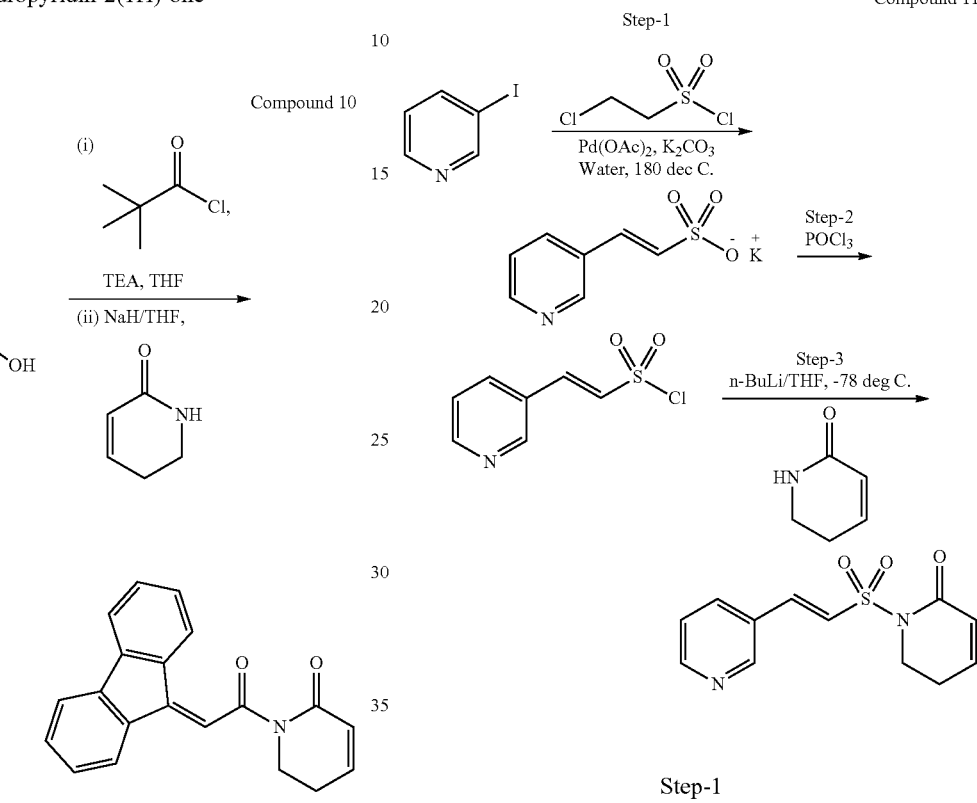

Compound 11

Step-1

To a suspension of anhydrous K$_2$CO$_3$ (402 mg, 2.91 mmol, 3 eq), palladium(II) acetate (11 mg, 0.049 mmol, 0.02 eq) and 3-iodopyridine (200 mg, 0.97 mmol) in water (5 mL) in a 30 mL microwave vial with a magnetic stir bar was added 2-chloroethanesulfonyl chloride (0.1 mL 0.97 mmol) dropwise. The vial was sealed and heated to 180° C. by microwave irradiation for 10 min. The vial was cooled to room temperature and to it was added a fresh portion of palladium(II) acetate (11 mg, 0.049 mmol, 0.02 eq). The vial was then resealed and heated under same conditions for an additional 10 min. Progress was monitored by TLC. After completion, the reaction mixture was diluted with water (50 mL) and the mixture was filtered through a bed of Celite. The filtrate was lyophilized to afford crude potassium (E)-2-(pyridin-3-yl)ethenesulfonate (500 mg) which was used in the next step without further purification.

Step-2

A mixture of (E)-2-(pyridin-3-yl)ethenesulfonate (500 mg) and POCl$_3$ (10 mL) was allowed to stir at 80° C. for 1 h. Progress was monitored by TLC. After completion, the reaction mixture was cooled to room temperature and POCl$_3$ was evaporated under reduced pressure to give an oily residue. The residue was dissolved in EtOAc (50 mL). The solution was washed water (3×50 mL), dried over anhydrous Na$_2$SO$_4$ and filtered. Removal of the solvent under reduced pressure afforded (E)-2-(pyridin-3-yl)ethenesulfonyl chloride (250 mg) which was used in the next step without further purification.

Step-3

To solution of 5,6-dihydropyridin-2(1H)-one (100 mg, 1.03 mmol) in THF (5 mL) at −78° C. was added n-BuLi (2.5 M in THF, 0.5 mL, 1.03 mmol, 1.2 eq) dropwise and the reaction mixture was allowed to stir at the same temperature for 30 min. To this solution was added a solution of (E)-2-(pyridin-3-yl)ethenesulfonyl chloride (209 mg, 1.2 eq) in THF (5 mL) and the reaction mixture was allowed to stir at −78° C. for 2 h. Progress was monitored by TLC and LCMS. After completion, the reaction mixture was diluted with water (30 mL) and extracted with EtOAc (3×50 mL). The combined organic layers were dried over anhydrous $Na_2SO_4$ and filtered. Removal of the solvent under reduced pressure afforded a crude oil which was purified by reversed phase HPLC to provide the title compound (12 mg, 4.4%).

LCMS: 265 [M+1]$^+$ $^1$H NMR: (400 MHz, CDCl$_3$) δ 8.77 (s, 1H), 8.66 (d, 1H), 7.85 (d, 1H), 7.67 (d, 1H), 7.40-7.35 (m, 1H), 7.30 (d, 1H), 6.90-6.80 (m, 1H), 6.00 (d, 1H), 4.05-3.98 (m, 2H), 2.62-2.50 (m, 2H).

Example 12

Preparation of (E)-1-(3-(isoquinolin-4-yl)acryloyl)-1,5,6,7-tetrahydro-2H-azepin-2-one Compound 12

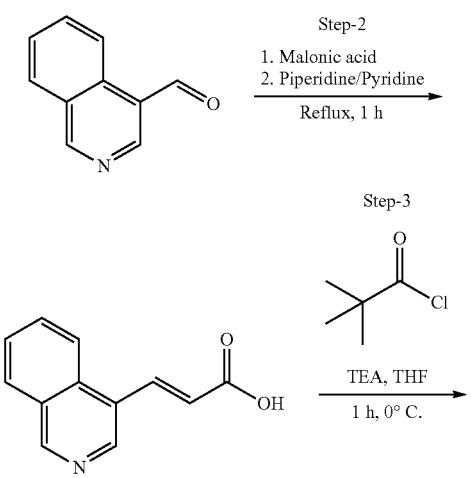

Step-4

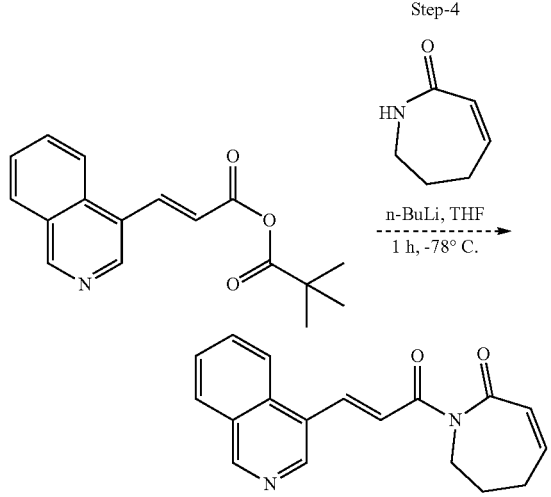

Step-1

To a solution of 4-bromoisoquinoline (1 g, 4.80 mmol) in a solution of THF-diethyl ether (60 mL, 2:1) at −78° C. was added n-BuLi (2.5 M in THF, 3.8 mL, 9.62 mmol) dropwise and the mixture was allowed to stir at the same temperature for 1 h. To this solution was added a solution of DMF (0.9 mL, 12 mmol. 2.5 eq) in THF (5 mL) dropwise and the resulting mixture was allowed to stir at −78° C. for 2 h. Progress was monitored by TLC and LCMS. After completion, the reaction mixture was diluted with saturated, aqueous NH$_4$Cl (50 mL) and extracted with EtOAc (3×100 mL). The combined organic layers were washed with brine (100 mL), dried over anhydrous Na$_2$SO$_4$ and filtered. Removal of solvent gave the crude product which was purified by CombiFlash to afford isoquinoline-4-carbaldehyde (553 mg, 73%).

LCMS: 158 [M+1]$^+$

Step-2

To the stirred solution of isoquinoline-4-carbaldehyde (530 mg, 3.37 mmol) in pyridine (15 mL) and piperidine (3 mL) at room temperature was added malonic acid (737 mg, 7.08 mmol, 2.1 eq) and the reaction mixture was stirred at 110° C. for 1 h. Progress was monitored by TLC. After completion, the reaction mixture was diluted with 1N HCl (50 mL) and extracted with EtOAc (2×200 mL). The combined organic layers were washed with water, dried over anhydrous Na$_2$SO$_4$, filtered and concentrated under reduced pressure. The crude material was purified by CombiFlash to afford (E)-3-(isoquinolin-4-yl)acrylic acid (433 mg, 65%).

LCMS: 200 [M+1]$^+$

Step-3

To a stirred solution of (E)-3-(isoquinolin-4-yl)acrylic acid (200 mg, 1.00 mmol) in THF (20 mL) at 0° C. was added triethylamine (0.21 mL, 1.50 mmol, 1.5 eq) followed by pivaloyl chloride (0.14 mL, 1.11 mmol, 1.1 eq) and the reaction mixture was allowed to stir at 0° C. for 1 h. Progress was monitored by TLC. After completion, the reaction mixture was filtered and the filtrate was carried to the next step without any further purification.

LCMS: 284 [M+1]$^+$

Step-4

To the stirred solution of 1,5,6,7-tetrahydro-2H-azepin-2-one (100 mg, 0.90 mmol) in THF (15 mL) at −78° C. was added n-BuLi (2.5 M in hexane, 0.47 mL, 1.17 mmol, 1.3 eq) and the reaction mixture was stirred at the same temperature for 30 min. To this mixture was added a solution of (E)-3-(isoquinolin-4-yl)acrylic pivalic anhydride (280 mg, 0.99 mmol, 1.1 eq) in THF (20 mL) and the resulting solution was allowed to stir at −78° C. for 2 h. Progress was monitored by TLC and LCMS. After completion, the reaction mixture was diluted with water (20 mL) and extracted with EtOAc (3×50 mL). The combined organic layers were washed with brine, dried over Na$_2$SO$_4$, filtered and concentrated under reduced pressure. The crude product was purified by CombiFlash to afford the title compound (21 mg, 7%) as a sticky solid.

LCMS: 293 [M+1]$^+$ $^1$H NMR: (400 MHz, CDCl$_3$) δ 9.23 (s, 1H), 8.80 (s, 1H), 8.41 (d, 1H), 8.23 (d, 1H), 8.01 (d, 1H), 7.80 (t, 1H), 7.65 (t, 1H), 7.58 (d, 1H), 6.60-6.50 (m, 1H), 6.17 (d, 1H), 4.00-4.10 (m, 2H), 2.50-2.40 (m, 2H), 2.10-2.00 (m, 2H).

Example 13

Preparation of (E)-1-(3-(pyrimidin-2-yl)acryloyl)-1,5,6,7-tetrahydro-2H-azepin-2-one

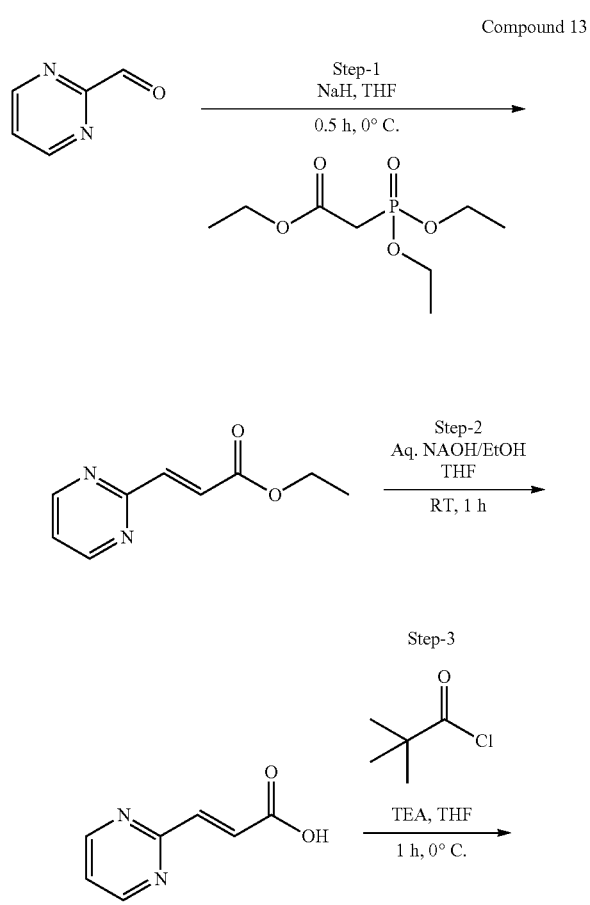

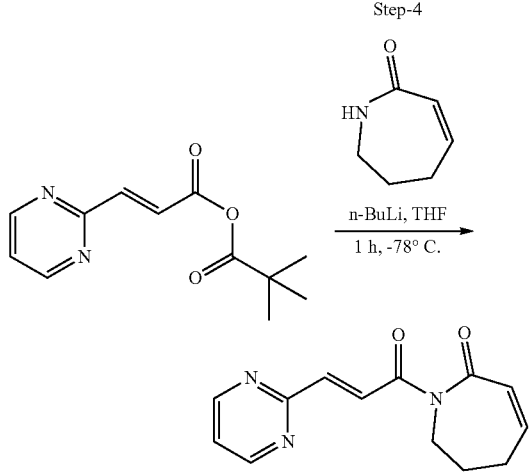

Step-1

To a suspension of NaH (60% in mineral oil, 178 mg, 4.45 mmol, 1.2 eq) in THF (15 mL) at 0° C. was added ethyl 2-(diethoxyphosphoryl)acetate (0.82 mL, 4.07 mmol, 1.1 eq) dropwise and the reaction mixture was allowed to stir at the same temperature for 20 min. To this mixture was added a solution of pyrimidine-2-carbaldehyde (400 mg, 3.70 mmol) in THF (10 mL) and the reaction mixture was allowed to stir at 0° C. for 30 min. Progress was monitored by TLC and LCMS. After completion, the reaction mixture was diluted with water (50 mL) and extracted with EtOAc (3×50 mL). The combined organic layers were washed with brine (20 mL) and dried over anhydrous Na$_2$SO$_4$ and filtered. Removal of solvent gave (E)-ethyl 3-(pyrimidin-2-yl)acrylate (520 mg, 79%) which was used in the next step without further purification. LCMS: 179 [M+1]$^+$ Step-2

To the stirred solution of (E)-ethyl 3-(pyrimidin-2-yl)acrylate (500 mg, 2.81 mmol) in EtOH-THF (1:1) was added aqueous 5N NaOH (3 mL) dropwise at 0° C. and the reaction mixture was stirred at room temperature for 1 h. Progress was monitored by TLC. After completion, the reaction mixture was diluted with 3N HCl (20 mL) and extracted with EtOAc (2×100 mL). The combined organic layers were washed with water, dried over Na$_2$SO$_4$, filtered and concentrated under reduced pressure to afford (E)-3-(pyrimidin-2-yl)acrylic acid (370 mg, 88%) as white solid.

LCMS: 151 [M+1]$^+$

Step-3

To a stirred solution of (E)-3-(pyrimidin-2-yl)acrylic acid (150 mg, 0.99 mmol) in THF (5 mL) at 0° C. were added triethylamine (0.2 mL, 1.50 mmol, 1.5 eq) and pivaloyl chloride (0.13 mL, 1.10 mmol, 1.1 eq) and the reaction mixture was allowed to stir at 0° C. for 1 h. Progress was monitored by TLC. After completion, the reaction mixture was filtered and the filtrate was carried to next step without any further purification.

LCMS: 235 [M+1]$^+$

Step-4

To a stirred solution of 6,7-dihydro-1H-azepin-2(5H)-one (100 mg, 0.90 mmol) in THF (5 mL) at −78° C. was added n-BuLi (2.5 M in hexane, 0.47 mL, 1.17 mmol, 1.3 eq) and the reaction mixture was stirred at same temperature for 30 min. To this mixture was added a solution of pivalic (E)-3-(pyrimidin-2-yl)acrylic anhydride (211 mg, 0.90 mmol, 1.1 eq) in THF (5 mL) and the resulting mixture was stirred at −78° C. for 2 h. Progress was monitored by TLC and LCMS. After completion, the reaction mixture was diluted with water (20 mL) and extracted with EtOAc (2×100 mL). The combined organic layers were washed with brine, dried over Na$_2$SO$_4$, filtered and concentrated under reduced pressure. The crude material was purified by CombiFlash to afford the title compound (48 mg, 22%) as a semi-solid.

LCMS: 244 [M+1]$^+$ $^1$H NMR: (400 MHz, CDCl$_3$) δ 8.78 (d, 2H), 8.01 (d, 1H), 7.65 (d, 1H), 7.20 (t, 1H), 6.65-6.50 (m, 1H), 6.12 (d, 1H), 4.03-3.96 (m, 2H), 2.46-2.38 (m, 2H), 2.05-1.98 (m, 2H).

Example 14

Preparation of (E)-1-(styrylsulfonyl)-1,5,6,7-tetrahydro-2H-azepin-2-one

Compound 14

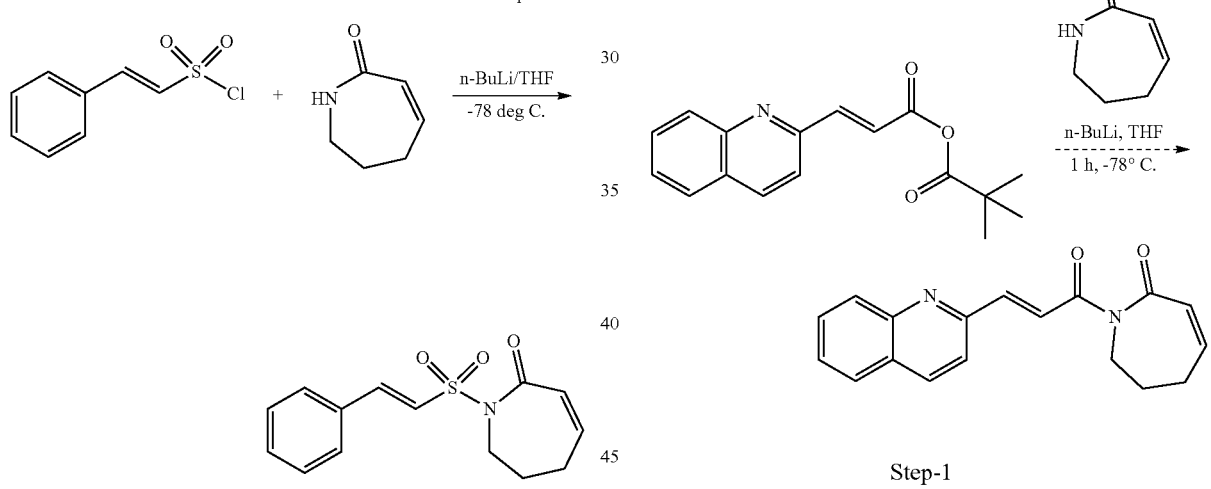

To a solution of 6,7-dihydro-1H-azepin-2(5H)-one (100 mg, 0.90 mmol) in THF (10 mL) at −78° C. was added n-BuLi (2.5 M in THF, 0.47 mL, 1.17 mmol, 1.3 eq) and the reaction mixture was allowed to stir at the same temperature for 30 min. To this was added a solution of (E)-2-phenylethenesulfonyl chloride (201 mg, 1.1 eq) in THF (5 mL) and the reaction mixture was allowed to stir at −78° C. for 2 h. Progress was monitored by TLC and LCMS. After completion, the reaction mixture was diluted with water (30 mL) and extracted with EtOAc (3×50 mL). The combined organic layers were dried over anhydrous sodium sulfate. Removal of solvent gave a crude oil which was purified by reversed phase HPLC to afford the title compound (12 mg, 4%) as a semi-solid.

LCMS: 278 [M+1]$^+$ $^1$H NMR: (400 MHz, CDCl$_3$) δ 7.63 (d, 1H), 7.56-7.46 (m, 2H), 7.45-7.38 (m, 3H), 7.27 (d, 1H), 6.55-6.45 (m, 1H), 6.00 (d, 1H), 3.92-3.81 (m, 2H), 250-2.40 (m, 2H), 2.12-2.02 (m, 2H).

Example 15

Preparation of (E)-1-(3-(quinolin-2-yl)acryloyl)-1,5,6,7-tetrahydro-2H-azepin-2-one Compound 15

Step-1

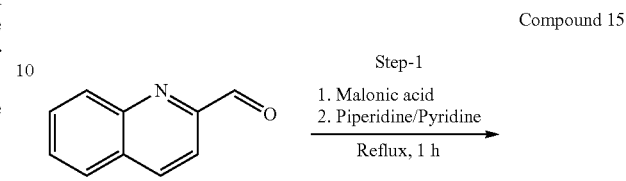

Step-2

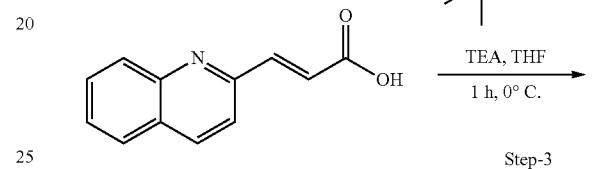

Step-3

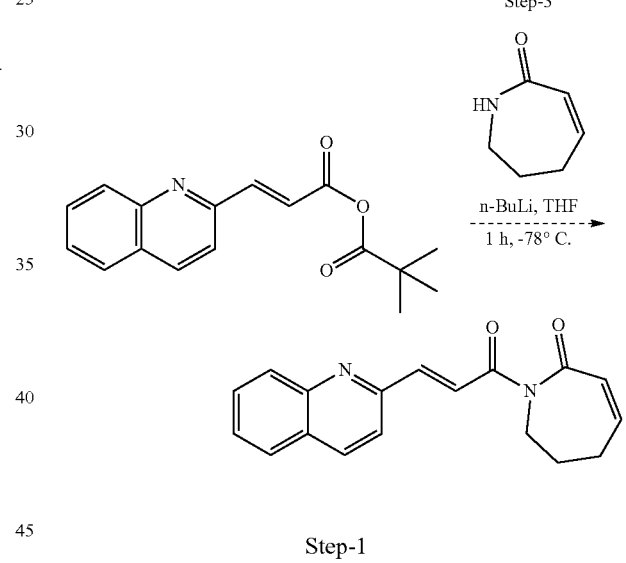

Step-1

To the stirred solution of quinoline-2-carbaldehyde (2 g, 12.7 mmol) in pyridine (27 mL) and piperidine (5 mL) at room temperature was added malonic acid (2.78 g, 26.7 mmol, 2.1 eq) and the reaction mixture was stirred at 110° C. for 1 h. Progress was monitored by TLC. After completion, the reaction mixture was diluted with 1N HCl (50 mL) and extracted with EtOAc (2×200 mL). The combined organic layers were washed with water, dried over Na$_2$SO$_4$, filtered and concentrated under reduced pressure. The crude product was purified by CombiFlash to afford (E)-3-(quinolin-2-yl)acrylic acid (470 mg, 18.5%).

LCMS: 200 [M+1]$^+$

Step-2

To a stirred solution of (E)-3-(quinolin-2-yl)acrylic acid (200 mg, 1.00 mmol) in THF (5 mL) at 0° C. was added triethylamine (0.21 mL, 1.50 mmol, 1.5 eq) and pivaloyl chloride (0.14 mL, 1.11 mmol, 1.1 eq) and the reaction mixture was allowed to stir at 0° C. for 1 h. Progress was monitored by TLC. After completion, the reaction mixture was filtered and the filtrate was carried to next step without any further purification.

LCMS: 284 [M+1]$^+$

Step-3

To the stirred solution of 1,5,6,7-tetrahydro-2H-azepin-2-one (100 mg, 0.90 mmol) in THF (5 mL) at −78° C. was added n-BuLi (2.5 M in hexane, 0.47 mL, 1.17 mmol, 1.3 eq) and the reaction mixture was stirred at the same temperature for 30 min. To this reaction mixture was added a solution of pivalic (E)-3-(quinolin-2-yl)acrylic anhydride (280 mg, 0.99 mmol, 1.1 eq) in THF and the resulting mixture was allowed to stir at −78° C. for 2 h. Progress was monitored by TLC and LCMS. After completion, the reaction mixture was diluted with water (20 mL) and extracted with EtOAc (2×100 mL). The combined organic layers were washed with brine, dried over Na$_2$SO$_4$, filtered and concentrated under reduced pressure. The crude material was purified by reversed phase HPLC to afford the title compound (17 mg, 6.4%) as a white solid.

LCMS: 293 [M+1]$^+$ $^1$H NMR: (400 MHz, CDCl$_3$) δ 8.19 (d, 1H), 8.16 (d, 1H), 7.95-7.85 (m, 2H), 7.80 (d, 1H), 7.78-7.65 (m, 2H), 7.55 (t, 1H), 6.61-6.65 (m, 1H), 6.17 (d, 1H), 4.08-3.98 (m, 2H), 2.45-2.38 (m, 2H), 2.10-1.98 (m, 2H).

Example 16

Preparation of (E)-1-(3-(3-methyl-1,2,4-oxadiazol-5-yl)acryloyl)-5,6-dihydropyridin-2(1H)-one Compound 16

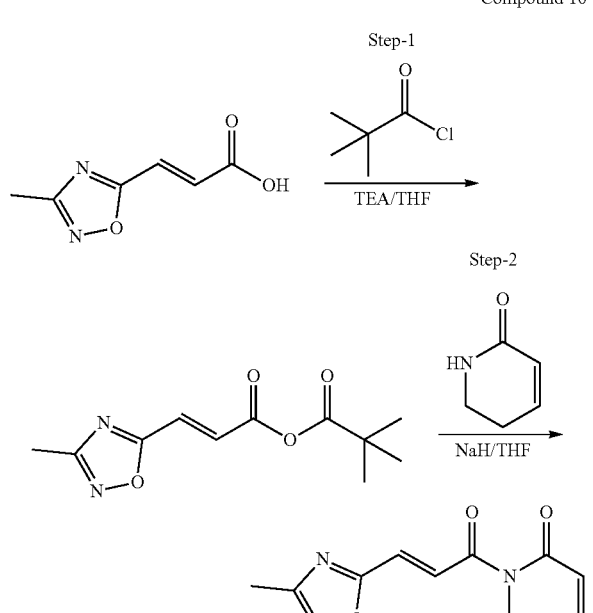

Step-1

To a stirred solution of (E)-3-(1,2,4-oxadiazol-5-yl) acrylic acid (250 mg, 1.62 mmol) in THF (10 mL) at 0° C. was added triethylamine (0.23 mL, 1.78 mmol, 1.1 eq) followed by pivaloyl chloride (0.23 mL, 1.78 mmol, 1.1 eq) and the reaction mixture was allowed to stir at 0° C. for 1 h. Progress was monitored by TLC. After completion, the mixture was filtered and the filtrate was used in the next step without any further purification.

Step-2

To the stirred solution of 5,6-dihydropyridin-2(1H)-one (143 mg, 1.48 mmol) in THF (10 mL) at 0° C. was added NaH (60% in mineral oil, 118 mg, 3.24 mmol, 2 eq) and the reaction mixture was stirred 0° C. for 30 minutes. To this was added a solution of (E)-3-(3-methyl-1,2,4-oxadiazol-5-yl)acrylic pivalic anhydride in THF (10 mL) and the reaction mixture was allowed to stir at 0° C. for 2 h. Progress was monitored by TLC. After completion, the mixture was diluted with water (20 mL) and extracted with EtOAc (3×50 mL). The combined organic layers were washed with brine, dried over Na$_2$SO$_4$, filtered and concentrated under reduced pressure. The crude material was purified by CombiFlash to afford the title compound (35 mg, 10%).

LCMS: 234 [M+1]$^+$ $^1$H NMR: (400 MHz, CDCl$_3$) δ 7.90 (d, 1H), 7.38 (d, 1H), 7.05-6.95 (m, 1H), 6.05 (d, 1H), 4.08-4.00 (m, 2H), 2.52-2.45 (m, 2H), 2.41 (s, 3H).

Example 17

Compound 17

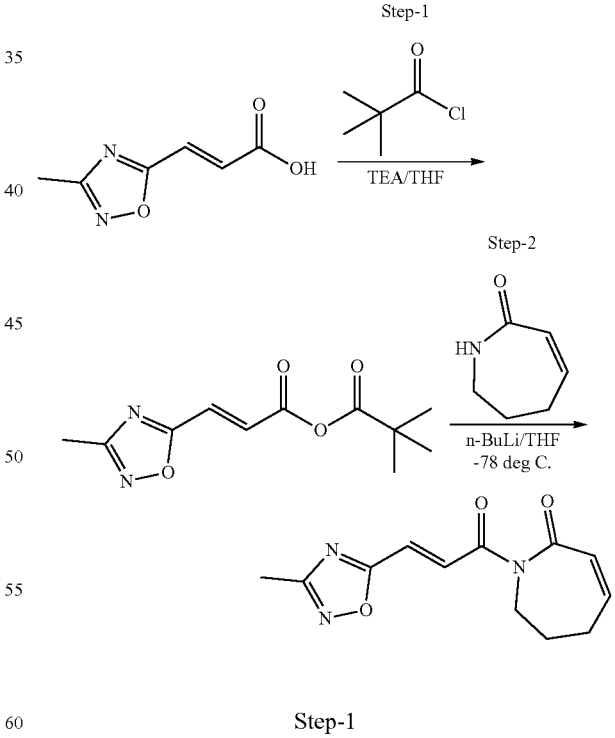

Step-1

To a stirred solution of (E)-3-(1,2,4-oxadiazol-5-yl) acrylic acid (250 mg, 1.62 mmol) in THF (10 mL) at 0° C. was added triethylamine (0.23 mL, 1.78 mmol, 1.1 eq) followed by pivaloyl chloride (0.23 mL, 1.78 mmol, 1.1 eq) and the reaction mixture was allowed to stir at 0° C. for 1 h. Progress was monitored by TLC. After completion, the mixture was filtered and the filtrate was used in the next step without any further purification.

Step-2

To the stirred solution of 6,7-dihydro-1H-azepin-2(5H)-one (100 mg, 0.90 mmol) in THF (10 mL) at −78° C. was added n-BuLi (2.5 M in hexane, 0.44 mL, 1.1 mmol, 1.2 eq) and the reaction mixture was stirred −78° C. for 30 minutes. To this reaction mixture was added a solution of (E)-3-(3-methyl-1,2,4-oxadiazol-5-yl)acrylic pivalic anhydride in THF (10 mL) and the reaction mixture was allowed to stir at 0° C. for 2 h. Progress was monitored by TLC. After completion, the reaction mixture was diluted with water (20 mL) and extracted with EtOAc (3×50 mL). The combined organic layers were washed with brine, dried over Na$_2$SO$_4$, filtered and concentrated under reduced pressure. The crude material was purified by CombiFlash by CombiFlash to obtain the title compound (80 mg, 36%).

LCMS: 248 [M+1]$^+$ $^1$H NMR: (400 MHz, CDCl$_3$) δ 7.82 (d, 1H), 7.40 (d, 1H), 6.65-6.56 (m, 1H), 6.10 (d, 1H), 4.03-3.95 (m, 2H), 2.45-2.37 (m, 2H), 2.42 (s, 3H), 2.06-1.95 (m, 2H).

Example 18

Preparation of (E)-1-(3-cyclopropylacryloyl)-5,6-dihydropyridin-2(1H)-one

Compound 18

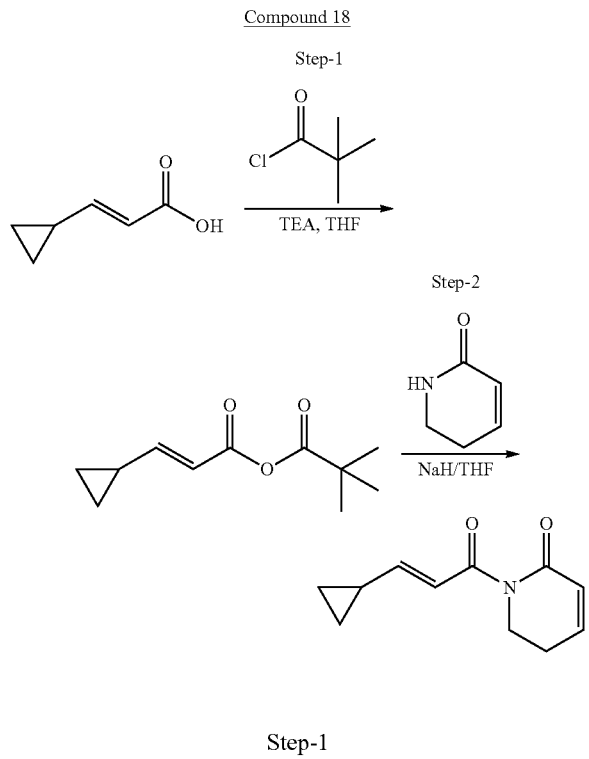

Step-1

To a solution of (2E)-3-cyclopropylprop-2-enoic acid (300 mg, 2.67 mmol) in dry THF (10 mL) was added triethylamine (0.41 mL, 2.94 mmol, 1.1 eq) followed by pivaloyl chloride (0.35 mL, 2.94 mmol, 1.1 eq) and the reaction mixture was stirred at 0° C. for 45 min. Progress was monitored by TLC. After completion, the reaction mixture was filtered and the filtrate was used directly for the next step.

Step-2

To a stirred solution of 5,6-dihydropyridin-2(1H)-one (150 mg, 1.54 mmol) in dry THF (10 mL) at 0° C. was added NaH (60% in mineral oil, 68 mg, 1.70 mmol, 1.1 eq.) and the mixture was allowed to stir at the same temperature for 30 min. To this solution was added a solution of (2E)-3-cyclopropylprop-2-enoic 2,2-dimethylpropanoic anhydride (333 mg, 1.70 mmol, 1.1 eq.) in THF (10 mL) and the resulting mixture was allowed to stir at 0° C. for 1 h. Progress was monitored by TLC and LCMS. After completion, the reaction mixture was brought to RT, diluted with water (30 mL) and extracted with EtOAc (3×30 mL). The combined organic layers were washed with brine (30 mL), dried over anhydrous Na$_2$SO$_4$, filtered and evaporated to dryness. The crude material was purified by CombiFlash to afford the title compound (22 mg, 15%).

LCMS: 192 [M+1]$^+$ $^1$H NMR: (400 MHz, CDCl$_3$) δ 6.97 (d, 1H), 6.92-6.82 (m, 1H), 656-6.43 (m, 1H), 6.00 (d, 1H), 4.04-3.91 (m, 2H), 2.43-2.37 (m, 2H), 1.68-1.58 (m, 1H), 2.00-1.92 (m, 2H), 0.66-0.60 (m, 2H).

Example 19

Preparation of (E)-1-(3-(piperidin-4-yl)acryloyl)-5,6-dihydropyridin-2(1H)-one and tert-butyl (E)-4-(3-oxo-3-(6-oxo-3,6-dihydropyridin-1(2H)-yl)prop-1-en-1-yl)piperidine-1-carboxylate Compound 19 and 20

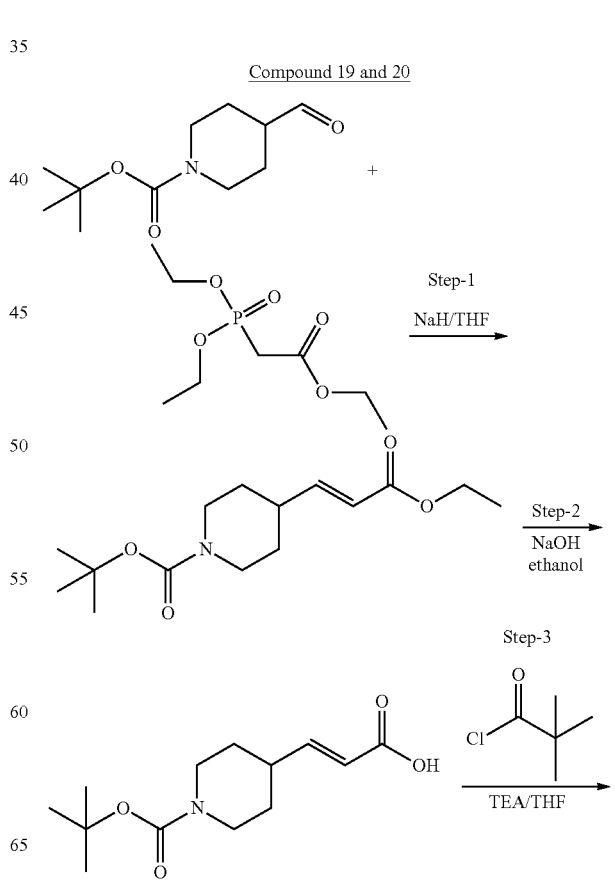

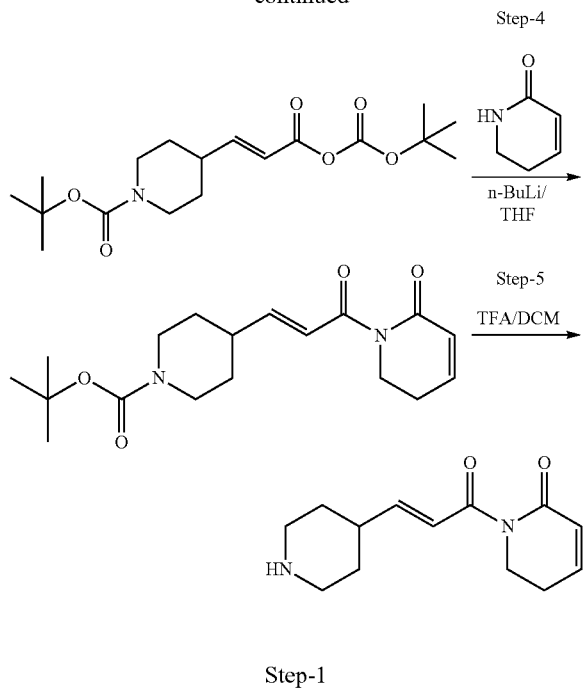

Step-1

To a suspension of NaH (60% in mineral oil, 1.03 g, 25.8 mmol, 1.1 eq.) in THF (50 mL) was added ethyl 2-(diethoxyphosphoryl)acetate (10.51 g, 46.9 mmol, 2 eq.) dropwise at 0° C. and the mixture was allowed to stir at the same temperature for 30 min. To this mixture was added a solution of tert-butyl 4-formylpiperidine-1-carboxylate (5 g, 23.5 mmol) in THF (5 mL) and the resulting mixture was allowed to stir at room temperature for 1 h. Progress was monitored by TLC. After completion, the mixture was diluted with saturated aqueous $NH_4Cl$ (100 mL) and extracted with EtOAc (3×50 mL). The combined organic layers were washed with brine, dried over anhydrous $Na_2SO_4$, filtered and evaporated. The crude material was purified by CombiFlash to afford tert-butyl (E)-4-(3-ethoxy-3-oxoprop-1-en-1-yl)piperidine-1-carboxylate (3.5 g, 52.7%).

LCMS: 284 [M+1]$^+$

Step-2

To a solution of tert-butyl (E)-4-(3-ethoxy-3-oxoprop-1-en-1-yl)piperidine-1-carboxylate (1 g, 3.53 mmol) in EtOH (20 mL) was added a solution of NaOH (2 M, 1.6 mL) in water and the reaction mixture was stirred at 70° C. for 4 h. The mixture was concentrated under vacuum and then acidified with 2N HCl to pH 3. The mixture was then diluted with saturated aqueous $NH_4Cl$ (30 mL) and extracted with $CH_2Cl_2$ (3×30 mL). The combined organic layers were washed with brine (50 mL), dried over anhydrous $Na_2SO_4$ and filtered. Removal of solvent under reduced pressure afforded (E)-3-(1-(tert-butoxycarbonyl) piperidin-4-yl) acrylic acid (0.43 g, 47%) as crystalline solid.

LCMS: 256 [M+1]$^+$

Step-3

To a solution of (E)-3-(1-(tert-butoxycarbonyl) piperidin-4-yl)acrylic acid (0.4 g, 1.56 mmol) in dry THF was added triethylamine (0.24 mL, 1.72 mmol, 1.1 eq.) followed by pivaloyl chloride (0.21 mL, 1.72 mmol, 1.1 eq.) and the reaction mixture was stirred at 0° C. for 45 min. Progress was monitored by TLC. After completion, the mixture was filtered and the filtrate was used directly for the next step.

Step-4

To a stirred solution of 5,6-dihydropyridin-2(1H)-one (0.18 g, 1.85 mmol) in dry THF at −78° C. was added n-BuLi (2.5 M in hexane, 0.81 mL, 2.04 mmol, 1.1 eq.) and the mixture was allowed to stir at the same temperature for 30 min. To this solution was added a solution of (E)-3-(1-(tert-butoxycarbonyl)piperidin-4-yl)acrylic(tert-butyl carbonic) anhydride in THF and the reaction mixture was allowed to stir at −78° C. for 1 h. Progress was monitored by TLC and LCMS. After completion, the mixture was brought to 0° C., diluted with water (30 mL) and extracted with EtOAc (3×30 mL). The combined organic layers were washed with brine, dried over anhydrous $Na_2SO_4$, filtered and evaporated to dryness. The crude material was purified by reversed phase HPLC to afford tert-butyl (E)-4-(3-oxo-3-(6-oxo-3,6-dihydropyridin-1(2H)-yl)prop-1-en-1-yl)piperidine-1-carboxylate (0.160 g, 30.6%).

LCMS: 335 [M+1]$^+$

Step-5

To a solution of tert-butyl (E)-4-(3-oxo-3-(6-oxo-3,6-dihydropyridin-1(2H)-yl)prop-1-en-1-yl)piperidine-1-carboxylate (0.16 g, 0.48 mmol) in $CH_2Cl_2$ (10 mL) was added trifluoroacetic acid (3.0 mL) at 0° C. and the resulting mixture was stirred at room temperature for 2 h. Progress was monitored by TLC. After completion, the mixture was evaporated under reduce pressure and the crude material was purified by reversed phase HPLC to afford the title compound (23 mg, 20.5%).

LCMS: 235 [M+1]$^+$ $^1$H NMR: (400 MHz, DMSO-d$_6$) δ 8.25-8.62 (br s, 2H), 7.12-7.03 (m, 1H), 6.80-6.67 (m, 2H), 5.93 (d, 1H), 3.87-3.79 (m, 2H), 3.40-3.20 (m, 2H), 2.96-2.80 (m, 2H), 2.60-2.38 (m, 3H), 1.96-1.80 (m, 2H), 1.59-1.40 (m, 2H).

Example 20

Preparation of (E)-1-(3-(2,3-dihydro-[1,4]dioxino[2,3-b]pyridin-6-yl)acryloyl)-5,6-dihydropyridin-2(1H)-one Compound 21

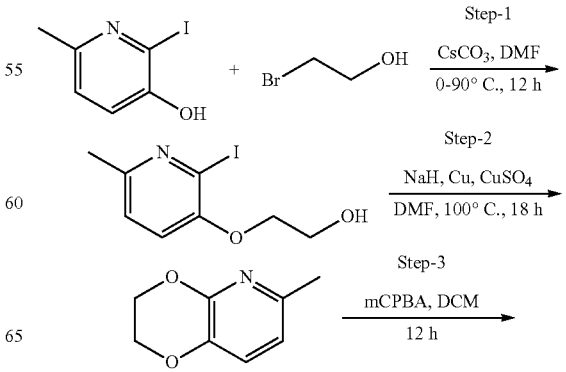

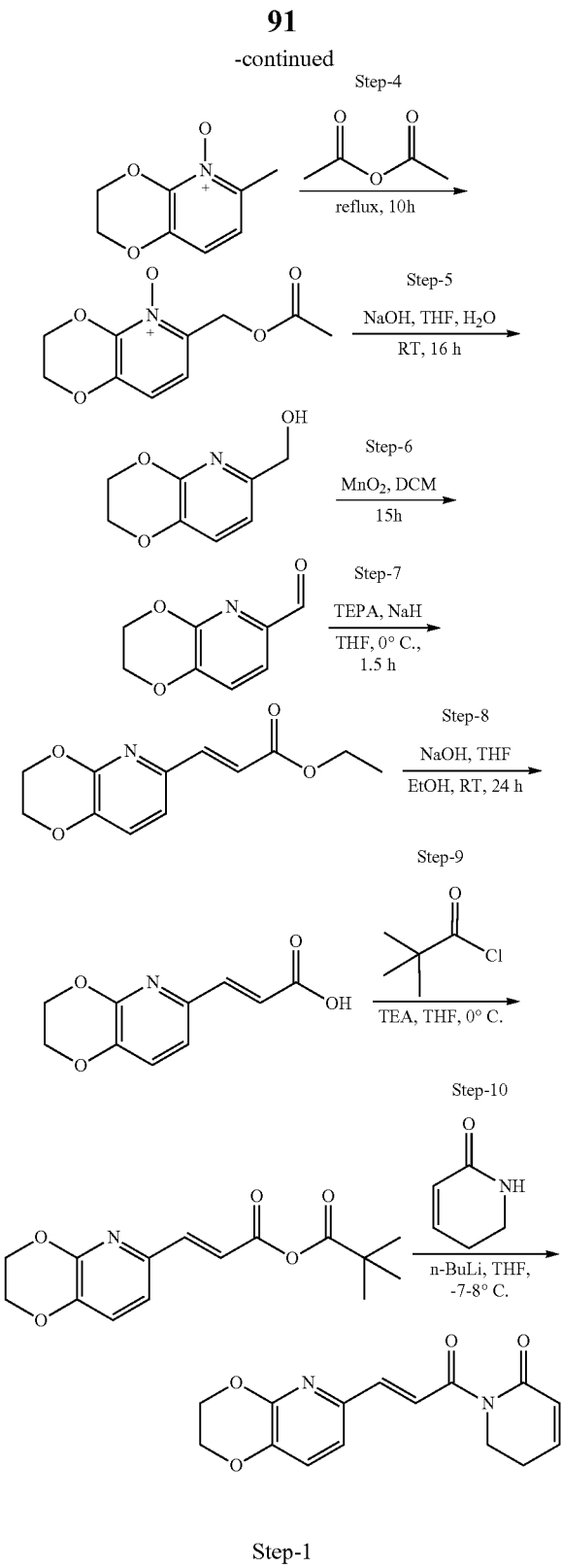

Step-1

To a solution of 2-iodo-6-methylpyridin-3-ol (10 g, 42.5 mmol) in DMF (250 mL) at room temperature was added Cs₂CO₃ (16.6 g, 51 mmol, 1.2 eq.) followed by 2-bromoethanol (5.99 mL, 85 mmol, 2 eq.) dropwise. The resulting mixture was stirred at 90° C. overnight. Progress was monitored by TLC. After completion, the reaction mixture was cooled to room temperature, diluted with ice cold water (300 mL) and extracted with CH₂Cl₂ (3×300 mL). The combined organic layers were washed with brine, dried over anhydrous Na₂SO₄ and filtered. Removal of solvent under reduced pressure afforded 2-(2-iodo-6-methylpyridin-3-yloxy)ethanol (9 g, 76.1%) which was used without further purification.

LCMS: 279 [M+1]⁺

Step-2

To a stirred solution of 2-(2-iodo-6-methylpyridin-3-yloxy)ethanol (6 g, 32.2 mmol) in anhydrous DMF (200 mL) at 0° C. was added NaH (60% in mineral oil, 0.928 g, 38.3 mmol, 1.2 eq.), Cu (0.81 g, 12.9 mmol, 0.4 eq.) and CuSO₄ (3.07 g, 19.3 mmol, 0.6 eq.). The resulting mixture was stirred at 100° C. overnight. Progress was monitored by TLC. After completion, the reaction mixture was cooled to room temperature, diluted with ice cold water (300 mL) and extracted with CH₂Cl₂ (3×300 mL). The combined organic layers were washed with brine, dried over anhydrous Na₂SO₄ and filtered. Removal of solvent under reduced pressure afforded the crude material which was purified by CombiFlash to afford 6-methyl-2,3-dihydro-[1,4]dioxino[2,3-b]pyridine (0.95 g, 19.5%).

LCMS: 152 [M+1]⁺

Step-3

To a stirred solution of 6-methyl-2,3-dihydro-[1,4]dioxino[2,3-b]pyridine (0.95 g, 6.27 mmol) in anhydrous DMF (200 mL) at 0° C. was added m-CPBA (1.29 g, 7.5 mmol, 1.2 eq.) portion-wise. After addition the resulting mixture was stirred at room temperature overnight. Progress was monitored by TLC. After completion, the solvent was removed under reduced pressure to afford crude 6-methyl-2,3-dihydro-[1,4]dioxino[2,3-b]pyridine 5-oxide (0.95 g, 90%) which was used without further purification.

LCMS: 168 [M+1]⁺

Step-4

A stirred solution of 6-methyl-2,3-dihydro-[1,4]dioxino[2,3-b]pyridine 5-oxide (0.95 g, 5.68 mmol) in acetic anhydride (20 mL) was refluxed for 10 h. Progress was monitored by TLC. After completion, the volatiles were removed under reduced pressure to afford crude 6-(acetoxymethyl)-2,3-dihydro-[1,4]dioxino[2,3-b]pyridine 5-oxide (4 g) which used without further purification.

LCMS: 227 [M+1]⁺

Step-5

To a solution of 6-(acetoxymethyl)-2,3-dihydro-[1,4]dioxino[2,3-b]pyridine 5-oxide (4 g, 19.1 mmol) in a mixture of THF and water (1:1, 20 mL) was added NaOH (1.35 g, 38.3 mmol, 2 eq). The resulting mixture was stirred at room temperature for 12 h. Progress was monitored by TLC. After the completion, the solvent was removed under reduced pressure to afford (2,3-dihydro-[1,4]dioxino[2,3-b]pyridin-6-yl)methanol (1.1 g) which was used without further purification.

LCMS: 168 [M+1]⁺

Step-6

To a solution of (2,3-dihydro-[1,4]dioxino[2,3-b]pyridin-6-yl)methanol (0.3 g, 1.79 mmol) in CH₂Cl₂ (10 mL) was added activated MnO$_2$ (0.31 g, 3.59 mmol, 2 eq.) and the resulting slurry was stirred at room temperature for 15 h. Progress was monitored by TLC. After completion, the slurry was filtered through a bed of Celite. The Celite-bed was washed with CH$_2$Cl$_2$ (10 mL) and the filtrate was concentrated under reduced pressure to afforded 2,3-dihydro-[1,4]dioxino[2,3-b]pyridine-6-carbaldehyde (0.25 g) which was used without further purification.

LCMS: 166 [M+1]$^+$

Step-7

To a stirred suspension of NaH (60% in mineral oil, 47 mg, 1.96 mmol, 1.3 eq.) in anhydrous THF (10 mL) at 0° C. was added triethylphosphonoacetate (0.36 mL, 1.81 mmol, 1.2 eq.) and the mixture was stirred at the same temperature for 10 min. To this mixture was added a solution of 2,3-dihydro-[1,4]dioxino[2,3-b]pyridine-6-carbaldehyde (0.25 g, 1.51 mmol) in THF (10 mL). The resulting mixture was stirred at 0° C. 1.5 h. Progress was monitored by TLC. After completion, the reaction mixture was diluted with brine (50 mL) and extracted with EtOAc (3×50 mL). The combined organic layers were dried over anhydrous Na$_2$SO$_4$ and filtered. Removal of solvent under reduced pressure afforded a crude material which was purified by CombiFlash to afford of (E)-ethyl 3-(2,3-dihydro-[1,4]dioxino[2,3-b]pyridin-6-yl) acrylate (0.2 g, 56.2%). LCMS: 236 [M+1]$^+$ Step-8

To a solution of (E)-ethyl 3-(2,3-dihydro-[1,4]dioxino[2,3-b]pyridin-6-yl)acrylate (0.2 g, 0.851 mmol) in a mixture of THF:EtOH (1:1, 10 mL) was added a solution of NaOH (0.34 g, 8.51 mmol, 10 eq.) in water (1 mL). The resulting mixture was stirred at room temperature for 2 h. Progress was monitored by TLC. After completion, the reaction mixture was neutralized with 2 M aqueous HCl and extracted with EtOAc (3×50 mL). The combined organic layers were dried over Na$_2$SO$_4$, filtered and concentrated to afforded a crude material. Trituration with Et$_2$O and pentane afforded (E)-3-(2,3-dihydro-[1,4]dioxino[2,3-b]pyridin-6-yl)acrylic acid (0.1 g, 56.8%). LCMS: 208 [M+1]$^+$ Step-9

To a stirred solution of (E)-3-(2,3-dihydro-[1,4]dioxino[2,3-b]pyridin-6-yl)acrylic acid (0.1 g, 0.48 mmol) in THF (15 mL) at 0° C. was added triethylamine (0.07 mL, 0.579 mmol, 1.2 eq.) followed by pivaloyl chloride (0.07 mL, 0.579 mmol, 1.2 eq.) and the resulting mixture was stirred at 0° C. for 2 h. Progress was monitored by TLC. After completion, the reaction mixture was used directly in the next step.

Step-10

To a stirred solution of 5,6-dihydropyridin-2(1H)-one (0.08 g, 0.71 mmol, 2.1 eq.) in THF (10 mL) at −78° C. was added n-BuLi (0.3 mL, 0.75 mmol, 2.2 eq.) and the resulting mixture was stirred at the same temperature for 30 min. To this mixture was added a solution of (E)-3-(2,3-dihydro-[1,4]dioxino[2,3-b]pyridin-6-yl)acrylic pivalic anhydride in THF (15 mL) dropwise and the reaction mixture was stirred at −78° C. for 2 h. Progress was monitored by TLC. After completion, the reaction mixture was diluted with an aqueous NH$_4$Cl solution (50 mL) and extracted with EtOAc (3×50 mL). The combined organic layers were dried over Na$_2$SO$_4$ and filtered. Removal of the solvent provided crude material which was purified by reversed phase HPLC to afford the title compound (5 mg, 5%).

LCMS: 287 [M+1]$^+$ $^1$H NMR: (400 MHz, CDCl$_3$) δ 7.64 (d, 1H), 7.57 (d, 1H), 7.16 (d, 1H), 7.08 (d, 1H), 6.96-6.89 (m, 1H), 6.03 (d, 1H), 4.45-4.40 (m, 2H), 4.28-4.20 (m, 2H), 4.03-3.96 (m, 2H), 2.46-2.40 (m, 2H).

Example 21

Preparation of (E)-1-(3-(1-methylcyclohexyl)acryloyl)-5,6-dihydropyridin-2(1H)-one

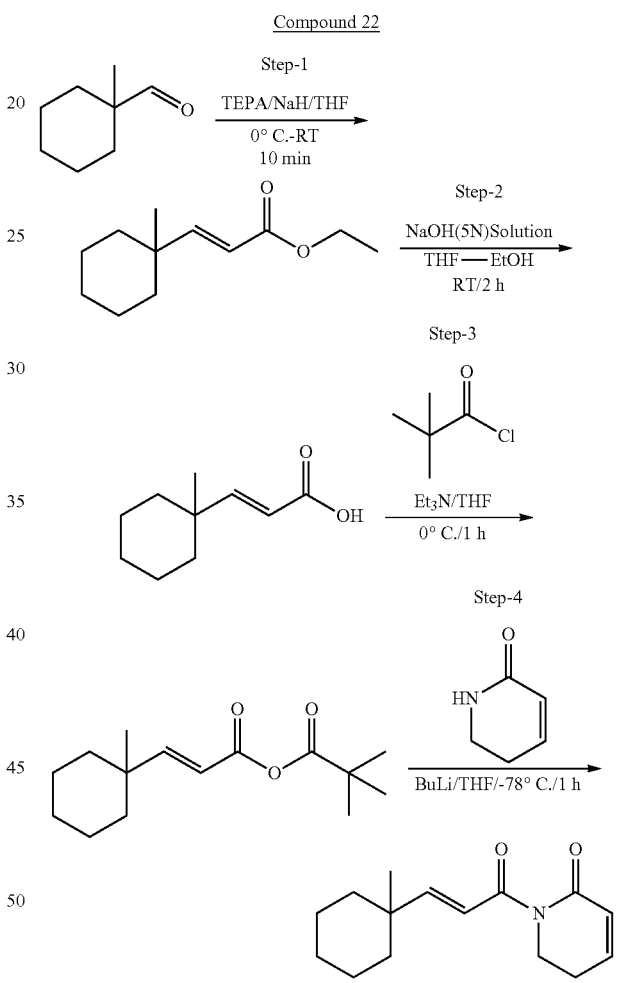

Step-1

To a solution of triethyl phosphonoacetate (TEPA) (1.95 g, 8.7 mmol, 1.1 eq.) in THF (8 mL) was added NaH (60% in mineral oil, 0.377 g, 9.5 mmol, 1.2 eq.) at 0° C. The mixture was stirred for 5 min. To this mixture was then added a solution of 1-methylcyclohexane-1-carbaldehyde (1 g, 7.9 mmol) in THF (2 mL) dropwise at 0° C. and the reaction mixture was stirred for 5 min. Progress was monitored by TLC. After completion, the reaction mixture was diluted with water (20 mL) and extracted with EtOAc (3×50 mL). The combined organic layers were washed with brine, dried over Na₂SO₄, filtered and concentrated under reduced pressure to obtain ethyl (F)-3-(1-methylcyclohexyl)acrylate (1.4 g, 93.3%) which was used without purification.
LCMS: 197 [M+1]⁺

Step-2

To the stirred solution of ethyl (E)-3-(1-methylcyclohexyl)acrylate (1 g, 5.0 mmol) in 1:1 THF-EtOH (10 mL) at room temperature was added 5N aqueous NaOH (10.2 mL, 50 mol, 10 eq.) and the mixture was stirred for 2 h. Progress was monitored by TLC. After completion, the reaction mixture was diluted with 1N HCl (15 mL) and extracted with EtOAc (2×100 mL). The combined organic layers were washed with water, dried over anhydrous Na₂SO₄, filtered and concentrated under to obtain (E)-3-(1-methylcyclohexyl)acrylic acid (0.33 g, 38.5%) which was used without purification.
LCMS: 169 [M+1]⁺

Step-3

To a stirred solution of (E)-3-(1-methylcyclohexyl)acrylic acid (330 mg, 1.96 mmol) in THF (5 mL) at 0° C. was added triethylamine (0.3 mL, 2.16 mmol, 1.1 eq) followed by pivaloyl chloride (0.26 mL, 2.16 mmol, 1.1 eq.) and the reaction mixture was allowed to stir at 0° C. for 1 h. Progress was monitored by TLC. After completion, the reaction mixture was filtered and carried to next step without any further purification.
LCMS: 251 [M+1]⁺

Step-4

To the stirred solution of 5,6-dihydropyridin-2(1H)-one (200 mg, 2.06 mmol) in THF (10 mL) at −78° C. was added n-BuLi (2.5 M in hexane, 0.98 mL, 2.47 mmol, 1.2 eq.) and the reaction mixture was stirred at the same temperature for 30 min. To this reaction mixture was added a solution of (E)-3-(1-methylcyclohexyl)acrylic pivalic anhydride (572 mg, 2.49 mmol, 1.1 eq.) in THF (10 mL) and the resulting mixture was allowed to stir at −78° C. for 2 h. Progress was monitored by TLC and LCMS. After completion, the reaction mixture was diluted with water (20 mL) and extracted with EtOAc (3×50 mL). The combined organic layers were washed with brine, dried over Na₂SO₄, filtered and concentrated. The crude material was purified by CombiFlash to afford the title compound (120 mg, 23.6%) as an oil.
LCMS: 248 [M+1]⁺
¹H NMR: (400 MHz, CDCl₃) δ 6.98 (d, 1H), 6.95-6.85 (m, 1H), 6.77 (d, 1H), 6.00 (d, 1H), 4.01-3.90 (m, 2H), 2.45-2.38 (m, 2H), 1.65-1.30 (m, 10H).

Example 22

Preparation of (E)-1-(3-(2,3-dihydro-[1,4]dioxino[2,3-b]pyridin-6-yl)acryloyl)-5,6-dihydropyridin-2(1H)-one Compound 23

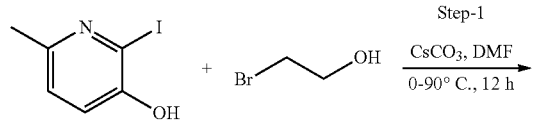

Step-1

To a solution of 2-iodo-6-methylpyridin-3-ol (10 g, 42.5 mmol, 1 eq.) in DMF (250 mL) at room temperature was added $Cs_2CO_3$ (16.57 g, 51 mmol, 1.2 eq.) followed by 2-bromoethanol (5.99 mL, 85 mmol, 2 eq.) dropwise. The resulting mixture was stirred at 90° C. overnight. Progress of reaction was monitored by TLC. After the completion, reaction mixture was cooled to room temperature, diluted with ice cold water (300 mL) and extracted with DCM (3×300 mL). Combined organic layer was washed with brine and dried over anhydrous sodium sulphate. Removal of solvent under reduced pressure afforded 2-(2-iodo-6-methylpyridin-3-yloxy)ethanol (9 g, 76.14%).

LCMS: 279 [M+1]$^+$

Step-2

To a stirred solution of 2-(2-iodo-6-methylpyridin-3-yloxy)ethanol (6 g, 32.2 mmol, 1 eq.) in anhydrous DMF (200 mL) at 0° C. were added NaH (0.928 g, 38.25 mmol, 1.2 eq.), Cu (0.81 g, 12.9 mmol, 0.4 eq.) and $CuSO_4$ (3.07 g, 19.3 mmol, 0.6 eq.) and the resulting mixture stirred at 100° C. overnight. Progress of reaction was monitored by TLC. After the completion, reaction mixture was cooled to room temperature, diluted with ice cold water (300 mL) and extracted with DCM (3×300 mL). Combined organic layer was washed with brine solution and dried over anhydrous sodium sulphate. Removal of solvent under reduced pressure afforded crude which was purified by Combi-Flash on silica gel chromatography using methanol-dichloromethane (0-10%) as eluents to afford 6-methyl-2,3-dihydro-[1,4]dioxino[2,3-b]pyridine (0.950 g, 19.50%).

LCMS: 152[M+1]$^+$

Step-3

To a stirred solution of 6-methyl-2,3-dihydro-[1,4]dioxino[2,3-b]pyridine (0.950 g, 6.27 mmol, 1 eq.) in anhydrous DMF (200 mL) at 0° C. was added m-CPBA (1.29 g, 7.5 mmol, 1.2 eq.) portionwise. After addition the resulting mixture was stirred at room temperature overnight. Progress of reaction was monitored by TLC. After completion, solvent was removed under reduced pressure to afford crude 6-methyl-2,3-dihydro-[1,4]dioxino[2,3-b]pyridine 5-oxide (0.950 g, 90%) which was used in the next step without further purification.

LCMS: 168[M+1]$^+$

Step-4

To a stirred solution of 6-methyl-2,3-dihydro-[1,4]dioxino[2,3-b]pyridine 5-oxide (0.950 g, 5.68 mmol, 1 eq.) in acetic anhydride (20 mL) and the mixture was reflux for 10 h. Progress of reaction was monitored by TLC. After completion, solvent was removed under reduced pressure to afford crude 6-(acetoxymethyl)-2,3-dihydro-[1,4]dioxino[2,3-b]pyridine 5-oxide (4 g) which used in next step without further purification.

LCMS: 227[M+1]$^+$

Step-5

To a solution of 6-(acetoxymethyl)-2,3-dihydro-[1,4]dioxino[2,3-b]pyridine 5-oxide (4 g, 19.13 mmol, 1 eq.) in a mixture of THF and water (1:1, 20 mL) was added with NaOH (1.35 g, 38.27 mmol, 2 eq.). The resulting mixture was stir at room temperature for 12 h. Progress of reaction was monitored by TLC. After the completion, solvent was removed under reduced pressure to afford (2,3-dihydro-[1,4]dioxino[2,3-b]pyridin-6-yl)methanol (1.1 g crude).

LCMS: 168[M+1]$^+$

Step-6

To a solution of (2,3-dihydro-[1,4]dioxino[2,3-b]pyridin-6-yl)methanol (0.300 g, 1.79 mmol, 1 eq.) in dichloromethane (10 mL) was added activated $MnO_2$ (0.31 g, 3.59 mmol, 2 eq.) and the resulting slurry was stirred at room temperature for 15 h. Progress of reaction was monitored by TLC. After the completion, the slurry was filtered through celite-bed. The celite-bed was washed with dichloromethane (10 mL) and filtrate was removed under reduced pressure to afford afforded crude 2,3-dihydro-[1,4]dioxino[2,3-b]pyridine-6-carbaldehyde (0.25 g crude) which was used in the next step without further purification.

LCMS: 166[M+1]$^+$

Step-7

To a stirred suspension of NaH (0.047 g, 1.96 mmol, 1.3 eq.) in anhydrous THF (10 mL) at 0° C. were added triethylphosphono acetate (0.36 mL, 1.81 mmol, 1.2 eq.) and the mixture was stirred at the same temperature for 10 minutes. To this mixture was added a solution of 2,3-dihydro-[1,4]dioxino[2,3-b]pyridine-6-carbaldehyde (0.25 g, 1.51 mmol, 1 eq.) in THF (10 mL). The resulting mixture was stir for at 0° C. 1.5 h. Progress of reaction was monitored by TLC. After the completion, reaction mixture was diluted with brine (50 mL), extracted with ethyl acetate (3×50 mL). Combined organic layer was dried over $Na_2SO_4$. Removal of solvent under reduced pressure afforded crude which was purified by Combi-Flash on silica gel using ethyl acetate-hexane (0-50%) as eluents to afford of (E)-ethyl 3-(2,3-dihydro-[1,4]dioxino[2,3-b]pyridin-6-yl)acrylate (0.200 g, 56.17%).

LCMS: 236[M+1]$^+$

Step-8

To a solution of (E)-ethyl 3-(2,3-dihydro-[1,4]dioxino[2,3-b]pyridin-6-yl)acrylate (0.2 g, 0.851 mmol, 1 eq.) in a mixture of THF-ethanol (1:1, 10 mL) was added a solution of NaOH (0.34 g, 8.51 mmol, 10 eq.) in water (1 mL). The resulting mixture was stirred at room temperature for 2 h. Progress of reaction was monitored by TLC. After completion, reaction mixture was neutralized with 2M aq. HCl and extracted with acetate (3×50 mL). Combined organic layer was dried over sodium sulphate, removal of solvent under reduced pressure afforded crude which was purified by trituration with diethyl ether and pentane to afford (E)-3-(2,3-dihydro-[1,4]dioxino[2,3-b]pyridin-6-yl)acrylic acid (0.1 g, 56.81%).

LCMS: 208[M+1]$^+$

Step-9

To a stirred solution of (E)-3-(2,3-dihydro-[1,4]dioxino[2,3-b]pyridin-6-yl)acrylic acid (0.1 g, 0.48 mmol, 1 eq.) in THF (15 mL) at 0° C. was added triethylamine (0.07 mL, 0.579 mmol, 1.2 eq.) followed by pivaloyl chloride (0.07 mL, 0.579 mmol, 1.2 eq.) and the resulting mixture was stirred stir at 0° C. for 2 h. Progress of reaction was monitored by TLC. After the completion, reaction mixture was used as such in the next reaction.

Step-10

To a stirred solution of 5,6-dihydropyridin-2(1H)-one (0.08 g, 0.71 mmol, 2.1 eq.) in THF (10 mL) at −78° C. was added n-BuLi (0.3 mL, 0.75 mmol, 2.2 eq.) and the resulting mixture was stirred at the same temperature for 30 minutes. To this mixture was added a solution of (E)-3-(2,3-dihydro-[1,4]dioxino[2,3-b]pyridin-6-yl)acrylic pivalic anhydride in THF (15 mL) dropwise and the reaction mixture was stirred at −78° C. for 2 h. Progress of reaction was monitored by TLC. After completion, reaction mixture was diluted with ammonium chloride solution (50 mL) and extracted with ethyl acetate (3×50 mL). Combined organic layer was dried over sodium sulphate. Removal of solvent under reduced pressure crude which was purified by reversed phase HPLC to afford (E)-1-(3-(2,3-dihydro-[1,4]dioxino[2,3-b]pyridin-6-yl)acryloyl)-5,6-dihydropyridin-2(1H)-one (5 mg, 5%) LCMS: 287[M+1]$^+$ $^1$H NMR (400 MHz, CDCl$_3$) δ 7.64 (d, 1H), 7.57 (d, 1H), 7.16 (d, 1H), 7.08 (d, 1H), 6.96-6.89 (m, 1H), 6.03 (d, 1H), 4.45-4.40 (m, 2H), 4.28-4.20 (m, 2H), 4.03-3.96 (m, 2H), 2.46-2.40 (m, 2H).

Example 23

Preparation of (E)-1-(3-(2,3-dihydro-[1,4]dioxino[2,3-b]pyridin-7-yl)acryloyl)-5,6-dihydropyridin-2(1H)-one Compound 24

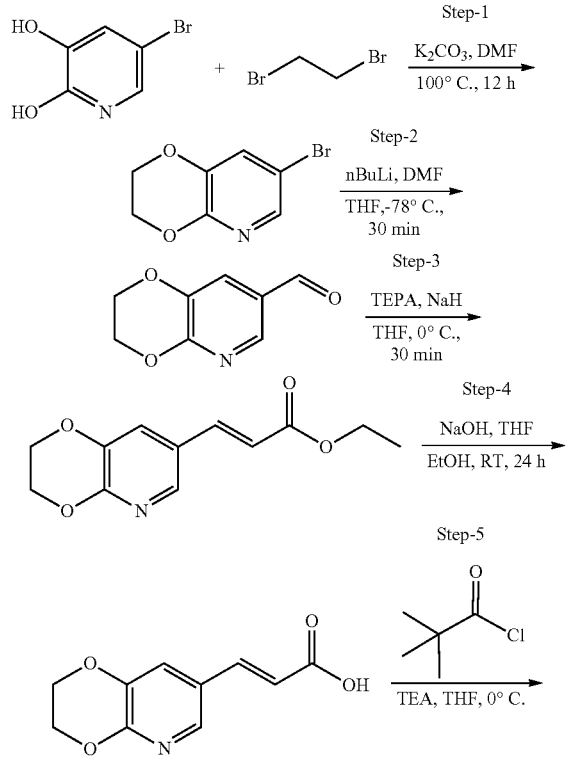

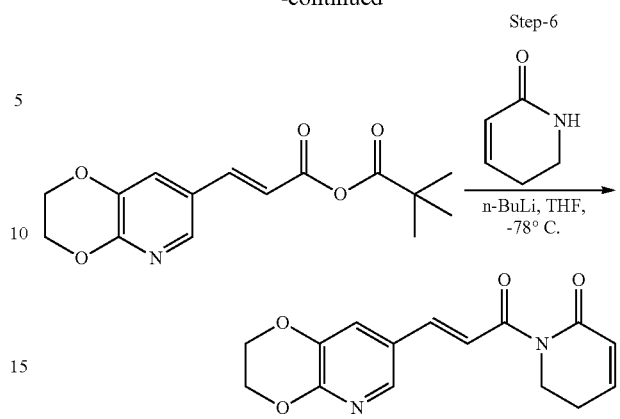

Step-1

To a solution of 5-bromopyridine-2,3-diol (10 g, 53.19 mmol, 1 eq.) in DMF (250 mL) at room temperature was added K$_2$CO$_3$ (21 g, 159.57 mmol, 3 eq.) followed by 1,2-dibromoethane (5.5 mL, 63.82 mmol, 1.2 eq.) dropwise. The resulting mixture was stirred at 100° C. overnight. Progress of reaction was monitored by TLC. After the completion, reaction mixture was cooled to room temperature, diluted with ice cold water (300 mL) and extracted with DCM (3×300 mL). Combined organic layer was washed with brine and dried over anhydrous sodium sulphate. Removal of solvent under reduced pressure afforded crude was purified by Combi-Flash on silica gel using methanol-dichloromethane (0-50%) as eluents to afford 7-bromo-2,3-dihydro-[1,4]dioxino[2,3-b]pyridine (2.9 g, 25.26%).
LCMS: 215 [M+1]$^+$ Step-2

To a solution of 7-bromo-2,3-dihydro-[1,4]dioxino[2,3-b]pyridine (0.500 g, 2.31 mmol, 1 eq.) in THF (15 mL) at −78° C. was added n-BuLi (1.43 mL, 0.50 mmol, 1.6 eq.) and the resulting mixture was allowed stirred at the same temperature for 30 minutes. To this solution was added a solution of DMF (0.43 mL, 5.54 mmol, 2.4 eq.) in THF (4 mL) and reaction mixture was allowed to stir at the same temperature for 2 h. Progress of reaction was monitored by TLC. After the completion, the reaction mixture was brought to 0° C., diluted with saturated NH$_4$Cl solution (50 mL) and extracted with ethyl acetate (3×50 mL). Combined organic layer dried over Na$_2$SO$_4$. Removal of solvent under reduced pressure afforded 2,3-dihydro-[1,4]dioxino[2,3-b]pyridine-7-carbaldehyde (0.35 g, 92.1%) which was used in the next step without further purification.
LCMS: 166 [M+1]$^+$ Step-3

To a solution of triethyl phosphonoacetate (0.618 g, 2.76 mmol, 1.3 eq.) in THF (30 mL) at 0° C. was added NaH (0.127 g, 3.18 mmol, 1.5 eq.) and the reaction mixture was allowed stirred at the same temperature for 10 minute. To this mixture was added a solution of 2,3-dihydro-[1,4]dioxino[2,3-b]pyridine-7-carbaldehyde (0.35 g, 2.76 mmol, 1 eq.) in THF (1 mL) and reaction mixture was allowed to stir at the same temperature for 30 minutes. Progress of reaction was monitored by TLC. After the completion, the reaction mixture was diluted with brine solution (50 mL) and extracted with ethyl acetate (3×50 mL). Combined organic layer was dried over Na$_2$SO$_4$. Removal of solvent under reduced pressure afforded (E)-ethyl 3-(2,3-dihydro-[1,4]dioxino[2,3-b]pyridin-7-yl)acrylate (0.45 g, 90.36%) which was used in the next step without further purification.

LCMS: 236 [M+1]$^+$

Step-4

To a solution of (E)-ethyl 3-(2,3-dihydro-[1,4]dioxino[2,3-b]pyridin-6-yl)acrylate (0.45 g, 1.91 mmol, 1 eq.) in a mixture of THF-ethanol (1:1, 10 mL) was added 5N aq. NaOH solution (3.82 mL, 19.1 mmol, 10 eq.) and mixture was stirred at room temperature overnight. Progress of reaction was monitored by TLC. After completion, reaction mixture was diluted with water (30 mL) and extracted with ethyl acetate (30 mL). Aqueous layer was acidified up to pH 6 and extracted with ethyl acetate (3×50 mL). Combined organic layer was washed with brine and dried over sodium sulphate. Removal of solvent under reduced pressure afforded crude (E)-3-(2,3-dihydro-[1,4]dioxino[2,3-b]pyridin-7-yl)acrylic acid (0.340 g, 39.6%) which was used in the next step without further purification.

LCMS: 208[M+1]$^+$

Step-5

To a stirred solution of (E)-3-(2,3-dihydro-[1,4]dioxino[2,3-b]pyridin-7-yl)acrylic acid (0.1 g, 0.48 mmol, 1 eq.) in THF (15 mL) at 0° C. was added triethylamine (0.07 mL, 0.579 mmol, 1.2 eq.) followed by pivaloyl chloride (0.07 mL, 0.579 mmol, 1.2 eq.) and the resulting mixture was stirred stir at 0° C. for 2 h. Progress of reaction was monitored by TLC. After the completion, reaction mixture was used as such in the next reaction.

Step-06

To a stirred solution of 5,6-dihydropyridin-2(1H)-one (0.07 g, 0.72 mmol, 1.5 eq.) in THF (10 mL) at −78° C. was added n-BuLi (0.3 mL, 0.75 mmol, 2.2 eq.) and the resulting mixture was stirred at the same temperature for 30 minutes. To this mixture was added a solution of (E)-3-(2,3-dihydro-[1,4]dioxino[2,3-b]pyridin-7-yl)acrylic pivalic anhydride in THF (15 mL) dropwise and the reaction mixture was stirred at −78° C. for 2 h. Progress of reaction was monitored by TLC. After completion, reaction mixture was diluted with ammonium chloride solution (50 mL) and extracted with ethyl acetate (3×50 mL). Combined organic layer was dried over sodium sulphate. Removal of solvent under reduced pressure crude which was purified by reversed phase HPLC to afford (E)-1-(3-(2,3-dihydro-[1,4]dioxino[2,3-b]pyridin-7-yl)acryloyl)-5,6-dihydropyridin-2(1H)-one (7 mg, 5%).

LCMS 287[M+1]$^+$ $^1$H NMR (400 MHz, CD$_3$OD) δ 7.98 (s, 1H), 7.80 (d, 1H), 7.79 (s, 1H), 7.38 (d, 1H), 7.10-6.98 (m, 1H), 4.50-4.42 (m, 2H), 4.32-4.28 (m, 2H), 3.95-4.03 (m, 2H), 2.47-2.40 (m, 2H).

Example 24

Preparation of 5-hydroxy-1-[(2E)-3-(8-methoxy-2,3-dihydro-1,4-benzodioxin-6-yl)prop-2-enoyl]-5,6-dihydropyridin-2(1H)-one Compound 25

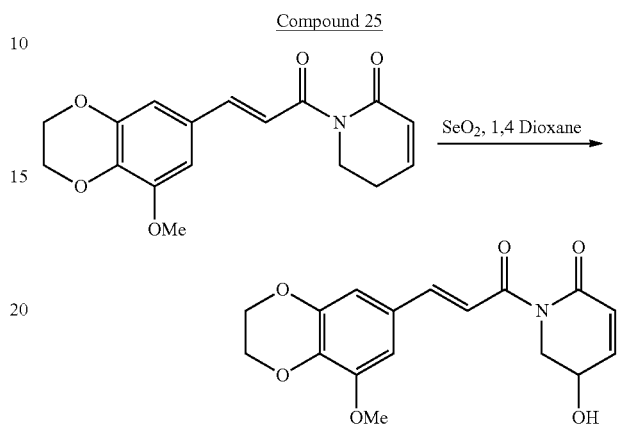

To the stirred solution of 1-[(2E)-3-(8-methoxy-2,3-dihydro-1,4-benzodioxin-6-yl)prop-2-enoyl]-5,6-dihydropyridin-2(1H)-one (300 mg, 0.95 mmol, 1 eq.) in 1,4 dioxane (6.0 mL) was added selenium dioxide (314 mg, 2.85 mmol, 3 eq.) portionwise. The reaction mixture was stirred at 120° C. in microwave for 2 h. Progress of the reaction was monitored by TLC and LCMS. After 40% completion, reaction mixture was diluted with water (20 mL) and extracted with ethyl acetate (2×50 mL). Combined organic layer was washed with brine, dried over Na$_2$SO$_4$ and concentrated under reduced pressure to obtain crude which was purified by reversed phase HPLC to afford 5-hydroxy-1-[(2E)-3-(8-methoxy-2,3-dihydro-1,4-benzodioxin-6-yl)prop-2-enoyl]-5,6-dihydropyridin-2(1H)-one (50 mg, 15.87%) as yellow solid.

LCMS: 332 [M+1]$^+$ $^1$H NMR (400 MHz, DMSO-d$_6$) δ 7.49 (d, 1H), 7.25 (d, 1H), 6.97 (dd, 1H), 6.86 (s, 1H) 6.81 (s, 1H), 5.96 (d, 1H), 5.59 (d, 1H), 4.38 (brs., 1H), 4.25 (brs, 3H), 3.90 (d, 1H), 3.84-3.71 (m, 2H).

Example 25

Preparation of (E)-1-(3-(2,3-dihydro-[1,4]dioxino[2,3-b]pyridin-7-yl)acryloyl)-6,7-dihydro-1H-azepin-2(5H)-one Compound 26

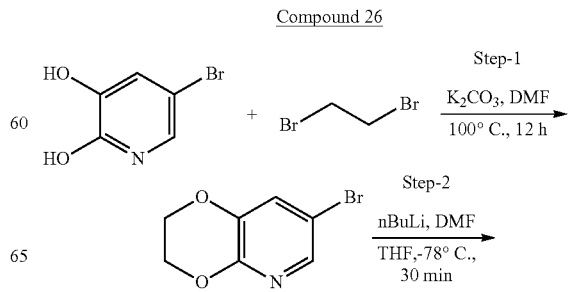

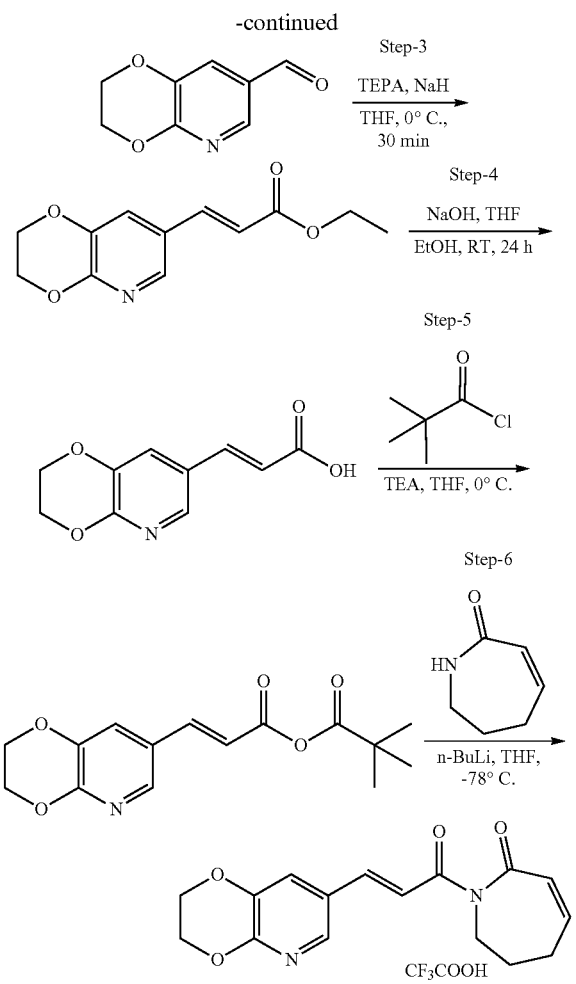

Step-1

To a solution of 5-bromopyridine-2,3-diol (10 g, 53.19 mmol, 1 eq.) in DMF (250 mL) at room temperature was added $K_2CO_3$ (21 g, 159.57 mmol, 3 eq.) followed by 1,2-dibromoethane (5.5 mL, 63.82 mmol, 1.2 eq.) dropwise. The resulting mixture was stirred at 100° C. overnight.

Progress of reaction was monitored by TLC. After the completion, reaction mixture was cooled to room temperature, diluted with ice cold water (300 mL) and extracted with DCM (3×300 mL). Combined organic layer was washed with brine and dried over anhydrous sodium sulphate. Removal of solvent under reduced pressure afforded crude was purified by Combi-Flash on silica gel using methanol-dichloromethane (0-50%) as eluents to afford 7-bromo-2,3-dihydro-[1,4]dioxino[2,3-b]pyridine (2.9 g, 25.26%).

LCMS: 215 [M+1]⁺

Step-2

To a solution of 7-bromo-2,3-dihydro-[1,4]dioxino[2,3-b]pyridine (0.500 g, 2.31 mmol, 1 eq.) in THF (15 mL) at −78° C. was added n-BuLi (1.43 mL, 0.50 mmol, 1.6 eq.) and the resulting mixture was allowed stirred at the same temperature for 30 minutes. To this solution was added a solution of DMF (0.43 mL, 5.54 mmol, 2.4 eq.) in THF (4 mL) and reaction mixture was allowed to stir at the same temperature for 2 h. Progress of reaction was monitored by TLC. After completion, the reaction mixture was brought to 0° C., diluted with saturated $NH_4Cl$ solution (50 mL) and extracted with ethyl acetate (3×50 mL). The combined organic layer was dried over $Na_2SO_4$. Removal of solvent under reduced pressure afforded 2,3-dihydro-[1,4]dioxino[2,3-b]pyridine-7-carbaldehyde (0.35 g, 92.1%) which was used in the next step without further purification.

LCMS: 166 [M+1]⁺

Step-3

To a solution of triethyl phosphonoacetate (0.618 g, 2.76 mmol, 1.3 eq.) in THF (30 mL) at 0° C. was added NaH (0.127 g, 3.18 mmol, 1.5 eq.) and the reaction mixture was allowed stirred at the same temperature for 10 minutes. To this mixture was added a solution of 2,3-dihydro-[1,4]dioxino[2,3-b]pyridine-7-carbaldehyde (0.35 g, 2.76 mmol, 1 eq.) in THF (1 mL) and reaction mixture was allowed to stir at the same temperature for 30 minutes. Progress of reaction was monitored by TLC. After the completion, the reaction mixture was diluted with brine solution (50 mL) and extracted with ethyl acetate (3×50 mL). Combined organic layer was dried over $Na_2SO_4$. Removal of solvent under reduced pressure afforded (E)-ethyl 3-(2,3-dihydro-[1,4]dioxino[2,3-b]pyridin-7-yl)acrylate (0.45 g, 90.36%) which was used in the next step without further purification.

LCMS: 236 [M+1]⁺

Step-4

To a solution of (E)-ethyl 3-(2,3-dihydro-[1,4]dioxino[2,3-b]pyridin-6-yl)acrylate (0.45 g, 1.91 mmol, 1 eq.) in a mixture of THF-ethanol (1:1, 10 mL) was added 5N aq. NaOH solution (3.82 mL, 19.1 mmol, 10 eq.) and mixture was stirred at room temperature overnight. Progress of reaction was monitored by TLC. After completion, reaction mixture was diluted with water (30 mL) and extracted with ethyl acetate (30 mL). Aqueous layer was acidified up to pH 6 and extracted with ethyl acetate (3×50 mL). Combined organic layer was washed with brine and dried over sodium sulphate. Removal of solvent under reduced pressure afforded crude (E)-3-(2,3-dihydro-[1,4]dioxino[2,3-b]pyridin-7-yl)acrylic acid (0.340 g, 39.6%) which was used in the next step without further purification.

LCMS: 208[M+1]⁺

Step-5

To a stirred solution of (E)-3-(2,3-dihydro-[1,4]dioxino[2,3-b]pyridin-7-yl)acrylic acid (0.1 g, 0.48 mmol, 1 eq.) in THF (15 mL) at 0° C. was added triethylamine (0.07 mL, 0.579 mmol, 1.2 eq.) followed by pivaloyl chloride (0.07 mL, 0.579 mmol, 1.2 eq.) and the resulting mixture was stirred stir at 0° C. for 2 h. Progress of reaction was monitored by TLC. After the completion, reaction mixture was used as such in the next reaction.

Step-6

To a stirred solution of 6,7-dihydro-1H-azepin-2(5H)-one (0.08 g, 0.71 mmol, 1.5 eq.) in THF (10 mL) at −78° C. was added n-BuLi (0.3 mL, 0.75 mmol, 2.2 eq.) and the resulting mixture was stirred at the same temperature for 30 minutes. To this mixture was added a solution of (E)-3-(2,3-dihydro-[1,4]dioxino[2,3-b]pyridin-7-yl)acrylic pivalic anhydride in THF (15 mL) dropwise and the reaction mixture was stirred at -78° C. for 2 h. Progress of reaction was monitored by TLC. After completion, reaction mixture was diluted with ammonium chloride solution (50 mL) and extracted with ethyl acetate (3×50 mL). Combined organic layer was dried over sodium sulphate. Removal of solvent under reduced pressure crude which was purified by reversed phase HPLC to afford (E)-1-(3-(2,3-dihydro-[1,4]dioxino[2,3-b]pyridin-7-yl)acryloyl)-6,7-dihydro-1H-azepin-2(5H)-one (11 mg, 6%) as TFA salt.

LCMS: 301[M+1]+

$^1$H NMR (400 MHz, DMSO-d$_6$) δ 8.01 (s, 1H), 7.60 (s, 1H), 7.37 (d, 1H), 7.23 (d, 1H), 6.65-6.55 (m, 1H), 6.03 (m, 1H), 4.45 (brs, 2H), 4.26 (brs, 2H), 3.90-3.80 (m, 2H), 2.41-2.30 (m, 2H), 1.90-1.80 (m, 2H).

Example 26

Preparation of (E)-1-(3-(pyridazin-3-yl)acryloyl)-5,6-dihydropyridin-2(1H)-one

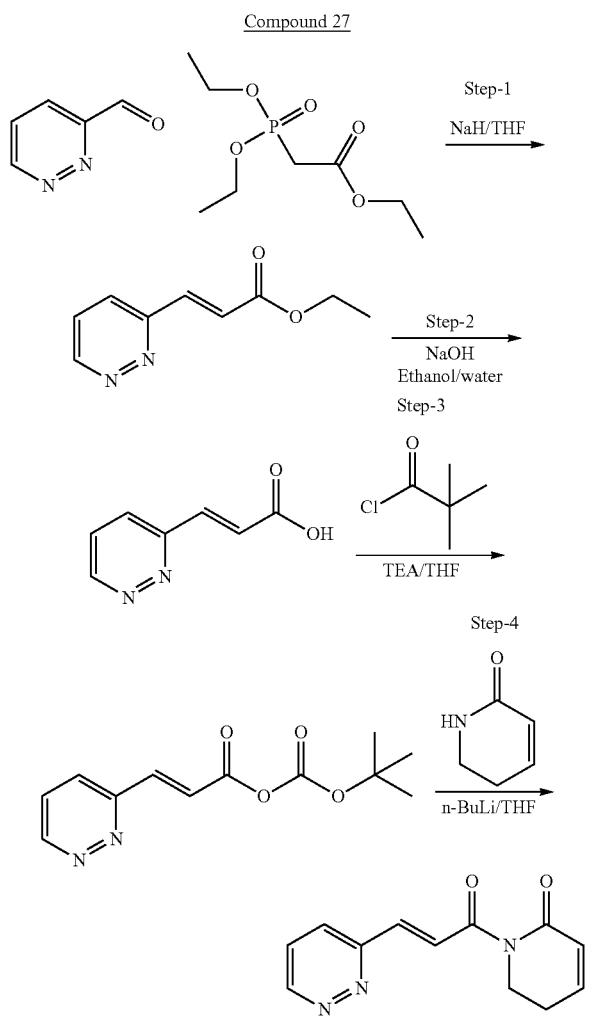

Compound 27

Step-1

To a suspension of sodium hydride (60% in mineral oil, 0.203 g, 5.09 mmol, 1.1 eq.) in THF (50 mL) was added ethyl 2-(diethoxyphosphoryl)acetate (2.07 g, 9.25 mmol, 2.0 eq.) dropwise at 0° C. and the mixture was allowed to stir at the same temperature for 30 minutes. To this mixture was added a solution of pyridazine-3-carbaldehyde (0.5 g, 4.62 mmol, 1.0 eq.) in THF (5 mL) and the resulting mixture was allowed to stir at room temperature for 1 h. Progress of reaction was monitored by TLC. After completion, reaction mixture was diluted with saturated aq. NH$_4$Cl (100 mL) and extracted with ethyl acetate (3×50 ml). Combined organic layer was washed with brine, dried over anhydrous Na$_2$SO$_4$ and evaporated to dryness under vacuum to afford crude which was purified by Combi-Flash to using ethyl acetate-hexane system as eluent to afford ethyl (E)-3-(pyridazin-3-yl)acrylate (0.42 g, 50.97%).

LCMS: 179 [M+1]+

Step-2

To a solution of ethyl (E)-3-(pyridazin-3-yl)acrylate (0.4 g, 2.24 mmol, 1.0 eq.) in ethanol (200 mL) was added a solution of sodium hydroxide (2M, 2.0 ml) in water (10 mL) and the reaction mixture was stirred at 70° C. for 3 h. Reaction mixture was concentrated under vacuum and then acidified with 2N HCl to make pH 3. The mixture was diluted saturated aq. NH$_4$Cl (25 mL) and extracted with dichloromethane (3×25 ml). The combined organic layer was washed with brine solution (50 mL) and dried over anhydrous Na$_2$SO$_4$. Removal of solvent under reduced pressure to obtain (E)-3-(pyridazin-3-yl)acrylic acid (0.29 g, 86%) as crystalline solid.

LCMS: 151 [M+1]+

Step-3

To a solution of (E)-3-(pyridazin-3-yl)acrylic acid (0.29 g, 1.93 mmol, 1.0 eq.) in dry THF was added triethylamine (0.27 ml, 2.12 mmol, 1.1 eq.) followed by pivaloyl chloride (0.26 ml, 2.12 mmol, 1.1 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.18 g, 1.85 mmol, 1.0 eq.) in dry THF at -78° C. was added n-butyllithium (2.5 M in hexane, 0.81 ml, 2.04 mmol, 1.1 eq.) and the mixture was allowed to stir at the same temperature for 30 minutes. To this solution was added a solution of (E)-pivalic (E)-3-(pyridazin-3-yl)acrylic anhydride (0.390 g, 1.67 mmol, 0.9 eq.) in THF and the reaction mixture was allowed to stir at -78° C. for 1 h. Progress of reaction was monitored by TLC and LCMS. After completion, reaction mixture was brought to 0° C., diluted with water (30 mL) and extracted with ethyl acetate (3×30 ml). Combined organic layer was washed with brine, dried over anhydrous Na$_2$SO$_4$ and evaporated to dryness under vacuum to afford crude which was purified by reversed phase HPLC to afford (E)-1-(3-(pyridazin-3-yl)acryloyl)-5,6-dihydropyridin-2(1H)-one (0.015 g, 3.52%).

LCMS: 230 [M+1]+

$^1$H NMR (400 MHz, DMSO-d$_6$) δ 9.21 (d, 1H), 8.02 (d, 1H), 7.85 (d, 1H), 7.76 (dd, 1H), 7.65 (d, 1H), 7.09-7.18 (m, 1H), 6.00 (d, 1H), 3.93 (t, 2H).

Example 27

Preparation of (E)-1-(4,4-dimethylpent-2-enoyl)-5,6-dihydropyridin-2(1H)-one Compound 28

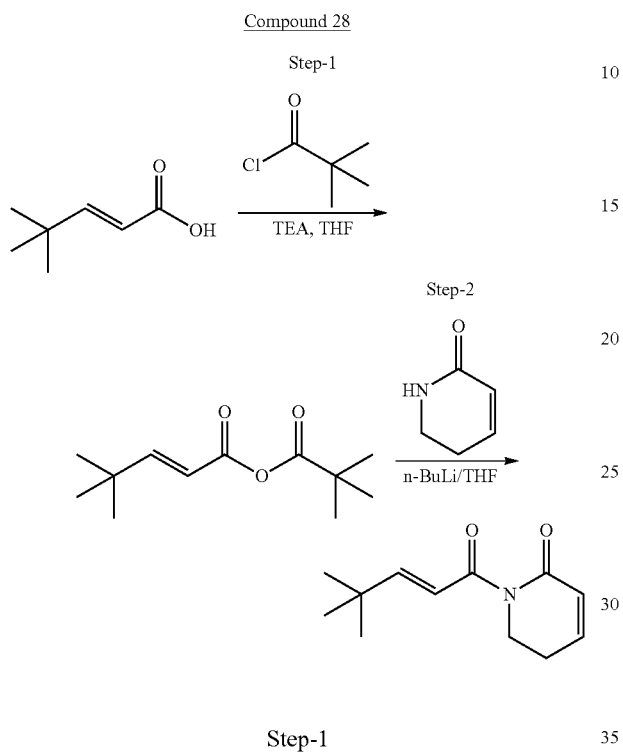

Step-1

To a solution of (E)-4,4-dimethylpent-2-enoic acid (0.3 g, 2.34 mmol, 1.0 eq.) in dry THF (10 mL) was added triethylamine (0.33 ml, 2.57 mmol, 1.1 eq.) followed by pivaloyl chloride 2 (0.30 mL, 2.57 mmol, 1.1 eq.) and the reaction mixture was stirred at 0° C. for 45 minutes. Progress of reaction was monitored by TLC. After completion, reaction mixture was filtered and the filtrate was used directly for the next step.

Step-2

To a stirred solution of 5,6-dihydropyridin-2(1H)-one (0.100 g, 1.03 mmol, 1.0 eq.) in dry THF at −78° C. was added n-butyllithium (2.5 M in hexane, 0.45 ml, 1.13 mmol, 1.1 eq.) and the mixture was allowed to stir at the same temperature for 30 minutes. To this solution was added a solution of (E)-(tert-butyl carbonic) (E)-4,4-dimethylpent-2-enoic anhydride (0.221 g, 0.92 mmol, 1.1 eq.) in THF (10 mL) and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×30 ml). Combined organic layer was washed with brine, dried over anhydrous $Na_2SO_4$ and evaporated to dryness under vacuum to afford crude which was purified by reversed phase HPLC to afford (E)-1-(4,4-dimethylpent-2-enoyl)-5,6-dihydropyridin-2(1H)-one (0.011 g, 6%).

LCMS: 208 ([M+1]+)

$^1$H NMR (500 MHz, $CDCl_3$) δ 7.02 (d, 1H), 6.84-6.96 (m, 1H), 6.78 (d, 1H), 6.00 (d, 1H), 3.98 (t, 2H), 2.44 (d, 2H), 1.11 (s, 9H).

Example 28

Preparation of 1-(3,3-diphenylacryloyl)-5,6-dihydropyridin-2(1H)-one

Compound 29

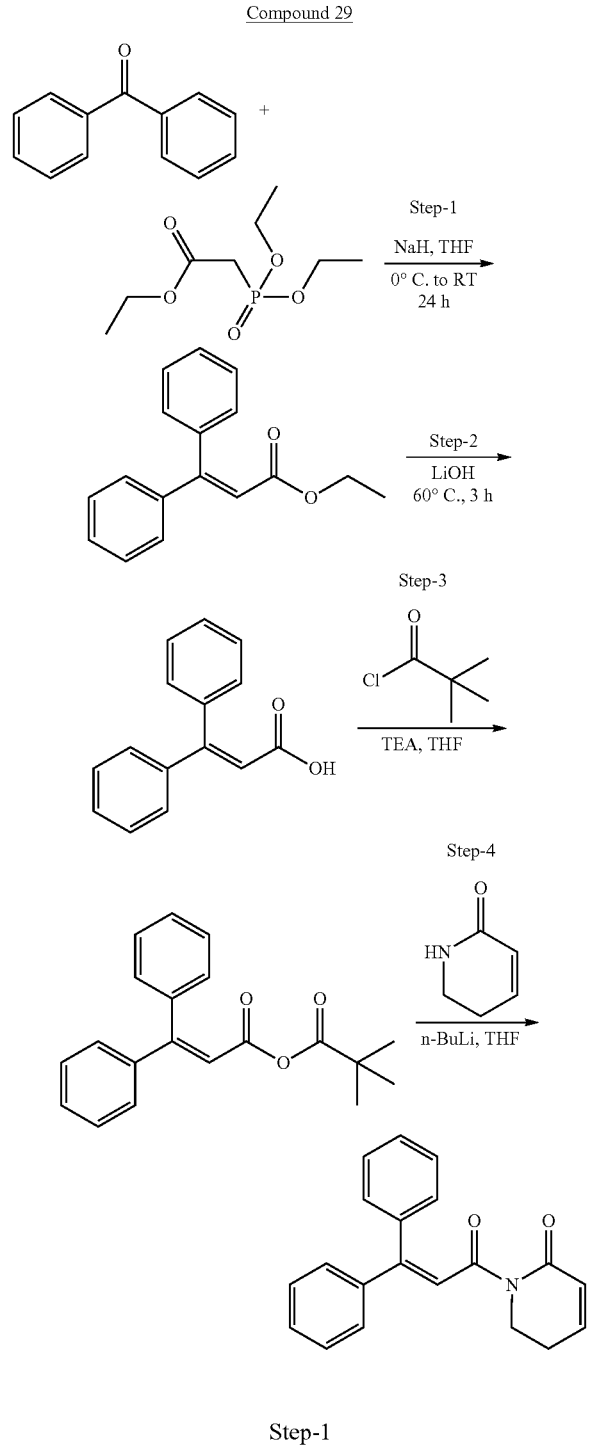

Step-1

To a suspension of sodium hydride (60% in mineral oil, 0.439 g, 10.98 mmol, 2.0 eq.) in THF (50 mL) was added ethyl 2-(diethoxyphosphoryl)acetate (2.08 mL, 10.98 mmol, 2.0 eq.) dropwise at 0° C. and the mixture was allowed to stir at the same temperature for 30 minutes. To this mixture was added a solution of diphenylmethanone (1.0 g, 5.49 mmol, 1.0 eq.) in THF (5 mL) and the resulting mixture was allowed to stir at room temperature for 24 h. Progress of reaction was monitored by TLC. After completion, reaction mixture was diluted with saturated aq. NH$_4$Cl (100 mL) and extracted with ethyl acetate (3×50 ml). Combined organic layer was washed with brine, dried over anhydrous Na$_2$SO$_4$ and evaporated to dryness under vacuum to afford crude which was purified by Combi-Flash using ethyl acetate-hexane system as eluent to afford ethyl 3,3-diphenylprop-2-enoate (0.53 g, 38.4%).

LCMS: 253 [M+1]$^+$

Step-2

To a solution of ethyl 3,3-diphenylprop-2-enoate (0.530 g, 2.10 mmol, 1.0 eq.) in ethanol (100 mL) was added a solution of lithium hydroxide (0.2 g) in water (2 mL) and the reaction mixture was stirred at 70° C. for 3 h. Progress of reaction was monitored by TLC. After completion, reaction mixture was concentrated under vacuum, acidified with 1N HCl (50 mL) and extracted with ethyl acetate (3×50 ml). Combined organic layer was washed with brine solution (50 mL) and dried over anhydrous Na$_2$SO$_4$. Removal of solvent under reduced pressure afforded 3,3-diphenylprop-2-enoic acid (0.450 g, 95.54%) as crystalline solid.

LCMS: 225 [M+1]$^+$

Step-3

To a solution of 3,3-diphenylprop-2-enoic acid (0.45 g, 2.00 mmol, 1.0 eq.) in dry THF (10 mL) was added triethylamine (0.34 ml, 2.4 mmol, 1.2 eq.) followed by pivaloyl chloride (0.284 ml, 2.4 mmol, 1.2 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.2 g, 2.05 mmol, 1.0 eq.) in dry THF at −78° C. was added n-butyllithium (2.5 M in hexane, 0.9 ml, 2.26 mmol, 1.1 eq.) and the mixture was allowed to stir at the same temperature for 30 minutes. To this solution was added a solution of 2,2-dimethylpropanoic 3,3-diphenylprop-2-enoic anhydride (0.698 g, 2.26 mmol, 1.1 eq.) in THF and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×50 mL). Combined organic layer was washed with brine, dried over anhydrous Na$_2$SO$_4$ and evaporated to dryness under vacuum to afford crude which was purified by combi flash to afford 1-(3,3-diphenylacryloyl)-5,6-dihydropyridin-2(1H)-one (0.22 g, 32.06%).

LCMS: 304 [M+1]$^+$ $^1$H NMR (400 MHz, CDCl$_3$) δ 7.39-7.19 (m, 10H), 6.90 (s, 1H), 6.85-7.75 (m, 1H), 5.97 (d, 1H), 3.80 (t, 2H), 2.25-2.18 (m, 2H).

Example 29

Preparation of (E)-1-(3-(8-methoxy-2,3-dihydrobenzo[b][1,4]dioxin-6-yl)acryloyl)-5,5-dimethyl-5,6-dihydropyridin-2(1H)-one Compound 30

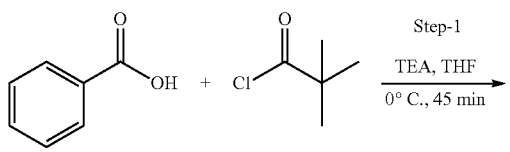

Step-1

TEA, THF

0° C., 45 min

Step-2

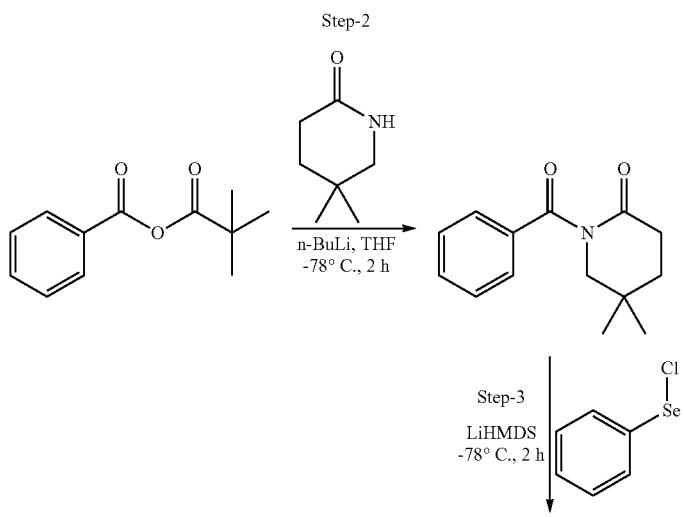

Step-3

LiHMDS

−78° C., 2 h

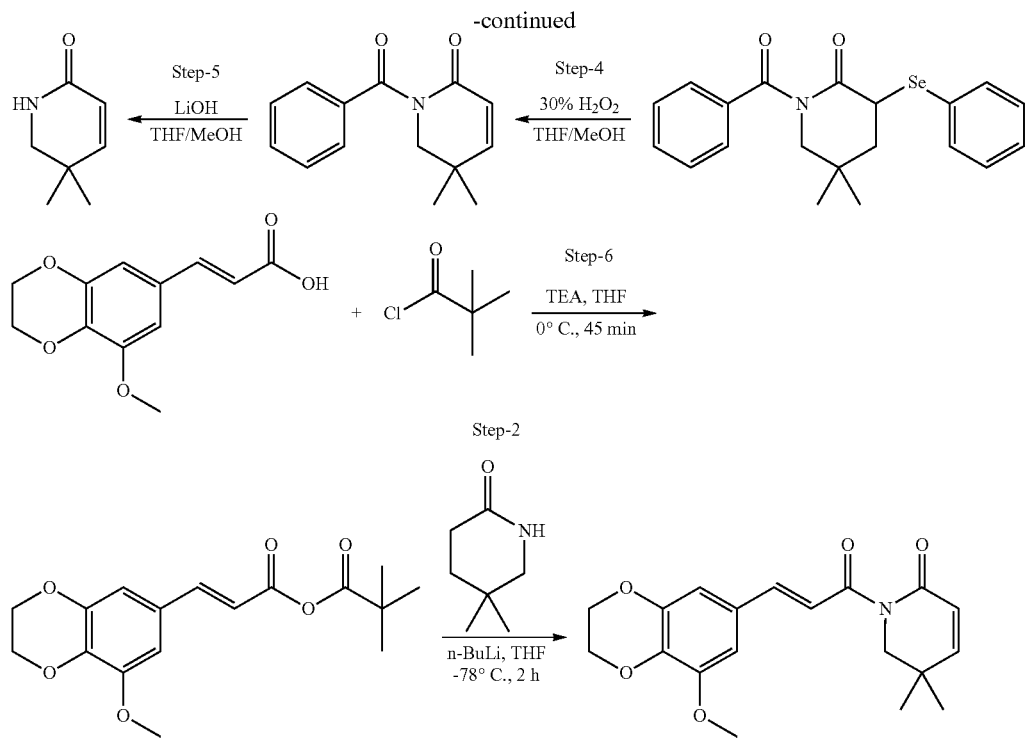

Step-1

To a solution of benzoic acid (1.15 g, 9.41 mmol, 1.0 eq.) in dry THF was added triethylamine (1.50 mL, 11.30 mmol, 1.2 eq.) and pivaloyl chloride (1.39 mL, 11.30 mmol, 1.2 eq.) and the reaction mixture was stirred at 0° C. for 45 minutes. Progress of reaction was monitored by TLC. After completion, reaction mixture was filtered and the filtrate was used directly for the next step.

Step-2

To a stirred solution of 5,5-dimethylpiperidin-2-one (1 g, 7.48 mmol, 0.8 eq.) in dry THF at −78° C. was added n-butyllithium (2.5 M in hexane, 3 mL, 7.50 mmol, 0.8 eq.) and the mixture was allowed to stir at the same temperature for 30 minutes. To this solution was added benzoic pivalic anhydride (1.93 g, 9.35 mmol, 1 eq.). Reaction mixture was allowed to stir at −78° C. for 90 minutes. Progress of reaction was monitored by TLC and LCMS. After completion, reaction mixture was brought to 0° C., diluted with water (40 mL) and extracted with ethyl acetate (3×50 mL). Combined organic layer was washed with brine, dried over anhydrous $Na_2SO_4$ and evaporated to dryness under vacuum to afford crude which was purified by CombiFlash on silica gel using ethyl acetate-hexane system as eluent to afford 1-benzoyl-5,5-dimethylpiperidin-2-one (0.550 g, 25.46%).

Step-3

To a stirred solution of 1-benzoyl-5,5-dimethylpiperidin-2-one (0.3 g, 1.29 mmol, 1 eq.) in dry THF at −78° C. was added LiHMDS (1 M in THF, 2.59 mL, 2.59 mmol, 2 eq.) and the mixture was allowed to stir at the same temperature for 30 minutes. To this solution was added phenyl hypochloroselenoite (0.496 g, 2.59 mmol, 2 eq.). Reaction mixture was allowed to stir at −78° C. for 90 min. Progress of reaction was monitored by TLC and LCMS. Reaction mixture was brought to 0° C., diluted with water (35 mL) and extracted with ethyl acetate (3×40 mL). Combined organic layer was washed with brine, dried over anhydrous $Na_2SO_4$ and evaporated to dryness under vacuum to afford crude which was purified by CombiFlash on silica gel using ethyl acetate-hexane system as eluent to afford 1-benzoyl-5,5-dimethyl-3 (phenyl selanyl)piperidin-2-one (0.3 g, 60%).

Step-4

To a stirred solution of 1-benzoyl-5,5-dimethyl-3-(phenylselanyl)piperidin-2-one (0.3 g, 0.77 mmol, 1 eq.) in dry THF at 0° C. was added 30% aq. $H_2O_2$ (0.4 mL, 3.88 mmol, 5 eq.) and the mixture was allowed to stir at the same temperature for 10 minutes followed by stirring at room temperature for 20 min. Progress of reaction was monitored by TLC and LCMS. Reaction mixture was diluted with water (20 mL) and extracted with ethyl acetate (3×25 mL). Combined organic layer was washed with brine, dried over anhydrous $Na_2SO_4$ and evaporated to dryness under vacuum to afford crude 1-benzoyl-5,5-dimethyl-5,6-dihydropyridin-2(1H)-one (0.250 g crude) which is used in next step without purification.

Step-5

To a stirred solution of 1-benzoyl-5,5-dimethyl-5,6-dihydropyridin-2(1H)-one (0.230 g, 1.00 mmol, 1 eq.) in mixture of MeOH (5 mL) and THF (5 mL) and the mixture was allowed to stir at room temperature for 10 minutes followed by addition of LiOH (0.144 g, 6.01 mmol, 6 eq.). Reaction mixture was allowed to at same temperature for 1 h. Progress of reaction was monitored by TLC and LCMS. Reaction mixture was diluted with water (20 mL) and extracted with ethyl acetate (3×35 mL). Combined organic layer was washed with brine, dried over anhydrous $Na_2SO_4$ and evaporated to dryness under vacuum to afford crude 5,5-dimethyl-5,6-dihydropyridin-2(1H)-one (0.11 g, 88%) which was used in the next step without purification.

Step-6

To a solution of (E)-3-(8-methoxy-2,3-dihydrobenzo[b][1,4]dioxin-6-yl)acrylic acid (0.205 g, 0.869 mmol, 1.0 eq.) in dry THF was added triethylamine (0.14 mL, 1.04 mmol, 1.2 eq.) and pivaloyl chloride (0.14 mL, 1.04 mmol, 1.2 eq.) and the reaction mixture was stirred at 0° C. for 45 minutes. Progress of reaction was monitored by TLC. After completion, reaction mixture was filtered and the filtrate was used directly for the next step.

Step-7

To a stirred solution of 5,5-dimethyl-5,6-dihydropyridin-2(1H)-one (0.110 g, 0.867 mmol, 1 eq.) in dry THF at −78° C. was added n-butyllithium (2.5 M in hexane, 0.38 mL, 0.953 mmol, 1.1 eq.) and the mixture was allowed to stir at the same temperature for 30 minutes. To this solution was added (E)-3-(8-methoxy-2,3-dihydrobenzo[b][1,4]dioxin-6-yl)acrylic pivalic anhydride (0.277 g, 0.867 mmol, 1 eq.). Reaction mixture was allowed to stir at −78° C. for 90 min. Progress of reaction was monitored by TLC and LCMS. Reaction mixture was brought to 0° C., diluted with water (35 mL) and extracted with ethyl acetate (3×40 mL). Combined organic layer was washed with brine, dried over anhydrous $Na_2SO_4$ and evaporated to dryness under vacuum to afford crude which was purified by reversed phase HPLC to afford (E)-1-(3-(8-methoxy-2,3-dihydrobenzo[b][1,4]dioxin-6-yl)acryloyl)-5,5-dimethyl-5,6-dihydropyridin-2(1H)-one (20 mg, 6.75%).

LCSM: 344[M+1]$^+$ $^1$H NMR (400 MHz, CDCl$_3$) δ 7.62 (d, 1H), 7.42 (d, 1H), 6.80 (s, 1H), 6.75 (s, 1H), 6.62 (d, 1H), 5.87 (d, 1H), 4.39-4.31 (m, 2H), 4.30-4.25 (m, 2H), 3.93 (s, 3H), 3.79 (s, 3H), 1.18 (s, 6H).

Example 30

Preparation of (E)-1-(3-(2,3-dihydro-[1,4]dioxino[2,3-b]pyridin-6-yl)acryloyl)-1,5,6,7-tetrahydroazepin-2-one Compound 31

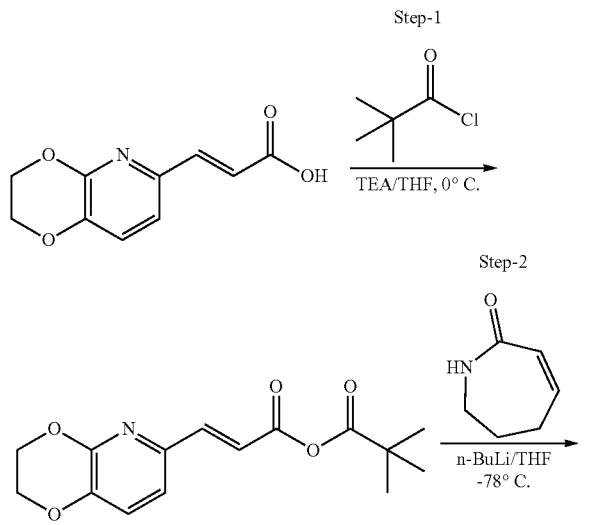

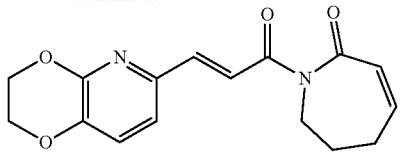

Step-1

To a stirred solution of (E)-3-(2,3-dihydro-[1,4]dioxino[2,3-b]pyridin-6-yl)acrylic acid (0.7 g, 3.38 mmol, 1 eq.) in THF (15 mL) at 0° C. was added triethylamine (0.5 mL, 4.05 mmol, 1.2 eq.) followed by pivaloyl chloride (0.5 mL, 4.05 mmol, 1.2 eq.) and the resulting mixture was stirred stir at 0° C. for 2 h. Progress of reaction was monitored by TLC. After the completion, reaction mixture was used as such in the next reaction.

Step-2

To a stirred solution of 1,5,6,7-tetrahydroazepin-2-one (0.4 g, 1.37 mmol, 1.5 eq.) in THF (15 mL) at −78° C. was added n-BuLi (1.2 mL, 3.02 mmol, 2.2 eq.) and the resulting mixture was stirred at the same temperature for 30 minutes. To this mixture was added a solution of (E)-3-(2,3-dihydro-[1,4]dioxino[2,3-b]pyridin-6-yl)acrylic pivalic anhydride in THF (15 mL) dropwise and the reaction mixture was stirred at −78° C. for 2 h. Progress of reaction was monitored by TLC. After completion, reaction mixture was diluted with ammonium chloride solution (50 mL) and extracted with ethyl acetate (3×50 mL). Combined organic layer was dried over sodium sulphate. Removal of aolvent under reduced pressure crude which was purified by reversed phase HPLC to afford (E)-1-(3-(2,3-dihydro-[1,4]dioxino[2,3-b]pyridin-6-yl)acryloyl)-1,5,6,7-tetrahydroazepin-2-one (20 mg, 4.8%).

LCMS: 301[M+1]$^+$ $^1$H NMR (400 MHz, CDCl$_3$) δ 7.59 (s, 2H), 7.17 (d, 2H), 7.03 (d, 2H), 6.60-6.48 (m, 1H), 6.08 (d, 1H), 4.45-4.40 (m, 2H), 4.25-4.20 (m, 2H), 3.99-3.92 (m, 2H), 2.42-2.35 (m, 2H), 2.20-1.92 (m, 2H).

Example 31

Preparation of 5-hydroxy-1-[(2E)-3-(pyrimidin-2-yl)prop-2-enoyl]-5,6-dihydropyridin-2(1H)-one Compound 32

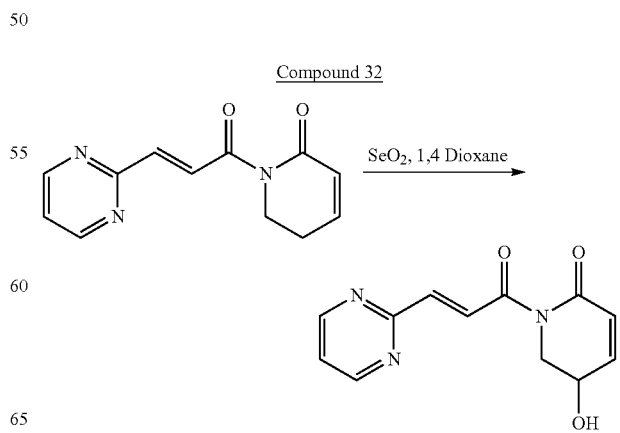

To the stirred solution of 1-[(2E)-3-(pyrimidin-2-yl)prop-2-enoyl]-5,6-dihydropyridin-2(1H)-one (500 mg, 2.18 mmol, 1 eq.) in 1,4 dioxane (15 mL) was added selenium dioxide (720 mg, 6.54 mmol, 3 eq.) portionwise. The reaction mixture was stirred at 120° C. in microwave for 2 h. Progress of the reaction was monitored by TLC and LCMS. After 40% completion, reaction mixture was diluted with water (20 mL) and extracted with ethyl acetate (2×50 mL). Combined organic layer was washed with brine, dried over $Na_2SO_4$ and concentrated under reduced pressure to obtain crude which was purified by reversed phase HPLC to afford 5-hydroxy-1-[(2E)-3-(pyrimidin-2-yl)prop-2-enoyl]-5,6-dihydropyridin-2(1H)-one (100 mg, 18.87%) as white solid.

LCMS: 246 [M+1]$^+$ $^1$H NMR (400 MHz, CDCl$_3$) δ 8.87 (d, 2H), 8.00 (d, 1H), 7.47 (t, 1H), 7.39 (d, 1H), 7.10-6.95 (m, 1H), 5.99 (d, 1H), 5.62 (d, 1H), 4.40 (brs, 1H), 4.00-3.82 (m, 2H).

Example 32

Preparation of (E)-5,5-dimethyl-1-(3-(pyrimidin-2-yl)acryloyl)-5,6-dihydropyridin-2(1H)-one

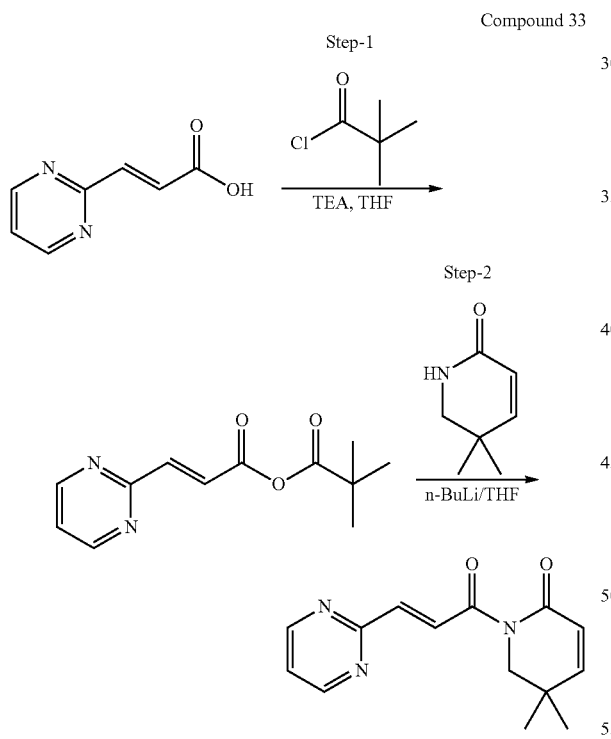

Compound 33

Step-1

To a solution of (E)-3-(pyrimidin-2-yl)acrylic acid (0.150 g, 0.99 mmol, 0.99 eq.) in dry THF was added triethylamine (0.16 mL, 1.198 mmol, 1.2 eq.) and pivaloyl chloride (0.14 mL, 1.198 mmol, 1.2 eq.) the reaction mixture was stirred at 0° C. for 45 minutes. Progress of the reaction was monitored by TLC. After completion, reaction mixture was filtered and the filtrate was used directly for the next step.

Step-2

To a stirred solution of 5,5-dimethyl-5,6-dihydropyridin-2(1H)-one (0.1 g, 0.80 mmol, 0.8 eq.) in dry THF at −78° C. was added n-butyllithium (2.5 M in hexane, 0.3 mL, 0.80 mmol, 0.8 eq.) and the mixture was allowed to stir at the same temperature for 30 minutes. To this solution was added (E)-pivalic (E)-3-(pyrimidin-2-yl)acrylic anhydride (0.234 g, 1.00 mmol, 1 eq.). Reaction mixture was allowed to stir at −78° C. for 1 h. Progress of reaction was monitored by TLC and LCMS. Reaction mixture was brought to 0° C., diluted with water (30 mL) and extracted with ethyl acetate (3×30 mL). Combined organic layer was washed with brine, dried over anhydrous $Na_2SO_4$ and evaporated to dryness under vacuum to afford crude which was purified by Combi-Flash to afford (E)-5,5-dimethyl-1-(3-(pyrimidin-2-yl)acryloyl)-5,6-dihydropyridin-2(1H)-one (80 mg, 34.18%).

LCMS: 258 [M+1]$^+$ $^1$H NMR (400 MHz, CDCl$_3$) δ 8.78 (d, 2H), 8.11 (d, 1H), 7.67 (d, 1H), 7.19 (t, 1H), 6.65 (d, 1H), 5.88 (d, 1H), 3.80 (s, 2H), 1.19 (s, 6H).

Example 33

Preparation of 1-[(2E)-3-(tetrahydro-2H-pyran-4-yl)prop-2-enoyl]-5,6-dihydropyridin-2(1H)-one

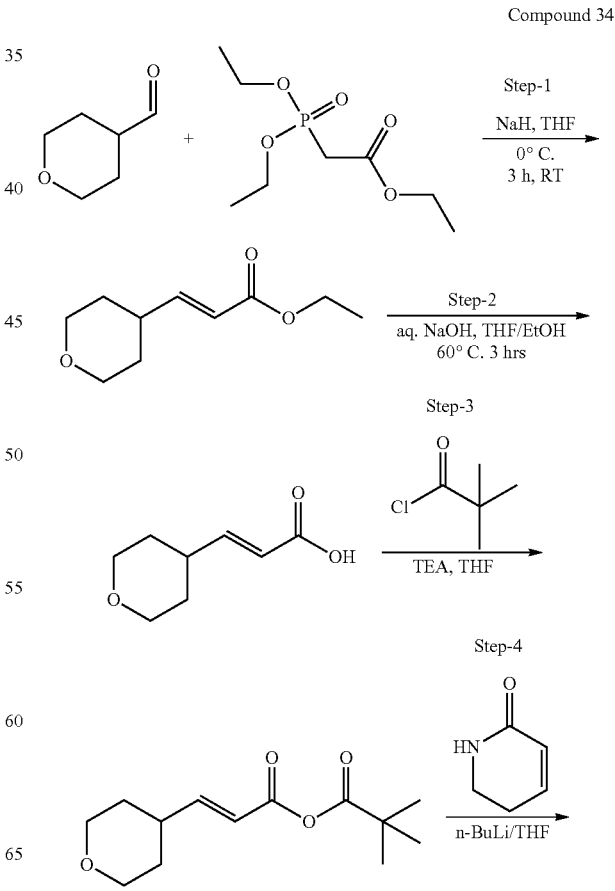

Compound 34

117

-continued

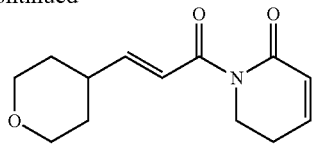

Step-1

To a suspension of sodium hydride (60% in mineral oil, 0.44 g, 10.72 mmol, 1.2 eq.) in THF (20 mL) was added ethyl 2-(diethoxyphosphoryl)acetate (2.1 g, 9.38 mmol, 1.05 eq.) dropwise at 0° C. and the mixture was allowed to stir at the same temperature for 30 minutes. To this mixture was added a solution of tetrahydro-2H-pyran-4-carbaldehyde (1.0 g, 0.93 mmol, 1.0 eq.) in THF (5 mL) and the resulting mixture was allowed to stir at room temperature for 2 h.

Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash to using ethyl acetate-hexane system as eluent to afford ethyl (2E)-3-(tetrahydro-2H-pyran-4-yl)prop-2-enoate (1.2 g, 74.53%).

LCMS: 185 [M+1]$^+$

Step-2

To a solution of ethyl (2E)-3-(tetrahydro-2H-pyran-4-yl) prop-2-enoate (1.2 g, 2.10 mmol, 1.0 eq.) in ethanol:THF (1:1, 20 mL) was added sodium hydroxide (1.5 g) in water (6.0 mL) and the reaction mixture was stirred at room temperature for 3 h. Reaction mixture was concentrated under vacuum and then acidified with 1N HCL. The mixture was diluted with water (100 mL) and extracted with ethyl acetate (3×50 mL). The combined organic layer was washed with brine solution (50 mL) and dried over anhydrous Na$_2$SO$_4$. Removal of solvent under reduced pressure to obtain (2E)-3-(tetrahydro-2H-pyran-4-yl)prop-2-enoic acid (0.80 g, 79.20%).

LCMS: 157 [M+1]+

Step-3

To a solution of (2E)-3-(tetrahydro-2H-pyran-4-yl)prop-2-enoic acid (0.20 g, 1.28 mmol, 1.0 eq.) in dry THF (20 mL) was added triethylamine (0.21 mL, 1.53 mmol, 1.2 eq.) followed by pivaloyl chloride (0.189 mL, 1.53 mmol, 1.2 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.109 g, 1.12 mmol, 0.9 eq.) in dry THF at −78° C. was added n-butyllithium (2.5 M in hexane, 0.45 mL, 1.1 eq.) and the mixture was allowed to stir at the same temperature for 30 minutes. To this solution was added a solution of 2,2-dimethylpropanoic (2E)-3-(tetrahydro-2H-pyran-4-yl) prop-2-enoic anhydride (0.300 g, 1.24 mmol, 1.0 eq.) in THF and the reaction mixture was allowed to stir at −78° C.

118 for 1 h. Progress of reaction was monitored by TLC and LCMS. After completion, reaction mixture was brought to 0° C., diluted with water (30 mL) and extracted with ethyl acetate (3×50 mL). Combined organic layer was washed with brine, dried over anhydrous Na$_2$SO$_4$ and evaporated to dryness under vacuum to afford crude which was purified by Combi-flash to afford 1-[(2E)-3-(tetrahydro-2H-pyran-4-yl) prop-2-enoyl]-5,6-dihydropyridin-2(1H)-one (0.05 g, 17.06%). LCMS: 236 [M+1]$^+$ $^1$H NMR (400 MHz, CDCl$_3$) δ 6.98-6.90 (m, 2H), 6.83 (d, 1H), 6.00 (d, 1H), 4.10-3.90 (m, 4H), 3.50-3.38 (m, 2H), 2.50-2.38 (m, 3H), 1.78-1.65 (m, 2H), 1.62-1.50 (m, 2H).

Example 34

(E)-3-chloro-1-(3-(pyrimidin-2-yl)acryloyl)-5,6-dihydropyridin-2(1H)-one

Compound 35

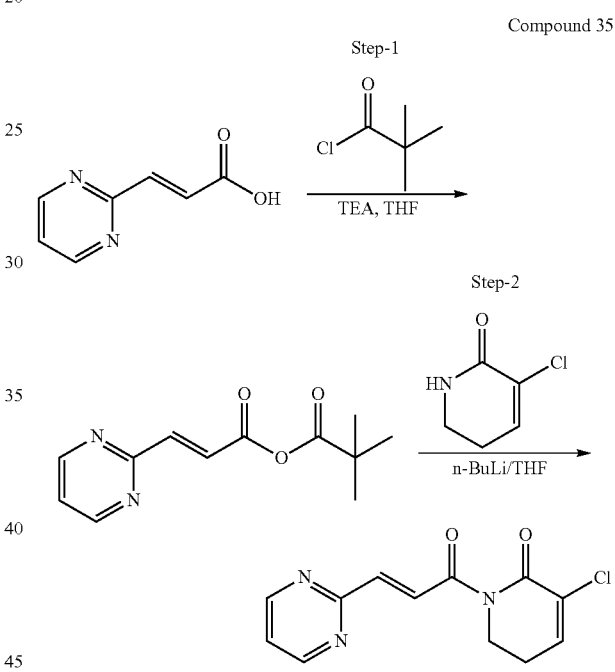

Step-1

To a solution of (E)-3-(pyrimidin-2-yl)acrylic acid (0.126 g, 0.839 mmol, 1 eq.) in dry THF was added triethylamine (0.14 mL, 1.00 mmol, 1.2 eq.) and pivaloyl chloride (0.1 mL, 0.755 mmol, 0.9 eq.) the reaction mixture was stirred at 0° C. for 45 minutes. Progress of reaction was monitored by TLC. After completion, reaction mixture was filtered and the filtrate was used directly for the next step.

Step-2

To a stirred solution of 3-chloro-5,6-dihydropyridin-2 (1H)-one (0.1 g, 0.755 mmol, 0.9 eq.) in dry THF at −78° C. was added n-butyllithium (1.8 M in hexane, 0.41 mL, 0.755 mmol, 0.9 eq.) and the mixture was allowed to stir at the same temperature for 30 minutes. To this solution was added (E)-pivalic (E)-3-(pyrimidin-2-yl)acrylic anhydride (0.196 g, 0.839 mmol, 1 eq.). Reaction mixture was allowed to stir at −78° C. for 1 h. Progress of reaction was monitored by TLC and LCMS. Reaction mixture was brought to 0° C., diluted with water (30 mL) and extracted with ethyl acetate (3×25 mL). Combined organic layer was washed with brine, dried over anhydrous Na$_2$SO$_4$ and evaporated to dryness under vacuum to afford crude which was purified by Combi-Flash to afford (E)-3-chloro-1-(3-(pyrimidin-2-yl)acryloyl)-5,6-dihydropyridin-2(1H)-one (55 mg, 25%).

LCMS: 264[M+1]$^+$ $^1$H NMR (400 MHz, CDCl$_3$) δ 8.78 (d, 1H), 8.08 (d, 1H), 7.65 (d, 1H), 7.20 (t, 1H), 7.10 (t, 1H), 4.09 (t, 2H), 2.61-2.55 (m, 2H).

Example 35

Preparation of (E)-4-chloro-1-(3-(pyrimidin-2-yl)acryloyl)-5,6-dihydropyridin-2(1H)-one

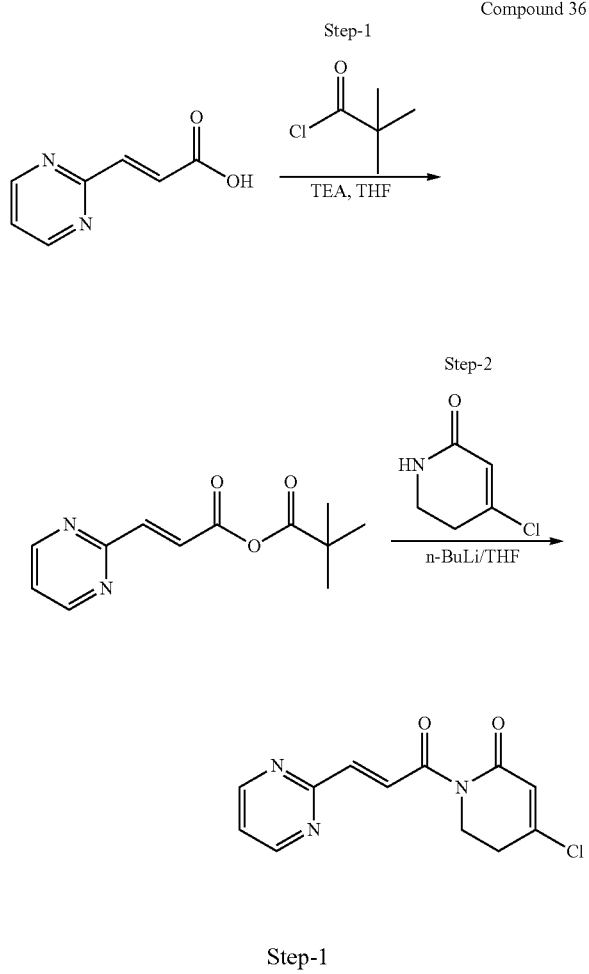

Step-1

To a solution of (E)-3-(pyrimidin-2-yl)acrylic acid (0.126 g, 0.839 mmol, 1 eq.) in dry THF was added triethylamine (0.14 mL, 1.00 mmol, 1.2 eq.) and pivaloyl chloride (0.1 mL, 0.755 mmol, 0.9 eq.) the reaction mixture was stirred at 0° C. for 45 minutes. Progress of reaction was monitored by TLC. After completion, reaction mixture was filtered and the filtrate was used directly for the next step.

Step-2

To a stirred solution of 4-chloro-5,6-dihydropyridin-2(1H)-one (0.1 g, 0.755 mmol, 0.9 eq.) in dry THF at −78° C. was added n-butyllithium (1.8 M in hexane, 0.41 mL, 0.755 mmol, 0.9 eq.) and the mixture was allowed to stir at the same temperature for 30 minutes. To this solution was added (E)-pivalic (E)-3-(pyrimidin-2-yl)acrylic anhydride (0.196 g, 0.839 mmol, 1 eq.). Reaction mixture was allowed to stir at −78° C. for 1 h. Progress of reaction was monitored by TLC and LCMS. Reaction mixture was brought to 0° C., diluted with water (30 mL) and extracted with ethyl acetate (3×25 ml). Combined organic layer was washed with brine, dried over anhydrous Na$_2$SO$_4$ and evaporated to dryness under vacuum to afford crude which was purified by CombiFlash to afford (E)-4-chloro-1-(3-(pyrimidin-2-yl)acryloyl)-5,6-dihydropyridin-2(1H)-one (120 mg, 61.22%).

LCMS: 264[M+1]$^+$ $^1$H NMR (400 MHz, CDCl$_3$) δ 8.79 (d, 2H), 8.07 (d, 1H), 7.65 (d, 1H), 7.20 (t, 1H), 6.22 (s, 1H), 4.18-4.08 (m, 2H), 2.85-2.75 (m, 2H).

Example 36

Preparation of (E)-5-fluoro-1-(3-(pyrimidin-2-yl)acryloyl)-5,6-dihydropyridin-2(1H)-one

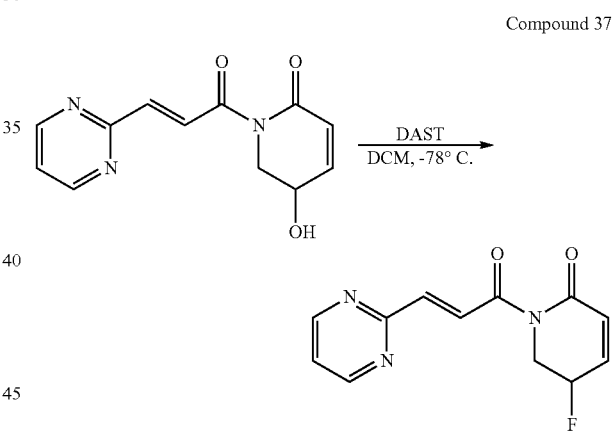

To a stirred solution of (E)-5-hydroxy-1-(3-(pyrimidin-2-yl)acryloyl)-5,6-dihydropyridin-2(1H)-one (0.07 g, 0.285 mmol, 1 eq.) in DCM (8 mL) was added DAST (0.15 mL, 1.14 mmol, 4 eq.) and the reaction mixture was stirred at −78° C. for 1 h. Progress of reaction was monitored by TLC. Reaction mixture was brought to room temperature, diluted with ammonium chloride solution (15 mL) and extracted using ethyl acetate (2×20 mL). Combined organic layer was washed with brine and dried over anhydrous sodium sulphate. Removal of solvent under reduced pressure afforded crude which was purified by Combi-Flash on silica gel using ethyl acetate-hexane system as eluent to afford (E)-5-fluoro-1-(3-(pyrimidin-2-yl)acryloyl)-5,6-dihydropyridin-2(1H)-one (15 mg, 21.42%).

LCMS: 248 [M+1]$^+$ $^1$H NMR (CDCl$_3$, 400 MHz) δ (8.88 (d, 2H), 8.10 (d, 1H), 7.70 (d, 2H), 7.20 (t, 1H), 6.99-6.90 (m 1H), 6.30-6.20 (m, 1H), 5.35-5.28 (m, 1H), 4.60-4.43 (m, 1H), 4.10-3.90 (m, 1H).

Example 37

Preparation (E)-1-(3-(piperidin-4-yl)acryloyl)-6,7-dihydro-1H-azepin-2(5H)-one

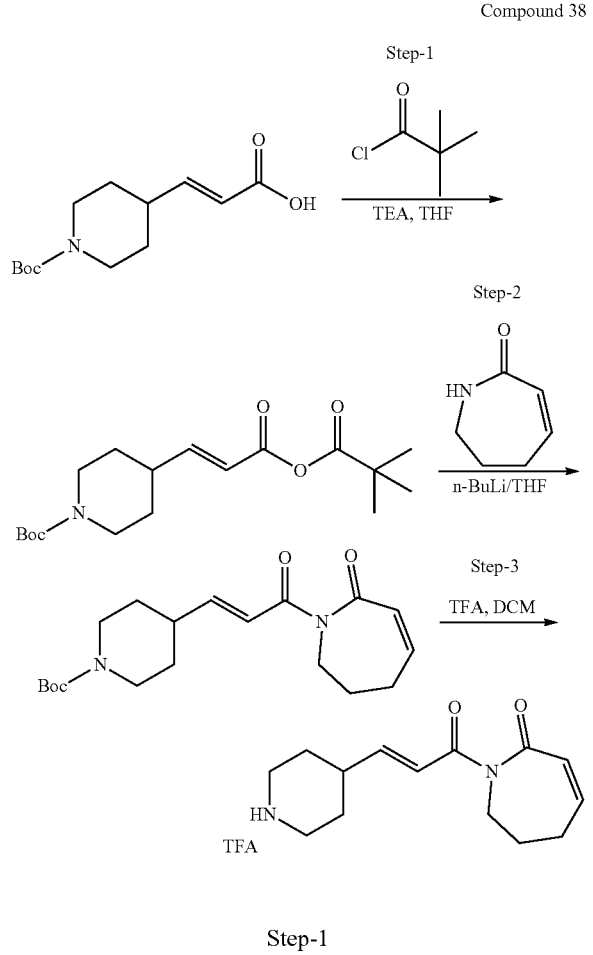

Compound 38

Step-1

To a solution of (2E)-3-[1-(tert-butoxycarbonyl)piperidin-4-yl]prop-2-enoic acid (0.90 g, 3.52 mmol, 1.0 eq.) in dry THF (20 mL) was added triethylamine (0.60 mL, 4.23 mmol, 1.2 eq.) followed by pivaloyl chloride (0.509 mL, 4.23 mmol, 1.2 eq.) and the reaction mixture was stirred at 0° C. for 45 minutes. Progress of reaction was monitored by TLC. After completion, reaction mixture was filtered and the filtrate was used directly for the next step.

Step-2

To a stirred solution of 1,5,6,7-tetrahydro-2H-azepin-2-one (0.324 g, 2.91 mmol, 0.9 eq.) in dry THF at −78° C. was added n-butyllithium (2.5 M in hexane, 1.16 mL, 1.1 eq.) and the mixture was allowed to stir at the same temperature for 30 minutes. To this solution was added a solution of anhydride (1.1 g, 3.24 mmol, 1.0 eq.) in THF and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×50 mL). Combined organic layer was washed with brine, dried over anhydrous $Na_2SO_4$ and evaporated to dryness under vacuum to afford crude which was purified by Combi-flash to afford (0.8 g, 71.42%).

LCMS: 349 [M+1]$^+$

Step-3

To a stirred solution of 5,6-dihydropyridin-2(1H)-one (0.324 g, 2.91 mmol, 0.9 eq.) in dry DCM at 0° C. was added TFA (0.27 mL, 6.0 eq.) and the mixture was allowed to stir at room temperature for 30 minutes. Progress of reaction was monitored by TLC and LCMS. Solvent was removed under reduced pressure to give oily residue. Residue was dissolved in ethanol (3 mL) and diluted with pentane (10 mL). Solid was filtered and lyophilized to give (E)-1-(3-(piperidin-4-yl)acryloyl)-6,7-dihydro-1H-azepin-2(5H)-one (150 mg, 75.75%).

LCMS: 249 [M+1]$^+$ $^1$H NMR (400 MHz, DMSO-$d_6$) δ 8.58 (brs, 1H), 8.23 (brs, 1H), 6.85-6.55 (m, 3H), 6.00 (d, 1H), 3.85-3.76 (m, 2H), 3.40-3.22 (m, 2H), 3.00-2.81 (m, 2H), 2.40-2.25 (m, 2H), 1.95-1.79 (m, 5H), 1.60-1.40 (m, 2H).

Example 38

Preparation of (E)-1-(3-(pyridazin-4-yl)acryloyl)-5,6-dihydropyridin-2(1H)-one

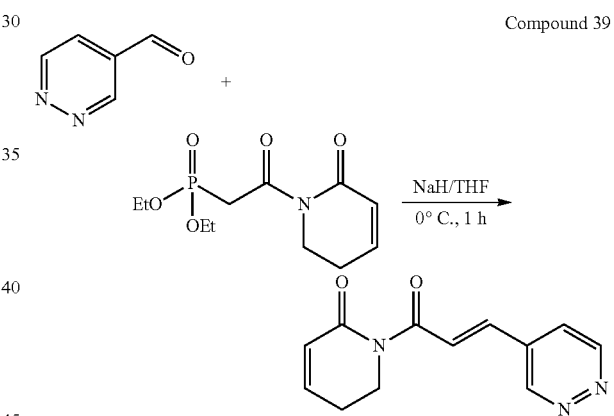

Compound 39

To a solution of diethyl 2-oxo-2-(2-oxo-5,6-dihydropyridin-1(2H)-yl)ethylphosphonate (350 mg, 1.27 mmol, 0.69 eq.) in THF (10 mL) at 0° C. was added NaH (80 mg, 2.00 mmol, 1.08 eq.) and the reaction mixture was allowed to stir at the same temperature for 10 minutes. To this mixture was added a solution of pyridazine-4-carbaldehyde (200 mg, 1.85 mmol, 1 eq.) in THF (5 mL) and the reaction mixture was allowed to stir at the same temperature for 1 h. Progress of reaction was monitored by TLC. After completion, reaction mixture was diluted with saturated aq. Ammonium chloride (30 mL) and extracted with ethyl acetate (3×30 mL). Combined organic layer was washed with brine (30 mL) and dried over anhydrous sodium sulfate. Removal of solvent under reduced pressure afforded crude which was purified by Combi-Flash on silica gel using ethyl acetate-hexane system as eluent to afford (E)-1-(3-(pyridazin-4-yl)acryloyl)-5,6-dihydropyridin-2(1H)-one (45 mg, 27%).

LCMS: 230 [M+1]$^+$ $^1$H NMR (CDCl$_3$, 400 MHz) δ 9.33 (s, 1H), 9.22 (s, 1H), 7.73 (d, 1H), 7.58 (d, 1H), 7.55 (d, 1H), 7.03-6.97 (m, 1H), 6.03 (d, 1H), 4.05-4.00 (m, 2H), 2.58-2.45 (m, 2H).

Example 39

Preparation 3-bromo-1-[(2E)-3-(pyrimidin-2-yl)prop-2-enoyl]-5,6-dihydropyridin-2(1H)-one

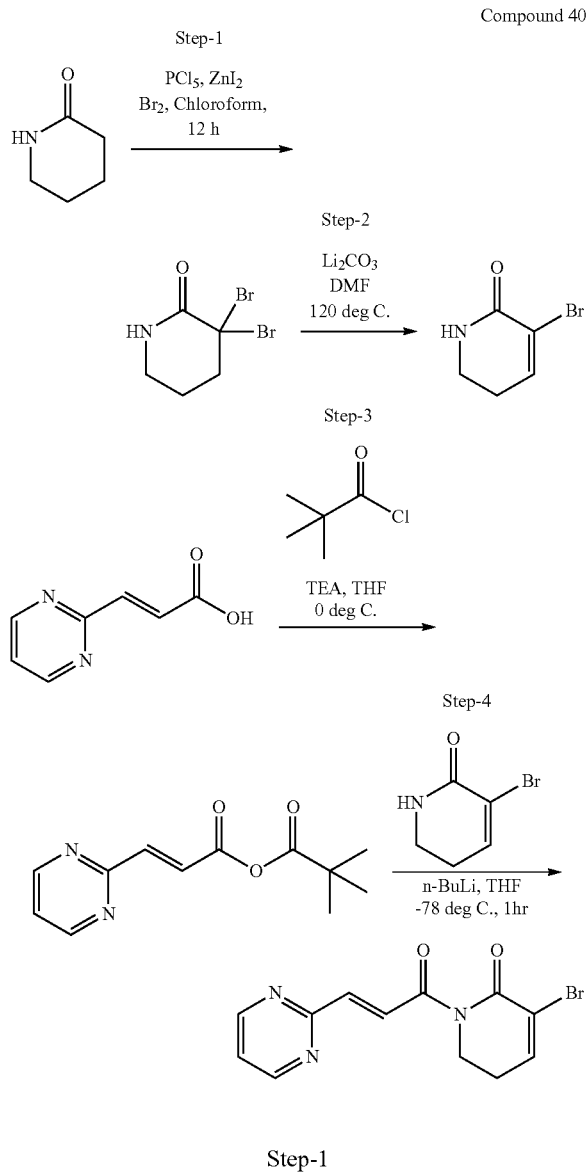

Compound 40

Step-1

To a stirred solution of piperidin-2-one (10 g, 101.01 mmol, 1 eq.) in chloroform (300 mL) was added $PCl_5$ (42 g, 202.02 mmol, 2 eq.) at 0-5° C. for 10 minutes. To this suspension was added $ZnI_2$ (0.96 g, 3.03 mmol, 0.03 eq.) under nitrogen at 0-5° C. and then allowed to stir at room temperature for 1 h. To this reaction mixture was added a solution of $Br_2$ (32.11 g, 202.02 mmol, 2 eq.) in chloroform (5 mL) dropwise and the reaction mixture was stirred overnight. Progress of reaction was monitored by TLC and LCMS. After completion, reaction mixture was diluted with ice-cold water and extracted with dichloromethane (3×50 mL). Combined organic layer was washed with brine and dried over sodium sulphate. Removal of solvent under reduced pressure afforded 3,3-dibromopiperidin-2-one (12 g, 46.17%) as brown liquid which was used in the next step without purification.

LCMS: 258 [M+1]+

Step-2

To a stirred solution of 3,3-dibromopiperidin-2-one (12 g, 46.87 mmol, 1 eq.) in DMF (100 mL) was added $Li_2CO_3$ (6.8 g, 93.75 mmol, 2 eq.) at room temperature and the resulting reaction mixture was stirred at 120° C. for 7 h. Progress of reaction was monitored by LCMS. After completion, reaction mixtures were diluted with ice-cold water (200 mL) and extracted with dichloromethane (3×100 mL). Combined organic layer was washed with brine (50 mL) and dried over anhydrous sodium sulfate. Removal of solvent under reduced pressure afford crude oil which was purified by Combi-Flash on silica gel using ethyl acetate-hexane system as eluent to afford 3-bromo-5,6-dihydropyridin-2(1H)-one (1 g, 12.18%) as brown oil.

LCMS: 177 [M+1]+

Step-3

To a stirred solution of (2E)-3-(pyrimidin-2-yl)prop-2-enoic acid (200 mg, 1.33 mmol, 1 eq) in a THF (20 mL) at 0° C. was added triethylamine (0.2 mL, 1.47 mmol, 1.1 eq.) followed by 2,2-dimethylpropanoyl chloride (159 mg, 1.33 mmol, 1 eq.) and the resulting mixture was allowed to stir at the same temperature for mixture for 1 h. Progress of reaction was monitored by TLC. After completion, reaction mixture was filtered through cotton plug and used directly in the next reaction.

Step-4

To a stirred solution of 3-bromo-5,6-dihydropyridin-2(1H)-one (234 mg, 1.329 mmol, 1 eq) in THF (20 mL) at −78° C. was added n-BuLi (0.53 mL, 1.329 mmol, 1 eq.) drop wise at and the resulting mixture was stirred at same temperature for 1 h. To this mixture was added a solution of 2,2-dimethylpropanoic (2E)-3-(pyrimidin-2-yl)prop-2-enoic anhydride (443 mg, 1.33 mmol, 1 eq.) in THF dropwise and the mixture was stirred at −78° C. for another 1 h. Progress of reaction was monitored by TLC and LCMS. After completion, reaction mixture was diluted with saturated ammonium chloride solution (50 mL) and extracted with dichloromethane (3×100 mL). Combined organic layer was dried over anhydrous sodium sulfate and concentrate under reduced pressure to yield crude product, which was purified by reversed phase HPLC to afford 3-bromo-1-[(2E)-3-(pyrimidin-2-yl)prop-2-enoyl]-5,6-dihydropyridin-2(1H)-one (20 mg, off white solid, 5% yield).

LCMS: 309[M+1]+

$^1$H NMR (400 MHz, DMSO-$d_6$) δ 8.88 (d, 2H), 7.90 (d, 1H), 7.60 (t, 1H), 7.49 (t, 1H), 7.38 (d, 1H), 3.99 (t, 2H) 2.52-2.60 (m, 2H).

Example 40

Preparation of (E)-1-(3-(1-methylpiperidin-4-yl)acryloyl)-5,6-dihydropyridin-2(1H)-one

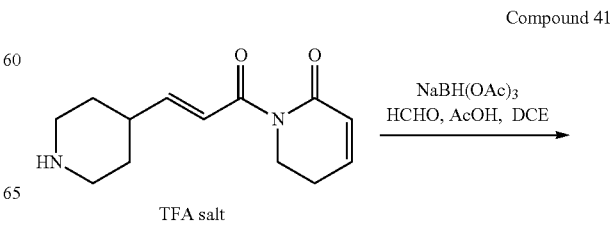

Compound 41

TFA salt

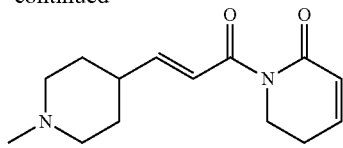

To a stirred solution of (E)-1-(3-(piperidin-4-yl)acryloyl)-5,6-dihydropyridin-2(1H)-one (0.100 g, 0.427 mmol, 1.0 eq.) in 1,2-dichloroethane (4 mL) was added HCHO in water (0.04 mL, 1.28 mol, 3.0 eq.), acetic acid (0.012 mL, 2.13 mol, 5.0 eq.). The reaction mixture was allowed to stir at room temperature for 1 h and followed by the addition of NaBH(OAc)₃ (0.271 g, 1.282 mmol, 3.0 eq.) and stirring was continued at room temperature for additional 1 h. Progress of the reaction was monitored by TLC and LCMS. After completion, the reaction mixture was diluted with water (30 mL) and extracted with ethyl acetate (2×30 mL). Organic layer was washed with brine solution (30 mL) and dried over anhydrous sodium sulphate. Removal of solvent under reduced pressure gave crude which was purified by reversed phase HPLC to afford (E)-1-(3-(1-methylpiperidin-4-yl)acryloyl)-5,6-dihydropyridin-2(1H)-one as a TFA salt (30 mg, 29%).

LCMS: 249 [M+1]⁺

¹H NMR (400 MHz, CD₃OD) δ 1.58-1.72 (m, 2H) 2.09 (d, 2H) 2.39-2.51 (m, 2H) 2.54 (d, 1H) 2.88 (s, 3H) 3.00-3.16 (m, 2H) 3.56 (d, 2H) 3.94 (t, 2H) 5.97 (d, 1H) 6.76-6.90 (m, 2H) 7.02-7.11 (m, 1H).

Example 41

Preparation of (E)-1-(2-methyl-3-(pyrimidin-2-yl)acryloyl)-5,6-dihydropyridin-2(1H)-one Compound 42

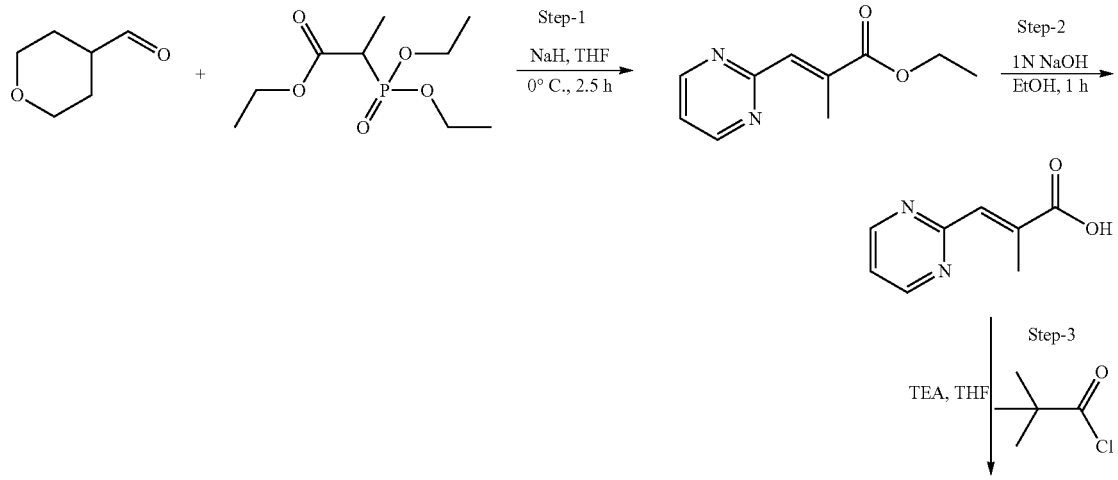

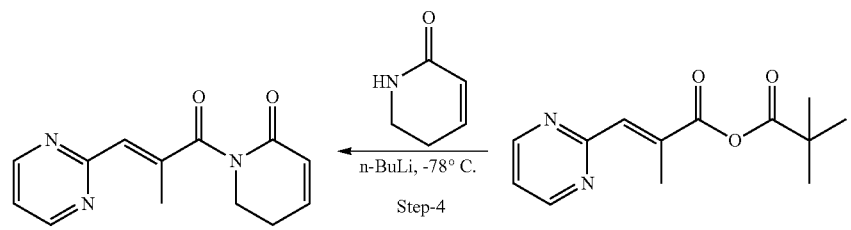

Step-1

To a solution of ethyl 2-(diethoxyphosphoryl)propanoate (0.66 g, 2.77 mmol, 1.2 eq.) in THF (20 mL) was added sodium hydride (0.110 g, 2.77 mmol, 1.2 eq.) portionwise at 0° C. and the reaction mixture was allowed to stir at 0° C. for 20 minutes. To this solution was added pyrimidine-2-carbaldehyde (0.25 g, 2.31 mmol, 1 eq.). Reaction mixture stirred at 0° C. for 2 h. Progress of reaction was monitored by TLC. After completion, reaction mixture was diluted saturated ammonium chloride (30 mL) and extract with ethyl acetate (3×30 mL). Combined organic layer was washed with brine (50 mL) and dried over anhydrous sodium sulfate. Removal of solvent afforded crude which was purified by CombiFlash on silica gel using ethyl acetate-hexane system as eluent to afford ethyl (E)-2-methyl-3-(pyrimidin-2-yl)acrylate (0.2 g, 45%).

Step-2

To a solution of ethyl (E)-2-methyl-3-(pyrimidin-2-yl) acrylate (0.2 g, 1.04 mmol, 1 eq.) in ethanol (10 mL) was added 1N sodium hydroxide (2.08 mL, 2.08 mmol, 2 eq.) at room temperature and the reaction mixture was allowed to stir at the same temperature for 1 h. Progress of reaction was monitored by TLC. After completion, reaction mixture was acidified with 1N HCl and extract with ethyl acetate (3×25 mL). Combined organic layer was washed with brine (50 mL) and dried over anhydrous sodium sulfate. Removal of solvent afforded (E)-2-methyl-3-(pyrimidin-2-yl)acrylic acid (0.180 g, crude) which was used in the next step without further purification.

Step-3

To a solution of (E)-2-methyl-3-(pyrimidin-2-yl)acrylic acid (0.180 g, 1.09 mmol, 1.0 eq.) in dry THF was added triethylamine (0.18 mL, 1.30 mmol, 1.2 eq.) and pivaloyl chloride (0.12 mL, 0.980 mmol, 0.9 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.105 g, 1.09 mmol, 1 eq.) in dry THF at −78° C. was added n-butyllithium (2.5 M in hexane, 0.43 ml, 1.09 mmol, 1 eq.) and the mixture was allowed to stir at the same temperature for 30 minutes. To this solution was added (E)-(E)-2-methyl-3-(pyrimidin-2-yl)acrylic pivalic anhydride (0.270 g, 1.09 mmol, 1 eq.). Reaction mixture was allowed to stir at −78° C. for 90 min. Progress of reaction was monitored by TLC. Reaction mixture was brought to 0° C., diluted with ammonium chloride solution (30 mL) and extracted with ethyl acetate (3×40 ml). Combined organic layer was washed with brine, dried over anhydrous $Na_2SO_4$ and evaporated to dryness under vacuum to afford crude which was purified by Combi-Flash to afford (E)-1-(2-methyl-3-(pyrimidin-2-yl) acryloyl)-5,6-dihydropyridin-2(1H)-one (80 mg, 30.30%).

LCMS: 244 [M+1]+

$^1$H NMR (CDCl$_3$, 400 MHz) δ 8.77 (d, 2H), 7.07 (t, 1H), 6.99-6.90 (m, 1H), 6.70 (s, 1H), 5.98 (d, 1H), 4.00-3.90 (m, 2H), 2.54 (brs, 5H).

Example 42

Preparation of (E)-5-methyl-1-(3-(pyrimidin-2-yl) acryloyl)-5,6-dihydropyridin-2(1H)-one Compound 43

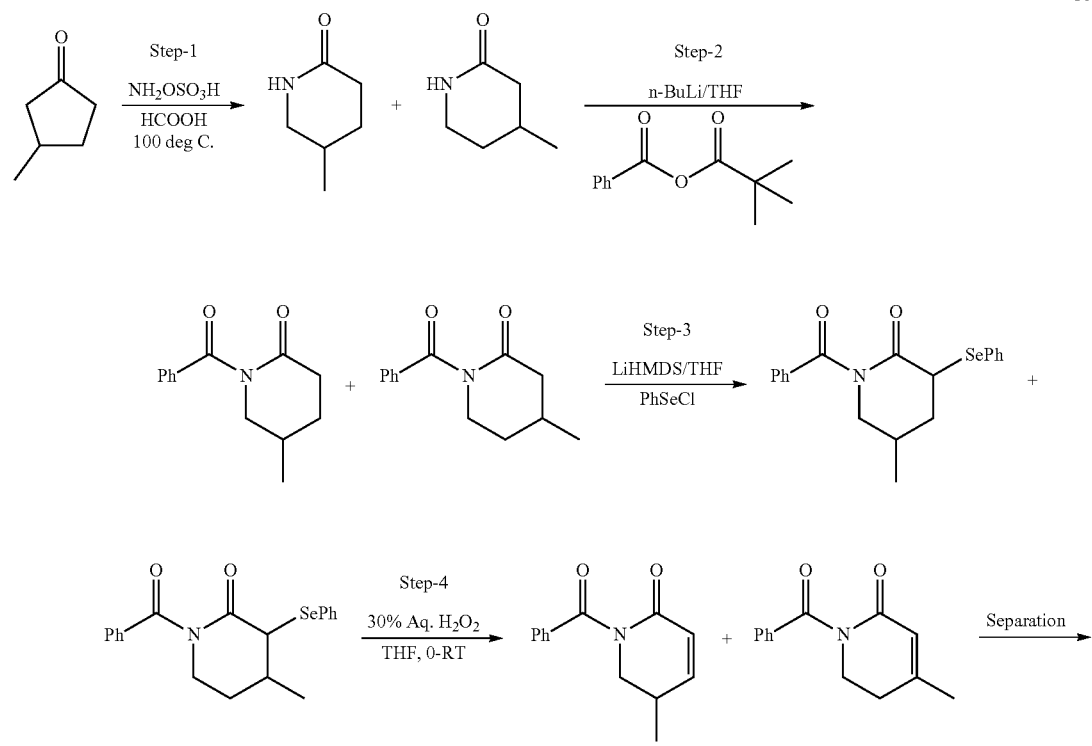

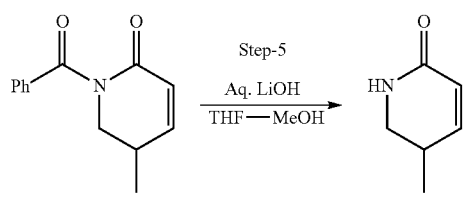 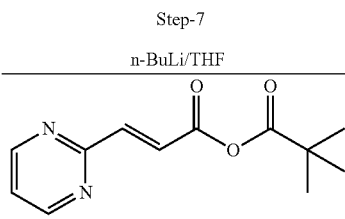 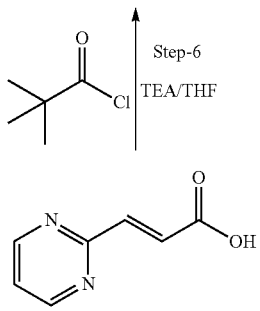

Step-1

To a stirred solution of 3-methylcyclopentanone (5 g, 51.02 mmol, 1 eq.) in formic acid (100 mL) was added hydroxyl amine-O-sulfonic acid (8.65 g, 76.53 mmol, 1.5 eq.) and the reaction mixture was refluxed for 12 h. Progress of reaction was monitored by TLC. After completion, reaction mixture was cool to room temperature, diluted with water (50 mL), basified with 5M aqueous NaOH and extracted with dichloromethane (3×100 mL). Combined organic layer was washed with brine solution (50 mL) and dried over anhydrous sodium sulphate. Removal of solvent under reduced pressure afforded a mixture of 5-methylpiperidin-2-one and 4-methylpiperidin-2-one (5 g, 87%).

LCMS: 114 [M+1]$^+$

Step-2

To a stirred solution of a mixture of 5-methylpiperidin-2-one and 4-methylpiperidin-2-one (4.6 g, 40.98 mmol, 1 eq.) in anhydrous THF (50 mL) at −78° C. was added n-BuLi (1.8 M in THF, 3.8 mL, 6.86 mmol, 1.2 eq.) dropwise and the reaction mixture was allowed to stir at same temperature for 30 minutes. To this mixture was added a solution of freshly prepared benzoic pivalic anhydride (8.4 g, 40.98 mmol, 1 eq.) and allow the reaction mixture was stirred at same temperature for 1 h. Progress of reaction was monitored by TLC. After completion, reaction mixture was brought to 0° C., diluted with saturated aqueous solution of ammonium chloride (200 mL) and extracted with ethyl acetate (3×200 mL). Organic layer was washed with brine and dried over anhydrous sodium sulphate. Removal of solvent under reduced pressure afforded a mixture of 1-benzoyl-5-methylpiperidin-2-one and 1-benzoyl-4-methylpiperidin-2-one as crude (8 g, 90%).

LCMS: 218 [M+1]$^+$

Step-3

To a stirred solution of a mixture of 1-benzoyl-5-methylpiperidin-2-one and 1-benzoyl-4-methylpiperidin-2-one (1.1 g, 5.07 mmol, 1 eq.) in anhydrous THF (25 mL) at −78° C. was added LiHMDS (1M in THF, 10.13 mL, 10.13 mmol, 2 eq.) dropwise and the reaction mixture was allowed to stir at same temperature for 30 minutes. To this solution was added phenyl selenium chloride (1.94 g, 10.13 mmol, 2 eq.) in THF (5 mL) dropwise. Reaction mixture was allowed to stir at same temperature for 1 h. Progress of reaction was monitored by TLC. After completion reaction mixture was brought to 0° C. and diluted with saturated aqueous solution of ammonium chloride (50 mL) and extracted with ethyl acetate (3×100 mL). Combined organic layer was washed with brine (100 mL) dried over anhydrous sodium sulphate. Removal of solvent under reduced pressure afforded a mixture of 1-benzoyl-5-methyl-3-(phenylselanyl)piperidin-2-one and 1-benzoyl-4-methyl-3-(phenylselanyl)piperidin-2-one as crude (1.4 g, 77.77%). LCMS 374 [M+1]$^+$

Step-4

To a stirred solution of a mixture of 1-benzoyl-5-methyl-3-(phenylselanyl)piperidin-2-one and 1-benzoyl-4-methyl-3-(phenylselanyl)piperidin-2-one (1.4 g, 3.76 mmol, 1 eq.) in THF (30 mL) at 0° C. was 30% aq. H$_2$O$_2$ (10 mL) dropwise and the resulting solution was allowed to stir at room temperature for 1 h. Progress of reaction was monitored by TLC. After completion, reaction mixture was diluted with water and extracted with ethyl acetate (3×100 mL). Combined organic layer was washed with brine (50 mL) and dried over anhydrous sodium sulphate. Removal of solvent under reduced pressure afforded 1-benzoyl-5-methyl-5,6-dihydropyridin-2(1H)-one and 1-benzoyl-4-methyl-5,6-dihydropyridin-2(1H)-one as crude which was purified by Combi-Flash on silica gel using ethyl acetate-hexane as eluent to afford 1-benzoyl-5-methyl-5,6-dihydropyridin-2(1H)-one (0.35 g, 43%).

LCMS 216 [M+1]$^+$

Step-5

To a stirred solution of 1-benzoyl-5-methyl-5,6-dihydropyridin-2(1H)-one (0.35 g, 1.63 mmol, 1 eq.) in a solution of 1:1 THF-MeOH (20 mL) was added LiOH (0.409 g, 9.77 mmol, 6 eq.) dissolved in minimum amount of water and the resulting mixture was allowed to stir at room temperature for 1 h. Progress of reaction was monitored by TLC. After completion, reaction mixture was diluted with water (50 mL) and extracted with ethyl acetate (3×50 mL). Combined organic layer was washed with brine (50 mL), dried over anhydrous sodium sulphate and concentrated under reduced pressure afforded crude which was purified by combi-Flash on silica gel using ethyl acetate-hexane as eluent to afford 5-methyl-5,6-dihydropyridin-2(1H)-one (0.130 g, 72%)

LCMS 112[M+1]$^+$

Step-6

To a stirred solution of (2E)-3-(pyrimidin-2-yl)prop-2-enoic acid (0.120 g, 0.80 mmol, 1 eq.) in THF (30 mL) in a 100 mL round bottom flask at 0° C. was added TEA (0.13 mL, 0.98 mmol, 1.2 eq.) followed by pivaloyl chloride (0.08 ml, 0.729 mmol, 1 eq.) and the resulting mixture was stirred at the same temperature for 1 h. Progress of reaction was monitored by TLC. After completion, the mixture was transferred to the reaction mixture of the next step drop wise via a syringe equipped with a cotton plug at the bottom.

Step-7

To a stirred solution 5-methyl-5,6-dihydropyridin-2(1H)-one (0.097 g, 0.88 mmol, 1 eq.) in anhydrous THF (10 mL) at −78° C. was added n-BuLi (2.5 M in THF, 0.3 mL, 0.88 mmol, 1 eq.) dropwise and the reaction mixture was allowed to stir at same temperature for 30 minute. To this solution was added freshly prepared anhydride of step-6 (0.21 g, 0.88 mmol, 1 eq.). The reaction mixture was allowed to stir at same temperature for 1 h. Progress of reaction was monitored by TLC. After completion reaction mixture was brought to 0° C. and diluted with saturated aqueous solution of ammonium chloride (50 mL) and extracted with ethyl acetate (3×50 mL). Organic layer was washed with brine and dried over anhydrous sodium sulphate. Removal of solvent under reduced pressure afforded crude which was purified by reversed phase HPLC to afford (E)-5-methyl-1-(3-(pyrimidin-2-yl)acryloyl)-5,6-dihydropyridin-2(1H)-one (20 mg, 21%).

LCMS: 244[M+1]$^+$
$^1$H NMR (400 MHz, CD$_3$OD) δ 8.69 (d, 2H), 8.1 (d, 1H), 7.7 (d, 1H), 7.2 (t, 1H), 6.8 (m, 1H), 6.0 (m, 1H), 4.2 (m, 1H), 3.59 (m, 2H), 2.7 (bs, 1H), 1.19 (d, 3H).

Example 43

(E)-1-(3-(1-(cyclopropylmethyl)piperidin-4-yl)acryloyl)-5,6-dihydropyridin-2(1H)-one Compound 44

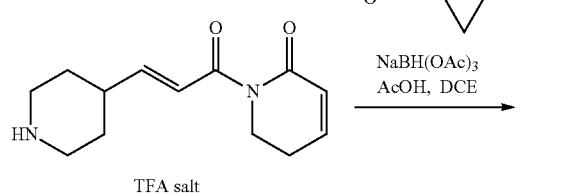

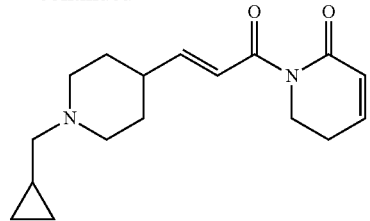

To a stirred solution of (E)-1-(3-(piperidin-4-yl)acryloyl)-5,6-dihydropyridin-2(1H)-one TFA salt (0.100 g, 0.427 mmol, 1.0 eq.) in DCE (4 mL), was added 2-Cyclopropanecarboxaldehyde (0.089 mL, 1.28 mmol, 3.0 eq.), acetic acid (0.061 ml, 2.14 mmol, 5.0 eq.). The reaction mixture was allowed to stir at room temperature for 1 h followed by the addition of NaBH(OAc)$_3$ (0.271 g, 1.282 mmol, 3.0 eq.) and stirring was continued at room temperature for additional 1 h. Progress of the reaction was monitored by TLC and LCMS. After completion, reaction mixture was diluted with water (30 mL) and extracted with ethyl acetate (2×30 ml). Organic layer was washed with brine solution (30 mL), dried over anhydrous sodium sulphate and concentrated under reduced pressure to obtain crude which was purified by reversed phase HPLC to afford (E)-1-(3-(1-(cyclopropylmethyl)piperidin-4-yl)acryloyl)-5,6-dihydropyridin-2(1H)-one as TFA salt (40 mg, 35%).

LCMS: 289 [M+1]$^+$
$^1$H NMR (400 MHz, CD$_3$OD) δ 7.01-7.12 (m, 1H), 6.75-6.93 (m, 2H), 5.97 (d, 1H), 3.94 (t, 2H), 3.72 (d, 2H), 2.97-3.11 (m, 3H), 2.52-2.63 (m, 1H), 2.40-2.52 (m, 2H), 2.11 (d, 2H), 1.63-1.80 (m, 2H), 1.29 (brs., 1H), 1.12 (d, 1H), 0.71-0.84 (m, 2H), 0.37-0.53 (m, 2H)

Example 44

Preparation of (E)-1-(3-(1-(oxetan-3-yl)piperidin-4-yl)acryloyl)-5,6-dihydropyridin-2(1H)-one Compound 45

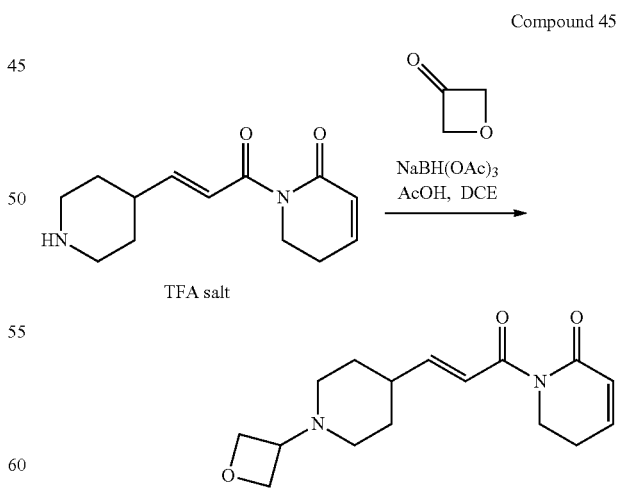

To a stirred solution of (E)-1-(3-(piperidin-4-yl)acryloyl)-5,6-dihydropyridin-2(1H)-one TFA salt (0.200 g, 0.85 mmol, 1.0 eq.) in DCE (4 mL), was added 3-Oxetanone (0.184 ml, 2.56 mmol, 3.0 eq.), acetic acid (0.24 mL, 4.27 mmol, 5.0 eq.). The reaction mixture was allowed to stir at room temperature for 1 h and followed by the addition of NaBH(OAc)₃ (0.543 g, 2.56 mol, 3.0 eq.) and stirring was continued at room temperature for additional 1 h. Progress of the reaction was monitored by TLC and LCMS. After completion, reaction mixture was diluted with water (30 mL) and extracted with ethyl acetate (2×30 mL). Organic layer was washed with brine solution (30 mL) and dried over anhydrous sodium sulphate. Removal of solvent under reduced pressure gave crude which was purified by reversed phase HPLC to afford (E)-1-(3-(1-(oxetan-3-yl)piperidin-4-yl)acryloyl)-5,6-dihydropyridin-2(1H)-one (40 mg, 17%) as TFA salt. LCMS: 291 [M+1]⁺

¹H NMR (400 MHz, DMSO-d₆) δ 10.16 (brs., 1H), 7.04-7.14 (m, 1H), 6.76 (s, 2H), 5.94 (d, 1H), 4.74 (d, 3H), 4.34 (brs, 2H), 3.84 (t, 2H), 3.43 (d, 2H), 2.85 (brs., 2H), 2.44 (brs., 3H), 1.99 (d, 2H), 1.56 (d, 2H).

Example 45

Preparation of (E)-3-chloro-1-(2-methyl-3-(pyrimidin-2-yl)acryloyl)-5,6-dihydropyridin-2(1H)-one Compound 46

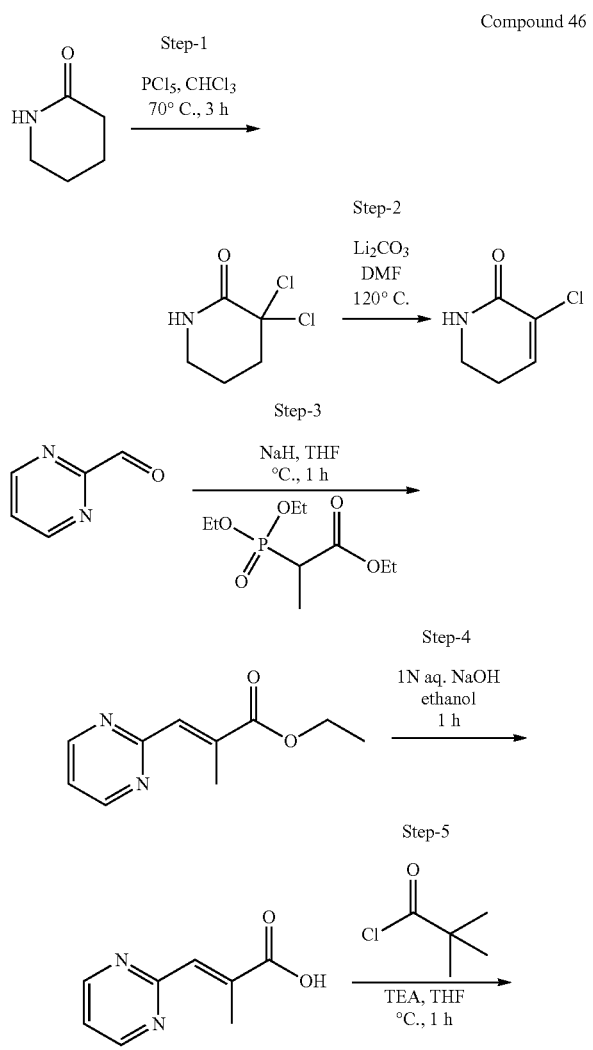

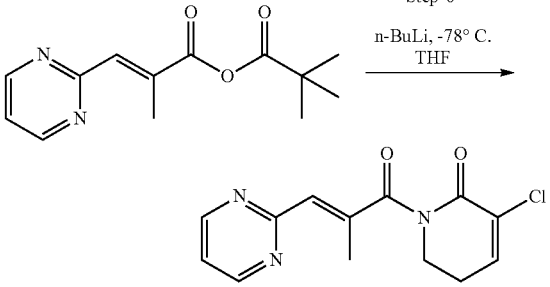

Step-1

To a stirred solution of piperidin-2-one (5 g, 50.50 mmol, 1 eq) in chloroform (200 mL) was added with PCl₅ (31.5 g, 151.5 mmol, 3 eq) at 0-5° C. portion-wise and the resulting mixture was allowed to stir at 70° C. for 3 h. Progress of reaction was monitored by TLC and LCMS. After completion, reaction mixture was diluted with dichloromethane (50 mL) and mixture was poured on ice-cold water. Organic layer was separated and aqueous layer was again extracted with dichloromethane (3×100 mL). Combined organic layer was washed with brine (100 mL) and dried over anhydrous sodium sulfate. Removal of solvent under reduced pressure afforded 3,3-dichloropiperidin-2-one (10 g, crude)

LCMS: 167 (M+1)

Step-2

To a stirred solution of 3,3-dichloropiperidin-2-one (5 g, 29.761 mmol, 1 eq) in DMF (30 mL) was added Li₂CO₃ (8.46 g, 119.04 mmol, 4 eq) at room temperature and the resulting reaction mixture was stirred at 120° C. for 7 h. Progress of reaction was monitored by TLC and LCMS. After completion, reaction mixture was diluted with ice-cold water and extracted with dichloromethane (3×100 mL). Combined organic layer was washed with brine (100 mL) and dried over anhydrous sodium sulphate and concentrate under reduced pressure to yield product 3-chloropiperidin-2-one (1 g, yellow liquid) which purified by Combi-Flash on silica gel using ethyl acetate-hexane system as eluent to afford 3-chloro-5,6-dihydropyridin-2(1H)-one (450 mg). LCMS: 132 (M+H)

Step-3

To a suspension of NaH (176 mg, 4.443 mmol, 1.2 eq) in THF (20 mL) at 0° C. was added ethyl 2-(diethoxyphosphoryl)propanoate (969 mg, 4.073 mmol, 1.1 eq) and the resulting mixture was stirred at the same temperature for 10 minutes. To this mixture was added pyrimidine-2-carbaldehyde (400 mg, 3.703 mmol, 1 eq) and the resulting reaction mixture for stirred at the same temperature for 1 h. Progress of reaction was monitored by TLC and LCMS. After completion, reaction mixture was diluted with ammonium chloride solution and extracted with ethyl acetate (3×50 mL). Combined organic layer was washed with brine (50 mL) and dried over anhydrous sodium sulphate. Removal of solvent under reduced afforded crude which was Combi-Flash on silica gel using ethyl acetate-hexane system as eluent to afford (E)-ethyl 2-methyl-3-(pyrimidin-2-yl)acrylate (350 mg).

LCMS: 193 (M+1)

Step-4

To a stirred solution of (E)-ethyl 2-methyl-3-(pyrimidin-2-yl)acrylate (350 mg, 1.82 mmol, 1 eq) in ethanol (10 mL) was added 1N aq. NaOH solution (3.6 mL, 3.644 mmol, 2 eq) and the resulting reaction mixture was stirred at room temperature for 1 h. Progress of reaction was monitored by TLC and LCMS. After completion, reaction mixture was acidified with 1N aq. HCl solution and extracted with ethyl acetate (3×50 mL). Combined organic layer was washed with brine solution (50 mL) and dried over anhydrous sodium sulphate. Removal of solvent under reduced pressure gave 2-methyl-3-(pyrimidin-2-yl)prop-2-enoic acid (300 mg).

LCMS: 165 (M+1)

Step-5

To a solution of (2E)-2-methyl-3-(pyrimidin-2-yl)prop-2-enoic acid (100 mg, 0.61 mmol, 1 eq) in THF (10 mL) was added triethylamine (73 mg, 0.73 mmol, 1.2 eq) and stirred the reaction mixture at 0° C. for 10 minute. To this solution was added pivaloyl chloride (73 mg, 0.6097 mmol, 1 eq) dropwise and the mixture was allowed to stir at 0° C. for 1 h. Progress of reaction was monitored by TLC. After completion, reaction mixture was filtered and the filtrate was used in the next step.

Step-6

To a stirred solution of 3-methyl-5,6-dihydropyridin-2(1H)-one (79 mg, 0.603 mmol, 1 eq) in THF (20 mL) was at −78° C. was added n-BuLi (0.24 mL, 0.603 mmol, 1 eq) dropwise and mixture was stirred 1 h. To this solution was added a solution of 2,2-dimethylpropanoic (2E)-2-methyl-3-(pyrimidin-2-yl)prop-2-enoic anhydride prepared above. Resulting mixture was stirred was stirred at the same temperature for 1 h. Progress of reaction was monitored by LCMS. After completion, reaction mixture was diluted with aq. ammonium chloride solution and extracted with ethyl acetate (3×50 mL). Combined organic layer was washed with brine (50 mL) and dried over sodium sulphate. Removal of solvent under reduced pressure gave crude product which was which was Combi-Flash on silica gel using ethyl acetate-hexane to afford (E)-3-chloro-1-(2-methyl-3-(pyrimidin-2-yl)acryloyl)-5,6-dihydropyridin-2(1H)-one (20 mg, 11.97%).

LCMS: 278.1 (M+1)

$^1$H NMR (400 MHz, CDCl$_3$) δ 8.74 (d, 2H), 7.03-7.13 (m, 2H), 6.72 (s, 1H), 3.99 (t, 2H), 2.57-2.72 (m, 2H), 2.49-2.57 (m, 3H).

Example 46

Preparation of 1-{(2E)-3-[1-(methylsulfonyl)piperidin-4-yl]prop-2-enoyl}-5,6-dihydropyridin-2(1H)-one Compound 47

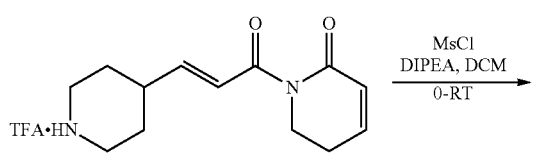

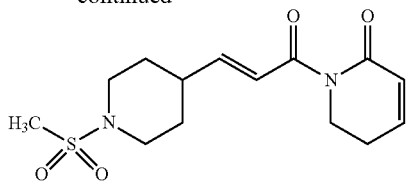

To a stirred solution of 1-[(2E)-3-(piperidin-4-yl)prop-2-enoyl]-5,6-dihydropyridin-2(1H)-one TFA salt (0.100 g, 0.28 mmol, 1.0 eq) in DCM (5.0 mL) was added diisopropylethylamine (0.074 mL, 0.43 mmol, 1.5 eq) dropwise at 0° C. and the mixture was allowed to stir at the same temperature for 30 minutes. To this mixture was added a solution of mesyl chloride (0.026 mL, 0.34 mmol, 1.2 eq) in DCM (2.0 mL) and the resulting mixture was allowed to stir at room temperature for 3 h. Progress of reaction was monitored by TLC. After completion, reaction mixture was evaporated to dryness under vacuum to afford crude which was purified by reversed phase HPLC to afford 1-{(2E)-3-[1-(methylsulfonyl)piperidin-4-yl]prop-2-enoyl}-5,6-dihydropyridin-2(1H)-one (0.028 g, 31.46%).

LCMS: 313 [M+1]$^+$ $^1$H NMR (400 MHz, DMSO-d$_6$) δ 7.10-7.01 (m, 1H), 6.85-6.70 (m, 2H), 6.91 (d, 1H), 3.83 (t, 2H), 3.60-3.50 (m, 2H), 2.85 (s, 3H), 2.80-2.70 (m, 2H), 2.50-2.40 (m, 3H), 1.85-1.77 (m, 2H), 1.46-1.35 (m, 2H).

Example 47

Preparation of (E)-1-(3-(quinazolin-2-yl)acryloyl)-5,6-dihydropyridin-2(1H)-one

Compound 48

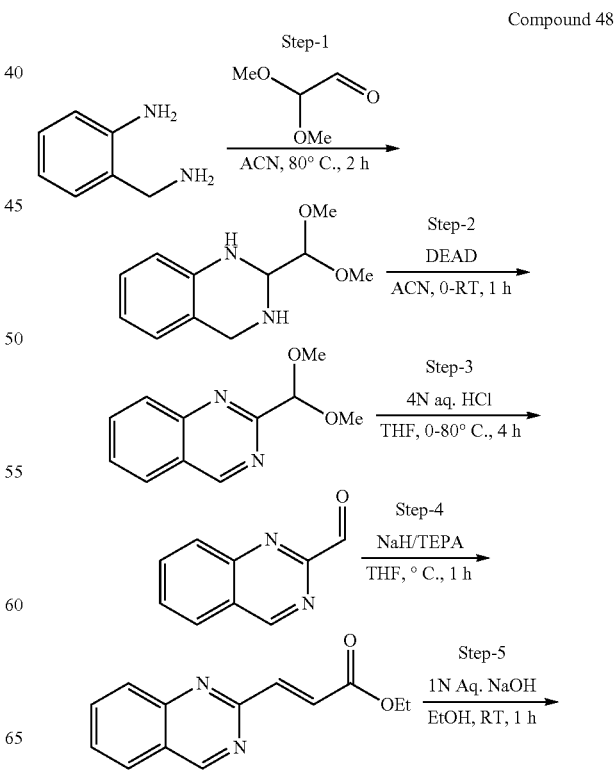

-continued

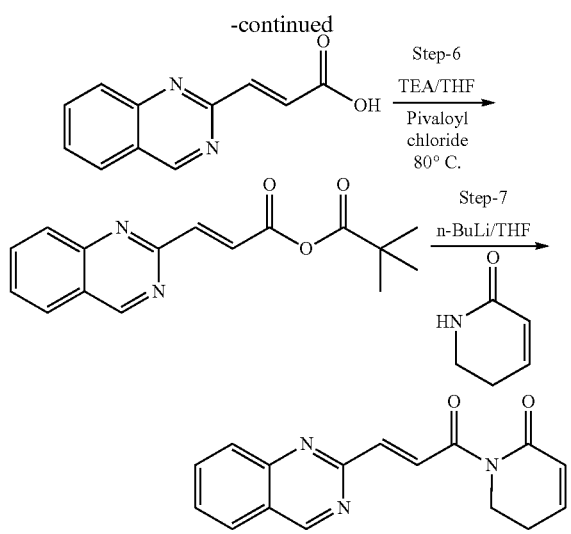

Step-1

A solution of 2-(aminomethyl)aniline (10 g, 81.83 mmol, 1 eq.) and 2,2-dimethoxyacetaldehyde (8.52 g, 81.83 mmol, 1 eq.) in acetonitrile (150 mL) was allowed to stir at 80° C. for 2 h. Progress of reaction was monitored by TLC. After completion, acetonitrile was removed under reduced pressure, the residue was diluted with ice cold water (150 mL) and extracted with ethyl acetate (2×500 mL). Combined organic layer was washed with water (3×100 mL) followed by brine solution (100 mL), and dried over anhydrous sodium sulphate. Removal of solvent under reduced pressure reduced pressure afforded crude which was purified by Combi-Flash on silica gel (100-200 mesh) using ethyl acetate-hexane system as eluent to afford 2-(dimethoxymethyl)-1,2,3,4-tetrahydroquinazoline (10.6 g, 62%) as brown solid.

Step-2

To a solution of 2-(dimethoxymethyl)-1,2,3,4-tetrahydroquinazoline (10.6 g, 50.89 mmol) in acetonitrile (50 mL) at 0° C. was added DEAD (19.5 g, 111.97 mmol, 2.2 eq.) portion-wise and then the resulting mixture was allowed to stir at room temperature for 1 h. Progress of reaction was monitored by TLC. After completion of reaction, reaction mixture was diluted with ice cold water (100 mL), acidified with 1N aq. HCl (100 mL) and extracted with ethyl acetate. Aqueous layer was basified with saturated sodium bicarbonate solution (100 mL) and extracted with ethyl acetate (3×200 mL). Combined organic layer was washed with water (100 mL) followed by brine (100 mL) and dried over anhydrous sodium sulphate. Removal of solvent under reduced pressure afforded 2-(dimethoxymethyl)quinazoline (6.2 g, 60%) as white solid.

Step-3

To a solution of 2-(dimethoxymethyl)quinazoline (6.2 g, 30.35 mmol, 1 eq.) in THF (50 mL) at 0° C. was added 4N aq. HCl (5 mL) and the reaction mixture was allowed to stir at 80° C. for 4 h. Progress of reaction was monitored by TLC. After completion, reaction mixture was concentrated under reduced pressure up to dryness and purified by Combi-Flash on silica gel (100-200 mesh) using ethyl acetate-hexane system as eluent to afford quinazoline-2-carbaldehyde (2.5 g, 52%).

Step-4

To a solution of triethyl phosphonoacetate (TEPA) (850 mg, 3.796 mmol, 1.2 eq) in THF (20 mL) was added NaH (163 mg, 4.113 mmol, 1.3 eq) at 0° C. and mixture was stirred for 5 minutes. To this mixture was then added a solution of quinazoline-2-carbaldehyde (500 mg, 3.164 mmol, 1 eq) in THF (2 mL) dropwise at 0° C. and the reaction mixture was stirred for 1 h. Progress of reaction was monitored by TLC. After completion, the reaction mixture was diluted with water (20 mL) and extracted with ethyl acetate (3×50 mL). Combined organic layer was washed with brine, dried over $Na_2SO_4$ and concentrated under reduced pressure to obtain crude which was purified by Combi-Flash on silica gel using ethyl acetate-hexane as eluent to afford ethyl (E)-ethyl 3-(quinazolin-2-yl)acrylate (300 mg, yellow liquid, 41.60%).

Step-5

To the stirred solution of (E)-ethyl 3-(quinazolin-2-yl) acrylate (300 mg, 1.315 mmol, 1 eq) in EtOH (10 mL) at RT was added 1N aq. NaOH (2.63 mL, 2.63 mmol, 2 eq) and the resulting mixture was stirred for at RT for 2 h. Progress of the reaction was monitored by TLC. After completion, the reaction mixture was diluted with 1 N HCl (15 mL) and extracted with ethyl acetate (2×100 mL). Combined organic layer was washed with water, dried over anhydrous $Na_2SO_4$ and concentrated under reduced pressure to obtain (E)-3-(quinazolin-2-yl)acrylic acid (200 mg, 76%).

Step-6

To a stirred solution of (E)-3-(quinazolin-2-yl)acrylic acid (90 mg, 0.45 mmol, 1 eq) in THF (5 mL) at 0° C. was added triethylamine (55 mg, 0.54 mmol, 1.2 eq) followed by pivaloyl chloride (56 mg, 0.45 mmol) and the reaction mixture was allowed to stir at 0° C. for 1 h. Progress of reaction was monitored by TLC. After completion, the reaction mixture was filtered and the filtrate was carried to next step without any further purification.

Step-7

To the stirred solution of 5,6-dihydropyridin-2(1H)-one (44 mg, 0.45 mmol, 1 eq) in THF (5 mL) at −78° C. was added n-BuLi (2.5 M in hexane, 0.18 mL, 0.45 mmol, 1 eq) and the reaction mixture was stirred at the same temperature for 30 minutes. To this reaction mixture was added a solution of pivalic (E)-3-(quinazolin-2-yl)acrylic anhydride (128 mg, 0.45 mmol, 1 eq) in THF (10 mL) and the resulting mixture was allowed to stir at −78° C. for 2 h. Progress of the reaction was monitored by TLC and LCMS. After completion, the reaction mixture was diluted with water (20 mL) and extracted with ethyl acetate (3×50 mL). Combined organic layer was washed with brine, dried over $Na_2SO_4$ and concentrated under reduced pressure to obtain crude which was purified by Combi-Flash on silica gel using ethyl acetate-hexane system as eluent to afford (E)-1-(3-(quinazolin-2-yl)acryloyl)-5,6-dihydropyridin-2(1H)-one (21 mg, 17%).

LCMS: 280 $[M+1]^+$

¹H NMR (CDCl₃, 400 MHz) δ 9.39 (s, 1H), 8.22 (d, 1H), 8.05 (d, 1H), 7.92-7.88 (m, 2H), 7.85 (d, 1H), 7.65 (t, 1H), 6.98 (dd, 1H), 6.08 (d, 1H), 4.09 (t, 2H), 2.55-2.45 (m, 2H).

Example 48

Preparation of 1-[(2E)-3-(4,5-dihydropyrimidin-2-yl)-2-methylprop-2-enoyl]-5,6-dihydropyridin-2(1H)-one Compound 49

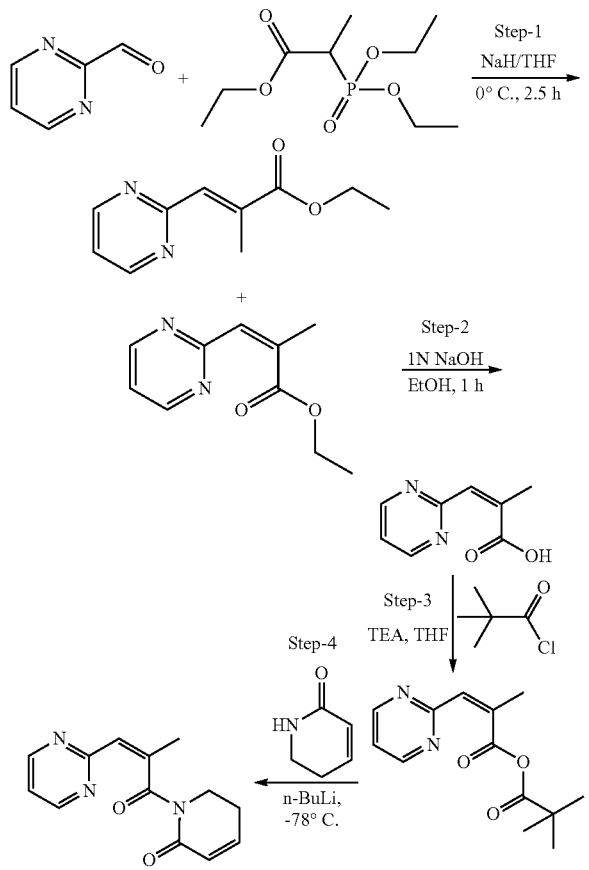

Step-1

To a solution of ethyl 2-(diethoxyphosphoryl)propanoate (0.95 g, 4.07 mmol, 1.1 eq) in THF (20 mL) was added sodium hydride (0.176 g, 4.443 mmol, 1.2 eq) slowly at 0° C. and the reaction mixture was allowed to stir at 0° C. for 20 minutes. To this solution was added pyrimidine-2-carbaldehyde (0.4 g, 3.7 mmol, 1 eq) and the reaction mixture stirred at 0° C. for 1 h. Progress of reaction was monitored by TLC. After completion, reaction mixture was diluted saturated ammonium chloride solution (30 mL) and extracted with ethyl acetate (3×30 mL). Combined organic layer was washed with brine and dried over anhydrous sodium sulfate. Removal of solvent afforded crude which was purified by Combi-Flash on silica gel using ethyl acetate-hexane system as eluent to afford ethyl (E)-ethyl 2-methyl-3-(pyrimidin-2-yl)acrylate (0.35 g, 49%) and ethyl (Z)-ethyl 2-methyl-3-(pyrimidin-2-yl)acrylate (0.15 g, 21%).

LCMS: 193 [M+1]⁺

Step-2

To a solution of ethyl (E)-2-methyl-3-(pyrimidin-2-yl)acrylate (0.26 g, 1.354 mmol, 1 eq) in ethanol (10 mL) was added 1N sodium hydroxide (2.7 mL, 2.71 mmol, 2 eq) at RT and the reaction mixture was allowed to stir at RT for 1 h. Progress of reaction was monitored by TLC. After completion, reaction mixture was acidified with 1N HCl (10 mL) and extracted with ethyl acetate (3×25 mL). Combined organic layer was washed with brine (50 mL) and dried over anhydrous sodium sulfate. Removal of solvent afforded (E)-2-methyl-3-(pyrimidin-2-yl)acrylic acid (0.07 g, 37%).

Step-3

To a solution of (E)-2-methyl-3-(pyrimidin-2-yl)acrylic acid (0.07 g, 0.426 mmol, 1.0 eq.) in dry THF was added triethylamine (0.051 g, 0.511 mmol, 1.2 eq.) and pivaloyl chloride (0.051 g, 0.426 mmol, 1 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.041 g, 0.426 mmol, 1 eq.) in dry THF at −78° C. was added n-butyllithium (2.5 M in hexane, 0.17 mL, 0.426 mmol, 1 eq.) and the mixture was allowed to stir at the same temperature for 1 h. To this solution was added (2E)-3-(4,5-dihydropyrimidin-2-yl)-2-methylprop-2-enoic 2,2-dimethylpropanoic anhydride (0.105 g, 0.426 mmol, 1 eq.) and the reaction mixture was allowed to stir at −78° C. for 1 h. Progress of reaction was monitored by TLC. After completion, reaction mixture was brought to 0° C., diluted with ammonium chloride solution (30 mL) and extracted with ethyl acetate (3×40 mL). Combined organic layer was washed with brine, dried over anhydrous Na₂SO₄ and evaporated to dryness under vacuum to afford crude which was purified by Combi-Flash to afford 1-[(2E)-3-(4,5-dihydropyrimidin-2-yl)-2-methylprop-2-enoyl]-5,6-dihydropyridin-2(1H)-one (10 mg, 10%).

LCMS: 266 [M+23]⁺

¹H NMR (400 MHz, CDCl₃) δ 8.55 (d, 2H), 6.98 (t, 1H), 6.83-6.93 (m, 1H), 6.36 (s, 1H), 5.92 (d, 1H), 4.15 (brs, 2H), 2.58-2.45 (m, 2H), 2.25 (s, 3H).

Example 49

Preparation of (E)-1-(3-(1-(4-fluorobenzoyl)piperidin-4-yl)acryloyl)-5,6-dihydropyridin-2(1H)-one Compound 50

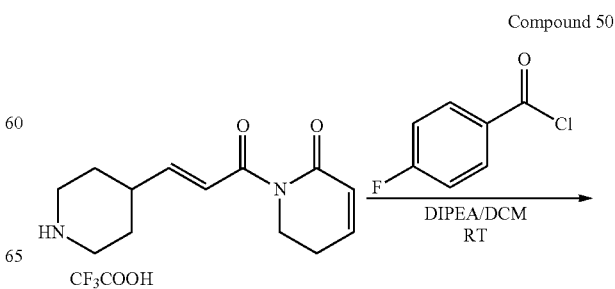

-continued

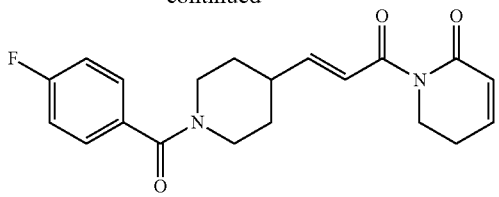

To a suspension of (E)-1-(3-(piperidin-4-yl)acryloyl)-5,6-dihydropyridin-2(1H)-one 2,2,2-trifluoroacetate (150 mg, 0.43 mmol, 1 eq) in dichloromethane (10 mL) was added 4-fluorobenzoyl chloride (68 mg, 0.43 mmol, 1 eq) followed by DIPEA (33 mg, 0.52 mmol, 1.2 eq) at 0° C. and the reaction mixture was allowed to stir at RT for 3 h. Progress of reaction was monitored by TLC and LCMS. After completion, reaction mixture was concentrated to get crude which was purified by Combi-Flash on silica gel (100-200 mesh) using ethyl acetate-hexane system as eluent to afford (E)-1-(3-(1-(4-fluorobenzoyl)piperidin-4-yl)acryloyl)-5,6-dihydropyridin-2(1H)-one (40 mg, 26%).

LCMS: 357 [M+1]$^+$ $^1$H NMR (400 MHz, CDCl$_3$) δ 7.43-7.36 (m, 2H), 7.35-7.25 (m, 2H), 6.98-6.80 (m, 3H), 6.00 (d, 1H), 4.80-4.35 (m, 1H), 3.98 (t, 2H), 3.97-3.60 (m, 1H), 3.20-2.80 (m, 2H), 2.60-2.40 (m, 3H), 2.00-1.70 (m, 2H), 1.60-1.35 (m, 2H).

Example 50

Preparation of (E)-1-(3-(1-(4-fluorophenylsulfonyl)piperidin-4-yl)acryloyl)-5,6-dihydropyridin-2(1H)-one Compound 51

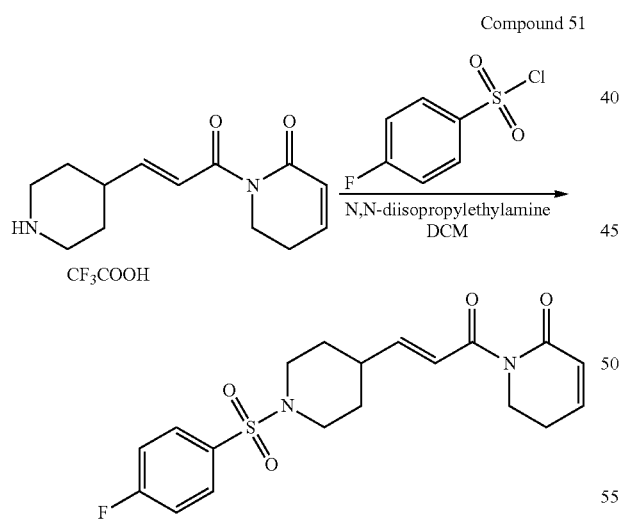

To a solution of (E)-1-(3-(piperidin-4-yl)acryloyl)-5,6-dihydropyridin-2(1H)-one 2,2,2-trifluoroacetate (0.150 g, 0.43 mmol, 1.0 eq.) and N,N-diisopropylethylamine (0.09 mL, 0.646 mmol, 1.5 eq.) in CH$_2$Cl$_2$ was added p-fluorobenzenesulfonyl chloride (0.100 mL, 0.58 mmol, 1.2 eq.) at 0° C. and the reaction mixture was stirred at room temperature for 4 h. Progress of reaction was monitored by TLC. After completion, reaction mixture was diluted with water (50 mL) and extracted with CH$_2$Cl$_2$ (3×30 ml). Combined organic layer was washed with brine (50 mL) and dried over Na$_2$SO$_4$. Removal of solvent under reduced pressure gave crude which was purified by Combi-Flash on silica gel using ethyl acetate-hexane system as eluent to afford (E)-1-(3-(1-(4-fluorophenylsulfonyl)piperidin-4-yl)acryloyl)-5,6-dihydropyridin-2(1H)-one (0.060 g, 36% yield).

LCMS: 393 [M+1]$^+$ $^1$H NMR (400 MHz, CDCl$_3$) δ 7.71-7.84 (m, 2H) 7.22 (t, 2H) 6.87-6.96 (m, 1H) 6.74-6.85 (m, 2H) 5.99 (d, 1H) 3.96 (t, 2H) 3.78 (d, 2H) 2.33-2.49 (m, 4H) 2.16 (d, 1H) 1.85 (d, 2H) 1.57-1.66 (m, 2H) 1.21-1.35 (m, 2H) 0.88 (t, 2H).

Example 51

Preparation of 1-[(2E)-3-(1-methyl-1H-indol-3-yl)prop-2-enoyl]-5,6-dihydropyridin-2(1H)-one Compound 52

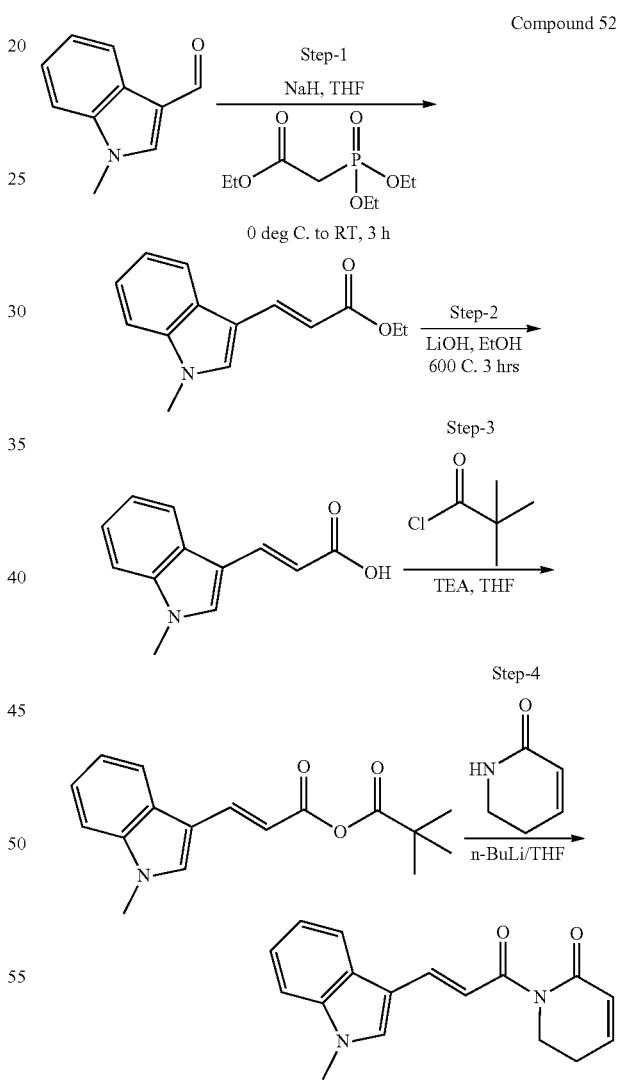

Step-1

To a suspension of sodium hydride (60% in mineral oil, 0.380 g, 9.42 mmol, 1.5 eq) in THF (20 mL) was added ethyl 2-(diethoxyphosphoryl)acetate (1.86 g, 9.42 mmol, 1.5 eq) dropwise at 0° C. and the mixture was allowed to stir at the same temperature for 30 minutes. To this mixture was added a solution of 1-methyl-1H-indole-3-carbaldehyde (1.0 g, 6.28 mmol, 1.0 eq) in THF (5 mL) and the resulting mixture was allowed to stir at room temperature for 2 h. Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash on silica gel (100-200 mesh) using ethyl acetate-hexane system as eluent to afford ethyl (2E)-3-(1-methyl-1H-indol-3-yl)prop-2-enoate (1.3 g, 90.27%).

LCMS: 230 [M+1]$^+$

Step-2

To a solution of ethyl (2E)-3-(1-methyl-1H-indol-3-yl)prop-2-enoate (1.3 g, 5.6 mmol, 1.0 eq) in ethanol (100 mL) was added lithium hydroxide (1.3 g) in water (6.0 mL) and the reaction mixture was stirred at 70° C. for 2 h. Progress of reaction was monitored by TLC. After completion, reaction mixture was concentrated under vacuum, diluted with water (20 mL), acidified with 1N HCL and extracted with ethyl acetate (3×50 mL). Combined organic layer was washed with brine solution (50 mL) and dried over anhydrous Na$_2$SO$_4$. Removal of solvent under reduced pressure afforded (2E)-3-(1-methyl-1H-indol-3-yl)prop-2-enoic acid (1.1 g, 96%) as crystalline solid.

LCMS: 202 [M+1]$^+$

Step-3

To a solution of (2E)-3-(1-methyl-1H-indol-3-yl)prop-2-enoic acid (0.30 g, 1.3 mmol, 1.0 eq.) in dry THF (20 mL) was added triethylamine (0.27 mL, 1.9 mmol, 1.5 eq.) followed by pivaloyl chloride (0.24 mL, 1.9 mmol, 1.5 eq.) and the reaction mixture was stirred at 0° C. for 45 minutes. Progress of reaction was monitored by TLC. After completion, reaction mixture was filtered, and the filtrate was used directly for the next step.

Step-4

To a stirred solution of 5,6-dihydropyridin-2(1H)-one (0.13 g, 1.32 mmol, 0.9 eq.) in dry THF at −78° C. was added n-butyllithium (2.5 M in hexane, 0.54 mL, 1.1 eq.) and the mixture was allowed to stir at the same temperature for 30 minutes. To this solution was added a solution of 2,2-dimethylpropanoic (2E)-3-(1-methyl-1H-indol-3-yl)prop-2-enoic anhydride (0.42 g, 1.48 mmol, 1.1 eq.) in THF and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash to afford 1-[(2E)-3-(1-methyl-1H-indol-3-yl)prop-2-enoyl]-5,6-dihydropyridin-2(1H)-one (0.019 g, 4.63%).

LCMS: 281 [M+1]$^+$ $^1$H NMR (400 MHz, DMSO-d$_6$) δ 7.91-7.80 (m, 3H), 7.60-7.47 (m, 2H), 7.35-7.20 (m, 2H), 7.10-1.02 (m, 1H), 5.99 (d, 1H), 3.93 (t, 2H), 3.83 (s, 1H), 2.50-2.40 (m, 2H).

Example 52

Preparation of 1-[(2E)-3-(1-methyl-1H-pyrazol-3-yl)prop-2-enoyl]-5,6-dihydropyridin-2(1H)-one Compound 53

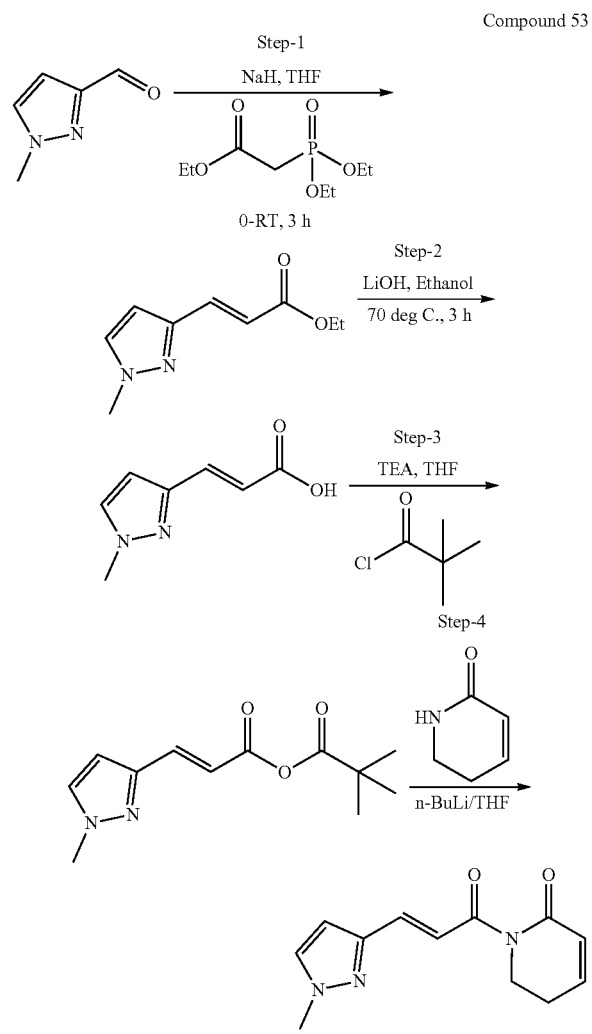

Step-1

To a suspension of sodium hydride (60% in mineral oil, 0.44 g, 10.9 mmol, 1.2 eq) in THF (50 mL) was added ethyl 2-(diethoxyphosphoryl)acetate (2.44 g, 10.9 mmol, 1.2 eq) dropwise at 0° C. and the mixture was allowed to stir at the same temperature for 30 minutes. To this mixture was added a solution of 1-methyl-1H-pyrazole-3-carbaldehyde (1.0 g, 9.09 mmol, 1.0 eq) in THF (5 mL) and the resulting mixture was allowed to stir at room temperature for 2 h. Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash on silica gel using ethyl acetate-hexane system as eluent to afford (2E)-3-(1-methyl-1H-indol-3-yl)prop-2-enoate (0.70 g, 61.11%).

LCMS: 181 [M+1]$^+$

Step-2

To a solution of ethyl (2E)-3-(1-methyl-1H-pyrazol-3-yl)prop-2-enoate (0.70 g, 3.88 mmol, 1.0 eq) in ethanol (100 mL) was added a solution of lithium hydroxide (0.28 g, 11.65 mmol, 3.0 eq) in water (6.0 mL) and the reaction mixture was stirred at 70° C. for 2 h. Reaction mixture was concentrated under vacuum and then acidified with 1N HCl (10 mL). The mixture was diluted with water (30 mL) and extracted with ethyl acetate (3×50 mL). Combined organic layer was washed with brine solution (50 mL) and dried over anhydrous $Na_2SO_4$. Removal of solvent under reduced pressure gave (2E)-3-(1-methyl-1H-pyrazol-3-yl)prop-2-enoic acid (0.32 g, 54%) as crystalline solid.

LCMS: 153 [M+1]$^+$

Step-3

To a solution of (2E)-3-(1-methyl-1H-pyrazol-3-yl)prop-2-enoic acid (0.30 g, 1.97 mmol, 1.0 eq.) in dry THF (20 mL) was added triethylamine (0.33 ml, 2.3 mmol, 1.2 eq.) followed by pivaloyl chloride (0.29 ml, 2.3 mmol, 1.2 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.17 g, 1.9 mmol, 1.0 eq) in dry THF at −78° C. was added nBuLi (0.77 mL, 1.92 mmol, 1.1 eq.) and the mixture was allowed to stir at the same temperature for 30 minutes. To this solution was added a solution of 2,2-dimethylpropanoic (2E)-3-(1-methyl-1H-pyrazol-3-yl)prop-2-enoic anhydride (0.46 g, 1.7 mmol, 1.0 eq.) in THF and the reaction mixture was allowed to stir at room temperature for 1 h. Progress of reaction was monitored by TLC and LCMS. After completion, reaction mixture was evaporated to dryness under vacuum to afford crude which was purified by reversed phase HPLC to afford 1-[(2E)-3-(1-methyl-1H-pyrazol-3-yl)prop-2-enoyl]-5,6-dihydropyridin-2(1H)-one (0.043 g, 9.34%).

LCMS: 232 [M+1]$^+$ $^1$H NMR (400 MHz, DMSO-$d_6$) δ 7.75 (s, 1H), 7.42 (d, 1H), 7.26 (d, 1H), 7.10-7.00 (m, 1H), 6.60 (s, 1H), 5.98 (d, 1H), 3.90-3.80 (m, 5H), 2.55-2.40 (m, 1H).

Example 53

Preparation of 1-[(2E)-3-(1-benzoylpiperidin-4-yl)prop-2-enoyl]-5,6-dihydropyridin-2(1H)-one Compound 54

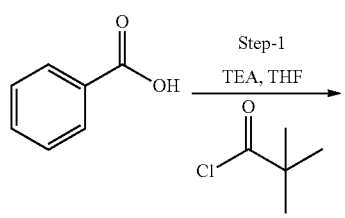

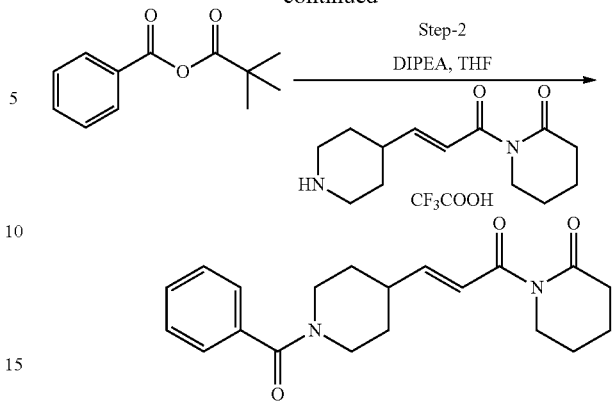

Step-1

To a solution of benzoic acid (0.20 g, 1.63 mmol, 1.0 eq.) in dry THF (20 mL) was added triethylamine (0.34 mL, 2.45 mmol, 1.5 eq.) followed by pivaloyl chloride (0.30 mL, 2.45 mmol, 1.5 eq.) and the reaction mixture was stirred at 0° C. for 45 minutes. Progress of reaction was monitored by TLC. After completion, reaction mixture was filtered, and the filtrate was used directly for the next step.

Step-2

To a stirred solution of 1-[(2E)-3-(piperidin-4-yl)prop-2-enoyl]-5,6-dihydropyridin-2(1H)-one (0.10 g, 0.28 mmol, 1.0 eq.) in dry THF at 0° C. was added DIPEA (0.77 mL, 0.34 mmol, 1.2 eq.) (20 mL) and the mixture was allowed to stir at the same temperature for 30 minutes. To this solution was added a solution of benzoic 2,2-dimethylpropanoic anhydride (0.33 g, 0.28 mmol, 1.0 eq.) in THF and the reaction mixture was allowed to stir at 0° C. for 1 h. Progress of reaction was monitored by TLC and LCMS. After completion, reaction mixture was evaporated to dryness under vacuum to afford crude which was purified by Combi-Flash to afford 1-[(2E)-3-(1-benzoylpiperidin-4-yl)prop-2-enoyl]-5,6-dihydropyridin-2(1H)-one (0.065 g, 11.6%).

LCMS: 339 [M+1]$^+$ $^1$H NMR (400 MHz, DMSO-$d_6$) δ 7.45-7.35 (m, 5H), 7.10-7.01 (m, 1H), 6.85-6.70 (m, 4H), 5.90 (d, 1H), 4.45 (brs, 1H), 3.88-3.80 (m, 2H), 3.60 (brs, 1H), 3.20-2.70 (m, 2H), 2.60-2.40 (m, 1H), 1.80-1.60 (m, 2H), 1.40-1.20 (m, 2H).

Example 54

Preparation of 1-[(2E)-3-(8-methoxy-2,3-dihydro-1,4-benzodioxin-6-yl)-2-methylprop-2-enoyl]-5,6-dihydropyridin-2(1H)-one Compound 55

Step-1

NaH, THF

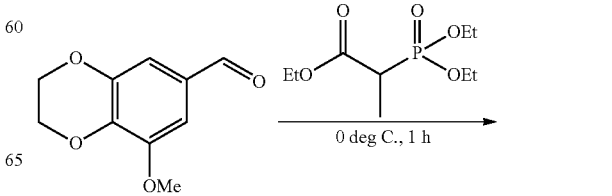

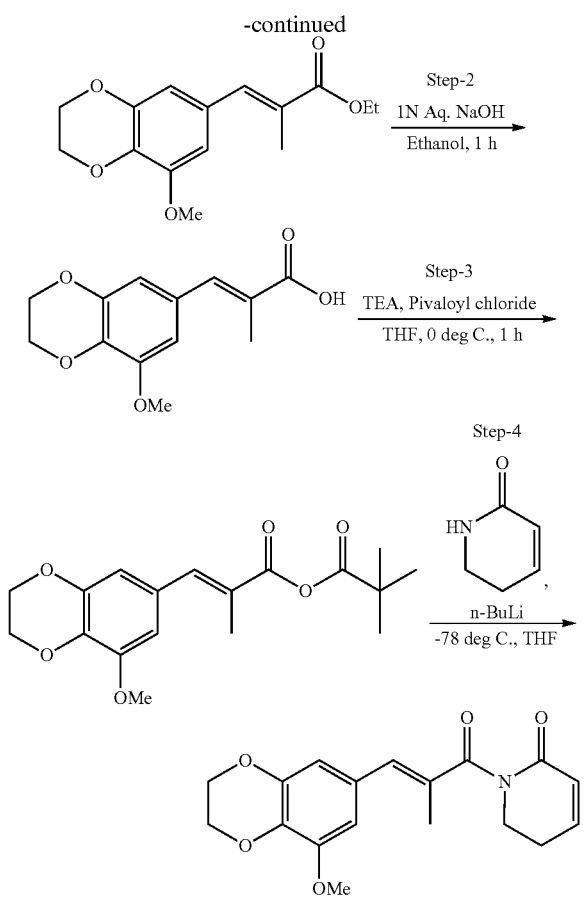

Step-1

To a stirred ice cold solution of NaH (0.543 g, 13.60 mmol, 1.2 eq) in THF (20 mL) was added ethyl 2-(diethoxyphosphoryl)propanoate (2.96 g, 12.47 mmol, 1.1 eq) and resulting mixture was stirred at 0° C. for 10 minutes. To this mixture was added a solution of 8-methoxy-2,3-dihydro-1,4-benzodioxine-6-carbaldehyde (2.2 g, 11.34 mmol, 1 eq) and reaction mixture was allowed to stir at the same temperature for 1 h. Progress of reaction was monitored by TLC and LCMS. After completion, reaction mixture was diluted with saturated aq. ammonium chloride solution (100 mL) and extracted with ethyl acetate (3×100 mL). Combined organic layer was dried over anhydrous. Removal of solvent under reduced pressure afforded crude which was purified by Combi-Flash on silica gel using ethyl acetate-hexane system as eluent to afford ethyl (2E)-3-(8-methoxy-2,3-dihydro-1,4-benzodioxin-6-yl)-2-methylprop-2-enoate (2.3 g, 73%).

Step-2

To a stirred solution of ethyl (2E)-3-(8-methoxy-2,3-dihydro-1,4-benzodioxin-6-yl)-2-methylprop-2-enoate (2.3 g, 8.27 mmol, 1 eq) in ethanol (20 mL) was added 1N aq. NaOH (16.54 mL) and the resulting mixture was stirred at room temperature for 1 h. Progress of reaction was monitored by TLC and LCMS. After completion, reaction mixture was diluted with water (50 mL) and acidified with 1N aq. HCl and extracted with ethyl acetate (3×100 mL). Combined organic layer was washed with brine (50 mL) and dried over anhydrous sodium sulfate. Removal of solvent under reduced pressure afforded (2E)-3-(8-methoxy-2,3-dihydro-1,4-benzodioxin-6-yl)-2-methylprop-2-enoic acid (2 g, 95%) which was used in the next step without further purification.

Step-3

To a stirred solution of (2E)-3-(8-methoxy-2,3-dihydro-1,4-benzodioxin-6-yl)-2-methylprop-2-enoic acid (300 mg, 1.2 mmol, 1 eq) in THF (20 mL) at 0° C. was added triethylamine (145 mg, 1.44 mmol, 1.2 eq) followed by 2,2-dimethylpropanoyl chloride (144 mg, 1.2 mmol, 1 eq) and the resulting mixture was allowed to stir at the same temperature for mixture for 1 h. Progress of reaction was monitored by TLC. After completion, reaction mixture was filtered through cotton plug and used directly in the next reaction.

Step-4

To a stirred solution of 5,6-dihydropyridin-2(1H)-one (116 mg, 1.2 mmol, 1 eq) in THF (20 mL) at −78° C. was added n-BuLi (0.48 mL, 1.2 mmol, 1 eq) dropwise at and the resulting mixture was stirred at same temperature for 1 h. To this mixture was added a solution of 2,2-dimethylpropanoic-3-(8-methoxy-2,3-dihydro-1,4-benzodioxin-6-yl)methyl-prop-2-enoic anhydride (400 mg, 1.2 mmol, 1 eq) in THF (20 mL) dropwise and the mixture was stirred at −78° C. for another 1 h. Progress of reaction was monitored by TLC and LCMS. After completion, reaction mixture was diluted with saturated ammonium chloride solution (50 mL) and extracted with dichloromethane (3×100 mL). Combined organic layer was dried over anhydrous sodium sulfate and concentrated under reduced pressure to yield crude product, which was purified by Combi-Flash on silica gel using ethyl acetate-hexane system as eluent to afford 1-[(2E)-3-(8-methoxy-2,3-dihydro-1,4-benzodioxin-6-yl)-2-methylprop-2-enoyl]-5,6-dihydropyridin-2(1H)-one (120 mg, 30.39%)

LCMS: 330.2 (M+H) $^1$H NMR (400 MHz, CDCl$_3$) δ 6.93 (dd, 1H), 6.81 (s, 1H), 6.65 (s, 1H), 6.54 (s, 1H), 5.99 (d, 1H), 4.29-4.39 (m, 2H), 4.27 (d, 2H), 3.78-3.96 (m, 5H), 2.53 (d, 2H), 2.13 (s, 3H).

Example 55

Preparation of (E)-1-(3-(1-methyl-1H-pyrazol-4-yl)acryloyl)-5,6-dihydropyridin-2(1H)-one Compound 56

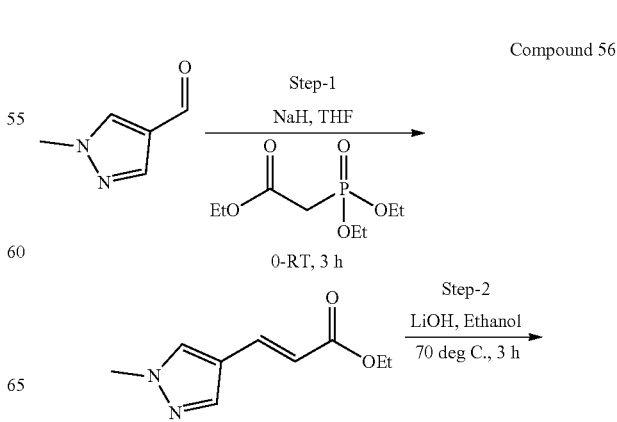

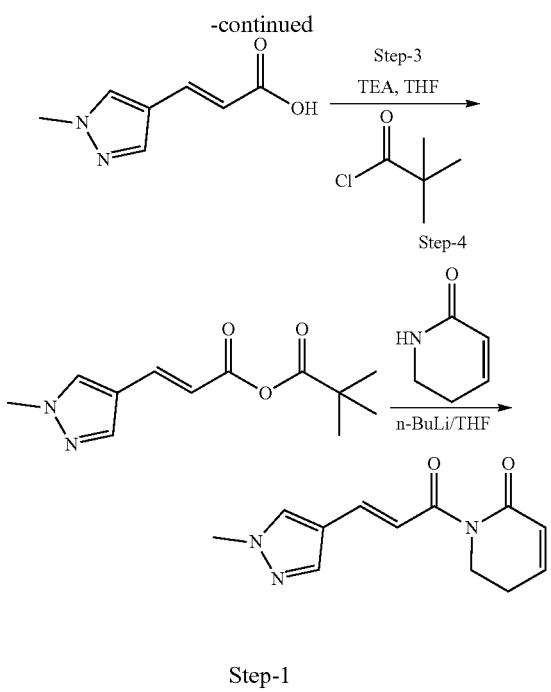

Step-1

To a solution of ethyl 2-(diethoxyphosphoryl)acetate (5.4 g, 22.7 mmol, 1 eq) in THF (100 mL) at 0° C. was added sodium hydride (60% in mineral oil, 1.2 g, 29.5 mmol, 1.3 eq) portion-wise and the mixture was allowed to stir at the same temperature for 30 minutes. To this mixture was added a solution of 1-methyl-1H-pyrazole-4-carbaldehyde (2.5 g, 22.7 mmol, 1.0 eq) in THF (10 mL) and the resulting mixture was allowed to stir at 0° C. for 1 h. Progress of reaction was monitored by TLC. After completion, reaction mixture was diluted with saturated aq. NH$_4$Cl (100 mL) and extracted with ethyl acetate (3×100 mL). Combined organic layer was washed with brine, dried over anhydrous Na$_2$SO$_4$ and evaporated to dryness under vacuum to afford ethyl (E)-3-(1-methyl-1H-pyrazol-4-yl)acrylate (3.9 g, 95%) which was used in the next step without further purification.
LCMS: 181 [M+1]$^+$

Step-2

To a solution of ethyl (E)-3-(1-methyl-1H-pyrazol-4-yl)acrylate (3.90 g, 21.67 mmol, 1.0 eq) in ethanol (100 mL) was added a solution of lithium hydroxide (1.6 g, 65.01 mmol, 3.0 eq) in water (25 mL) and the reaction mixture was stirred at 70° C. for 2 h. Reaction mixture was concentrated under vacuum and then acidified with 1N aq. HCl. The mixture was diluted with water (100 mL) and extracted with ethyl acetate (5×100 mL). Combined organic layer was washed with brine solution (50 mL) and dried over anhydrous Na$_2$SO$_4$. Removal of solvent under reduced pressure gave (E)-3-(1-methyl-1H-pyrazol-4-yl)acrylic acid (2.5 g, 76%) as crystalline solid.
LCMS: 153 [M+1]$^+$

Step-3

To a solution of (E)-3-(1-methyl-1H-pyrazol-4-yl)acrylic acid (1.5 g, 9.9 mmol, 1.0 eq.) in dry THF (50 mL) was added triethylamine (1.68 mL, 12 mmol, 1.2 eq.) followed by pivaloyl chloride (1.23 mL, 9.9 mmol, 1 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.96 g, 9.9 mmol, 1.0 eq.) in dry THF (60 mL) at −78° C. was added n-BuLi (3.9 mL, 9.9 mmol, 1 eq.) and the mixture was allowed to stir at the same temperature for 30 minutes. To this solution was added a solution of (E)-(E)-3-(1-methyl-1H-pyrazol-4-yl)acrylic pivalic anhydride (9.9 mmol, 1.0 eq.) in THF and the reaction mixture was allowed to stir at room temperature for 1 h. Progress of reaction was monitored by TLC and LCMS. After completion, reaction mixture was evaporated to dryness under vacuum to afford crude which was purified by Combi-Flash on silica gel using ethyl acetate-hexane system as eluent to afford 1.4 g (E)-1-(3-(1-methyl-1H-pyrazol-4-yl)acryloyl)-5,6-dihydropyridin-2(1H)-one with 90% LCMS purity. The residue was recrystallized with ethyl acetate and pentane to afford 99% pure (E)-1-(3-(1-methyl-1H-pyrazol-4-yl)acryloyl)-5,6-dihydropyridin-2(1H)-one (1.09 g, 48%).
LCMS: 232 [M+1]$^+$
$^1$H NMR (400 MHz, DMSO-d$_6$) δ 7.75 (s, 1H), 7.42 (d, 1H), 7.26 (d, 1H), 7.10-7.00 (m, 1H), 6.60 (s, 1H), 5.98 (d, 1H), 3.90-3.80 (m, 5H), 2.55-2.40 (m, 1H).

Example 56

Preparation of (E)-1-(3-(1-(phenyl sulfonyl)piperidin-4-yl)acryloyl)-5,6-dihydropyridin-2(1H)-one

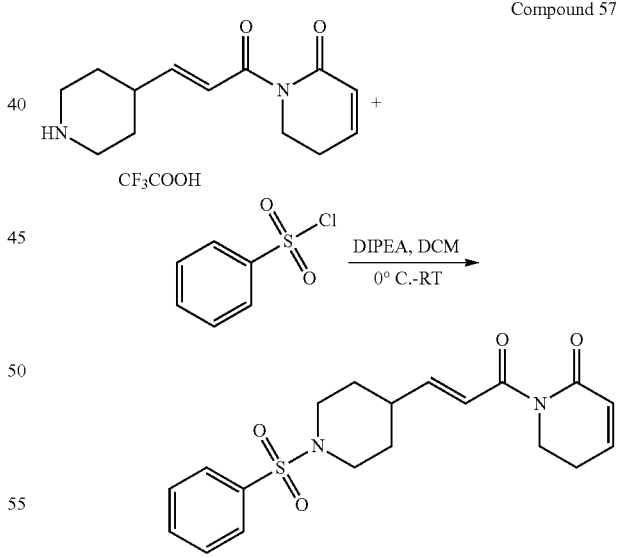

To a solution of (E)-1-(3-(piperidin-4-yl)acryloyl)-5,6-dihydropyridin-2(1H)-one 2,2,2-trifluoroacetate (0.1 g, 0.29 mmol, 1.0 eq.) in dichloromethane (20 mL) at 0° C. was added DIPEA (0.057 mL, 0.43 mmol, 1.5 eq.) followed by benzene sulfonyl chloride (51 mg, 0.29 mmol, 1 eq.) and the reaction mixture was stirred at room temperature for 2 h. Progress of reaction was monitored by TLC. After completion, reaction mixture was diluted with water (50 mL) and extracted with dichloromethane (3×20 mL). Combined organic layer was washed with brine (20 mL) and dried over anhydrous sodium sulfate. Removal of solvent gave crude which was purified by Combi-Flash on silica gel using ethyl acetate-hexane system as eluent to afford (E)-1-(3-(1-(phenylsulfonyl)piperidin-4-yl)acryloyl)-5,6-dihydropyridin-2 (1H)-one (50 mg, 46%).

LCMS: 375 [M+1]$^+$ $^1$H NMR (400 MHz, CDCl$_3$) δ 7.79 (d, 2H), 7.65-7.50 (m, 3H), 6.95-6.78 (m, 4H), 3.96 (t, 2H), 3.80 (d, 2H), 2.50-2.30 (m, 4H), 2.20-2.08 (m, 1H), 1.90-1.79 (m, 2H), 1.67-1.50 (m, 2H).

Example 57

Preparation of N-(4-fluorophenyl)-4-[(1E)-3-oxo-3-(6-oxo-3,6-dihydropyridin-1(2H)-yl)prop-1-en-1-yl]piperidine-1-carboxamide

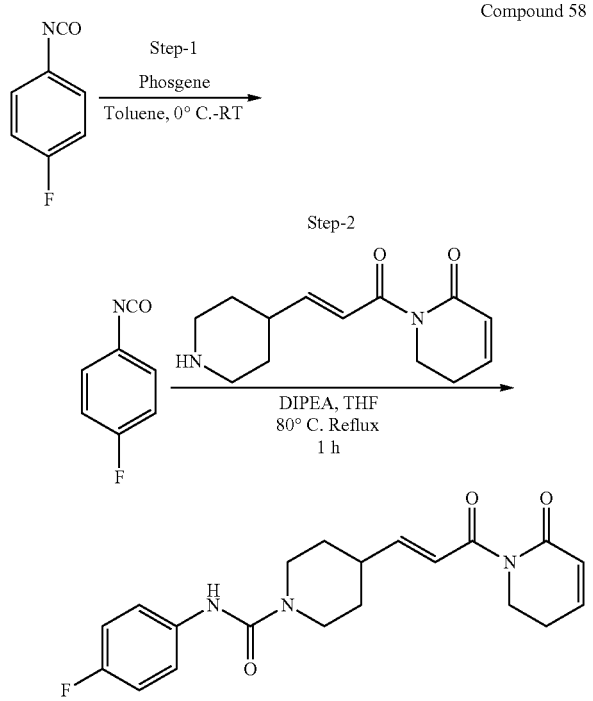

Compound 58

Step-1

To a stirred solution of 4-fluoroaniline (1.2 g, 10.81 mmol, 1 eq) in dry toluene (10 mL) was added phosgene (20% in toluene, 5.29 ml 10.81 mmol 1 eq) dropwise at 0° C. and the resulting mixture was stirred for 20 minutes. To this mixture was then added a solution of triethylamine (1.69 mL 12.97 mmol 1.2 eq) in toluene (5 mL) and the resulting mixture was stirred at room temperature for 1 h. Progress of reaction was monitored by TLC. After completion, reaction mixture was concentrated under reduced pressure to yield 1-fluoro-4-isocyanatobenzene which was used in the next step without purification.

Step-2

To a stirred solution of 1-[(2E)-3-(piperidin-4-yl)prop-2-enoyl]-5,6-dihydropyridin-2(1H)-one (0.1 g, 0.287 mmol, 1 eq) in THF (5 mL) was added DIPEA (0.075 mL, 0.430 mmol, 1.5 eq) and the resulting mixture was stirred for 10 minutes. To this mixture was then added a solution of 1-fluoro-4-isocyanatobenzene (0.039 g, 0.287 mmol, 1 eq) in THF (5 mL) and mixture was stirred under reflux 1 h. Progress of reaction was monitored by TLC. After completion, reaction mixture was diluted with ethyl acetate (80 mL), washed with brine (2×50 mL) and dried over sodium sulphate. Removal of solvent under reduced pressure afforded crude which was purified by Combi-Flash on silica gel using ethyl acetate-hexane system as eluent to afford N-(4-fluorophenyl)-4-[(1E)-3-oxo-3-(6-oxo-3,6-dihydropyridin-1(2H)-yl)prop-1-en-1-yl]piperidine-1-carboxamide (50 mg, 47.16% yield).

LCMS: 371 [M+l]$^+$ $^1$H NMR (400 MHz, DMSO-d$_6$) δ 8.51 (s, 1H), 7.45 (dd, 2H), 6.99-7.13 (m, 2H), 6.68-6.84 (m, 2H), 5.93 (d, 1H), 4.11 (d, 2H), 3.84 (t, 2H), 2.85 (t, 2H), 2.42 (d, 3H), 1.73 (d, 2H), 1.17-1.38 (m, 3H).

Example 58

Preparation of 1-{(2E)-3-[1-(2-hydroxy-2-methylpropyl)piperidin-4-yl]prop-2-enoyl}-5,6-dihydropyridin-2(1H)-one

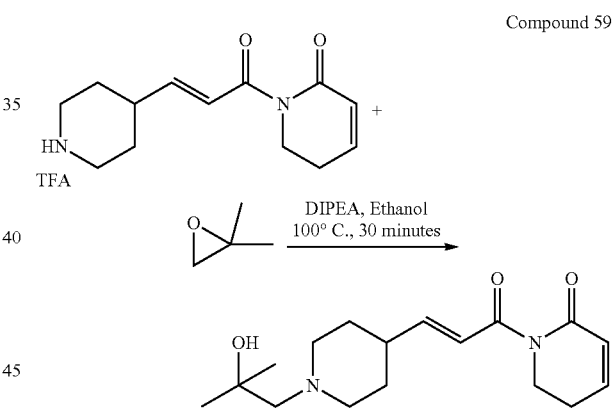

Compound 59

To a stirred solution of a (E)-1-(3-(piperidin-4-yl)acryloyl)-5,6-dihydropyridin-2(1H)-one 2,2,2-trifluoroacetate (200 mg, 0.57 mmol, 1 eq) in ethanol (10 mL) was added DIPEA (583 mg, 5.7 mmol, 10 eq) and the resulting mixture was stirred for 5 minute. To this mixture was added 2,2-dimethyloxirane (252 mg, 3.5 mmol, 6.1 eq) and reaction mixture was stirred at 100° C. for 30 minutes. Progress of reaction was monitored by TLC and LCMS. After completion, reaction mixture was concentrated under vacuum to afford crude oil which was purified by reversed phase chromatography to afford 1-{(2E)-3-[1-(2-hydroxy-2-methylpropyl)piperidin-4-yl]prop-2-enoyl}-5,6-dihydropyridin-2(1H)-one (20 mg, 11%).

LCMS: 307.3 [M+H]$^+$ $^1$H NMR (400 MHz, CDCl$_3$) δ 7.00-6.86 (m, 2H), 6.81 (d, 1H), 6.00 (d, 1H), 4.01-3.95 (m, 2H), 3.00-2.92 (m, 2H), 2.46-2.20 (m, 6H), 1.82-1.70 (m, 2H), 1.65-1.50 (m, 2H), 1.19 (s, 6H).

Example 59

Preparation of 1-{3-[1-(4-fluorobenzyl)piperidin-4-yl]prop-2-enoyl}-5,6-dihydropyridin-2(1H)-one Compound 60

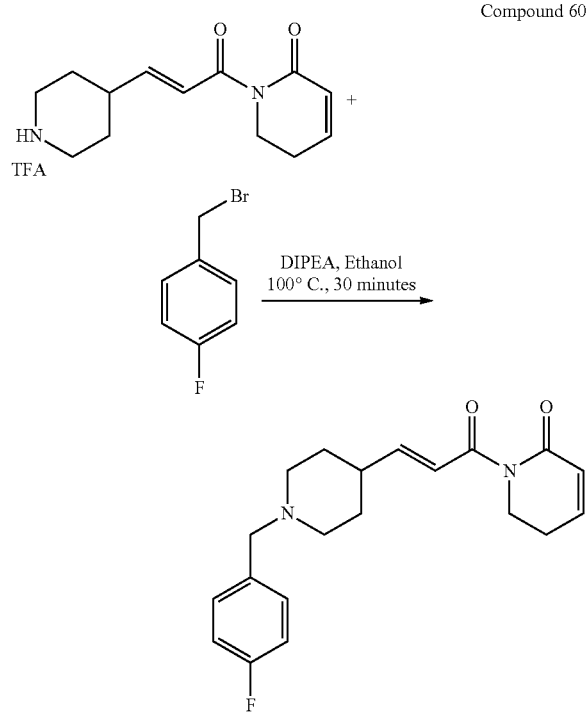

To a stirred solution of a (E)-1-(3-(piperidin-4-yl)acryloyl)-5,6-dihydropyridin-2(1H)-one 2,2,2-trifluoroacetate (200 mg, 0.57 mmol, 1 eq) in ethanol (10 mL) was added DIPEA (583 mg, 5.7 mmol, 10 eq) and the resulting mixture was stirred for 5 minute. To this mixture was added 1-(bromomethyl)-4-fluorobenzene (176 mg, 0.93 mmol, 1.6 eq) and heated the resulting reaction mixture at 100° C. for 60 minutes. Progress of reaction was monitored by TLC and LCMS. After completion, reaction mixture was concentrated under vacuum to afford crude oil which was purified by reversed phase chromatography to afford 1-{3-[1-(4-fluorobenzyl)piperidin-4-yl]prop-2-enoyl}-5,6-dihydropyridin-2(1H)-one (20 mg, 10%).

LCMS: 344.3 [M+H]

$^1$H NMR (400 MHz, CD$_3$OD) 7.53 (dd, 2H) 7.23 (t, 2H) 6.99-7.11 (m, 1H) 6.70-6.91 (m, 2H) 5.96 (d, 1H) 4.25 (brs, 2H) 3.93 (t, 2H) 3.43 (brs, 2H) 3.01 (brs, 2H) 2.54 (brs, 1H) 2.47 (d, 2H) 2.05 (d, 2H) 1.68 (brs, 2H).

Example 60

Preparation of 1-{3-[1-(4-fluorophenyl)piperidin-4-yl]prop-2-enoyl}-5,6-dihydropyridin-2(1H)-one Compound 61

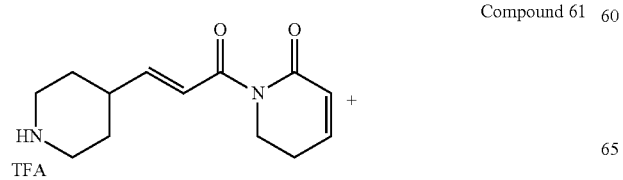

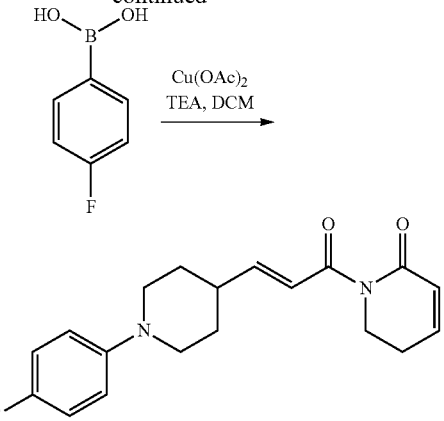

To a stirred solution of a 1-[3-(piperidin-4-yl)prop-2-enoyl]-5,6-dihydropyridin-2(1H)-one TFA salt (100 mg, 0.29 mmol, 1 eq) in DCM (20 mL) was added TEA (0.12 mL, 0.58 mmol, 2 eq) the resulting mixture was stirred for 5 minutes. To this mixture was added 4-fluorophenyl boronic acid (80 mg, 0.58 mmol, 2 eq) and reaction mixture was stirred at room temperature overnight. Progress of reaction was monitored by TLC and LCMS. After completion, reaction mixture was diluted with water (50 mL) and extracted with ethyl acetate (3×50 mL). Combined organic layer was dried over anhydrous sodium sulfate. Removal of solvent under reduced pressure gave crude which was purified by Combi-Flash on silica gel to afford 1-{3-[1-(4-fluorophenyl)piperidin-4-yl]prop-2-enoyl}-5,6-dihydropyridin-2(1H)-one (15 mg, 16%). LCMS: 329.2 [M+H]

$^1$H NMR (400 MHz, CDCl$_3$) δ 7.05-6.85 (m, 7H), 6.02 9 (d, 1H), 4.02-3.97 (m, 2H), 3.60-3.55 (m, 2H), 2.78-2.65 (m, 2H), 2.46-2.25 (m, 3H), 1.95-1.187 (m, 2H), 1.78-1.56 (m, 2H).

Example 61

Preparation of (E)-1-(3-(1-neopentylpiperidin-4-yl)acryloyl)-5,6-dihydropyridin-2(1H)-one Compound 62

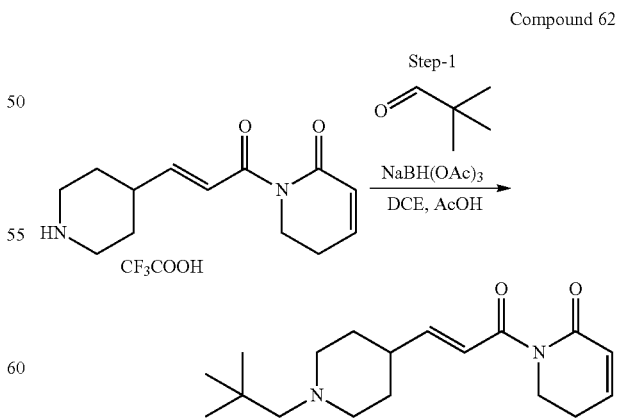

To a stirred solution of (E)-1-(3-(piperidin-4-yl)acryloyl)-5,6-dihydropyridin-2(1H)-one TFA Salt (0.150 g, 0.641 mmol, 1.0 eq) in DCE (20 mL) were added pivalaldehyde (0.165 ml, 1.923 mmol, 3.0 eq) and acetic acid (0.096 mL, 3.205 mmol, 5.0 eq). The reaction mixture was allowed to stir at RT for 1 h and followed by the addition of sodium triacetoxyborohydride (0.408 g, 1.933 mmol, 3.0 eq) and stirring was continued further at room temperature for 1 h. Progress of the reaction was monitored by TLC and LCMS. After completion of the reaction, the reaction mixture was diluted with water (30 mL) and extracted with ethyl acetate (2×30 mL). Organic layer was washed with brine solution (30 mL). Organic layer was dried over anhydrous sodium sulphate and concentrated under reduced pressure to obtain crude, which was purified by reversed phase HPLC to afford (E)-1-(3-(1-neopentylpiperidin-4-yl)acryloyl)-5,6-dihydropyridin-2(1H)-one (0.010 g, 5.1%) was obtained as off white solid.

LCMS: 305 [M+1]⁺

¹H NMR (400 MHz, DMSO-d₆) δ 7.04-7.10 (m, 1H) 6.76-6.83 (m, 1H) 6.66-6.73 (m, 1H) 5.92 (d, 1H) 3.83 (t, 2H) 2.76 (d, 2H) 2.42 (d, 2H) 2.18-2.25 (m, 2H) 2.09 (br. s., 1H) 1.62 (d, 2H) 1.32-1.41 (m, 2H) 0.83 (s, 9H).

Example 62

Preparation of (E)-1-(3-(5-methoxypyrimidin-2-yl)acryloyl)-5,6-dihydropyridin-2(1H)-one Compound 63

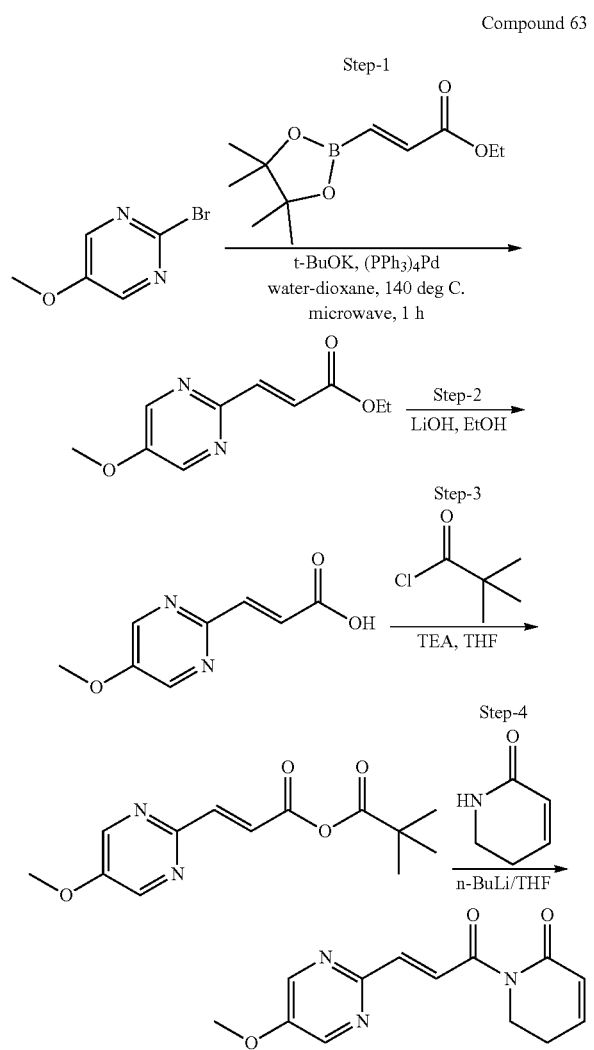

Step-1

To a solution of 2-bromo-5-methoxypyrimidine (0.5 g, 2.66 mmol, 1.0 eq) in 1,4-dioxane (15 mL) were added ethyl (E)-3-(4,4,5,5-tetramethyl-1,3,2-dioxaborolan-2-yl)acrylate (0.721 g, 3.19 mmol, 1.2 eq) and potassium tert-butoxide (0.595 g, 5.32 mmol, 2.0 eq) in water (2 mL) and the reaction mixture was deoxygenated using nitrogen gas for 10 minutes. Tetrakis(triphenylphosphine)palladium(0) (0.153 g, 0.132 mmol, 0.05 eq) was added and the reaction mixture was again deoxygenated for 10 minutes. Reaction mixture was allowed to stir at 140° C. for 1 h in microwave and progress of reaction was monitored by TLC, after completion the reaction mixture was cooled to RT. The mixture was diluted with water (30 mL) and extracted with ethyl acetate (3×30 mL). Combined organic layer was washed with brine solution (50 mL) and dried over anhydrous Na₂SO₄. Solvent was concentrated under reduced pressure to afford crude which was purified by Combi-Flash on silica gel using ethyl acetate-hexane as eluent to afford ethyl (E)-3-(5-methoxypyrimidin-2-yl)acrylate (0.4 g, 72.72%). LCMS: 209 [M+1]⁺

Step-2

To a solution of ethyl (E)-3-(5-methoxypyrimidin-2-yl)acrylate (0.4 g, 1.92 mmol, 1.0 eq) in ethanol (40 mL) was added a solution of lithium hydroxide (0.138 g, 5.769 mmol, 3.0 eq) in water (10.0 mL) and the reaction mixture was stirred at 70° C. for 2 h. Progress of reaction was monitored by TLC. After completion the reaction mixture was cooled to RT, The reaction mixture was concentrated under vacuum and then acidified with 1N HCl (10 mL). The mixture was diluted with water (30 mL) and extracted with ethyl acetate (3×30 ml). Combined organic layer was washed with brine solution (50 mL) and dried over anhydrous Na₂SO₄. Concentrated the solvent under reduced pressure gave (E)-3-(5-methoxypyrimidin-2-yl)acrylic acid (0.320 g, 86.70%) as crystalline solid.

LCMS: 181 [M+1]⁺

Step-3

To a solution of (E)-3-(5-methoxypyrimidin-2-yl)acrylic acid (0.3 g, 1.665 mmol, 1.0 eq.) in dry THF (10 mL) was added triethylamine (0.257 mL, 1.833 mmol, 1.1 eq.) followed by pivaloyl chloride (0.219 mL, 1.833 mmol, 1.1 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.100 g, 1.03 mmol, 1.0 eq.) in dry THF (10 mL) at −78° C. was added n-butyllithium (2.5 M in hexane, 0.45 mL, 1.13 mmol, 1.1 eq.) and the mixture was allowed to stir at the same temperature for 30 minutes. To this solution was added a solution of (E)-(E)-3-(5-methoxypyrimidin-2-yl)acrylic pivalic anhydride (0.299 g, 1.134 mmol, 1.1 eq.) in THF (10 mL) and the reaction mixture was allowed to stir at −78° C. for 1 h. Progress of reaction was monitored by TLC. After completion, reaction mixture was brought to 0° C., diluted with water (30 mL) and extracted with ethyl acetate (3×30 mL). Combined organic layer was washed with brine, dried over anhydrous Na₂SO₄ and evaporated to dryness under vacuum to afford crude which was purified by Combi-Flash to afford (E)-1-(3-(5-methoxypyrimidin-2-yl)acryloyl)-5,6-dihydropyridin-2(1H)-one (0.140 g, 52.23%) was obtained as off white solid.

LCMS: 260 [M+1]

$^1$H NMR (400 MHz, CDCl$_3$) δ 8.42 (s, 2H), 7.95 (d, 1H), 7.67 (d, 1H), 6.91-7.00 (m, 1H), 6.05 (d, 1H), 4.05 (t, 2H), 3.95 (s, 3H), 2.55-2.45 (m, 2H).

Example 63

Preparation of tert-butyl (E)-4-methyl-4-(3-oxo-3-(6-oxo-3,6-dihydropyridin-1(2H)-yl)prop-1-en-1-yl)piperidine-1-carboxylate

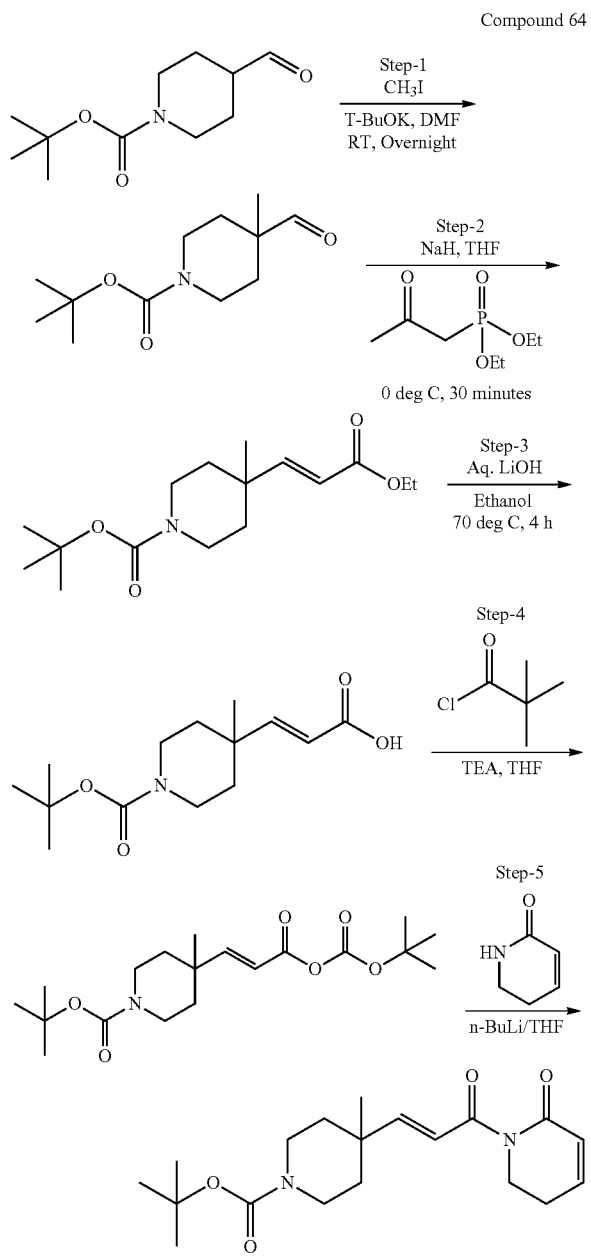

Step-1

To a solution of tert-butyl 4-formylpiperidine-1-carboxylate (3 g, 14.08 mmol) in DMF (30 mL) were added t-BuOK (1.56 g, 28 mmol, 2 eq) and methyl iodide (3.98 g, 28 mmol, 2 eq) at 0° C. The reaction mixture was stirred at RT overnight. Progress of reaction was monitored by TLC. After completion, reaction mixture was diluted with brine (50 mL) and extracted EtOAc (2×50 mL). Combine organic layer was washed with brine and dried over anhydrous sodium sulfate. Removal of solvent under reduced pressure gave tert-butyl 4-formyl-4-methylpiperidine-1-carboxylate (3 g, 94%) which was used in the next step without purification.

LCMS: 228 [M+1]$^+$

Step-2

To a suspension of sodium hydride (60% in mineral oil, 793 mg 19.83 mmol, 1.5 eq) in THF (50 mL) ethyl (diethoxyphosphoryl)acetate (3.77 g, 16.83 mmol, 1.3 eq) dropwise at 0° C. and the mixture was allowed to stir at the same temperature for 30 minutes. To this mixture was added a solution of tert-butyl 4-formyl-4-methylpiperidine-1-carboxylate (3 g, 13.22 mmol, 1.0 eq) in THF (5 mL) and the resulting mixture was allowed to stir at room temperature for 1 h. Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash using ethyl acetate-hexane system as eluent to afford tert-butyl 4-[(1E)-3-ethoxy-3-oxoprop-1-en-1-yl]-4-methylpiperidine-1-carboxylate (1.4 g, 36%).

LCMS: 298 [M+1]$^+$

Step-3

To a solution of tert-butyl 4-[(1E)-3-ethoxy-3-oxoprop-1-en-1-yl]-4-methylpiperidine-1-carboxylate (1.1 g, 3.7 mmol, 1.0 eq) in ethanol (200 mL) was added a solution of Lithium hydroxide (444 mg, 18.5 mmol, 5 eq) in water (20 mL) and the reaction mixture was stirred at 70° C. for 4 h. Progress of reaction was monitored by TLC. After completion, reaction mixture was concentrated under vacuum and then acidified with 2N HCl to make pH up to 3. The mixture was diluted saturated aq. NH$_4$Cl (30 mL) and extracted with dichloromethane (3×30 mL). Combined organic layer was washed with brine solution (50 mL) and dried over anhydrous Na$_2$SO$_4$. Removal of solvent under reduced pressure afforded (2E)-3-{4-methyl-1-[(propan-2-yloxy)carbonyl]piperidin-4-yl}prop-2-enoic acid as crystalline solid (0.65 g, 65%). LCMS: 270 [M+1]$^+$

Step-4

To a solution of (E)-3-(1-(tert-butoxycarbonyl)piperidin-4-yl)-2-methylacrylic acid (200 mg, 0.743 mmol, 1.0 eq) in dry THF was added triethylamine (0.1 mL, 0.817 mmol, 1.1 eq) followed by pivaloyl chloride (98 µL, 0.817 mmol, 1.1 eq) and the reaction mixture was stirred at 0° C. for 45 minutes. Progress of reaction was monitored by TLC. After completion, reaction mixture was filtered and the filtrate was used directly for the next step.

Step-5

To a stirred solution of 5,6-dihydropyridin-2(1H)-one (80 mg, 0.82 mmol, 1.1 eq.) in dry THF at −78° C. was added n-butyllithium (2.5 M in hexane, 0.33 ml, 0.82 mmol, 1.1 eq.) and the mixture was allowed to stir at the same temperature for 30 minutes. To this solution was added a solution of anhydride (0.743 mmol, 1 eq) in THF and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×30 mL). Combined organic layer was washed with brine, dried over anhydrous Na$_2$SO$_4$ and evaporated to dryness under vacuum to afford crude which was purified by reversed phase HPLC to afford tert-butyl (E)-4-methyl-4-(3-oxo-3-(6-oxo-3,6-dihydropyridin-1(2H)-yl)prop-1-en-1-yl)piperidine-1-carboxylate (50 mg, 19%).

LCMS: 349 [M+1]$^+$ $^1$H NMR (400 MHz, CDCl$_3$) δ 6.86-7.01 (m, 2H) 6.73-6.83 (m, 1H) 6.00 (dd, 1H) 3.98 (br. s, 2H), 3.54 (brs, 2H), 3.29 (t, 2H), 2.45 (dt, 2H), 1.64-1.80 (m, 2H), 1.57 (brs, 2H) 1.45 (s, 9H), 1.11 (s, 3H).

Example 64

Preparation of (E)-1-(3-(2,3-dihydro-[1,4]dioxino[2,3-b]pyrazin-6-yl)acryloyl)-5,6-dihydropyridin-2(1H)-one Compound 65

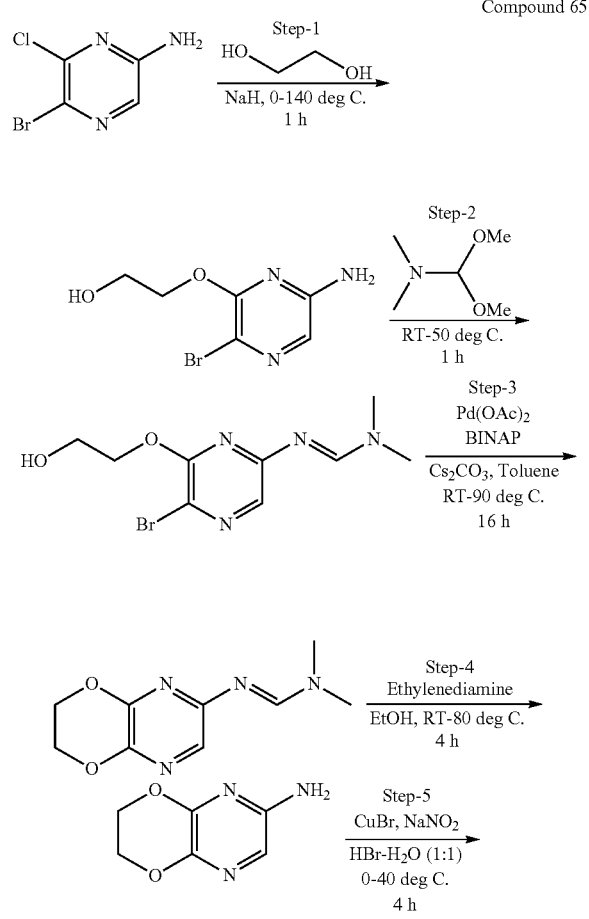

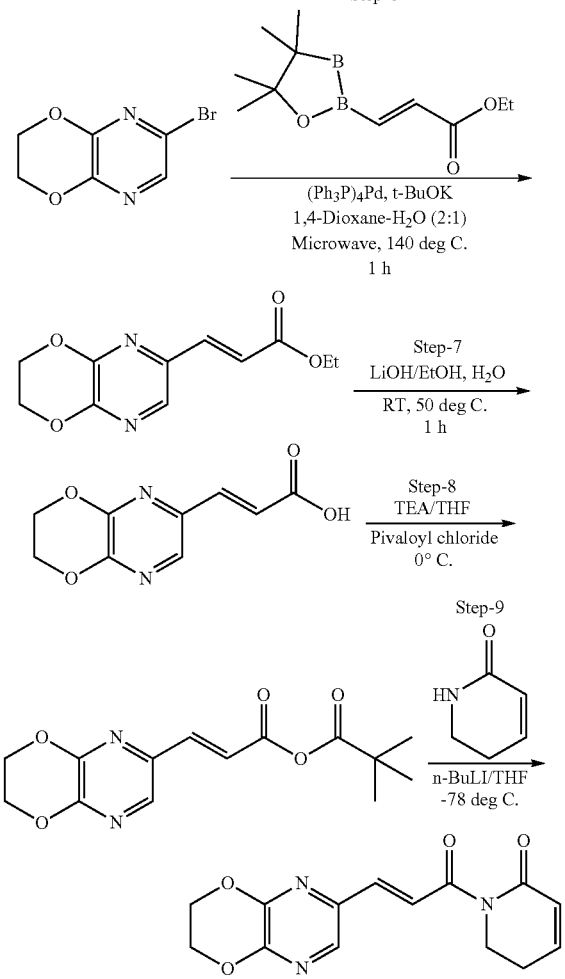

Step-1

NaH (60% in mineral oil) (1.84 g, 76.73 mmol, 2.0 eq) was added slowly to ethylene glycol (50 mL) at 0° C. over a period of 15 minutes under inert atmosphere and reaction mixture was allowed to stir at the same temperature for 30 minutes. To this mixture was added Then 5-bromo-6-chloropyrazin-2-amine (8 g, 38.36 mmol, 1 eq) at 0° C. and the resulting mixture was allowed to stir 140° C. for 1 h. Progress of reaction was monitored by TLC. After completion, reaction mixture was diluted with ice cold water (500 mL) and extract with ethyl acetate (2×500 mL). Combined organic layer was washed with brine and dried over anhydrous sodium sulfate. Removal of solvent under reduce pressure afforded 2-(6-amino-3-bromopyrazin-2-yloxy)ethanol (8.97 g, 99.66%) as white solid which was used in the next step without purification.

Step-2

A mixture of 2-(6-amino-3-bromopyrazin-2-yloxy)ethanol (8.97 g, 38.33 mmol, 1.0 eq.) and DMF-DMA (15 mL) was allowed to stir at 50° C. for 1 h. Progress of reaction was monitored by TLC. After completion, reaction mixture was diluted with ice-cold water (500 mL) and extract with ethyl acetate (2×500 mL). Combined organic layer was washed with brine and dried over anhydrous sodium sulfate. Removal of solvent under reduced pressure afforded gave (E)-N'-(5-bromo-6-(2-hydroxyethoxy)pyrazin-2-yl)-N,N-dimethylformimidamide (11 g, 99.66%) as white solid.

Step-3

To a solution of (E)-N'-(5-bromo-6-(2-hydroxyethoxy)pyrazin-2-yl)-N,N-dimethylformimidamide (11 g, 38 mmol, 1 eq) in toluene (80 ml) was added $Cs_2CO_3$ (37.33 g, 114 mmol, 3.0 eq) at room temperature. The reaction mixture was deoxygenated by purging nitrogen for 5 minutes. To this mixture were added $Pd(OAc)_2$ (850 mg, 3 mmol, 0.1 eq) and BINAP (4.75 g, 7 mmol, 0.2 eq) and reaction mixture was again deoxygenated allowed by purging nitrogen for 10 minutes. Then the reaction mixture was stirred at 90° C. for 16 h. Progress of reaction was monitored by TLC. After completion, reaction mixture was diluted with water (200 mL) and extract with ethyl acetate (3×250 mL). Combined organic layer was washed with brine and dried over anhydrous sodium sulfate. Removal of solvent under reduced pressure afforded crude which was purified by Combi-Flash on silica gel using ethyl acetate-hexane system as eluent to afford (E)-N'-(2,3-dihydro-[1,4]dioxino[2,3-b]pyrazin-6-yl)-N,N-dimethylformimidamide (2.5 g, 31.60%).

Step-4

To a solution of (E)-N'-(2,3-dihydro-[1,4]dioxino[2,3-b]pyrazin-6-yl)-N,N-dimethylformimidamide (4 g, 19 mmol, 1 eq) in EtOH (30 mL) was added ethylenediamine (2 mL, 38 mmol, 2 eq) at RT and the resulting reaction mixture was allowed to stir at 80° C. for 4 h. Progress of reaction was monitored by TLC. After completion, solvent was evaporated under reduced pressure, diluted with water (100 mL) and extracted with ethyl acetate (3×150 mL). Combined organic layer was washed with brine (100 mL) and dried over anhydrous sodium sulfate. Removal of solvent under reduced pressure afforded 2,3-dihydro-[1,4]dioxino[2,3-b]pyrazin-6-amine (2.85 g, 96.93%) as off white solid.

Step-5

To a solution of 2,3-dihydro-[1,4]dioxino[2,3-b]pyrazin-6-amine (2 g, 13.05 mmol, 1 eq) in a 1:1 mixture of 48% aq. HBr in water (10 mL) and water at 0° C. was added a solution $NaNO_2$ (1.35 g, 19.58 mmol, 1.5 eq) portion-wise. The reaction mixture was allowed to stir at the same temperature for 5 minutes. To this mixture was then added CuBr (3.73 g, 26.11 mmol, 2 eq) under nitrogen atmosphere at 0° C. and the reaction mixture was allowed to stir at 0° C. for 1 h. Progress of reaction was monitored by TLC. After completion, reaction mixture was diluted with water (30 mL) and extracted with ethyl acetate (3×250 mL). Combined organic layer was washed with brine and dried over anhydrous sodium sulfate. Removal of solvent under reduced pressure afforded 6-bromo-2,3-dihydro-[1,4]dioxino[2,3-b]pyrazine (300 mg, 10.93%) as brown solid.

Step-6

To a solution of 6-bromo-2,3-dihydro-[1,4]dioxino[2,3-b]pyrazine (250 mg, 1.15 mmol, 1 eq) in a mixture of 1,4-dioxane (5 mL) and $H_2O$ (2 mL) were added (E)-ethyl 3-(4,4,5,5-tetramethyl-1,3,2-dioxaborolan-2-yl)acrylate (312.6 mg, 1.38 mmol, 1.2 eq) and t-BuOK (193.91 mg, 1.72 mmol, 1.5 eq) at room temperature. The reaction mixture was deoxygenated by purging nitrogen for 5 minutes. To this mixture was added $(Ph_3P)_4Pd$ (66.6 mg, 0.05 mmol, 0.05 eq) and mixture was again deoxygenated by purging nitrogen for 10 minutes. The reaction mixture was stirred at 140° C. under microwave for 1 h. Progress of reaction was monitored by TLC. After completion, reaction mixture was diluted with water (50 mL) and extract with ethyl acetate (3×50 mL). Combined organic layer was washed with brine and dried over anhydrous sodium sulfate. Removal of solvent under reduced pressure afforded crude which was purified by Combi-Flash on silica gel using ethyl acetate-hexane system as eluent to afford (E)-ethyl dihydro-[1,4]dioxino[2,3-b]pyrazin-6-yl)acrylate (170 mg, 62.73%)

Step-7

To a solution of (E)-ethyl 3-(2,3-dihydro-[1,4]dioxino[2,3-b]pyrazin-6-yl)acrylate (250 mg, 0.97 mmol, 1 eq) in EtOH (10 mL) at RT was added a solution of LiOH (116.54 mg, 4.86 mmol, 5 eq) in water (1 mL) and the resulting mixture was allowed to stir at 50° C. for 1 h. Progress of reaction was monitored by TLC. After completion, reaction mixture was concentrated to remove ethanol, washed with diethyl ether (2×10 mL), acidified with 1N HCl up to pH 6 and extracted with mixture of ethanol and ethyl acetate (1:4) (3×50 mL). Combined organic layer was washed with brine and dried over anhydrous sodium sulfate. Removal of solvent afforded crude (E)-3-(2,3-dihydro-[1,4]dioxino[2,3-b]pyrazin-6-yl)acrylic acid (170 mg, 77.27%) as white solid which was used in the next step without purification.

Step-8

To a solution of (E)-3-(2,3-dihydro-[1,4]dioxino[2,3-b]pyrazin-6-yl)acrylic acid (0.170 g, 0.81 mmol, 1.0 eq.) in dry THF were added triethylamine (0.098 g, 0.97 mmol, 1.2 eq) and pivaloyl chloride (0.098 g, 0.81 mmol, 1 eq). The reaction mixture was stirred at 0° C. for 45 minutes. Progress of reaction was monitored by TLC. After completion, reaction mixture was filtered and the filtrate was used directly for the next step.

Step-9

To a stirred solution of 5,6-dihydropyridin-2(1H)-one (0.079 g, 0.81 mmol, 1 eq.) in dry THF at −78° C. was added n-butyl lithium (2.5 M in hexane, 0.32 mL, 0.81 mmol, 1 eq) and the mixture was allowed to stir at the same temperature for 30 minutes. To this solution was added anhydride (0.238 g, 0.81 mmol, 1 eq). Reaction mixture was allowed to stir at −78° C. for 90 minutes. Progress of reaction was monitored by TLC. After completion, reaction mixture was brought to 0° C., diluted with ammonium chloride solution (30 mL) and extracted with ethyl acetate (3×50 mL). Combined organic layer was washed with brine, dried over anhydrous $Na_2SO_4$ and evaporated to dryness under vacuum to afford crude which was purified by Combi-Flash on silica gel using ethyl acetate-hexane as eluent to afford (E)-1-(3-(2,3-dihydro-[1,4]dioxino[2,3-b]pyrazin-6-yl)acryloyl)-5,6-dihydropyridin-2(1H)-one (60 mg, 26%).

LCMS: 288 [M+1]+

$^1$HNMR (400 MHz, $CDCl_3$) δ 7.95 (s, 1H), 7.70 (d, 1H), 7.59 (d, 1H), 6.95-6.88 (m, 1H), 6.03 (d, 1H), 4.57-4.44 (m, 4H), 4.02 (t, 2H), 2.50-2.40 (m, 2H).

Example 65

Preparation of 1-{[(E)-2-(pyrimidin-2-yl)ethenyl]sulfonyl}-5,6-dihydropyridin-2(1H)-one Compound 66

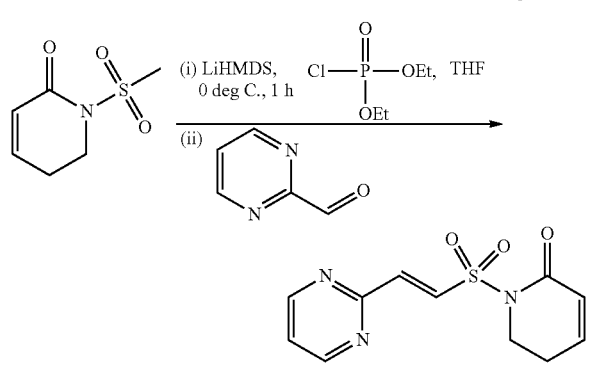

To a solution of 1-(methylsulfonyl)-5,6-dihydropyridin-2(1H)-one (150 mg, 0.85 mmol, 1.0 eq) and diethyl phosphorochloridate (147.8 mg, 0.85 mmol, 1 eq) in THF (10 mL) at 0° C. was added LiHMDS (1M in THF) (1.7 mL, 1.70 mmol, 2.0 eq) and the reaction mixture was stirred at 0° C. for 1 h. To this mixture was added a solution of pyrimidine-2-carbaldehyde (91.8 mg, 0.85 mmol, 1 eq) in THF (3 mL) and the reaction mixture was stirred at 0° C. for 1 h.

Progress of reaction was monitored by TLC. Reaction mixture was quenched with saturated ammonium chloride solution (20 mL) and extracted with ethyl acetate (3×50 mL). Combined organic layer was washed with brine solution (50 mL) and dried over anhydrous Na$_2$SO$_4$. Removal of solvent under reduced pressure gave crude which was purified by Combi-Flash on silica gel using ethyl acetate-hexane as eluent to afford 1-{[(E)-2-(pyrimidin-2-yl)ethenyl]sulfonyl}-5,6-dihydropyridin-2(1H)-one (12 mg, 5.3%)

LCMS: 266 [M+1]$^+$ $^1$H NMR (400 MHz, CD$_3$OD) δ 8.85 (d, 2H), 7.90 (d, 1H), 7.59 (d, 1H), 7.45 (t, 1H), 6.90-7.18 (m, 1H), 5.93 (d, 1H), 4.00 (t, 2H), 2.47-2.77 (m, 2H).

Example 66

Preparation of 1-{(2E)-3-[1-(pyrimidin-2-yl)piperidin-4-yl]prop-2-enoyl}-5,6-dihydropyridin-2(1H)-one Compound 67

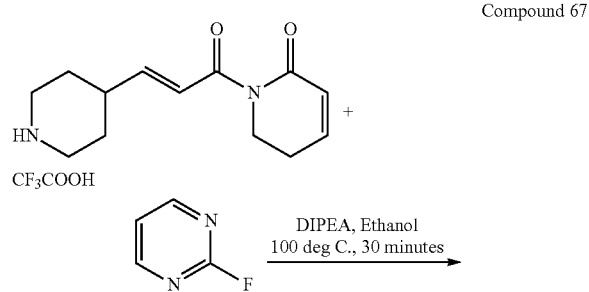

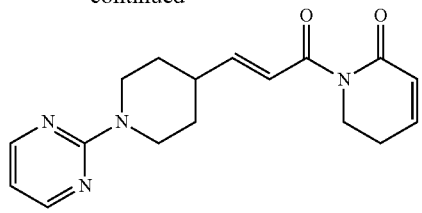

To a stirred solution of 1-[(2E)-3-(piperidin-4-yl)prop-2-enoyl]-5,6-dihydropyridin-2(1H)-one TFA salt (100 mg, 0.29 mmol, 1 eq) in ethanol (5 mL) was added DIPEA (0.22 mL, 1.281 mmol, 4.4 eq) and 2-fluoropyrimidine (45 mg, 0.469 mmol, 1.6 eq) and the reaction mixture was allowed to stir at 100° C. in microwave for 30 minutes. Progress of reaction was monitored by LCMS and TLC. After completion, reaction mixture was concentrated under reduced pressure to yield crude product which further purified by Combi-Flash on silica gel using ethyl acetate-hexane as eluent to yield 1-{(2E)-3-[1-(pyrimidin-2-yl)piperidin-4-yl]prop-2-enoyl}-5,6-dihydropyridin-2(1H)-one (30 mg, 23%).

LCMS: 313 [M+H]$^+$ $^1$H NMR (400 MHz, CHCl$_3$) δ 8.29 (d, 2H), 6.92 (m, 3H), 7.00-6.80 (m, 3H), 6.42 (t, 1H), 6.00 (d, 1H), 4.80-4.70 (m, 2H), 3.98 (t, 2H), 3.02-2.88 (m, 2H), 2.60-2.39 (m, 3H), 1.90-1.80 (m, 2H), 1.63-1.40 (m, 2H).

Example 67

Preparation of (E)-4-(3-oxo-3-(6-oxo-3,6-dihydropyridin-1(2H)-yl)prop-1-en-1-yl)piperidine-1-carboxamide Compound 68

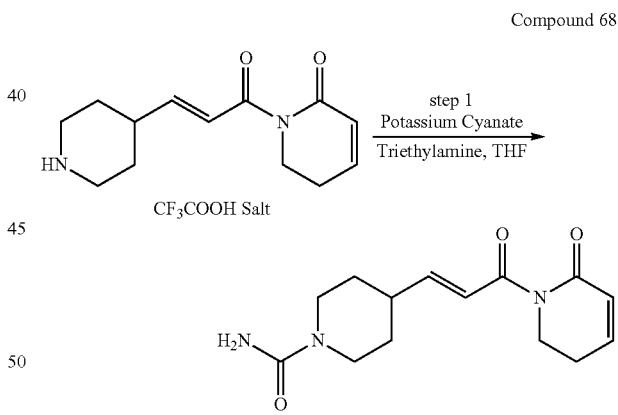

To a solution of the product of (E)-1-(3-(piperidin-4-yl)acryloyl)-5,6-dihydropyridin-2(1H)-one 2,2,2-trifluoroacetate (0.3 g, 0.862 mmol, 1.0 eq.) in tetrahydrofuran (20 mL) was added triethylamine (0.150 g, 2.586 mmol, 3.0 eq.) and potassium cyanate (0.209 g, 2.586 mmol, 3.0 eq.) and the reaction mixture was stirred at room temperature for 4 h. Progress of reaction was monitored by TLC. Reaction mixture was diluted with water (50 mL) and extracted with ethyl acetate (3×50 mL). Combined organic layer was washed with saturated aqueous sodium bicarbonate solution followed by brine (50 mL) and dried over anhydrous sodium sulfate. Removal of solvent under reduced pressure afforded crude which was purified by Combi-Flash on silica gel using ethyl acetate-hexane system as eluent to afford the (E)-4-

(3-oxo-3-(6-oxo-3,6-dihydropyridin-1(2H)-yl)prop-1-en-1-yl)piperidine-1-carboxamide (0.030 g, 12.60% yield).

LCMS: 278 [M+1]+

$^1$H NMR (400 MHz, DMSO-d$_6$) δ 7.03-7.10 (m, 1H), 6.74-6.82 (m, 1H), 6.70 (d, 1H), 5.88-5.95 (m, 2H), 3.92 (d, 2H), 3.83 (t, 2H), 3.16 (s, 1H), 2.65-2.76 (m, 2H), 2.42 (dt, 2H), 1.61-1.70 (m, 3H), 1.12-1.24 (m, 2H).

Example 68

Preparation of 1-[(2E)-2-methyl-3-(1-methyl-1H-pyrazol-4-yl)prop-2-enoyl]-5,6-dihydropyridin-2(1H)-one Compound 69

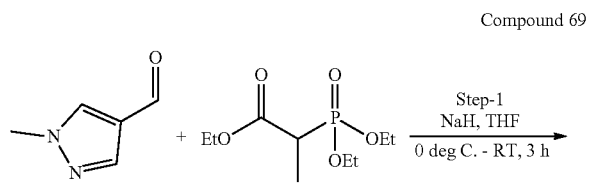

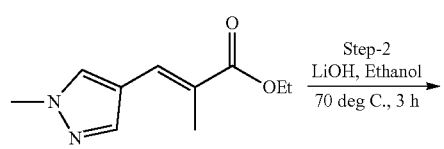

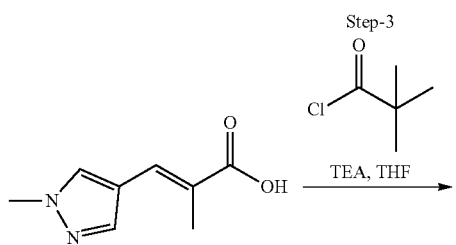

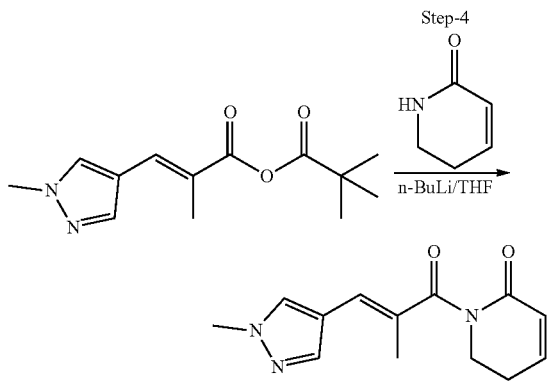

Step-1

To a suspension of sodium hydride (60% in mineral oil), (472 mg, 11.8 mmol, 1.2 eq) in THF (50 mL) was added ethyl 2-(diethoxyphosphoryl)propanoate (2.16 g, 9.08 mmol, 1.2 eq) dropwise at 0° C. and the mixture was allowed to stir at the same temperature for 30 minutes. To this mixture was added a solution of 1-methyl-1H-pyrazole-4-carbaldehyde (1.0 g, 9.08 mmol, 1.0 eq) in THF (5 mL) and the resulting mixture was allowed to stir at room temperature for 2 h. Progress of reaction was monitored by TLC. After completion, reaction mixture was diluted with saturated aq. NH$_4$Cl (100 mL) and extracted with ethyl acetate (3×50 mL). Combined organic layer was washed with brine (50 mL), dried over anhydrous Na$_2$SO$_4$ and evaporated to dryness under vacuum to afford crude which was purified by Combi-Flash on silica gel using ethyl acetate-hexane system as eluent to afford ethyl (2E)-2-methyl-3-(1-methyl-1H-pyrazol-4-yl)prop-2-enoate (1.6 g, 90.91%).

Step-2

To a solution of ethyl (2E)-2-methyl-3-(1-methyl-1H-pyrazol-4-yl)prop-2-enoate (1.6 g, 8.22 mmol, 1.0 eq) in ethanol (50 mL) was added a solution of lithium hydroxide (0.28 g, 11.65 mmol, 3.0 eq) in water (6.0 mL) and the reaction mixture was stirred at 70° C. for 2 h. Reaction mixture was concentrated under vacuum and then acidified with 1N HCl (10 mL). The mixture was diluted with water (30 mL) and extracted with ethyl acetate (3×50 mL). Combined organic layer was washed with brine solution (50 mL) and dried over anhydrous Na$_2$SO$_4$. Removal of solvent under reduced pressure gave (2E)-2-methyl-3-(1-methyl-1H-pyrazol-4-yl)prop-2-enoic acid (1.0 g 73%) as crystalline solid.

Step-3

To a solution of (2E)-2-methyl-3-(1-methyl-1H-pyrazol-4-yl)prop-2-enoic acid (200 mg, 1.20 mmol, 1.0 eq.) in dry THF (10 mL) was added triethylamine (0.35 mL, 2.76 mmol, 1.2 eq.) followed by pivaloyl chloride (0.20 mL, 1.44 mmol, 1.2 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (100 mg, 1.03 mmol, 1.0 eq.) in dry THF (10 mL) at −78° C. was added nBuLi (0.50 mL, 1.13 mmol, 1.2 eq.) and the mixture was allowed to stir at the same temperature for 30 minutes. To this solution was added a solution of 2,2-dimethylpropanoic (2E)-2-methyl-3-(1-methyl-1H-pyrazol-4-yl)prop-2-enoic anhydride (205 mg, 1.23 mmol, 12 eq.) in THF and the reaction mixture was allowed to stir at room temperature for 1 h. Progress of reaction was monitored by TLC and LCMS. After completion, reaction mixture was evaporated to dryness under vacuum to afford crude which was purified combi-flash chromatography (0-50% EtOAc-Hexane) to afford 1-[(2E)-2-methyl-3-(1-methyl-1H-pyrazol-4-yl)prop-2-enoyl]-5,6-dihydropyridin-2(1H)-one (50 mg, 25%).

LCMS: 246[M+1]$^+$

¹HNMR (400 MHz, CHCl₃) δ 7.63 (s, 1H), 7.52 (s, 1H), 6.94-7.07 (m, 1H), 6.91 (dd, 1H), 5.98 (d, 1H), 4.06-4.14 (m, 1H), 3.98 (s, 3H), 3.90 (t, 2H), 2.52 (d, 2H), 2.08 (s, 3H).

Example 69

Preparation of (E)-4-(3-(3,3-dimethyl-6-oxo-3,6-dihydropyridin-1(2H)-yl)-3-oxoprop-1-en-1-yl)-N-(4-fluorophenyl)piperidine-1-carboxamide

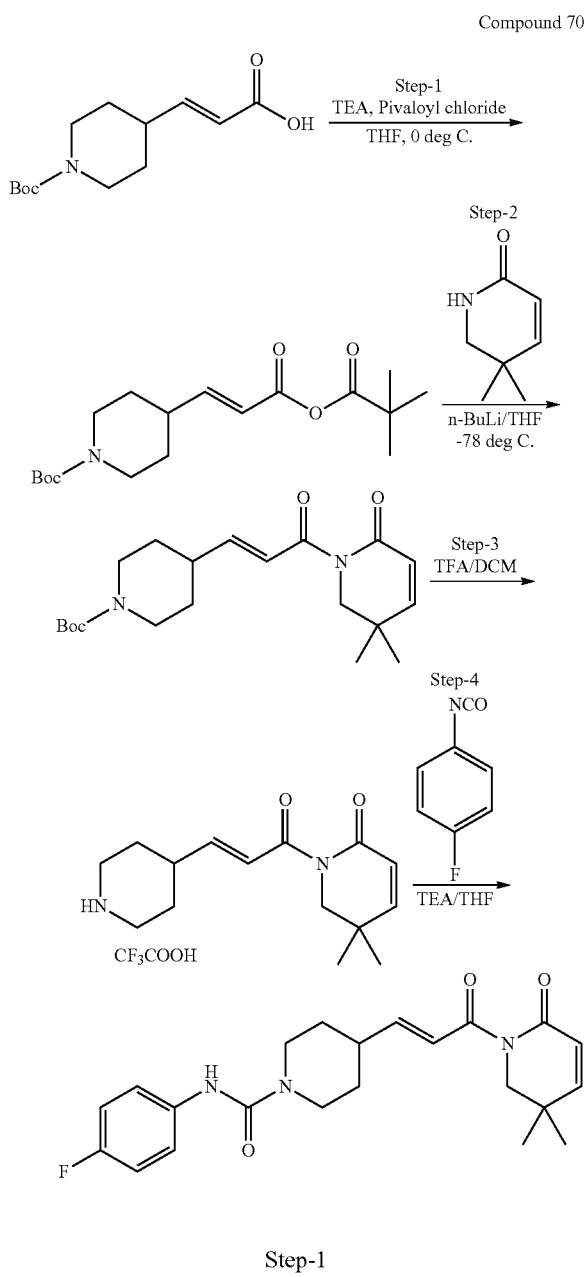

Step-1

To a solution of (E)-3-(1-(tert-butoxycarbonyl)piperidin-4-yl)acrylic acid (0.193 g, 0.717 mmol, 1.0 eq.) in dry THF (10 mL) was added triethylamine (0.257 mL, 0.717 mmol, 1.0 eq.) followed by pivaloyl chloride (0.086 mL, 0.717 mmol, 1.0 eq.) and the reaction mixture was stirred at 0° C. for 45 minutes. Progress of reaction was monitored by TLC. After completion, reaction mixture was filtered and the filtrate was used directly for the next step.

Step-2

To a stirred solution of 5,5-dimethyl-5,6-dihydropyridin-2(1H)-one (0.90 g, 0.72 mmol, 1.0 eq.) in dry THF (10 mL) at −78° C. was added n-butyllithium (2.5 M in hexane, 0.28 mL, 0.72 mmol, 1.0 eq.) and the mixture was allowed to stir at the same temperature for 30 minutes. To this solution was added a solution of (E)-(E)-3-(1-(tert-butoxycarbonyl)piperidin-4-yl)acrylic pivalic anhydride (0.254 g, 0.72 mmol, 1.0 eq.) in THF (10 mL) and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×30 mL). Combined organic layer was washed with brine, dried over anhydrous Na₂SO₄ and evaporated to dryness under vacuum to afford crude which was purified by reversed phase HPLC to afford tert-butyl (E)-4-(3-(3,3-dimethyl-6-oxo-3,6-dihydropyridin-1(2H)-yl)-3-oxoprop-1-en-1-yl)piperidine-1-carboxylate (0.2 g, 69.20%) was obtained as off white solid.

LCMS: 363 [M+1]⁺

Step-3

To a tert-butyl (E)-4-(3-(3,3-dimethyl-6-oxo-3,6-dihydropyridin-1(2H)-yl)-3-oxoprop-1-en-1-yl)piperidine-1-carboxylate (0.16 g, 0.48 mmol, 1.0 eq.) was dissolved in dichloromethane (10 mL) was added trifluoroacetic acid (3.0 mL) at 0° C. and resulting reaction mixture was stirred at room temperature for 2 h. Progress of reaction was monitored by TLC. After completion the reaction mixture was evaporated under reduce pressure to dryness, triturated with Et₂O to afford (E)-1-(3-(piperidin-4-yl)acryloyl)-5,6-dihydropyridin-2(1H)-one (0.015 g, 9.86%).

LCMS: 263 [M+1]⁺

Step-4

To a suspension of (E)-1-(3-(piperidin-4-yl)acryloyl)-5,6-dihydropyridin-2(1H)-one (0.1 g, 0.381 mmol, 1.0 eq) in tetrahydrofuran (10 mL) was added triethylamine (1.39 mL, 0.762 mmol, 2.0 eq). The mixture was cooled to 0° C., and 1-fluoro-4-isocyanatobenzene (1.10 mL, 0.762 mmol, 2.0 eq) was added slowly. The reaction was allowed to warm to room temperature and stirred for 1 h. Progress of reaction was monitored by TLC. After completion, reaction mixture was diluted with water (30 mL) and extracted with ethyl acetate (3×30 mL). Combined organic layer was washed with brine, dried over anhydrous Na₂SO₄ and evaporated to dryness under vacuum to afford crude which was purified by Combi-Flash to using ethyl acetate-hexane system as eluent to afford (E)-4-(3-(3,3-dimethyl-6-oxo-3,6-dihydropyridin-1(2H)-yl)-3-oxoprop-1-en-1-yl)-N-(4-fluorophenyl)piperidine-1-carboxamide (0.015 g, 9.86%) was obtained as off white solid.

LCMS: 400 [M+1]⁺

¹H NMR (400 MHz, CDCl₃) δ ppm 7.27-7.32 (m, 2H), 6.98 (t, 2H), 6.92-6.94 (m, 1H), 6.64 (d, 1H), 6.29 (br. s., 1H), 5.84 (d, 1H), 4.07 (d, 2H), 3.74 (s, 2H), 2.92-3.04 (m, 2H), 2.45 (br. s., 1H), 1.88 (d, 2H), 1.43-1.53 (m, 2H), 1.21-1.32 (m, 3H), 1.15 (s, 5H), 0.89 (d, 1H).

Example 70

Preparation of (Z)-tert-butyl 4-(2-methyl-3-oxo-3-(2-oxo-5,6-dihydropyridin-1(2H)-yl)prop-1-enyl)piperidine-1-carboxylate

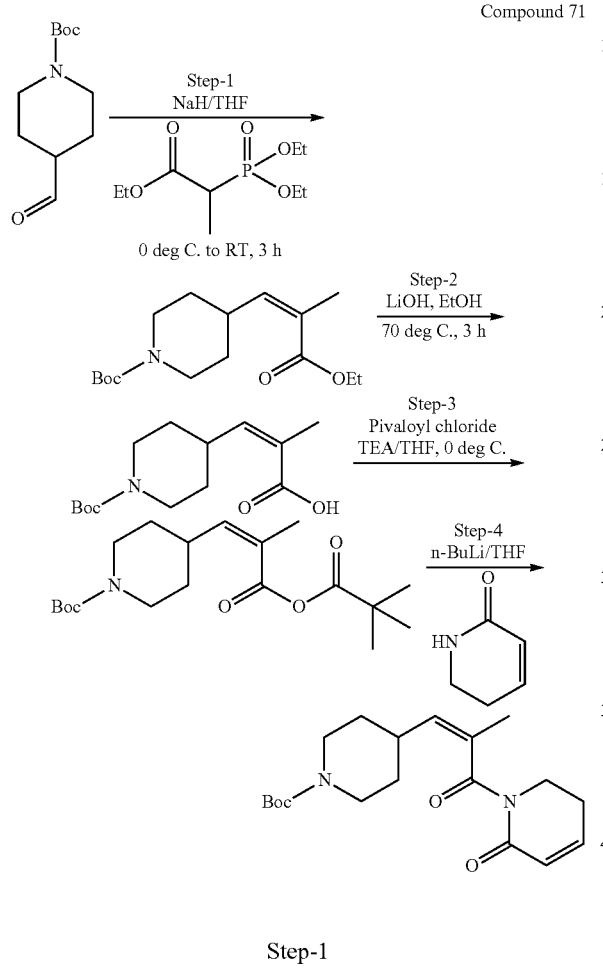

Compound 71

Step-1

To a suspension of sodium hydride (60% in mineral oil, 0.487 g, 12.81 mmol, 1.3 eq) in THF (50 mL) was added ethyl 2-(diethoxyphosphoryl)propanoate (2.23 g, 9.37 mmol, 1.0 eq) dropwise at 0° C. and the mixture was allowed to stir at the same temperature for 30 minutes. To this mixture was added a solution of tert-butyl 4-formylpiperidine-1-carboxylate (2.0 g, 9.37 mmol, 1.0 eq) in THF (5 mL) and the resulting mixture was allowed to stir at RT for 2 h. Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash on silica gel using ethyl acetate-hexane system as eluent to afford (Z)-tert-butyl 4-(3-ethoxy-2-methyl-3-oxoprop-1-enyl)piperidine-1-carboxylate (1.34 g, 48.2%).

LCMS: 298 [M+1]$^+$

Step-2

To a solution of (Z)-tert-butyl 4-(3-ethoxy-2-methyl-3-oxoprop-1-enyl)piperidine-1-carboxylate (0.75 g, 2.52 mmol, 1.0 eq) in ethanol (8.0 mL) was added lithium hydroxide (0.643 g, 8.0 mmol, 3.0 eq) in water (1.0 ml) and the reaction mixture was stirred at 70° C. for 2 h. Reaction mixture was concentrated under vacuum and then acidified with 1N HCl. The mixture was diluted with water and extracted with ethyl acetate (3×50 mL). The combined organic layer was washed with brine solution (50 mL) and dried over anhydrous Na$_2$SO$_4$. Removal of solvent under reduced pressure to obtain (Z)-tert-butyl 4-(3-ethoxy-2-methyl-3-oxoprop-1-enyl)piperidine-1-carboxylate (0.570 g, 83.82%) as crystalline solid.

LCMS: 270 [M+1]$^+$

Step-3

To a solution of (Z)-tert-butyl 4-(3-ethoxy-2-methyl-3-oxoprop-1-enyl)piperidine-1-carboxylate (0.20 g, 0.74 mmol, 1.0 eq.) in dry THF (10 mL) was added triethylamine (0.124 mL, 0.089 mmol, 1.2 eq.) followed by pivaloyl chloride (0.091 mL, 0.74 mmol, 1.0 eq.) and the reaction mixture was stirred at 0° C. for 45 minutes. Progress of reaction was monitored by TLC. After completion, reaction mixture was filtered through syringe filter and the filtrate was used directly for the next step.

Step-4

To a stirred solution of 5,6-dihydropyridin-2(1H)-one (0.071 g, 0.74 mmol, 1.0 eq.) in dry THF (20 mL) at −78° C. was added n-BuLi (0.30 mL, 0.74 mmol, 1.0 eq.) and the mixture was allowed to stir at the same temperature for 30 minutes. To this solution was added a solution of respective anhydride (0.262 g, 0.74 mmol, 1.0 eq.) in THF and the reaction mixture was allowed to stir at RT for 1 h. Progress of reaction was monitored by TLC and LCMS. After completion, reaction mixture was evaporated to dryness under vacuum to afford crude which was purified by reversed phase HPLC to afford (Z)-tert-butyl 4-(2-methyl-3-oxo-3-(2-oxo-5,6-dihydropyridin-1(2H)-yl)prop-1-enyl)piperidine-1-carboxylate (0.13 g, 49.6%).

LCMS: 349 [M+1]$^+$ $^1$H NMR (400 MHz, DMSO-d$_6$) δ 6.90-7.00 (m, 1H), 6.00 (d, 1H), 5.18 (d, 1H), 4.10-3.92 (m, 4H), 2.70-2.55 (m, 2H), 2.50-2.40 (m, 2H), 2.20-2.05 (m, 1H), 1.91 (s, 3H), 1.60-1.50 (m, 4H), 1.30-1.18 (m, 7H), 0.90-0.78 (m, 2H).

Example 71

Preparation of tert-butyl (E)-4-(2-methyl-3-oxo-3-(6-oxo-3,6-dihydropyridin-1(2H)-yl)prop-1-en-1-yl)piperidine-1-carboxylate

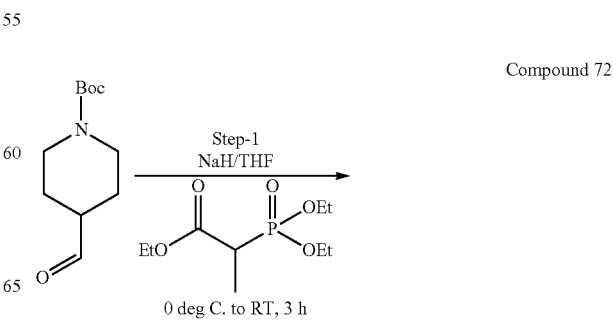

Compound 72

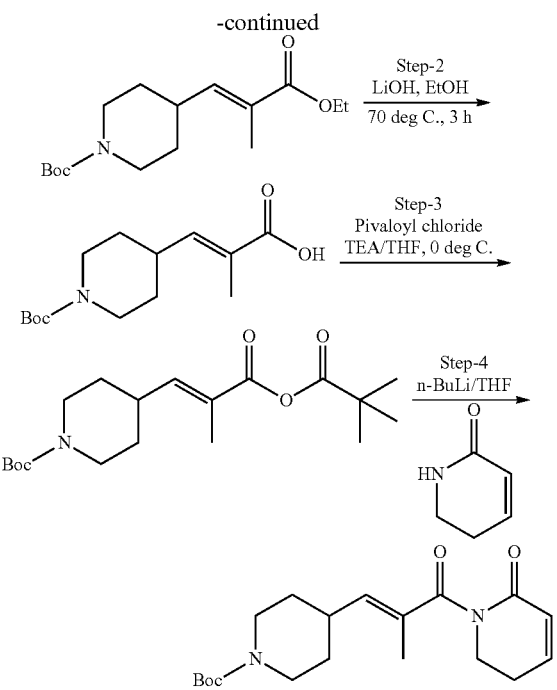

Step-1

To a suspension of sodium hydride (60% in mineral oil, 0.487 g, 12.81 mmol, 1.3 eq) in THF (50 mL) was added ethyl 2-(diethoxyphosphoryl)propanoate (2.23 g, 9.37 mmol, 1.0 eq) dropwise at 0° C. and the mixture was allowed to stir at the same temperature for 30 minutes. To this mixture was added a solution of tert-butyl 4-formylpiperidine-1-carboxylate (2.0 g, 9.37 mmol, 1.0 eq) in THF (5 mL) and the resulting mixture was allowed to stir at RT for 2 h. Progress of reaction was monitored by TLC. After completion, reaction mixture was diluted with saturated aq. $NH_4Cl$ (100 mL) and extracted with ethyl acetate (3×50 mL). Combined organic layer was washed with brine, dried over anhydrous $Na_2SO_4$ and evaporated to dryness under vacuum to afford crude which was purified by Combi-Flash on silica gel using ethyl acetate-hexane system as eluent to afford (Z)-tert-butyl 4-(3-ethoxy-2-methyl-3-oxoprop-1-enyl)piperidine-1-carboxylate (1.34 g, 48.2%).

LCMS: 298 [M+1]$^+$

Step-2

To a solution of tert-butyl 4-[(1E)-3-ethoxy-2-methyl-3-oxoprop-1-en-1-yl]piperidine-1-carboxylate (0.55 g, 1.85 mmol, 1.0 eq) in ethanol (5 mL) was added lithium hydroxide (0.543 g, 5.5 mmol, 3.0 eq) in water (1 mL) and the reaction mixture was stirred at 70° C. for 2 h. Reaction mixture was concentrated under vacuum and then acidified with 1N HCl. The mixture was diluted with water and extracted with ethyl acetate (3×50 mL). Combined organic layer was washed with brine solution (50 mL) and dried over anhydrous $Na_2SO_4$. Removal of solvent under reduced pressure gave (2E)-3-[1-(tert-butoxycarbonyl)piperidin-4-yl]-2-methylprop-2-enoic acid (0.24 g, 48.2%) as crystalline solid which was used in the next step without purification.

LCMS: 270 [M+1]$^+$

Step-3

To a solution of (2E)-3-[1-(tert-butoxycarbonyl)piperidin-4-yl]-2-methylprop-2-enoic acid (0.23 g, 0.85 mmol, 1 eq) in dry THF (20 mL) was added triethylamine (0.142 mL, 1.02 mmol, 1.2 eq.) followed by pivaloyl chloride (0.105 mL, 2.3 mmol, 1.0 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (0.82 g, 0.84 mmol, 1.0 eq.) in dry THF (20 mL) at −78° C. was added n-BuLi (0.34 mL, 0.84 mmol, 1 eq) and the mixture was allowed to stir at the same temperature for 30 minutes. To this solution was added a solution of anhydride (0.30 g, 0.84 mmol, 1.0 eq.) in THF and the reaction mixture was allowed to stir at RT for 1 h. Progress of reaction was monitored by TLC and LCMS. After completion, reaction mixture was evaporated to dryness under vacuum to afford crude which was purified by reversed phase HPLC to afford tert-butyl (E)-4-(2-methyl-3-oxo-3-(6-oxo-3,6-dihydropyridin-1(2H)-yl)prop-1-en-1-yl)piperidine-1-carboxylate (0.2 g, 67.8%).

LCMS: 349 [M+1]$^+$ $^1$H NMR (400 MHz, CDCl$_3$) δ 6.85-6.95 (m, 1H), 5.96 (d, 1H), 5.70 (d, 1H), 4.07 (brs, 2H), 3.83 (t, 2H), 2.85-2.70 (m, 2H), 2.50-2.37 (m, 2H), 1.87 (s, 3H), 1.70-1.58 (m, 2H), 1.42 (s, 9H), 1.39-1.20 (m, 3H).

Example 72

Preparation of (E)-N-(4-fluorophenyl)-4-(2-methyl-3-oxo-3-(6-oxo-3,6-dihydropyridin-1(2H)-yl)prop-1-en-1-yl)piperidine-1-carboxamide

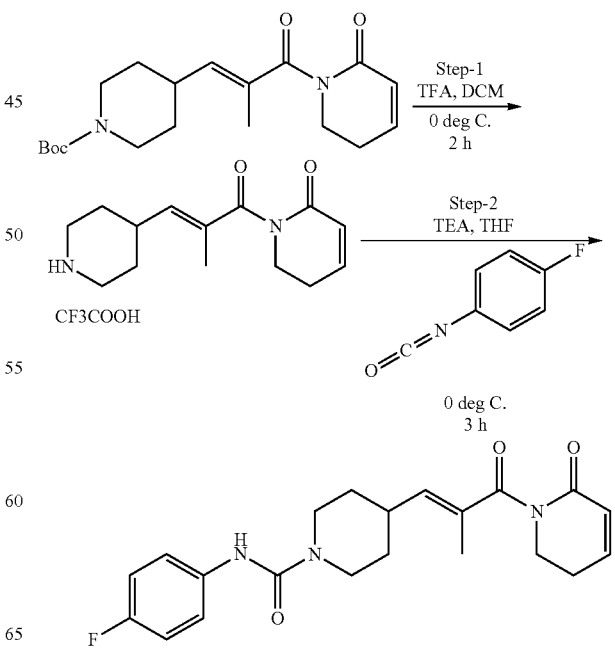

Compound 73

Step-1

To a solution of tert-butyl 4-[(1E)-3-ethoxy-3-oxoprop-1-en-1-yl]piperidine-1-carboxylate (0.20 g, 0.57 mmol, 1.0 eq) in DCM (10 mL) was added TFA (0.196 mL, 0.17 mmol, 3.0 eq) at 0° C. and RM was allowed to stir at the same temperature for 2 h. Progress of reaction was monitored by TLC. After completion, solvent was removed under reduced pressure to obtain (E)-1-(2-methyl-3-(piperidin-4-yl)acryloyl)-5,6-dihydropyridin-2(1H)-one (0.11 g, 55.0%) as solid which was used in the next step without purification.

LCMS: 249 [M+1]$^+$

Step-2

To a solution of (E)-1-(2-methyl-3-(piperidin-4-yl)acryloyl)-5,6-dihydropyridin-2(1H)-one (110 mg, 0.30 mmol, 1.0 eq.) in dry THF (15 mL) was added DIPEA (0.08 mL, 0.45 mmol, 1.5 eq) followed by 1-fluoro-4-isocyanatobenzene (62 mg, 0.45 mmol, 1.5 eq) and the reaction mixture was stirred at RT for 3 h. Progress of reaction was monitored by TLC. After completion, reaction mixture was diluted with water (20 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash on silica gel using ethyl acetate-hexane system as eluent to afford (E)-N-(4-fluorophenyl)-4-(2-methyl-3-oxo-3-(6-oxo-3,6-dihydropyridin-1(2H)-yl)prop-1-en-1-yl)piperidine-1-carboxamide.

LCMS: 386 [M+1]$^+$ $^1$H NMR (400 MHz, DMSO-d$_6$) δ 8.50 (brs, 1H), 7.48-7.40 (m, 2H), 7.10-7.00 (m, 3H), 5.88 (d, 1H), 5.67 (d, 1H), 4.10-4.00 (m, 2H), 3.68 (t, 2H), 2.90-2.80 (m, 2H), 2.40-2.50 (m, 2H), 1.80 (t, 3H), 1.60-1.52 (m, 2H), 1.30-1.15 (m, 3H).

Example 73

Preparation of (E)-1-(3-(1-(pyridin-2-yl)piperidin-4-yl)acryloyl)-5,6-dihydropyridin-2(1H)-one Compound 74

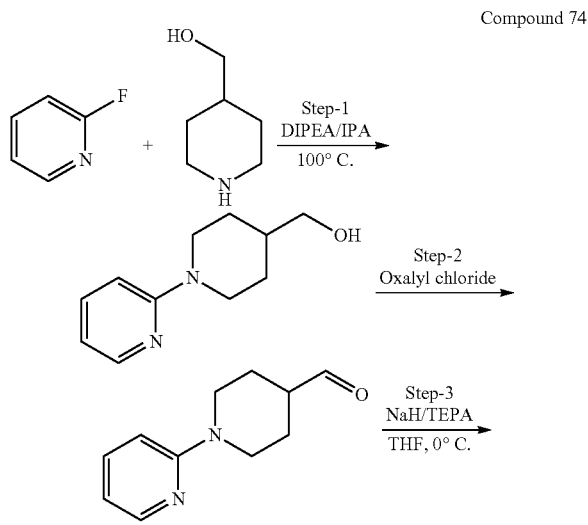

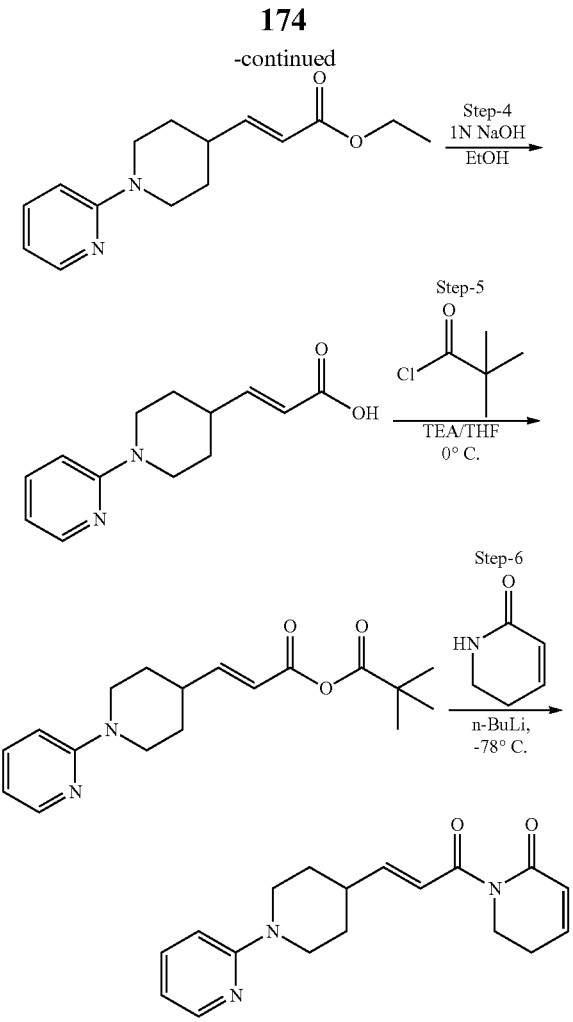

Step-1

To a solution of 2-fluoropyridine (2 g, 20.61 mmol, 1 eq) in 2-propanol (20 mL) were added DIPEA (10.77 mL, 61.83 mmol, 3 eq) and piperidin-4-ylmethanol (2.38 g, 20.61 mmol, 1 eq) and the reaction mixture was allowed to stir at 100° C. for 3 h. Progress of reaction was monitored by NMR. After completion reaction mixture was diluted with water extracted with ethyl acetate (3×20 mL). Combined organic layer was washed with brine (50 mL) and dried over anhydrous sodium sulfate. Removal of solvent afforded crude (1-(pyridin-2-yl)piperidin-4-yl)methanol (1.5 g, 37.97%) which was used in the next step without purification.

Step-2

To a solution of oxalyl chloride (1.34 mL, 15.62 mmol, 2 eq) in DCM (50 mL) at −78° C. was added DMSO (2.18 mL, 30.86 mmol, and 3.95 eq.) dropwise and the mixture was allowed to stir at the same temperature for 30 minutes. To this solution was added (1-(pyridin-2-yl)piperidin-4-yl)methanol (1.5 g, 7.81 mmol, 1 eq.). Reaction mixture was allowed to stir at −78° C. for 45 min. After that add TEA (4.30 mL, 30.86 mmol, 3.95 eq.) at same temperature. Reaction mixture was allowed to stir at RT for 30 minutes. Progress of reaction was monitored by TLC. Reaction mixture was diluted with water (30 mL) and extracted with DCM (3×40 mL). Combined organic layer was washed with brine and dried over anhydrous sodium sulfate. Removal of solvent to afford crude reaction mixture was purified by Combi-Flash to afford 1-(pyridin-2-yl)piperidine-4-carbaldehyde (1 g, 67.56%).

Step-3

To a solution of triethylphosphonoacetate (1.25 mL, 6.31 mmol, 1.2 eq) in THF (40 mL) at 0° C. was added NaH (0.315 g, 7.89 mmol, and 1.5 eq.) portion-wise and the mixture was allowed to stir at the same temperature for 20 minutes. To this solution was added 1-(pyridin-2-yl)piperidine-4-carbaldehyde (1 g, 5.26 mmol, 1 eq.). Reaction mixture was allowed to stir at 0° C. for 15 min followed by stirring at RT for 1 h. Progress of reaction was monitored by TLC. Reaction mixture was diluted with water (30 mL) and extracted with ethyl acetate (3×50 mL). Combined organic layer was washed with brine and dried over anhydrous sodium sulfate. Removal of solvent to afford crude reaction mixture was purified by Combi-Flash to afford ethyl (E)-3-(1-(pyridin-2-yl)piperidin-4-yl)acrylate (0.650 g, 47%).

Step-4

To a solution of ethyl (E)-3-(1-(pyridin-2-yl)piperidin-4-yl)acrylate (0.650 g, 2.5 mmol, 1 eq) in ethanol (10 mL) was added 1N NaOH (5 mL, 5.0 mmol, and 2 eq.) dropwise and the mixture was allowed to stir at the RT for 4 h. Progress of reaction was monitored by TLC. Reaction mixture was acidifying using 1N HCl up to pH 6 and extracted using mixture of ethanol and ethyl acetate (20:80) (3×50 mL). Combined organic layer was washed with brine and dried over anhydrous sodium sulfate. Removal of solvent afforded crude (E)-3-(1-(pyridin-2-yl)piperidin-4-yl)acrylic acid (0.3 g, 51.72%).

Step-5

To a solution of (E)-3-(1-(pyridin-2-yl)piperidin-4-yl) acrylic acid (0.1 g, 0.430 mmol, 1.0 eq.) in dry THF was added triethylamine (0.071 mL, 0.516 mmol, 1.2 eq.) and pivaloyl chloride (0.047 mL, 0.387 mmol, 0.9 eq.) the reaction mixture was stirred at 0° C. for 45 minutes. Progress of reaction was monitored by TLC. After completion, reaction mixture was filtered and the filtrate was used directly for the next step.

Step-6

To a stirred solution of 5,6-dihydropyridin-2(1H)-one (0.041 g, 0.430 mmol, 1 eq.) in dry THF at −78° C. was added n-butyl lithium (2.5 M in hexane, 0.17 mL, 0.430 mmol, 1 eq.) and the mixture was allowed to stir at the same temperature for 30 minutes. To this solution was added (E)-pivalic (E)-3-(1-(pyridin-2-yl)piperidin-4-yl)acrylic anhydride (0.136 g, 0.430 mmol, 1 eq.). Reaction mixture was allowed to stir at −78° C. for 90 min. Progress of reaction was monitored by TLC. Reaction mixture was brought to 0° C., diluted with ammonium chloride solution (30 mL) and extracted with ethyl acetate (3×40 mL). combined organic layer was washed with brine, dried over anhydrous $Na_2SO_4$ and evaporated to dryness under vacuum to afford crude which was purified by Combi-Flash to afford (E)-1-(3-(1-(pyridin-2-yl)piperidin-4-yl)acryloyl)-5,6-dihydropyridin-2(1H)-one (30 mg, 22.56%).

LCMS: 312 [M+1]+

$^1$H NMR (400 MHZ, CDCl$_3$) δ 8.19 (d, 1H), 7.43 (d, 1H), 7.00-6.80 (m, 3H), 6.65 (d, 1H), 6.60-6.55 (m, 1H), 6.00 (d, 1H), 4.36-4.24 (m, 2H), 3.98 (t, 2H), 2.93-2.82 (m, 2H), 2.50-2.39 (m, 3H), 1.90-1.80 (m, 2H), 1.80-1.40 (m, 2H).

Example 74

Preparation of 1-{[(E)-2-(1-methyl-1H-pyrazol-4-yl) ethenyl]sulfonyl}-5,6-dihydropyridin-2(1H)-one Compound 75

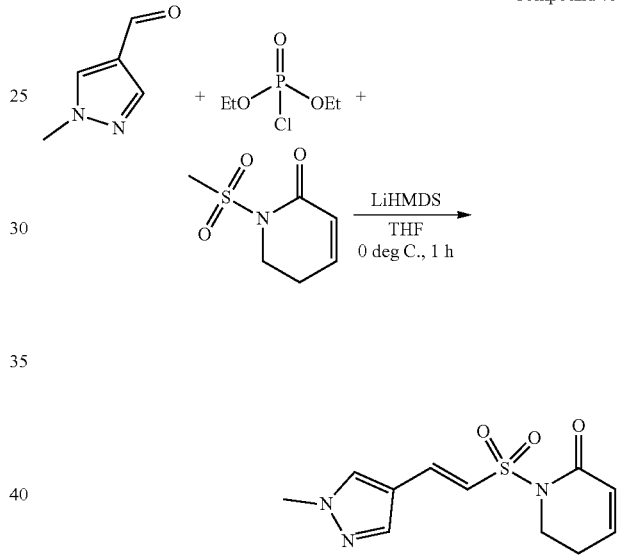

To a solution of 1-(methylsulfonyl)-5,6-dihydropyridin-2 (1H)-one (200 mg, 1.14 mmol, 1.0 eq), diethyl phosphorochloridate (197 mg, 1.14 mmol, 1 eq) and 1-methyl-1H-pyrazole-4-carbaldehyde (100 mg, 0.91 mmol, 0.8 eq) in THF (10 mL) at 0° C. was added LiHMDS 1M in THF (2.5 mL, 2.50 mmol, 2.0 eq). The reaction mixture was stirred at 0° C. for 1 h. Progress of reaction was monitored by TLC. Reaction mixture was quenched by saturated ammonium chloride solution 20 mL and extracted with ethyl acetate (3×50 mL). Combined organic layer was washed with brine solution (50 mL) and dried over anhydrous $Na_2SO_4$. Removal of solvent under reduced pressure gave the crude which was purified by flash column chromatograpy (0-70% EtOAc-hexane) as eluent to 1-{[(E)-2-(1-methyl-1H-pyrazol-4-yl)ethenyl]sulfonyl}-5,6-dihydropyridin-2(1H)-one (90 mg, 29.50%).

LCMS: 268[M+1]+

$^1$H NMR (400 MHz, CDCl$_3$) δ 7.69 (s, 1H), 7.59 (s, 1H), 7.55 (d, 1H), 6.91 (d, 1H), 6.81-6.86 (m, 1H), 5.97 (d, 1H), 3.96 (t, 2H), 3.92 (s, 3H), 2.51-2.57 (m, 2H),

Example 75

Preparation of 1-{[(E)-2-(8-methoxy-2,3-dihydro-1,4-benzodioxin-6-yl)ethenyl]sulfonyl}-5,6-dihydropyridin-2(1H)-one Compound 76

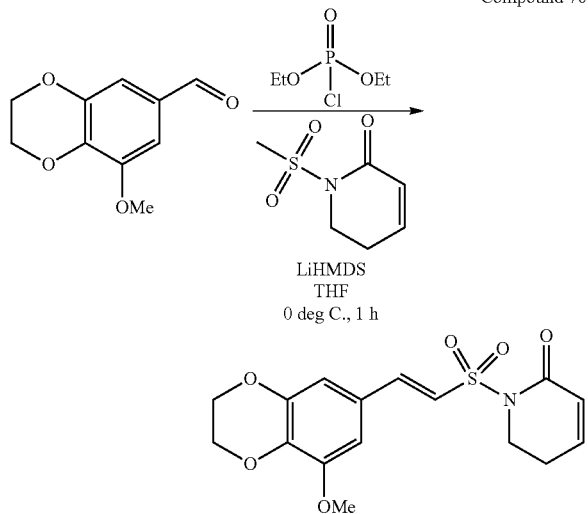

To a solution of 1-(methylsulfonyl)-5,6-dihydropyridin-2(1H)-one (250 mg, 1.43 mmol, 1.0 eq), diethyl phosphorochloridate (247 mg, 1.43 mmol, 1 eq) and 8-methoxy-2,3-dihydro-1,4-benzodioxine-6-carbaldehyde (222 mg, 1.14 mmol, 0.8 eq) in THF (10 mL) at 0° C. was added LiHMDS 1M in THF (3.15 mL, 3.15 mmol, 2.2 eq). The reaction mixture was stirred at 0° C. for 1 h. Progress of reaction was monitored by TLC. Reaction mixture was quenched by saturated ammonium chloride solution 20 mL and extracted with ethyl acetate (3×50 mL). Combined organic layer was washed with brine solution (50 mL) and dried over anhydrous $Na_2SO_4$. Removal of solvent under reduced pressure gave the crude which was purified by Combi-Flash on silica gel using ethyl acetate-hexane system as eluent to afford 1-{[(E)-2-(8-methoxy-2,3-dihydro-1,4-benzodioxin-6-yl)ethenyl]sulfonyl}-5,6-dihydropyridin-2(1H)-one (20 mg, 5%).

LCMS: 352[M+1]$^+$ $^1$H NMR (400 MHz, CDCl$_3$) δ 7.51 (d, 1H), 7.23 (d, 1H), 6.89-5.99 (m, 1H), 6.74 (s, 1H), 6.65 (s, 1H), 6.00 (d, 1H), 4.40-4.23 (m, 4H), 3.97 (t, 2H), 3.89 (s, 3H), 2.60-2.50 (m, 2H).

Example 76

Preparation of (E)-1-(3-(1-(cyclopropylmethyl)piperidin-4-yl)-2-methylacryloyl)-5,6-dihydropyridin-2(1H)-one Compound 77

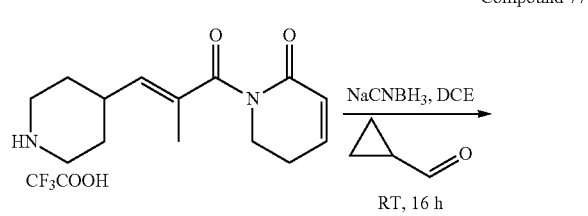

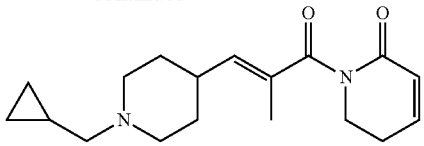

To a solution of (E)-1-(2-methyl-3-(piperidin-4-yl)acryloyl)-5,6-dihydropyridin-2(1H)-one 2,2,2-trifluoroacetate (80 mg, 0.22 mmol, 1.0 eq) in DCE (15 mL) was added (0.08 mL, 1.1 mmol, 5 eq) followed by AcOH (39 mg, 0.66 mmol, 3 eq) and the reaction mixture was stirred at RT for 1 h. To this mixture was added NaCNBH$_3$ (41 mg, 0.66 mmol, 3 eq) and the resulting mixture was allowed to stir for 16 h. Progress of reaction was monitored by TLC. After completion, reaction mixture was diluted with aq. sodium bicarbonate (20 mL) and extracted with ethyl acetate (3×50 mL). Combined organic layer was washed with brine, dried over anhydrous $Na_2SO_4$ and evaporated to dryness under vacuum to afford crude which was purified by reversed phase HPLC to afford (E)-1-(3-(1-(cyclopropylmethyl)piperidin-4-yl)-2-methylacryloyl)-5,6-dihydropyridin-2(1H)-one (10 mg, 15%).

LCMS: 303 [M+1]$^+$ $^1$H NMR (400 MHz, CD$_3$OD) δ 7.10-7.00 (m, 1H), 5.91 (d, 1H), 5.70 (d, 1H), 3.80 (t, 2H), 3.42-3.35 (m, 2H), 2.80-2.42 (m, 6H), 1.98-1.80 (m, 6H), 1.70-1.50 (m, 2H), 1.10-0.95 (m, 1H), 0.70-0.65 (m, 2H), 0.38-0.30 (m, 2H).

Example 77

Preparation of (Z)-1-(3-(1-(4-fluorophenyl)piperidin-4-yl)-2-methylacryloyl)-5,6-dihydropyridin-2(1H)-one Compound 78

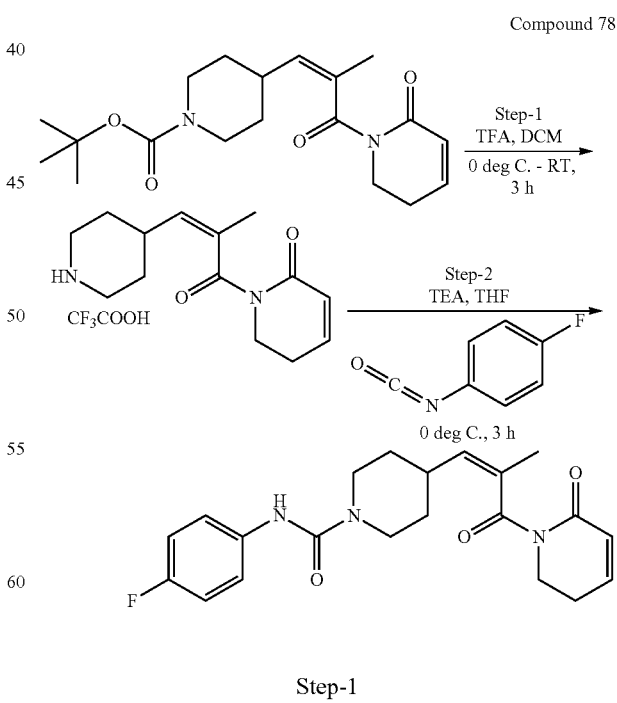

Step-1

To a solution of tert-butyl 4-[(1E)-3-ethoxy-3-oxoprop-1-en-1-yl]piperidine-1-carboxylate (0.40 g, 1.14 mmol, 1.0 eq) in DCM (20 mL) was added CF₃COOH (2.0 mL, 3.44 mmol, 3.0 eq) at 0° C. and reaction mixture was allowed to stir at the same temperature for 10 minutes. Ice batch was removed and then reaction mixture was allowed to stir at RT for 3 h. Progress of reaction was monitored by TLC. After completion, removal of CF₃COOH under reduced pressure gave ethyl (2E)-3-(piperidin-4-yl)prop-2-enoate (0.2 g, 57.7%) as solid which was used in the next step without purification.

LCMS: 249 [M+1]⁺

Step-2

To a solution of (Z)-1-(2-methyl-3-(piperidin-4-yl)acryloyl)-5,6-dihydropyridin-2(1H)-one 2,2,2-trifluoroacetate (0.1 g, 0.28 mmol, 1.0 eq.) in dry THF (15 mL) was added TEA (0.057 mL, 0.41 mmol, 1.5 eq.) followed by 1-fluoro-4-isocyanatobenzene (0.56 g, 0.41 mmol, 1.5 eq) and the reaction mixture was stirred at RT for 3 h. Progress of reaction was monitored by TLC. After completion, reaction mixture was diluted with water (20 mL) and extracted with ethyl acetate (3×50 mL). Combined organic layer was washed with brine, dried over anhydrous Na₂SO₄ and evaporated to dryness under vacuum to afford crude which was purified by Combi-Flash on silica gel using ethyl acetate-hexane system as eluent to afford (Z)-1-(3-(1-(4-fluorophenyl)piperidin-4-yl)-2-methylacryloyl)-5,6-dihydropyridin-2(1H)-one (65 mg, 61%).

LCMS: 386 [M+1]⁺
¹H NMR (400 MHz, DMSO-d₆) δ 8.43 (s, 1H), 7.45-7.39 (m, 2H), 7.16-6.90 (m, 3H), 5.95 (d, 1H), 5.11 (d, 1H), 4.08-3.97 (m, 2H), 3.90-3.80 (m, 2H), 2.78-2.40 (m, 2H), 2.22-2.10 (m, 1H), 1.60 (s, 3H), 1.45-1.10 (m, 4H).

Example 78

Preparation of (Z)-1-(3-(1-(cyclopropylmethyl)piperidin-4-yl)-2-methylacryloyl)-5,6-dihydropyridin-2(1H)-one Compound 79

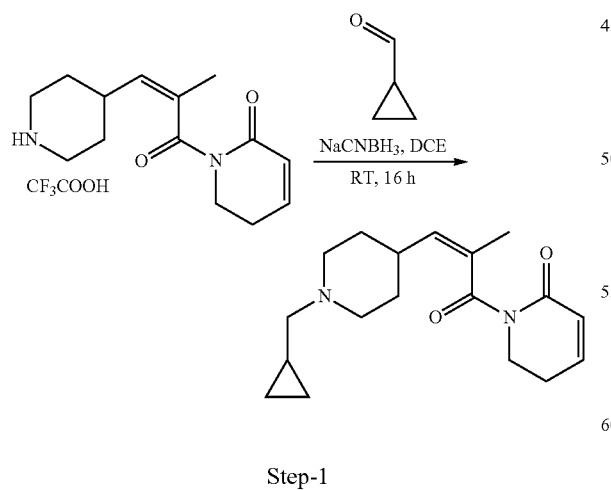

Step-1

To a solution of (Z)-1-(2-methyl-3-(piperidin-4-yl)acryloyl)-5,6-dihydropyridin-2(1H)-one 2,2,2-trifluoroacetate (0.05 g, 0.14 mmol, 1.0 eq.) in DCE (15 mL) was added (0.048 mL, 0.70 mmol, 5.0 eq) followed by AcOH (24 mg, 0.40 mmol, 3.0 eq) and the reaction mixture was stirred at RT for 1 h. To this mixture was added NaCNBH₃ (29 mg, 0.46 mmol, 3.4 eq) and reaction mixture was allowed to stir for 16 h. Progress of reaction was monitored by TLC. After completion, reaction mixture was diluted with aq. sodium bicarbonate (20 mL) and extracted with ethyl acetate (3×50 mL). Combined organic layer was washed with brine, dried over anhydrous Na₂SO₄ and evaporated to dryness under vacuum to afford crude which was purified by reversed phase HPLC to afford (Z)-1-(3-(1-(cyclopropylmethyl)piperidin-4-yl)-2-methylacryloyl)-5,6-dihydropyridin-2(1H)-one (20 mg, 50%).

LCMS: 303 [M+1]⁺
¹H NMR (400 MHz, CD₃OD) δ 8.58 (brs, 1H), 7.18-7.02 (m, 1H), 5.98 (d, 1H), 5.18 (d, 1H), 3.98 (t, 2H), 3.30-3.00 (m, 2H), 2.60-2.40 (m, 4H), 2.39-2.33 (m, 2H), 2.21-2.10 (m, 1H), 2.87 (s, 3H), 1.75-1.40 (m, 4H), 1.02-0.90 (m, 1H), 0.62-0.55 (m, 2H), 0.22-0.17 (m, 2H).

Example 79

Preparation of (E)-1-(3-(6,7-dihydro-[1,4]dioxino[2,3-d]pyrimidin-2-yl)acryloyl)-5,6-dihydropyridin-2(1H)-one Compound 80

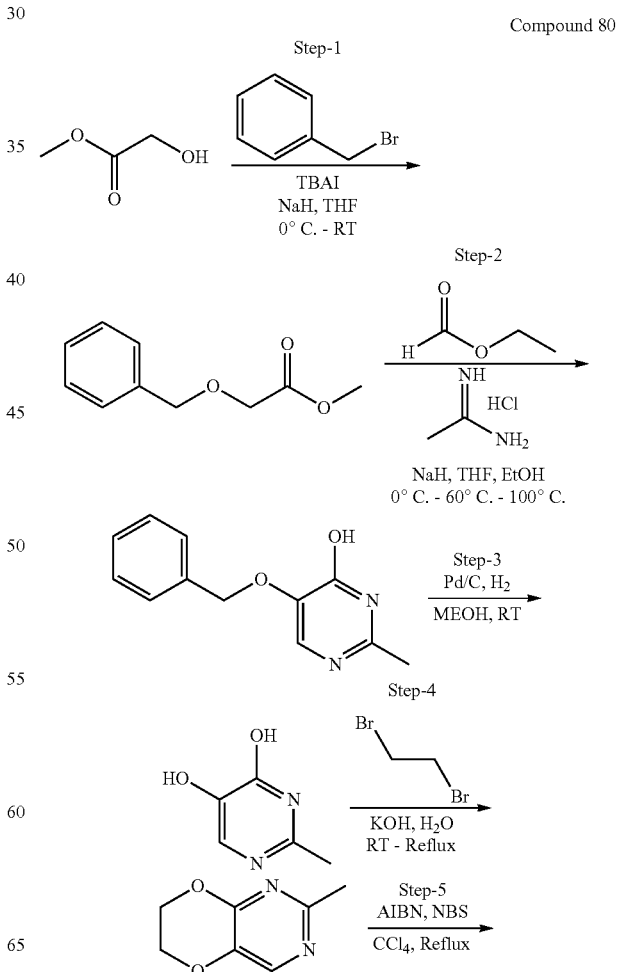

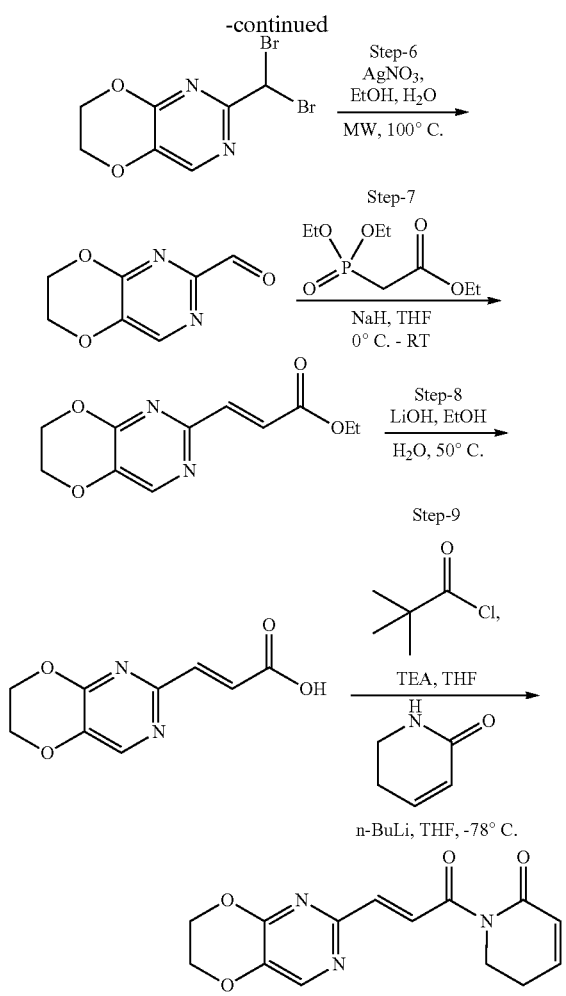

Step-1

To a solution of methyl 2-hydroxyacetate (20 g, 0.22 mol, 1.0 eq.) in dry THF (250 mL) was added NaH (60% in mineral oil) (6.4 g, 0.26 mol, 1.2 eq.) at 0° C. over a period of 15 minutes. The reaction mixture was allowed to stir at that temperature for 30 minutes. To that stirred solution were added TBAI (8.20 g, 0.022 mol, 0.1 eq.) followed by (bromomethyl)benzene (38 g, 0.22 mol, 1.0 eq.) at that temperature and allowed to stir at RT for 16 h. Progress of reaction was monitored by TLC (10% ethyl acetate-hexane). After completion, reaction mixture was diluted with ice-cold water (100 mL) and extracted with ethyl acetate (3×250 mL). Combined organic layer was washed with brine and dried over anhydrous sodium sulfate. Removal of solvent under reduced pressure afforded crude which was purified by Combi-Flash to afford methyl 2-(benzyloxy)acetate (28.4 g, 71%).

Step-2

To a solution of methyl 2-(benzyloxy)acetate (28.4 g, 0.157 mol, 1.0 eq.) and ethyl formate (11.67 g, 0.157 mol, 1.0 eq.) in dry THF (250 mL) was added NaH (60% in mineral oil) (4.92 g, 0.207 mol, 1.3 eq.) at 0° C. over a period of 15 minutes. The reaction mixture was allowed to stir at 50° C. for 30 minutes. Excess of solvent was evaporated under reduced pressure to get an oily residue. Sodium ethoxide was prepared by using Na (3.62 g, 0.157 mol, 1.0 eq.) and ethanol (150 mL) at 0° C. To it, acetimidamide.HCl (14.91 g, 0.157 mol, 1.0 eq.) was added at that temperature and allowed to stir at RT for 30 minutes. Acetimidamide solution in ethanol was filtered to remove solid and then it was added to the oily residue. The resulting reaction mixture was allowed to stir at 100° C. for 16 h. Progress of reaction was monitored by TLC (100% ethyl acetate). After completion, reaction mixture was diluted with ice-cold water (500 mL) and extract using ethyl acetate (2×150 mL). Aqueous layer was acidified with glacial acetic acid (pH=4-5). Solid precipitate was filtered, washed with water, dried under vacuum and azeotroped with toluene to afford 5-(benzyloxy)-2-methylpyrimidin-4-ol (15 g, 44%) as a white solid.

Step-3

To a solution of 5-(benzyloxy)-2-methylpyrimidin-4-ol (15 g, 69.34 mmol, 1.0 eq.) in methanol (250 mL) was added Pd/C (3 g, 28.19 mmol, 0.4 eq.) at RT. The reaction mixture was allowed to stir under hydrogen atmosphere at room temperature for 2 h. Progress of reaction was monitored by TLC (100% ethyl acetate). After completion, reaction mixture was filtered through celite-bed and filtrate was evaporated under reduce pressure to afford 2-methylpyrimidine-4,5-diol (7 g, 80%) as a brown solid.

Step-4

To a solution of 2-methylpyrimidine-4,5-diol (7 g, 55.55 mmol, 1.0 eq.) in water (100 mL) was added KOH (10.26 g, 183.33 mmol, 3.3 eq.) followed by 1,2-dibromoethane (23.5 g, 125 mmol, 2.25 eq.) at RT. The reaction mixture was allowed to stir at 100° C. temperature for 16 h. Progress of reaction was monitored by TLC (100% ethyl acetate). After completion, reaction mixture was diluted with water (20 mL) and extracted with ethyl acetate (3×200 mL). Combined organic layer was washed with brine and dried over anhydrous sodium sulfate. Removal of solvent under reduced pressure afforded crude which was purified by Combi-Flash to afford 2-methyl-6,7-dihydro-[1,4]dioxino[2,3-d]pyrimidine (4 g, 47.4%).

Step-5

To a solution of 2-methyl-6,7-dihydro-[1,4]dioxino[2,3-d]pyrimidine (4 g, 26.28 mmol, 1.0 eq.) in CCl$_4$ (40 mL) was added AIBN (1.29 g, 7.88 mmol, 0.3 eq.) followed by NBS (14.03 g, 78.84 mmol, 3.0 eq.) at RT. The reaction mixture was allowed to stir at 80° C. temperature for 2.5 h. Progress of reaction was monitored by TLC (50% ethyl acetate-hexane). After completion, solvent was evaporated under reduced pressure, poured on ice-water (50 mL) and extracted with ethyl acetate (3×150 mL). Combined organic layer was washed with brine and dried over anhydrous sodium sulfate. Removal of solvent under reduced pressure afforded crude which was purified by Combi-Flash to afford 2-(dibromomethyl)-6,7-dihydro-[1,4]dioxino[2,3-d]pyrimidine (3 g, 36.85%).

Step-6

To a solution of 2-(dibromomethyl)-6,7-dihydro-[1,4]dioxino[2,3-d]pyrimidine (3 g, 9.67 mmol, 1.0 eq.) in EtOH (30 mL) at RT was added a solution of AgNO$_3$ (3.29 g, 19.35 mmol, 2.0 eq.) in water (20 mL). The reaction mixture was allowed to stir at 100° C. in microwave for 30 minutes. Progress of reaction was monitored by TLC (100% ethyl acetate). After completion the reaction mixture was filtered through syringe filter and the filtrate was evaporated under reduced pressure, dried and azetroped to afford 6,7-dihydro-[1,4]dioxino[2,3-d]pyrimidine-2-carbaldehyde (0.8 g, 50%) which was used in the next step without purification.

Step-7

To a solution of ethyl 2-(diethoxyphosphoryl)acetate (1.3 g, 5.77 mmol, 1.2 eq.) in dry THF (30 mL) was added NaH (60% in mineral oil) (0.138 g, 5.77 mmol, 1.2 eq.) at 0° C. over a period of 10 minutes. The reaction mixture was allowed to stir at that temperature for 30 minutes. To that stirred solution was added 6,7-dihydro-[1,4]dioxino[2,3-d] pyrimidine-2-carbaldehyde (0.8 g, 4.81 mmol, 1.0 eq.) at that temperature and allowed to stir at RT for another 30 minutes. Progress of reaction was monitored by TLC (50% ethyl acetate-hexane). After completion, reaction mixture was diluted with ice-cold water (50 mL) and extracted using ethyl acetate (3×100 mL). Combined organic layer was washed with brine and dried over anhydrous sodium sulfate. Removal of solvent is done under reduce pressure to afford crude which was purified by Combi-Flash to afford ethyl (E)-3-(6,7-dihydro-[1,4]dioxino[2,3-d]pyrimidin-2-yl)acrylate (0.7 g, 61.94%).

Step-8

To a solution of ethyl (E)-3-(6,7-dihydro-[1,4]dioxino[2,3-d]pyrimidin-2-yl)acrylate (0.4 g, 1.69 mmol, 1.0 eq.) in EtOH (10 mL) at RT was added a solution of LiOH (0.203 g, 8.46 mmol, 5.0 eq.) in water (1 mL) and the resulting mixture was allowed to stir at 50° C. for 1 h. Progress of reaction was monitored by TLC (100% ethyl acetate). After completion, reaction mixture was concentrated to remove ethanol, washed with diethyl ether (2×10 mL), acidified with 1N HCl up to pH 6 and extracted with mixture of ethanol and ethyl acetate (1:4) (3×50 mL). Combined organic layer was washed with brine and dried over anhydrous sodium sulfate. Removal of solvent afforded crude (E)-3-(6,7-dihydro-[1,4]dioxino[2,3-d]pyrimidin-2-yl)acrylic acid (0.3 g, 85%) as white solid which was used in the next step without purification.

Step-9

To a solution of (E)-3-(6,7-dihydro-[1,4]dioxino[2,3-d]pyrimidin-2-yl)acrylic acid (0.350 g, 1.68 mmol, 1.0 eq.) in dry THF were added triethylamine (0.204 g, 2.01 mmol, 1.2 eq.) and pivaloyl chloride (0.203 g, 1.68 mmol, 1.0 eq.). The reaction mixture was stirred at 0° C. for 45 minutes. Progress of reaction was monitored by TLC. After completion, reaction mixture was filtered and the filtrate was used directly for the next step.

To a stirred solution of 5,6-dihydropyridin-2(1H)-one (0.164 g, 1.68 mmol, 1.0 eq.) in dry THF at −78° C. was added n-butyl lithium (2.5 M in hexane, 0.68 mL, 1.68 mmol, 1.0 eq.) and the mixture was allowed to stir at the same temperature for 30 minutes. To this solution was added anhydride (0.490 g, 1.68 mmol, 1.0 eq.). Reaction mixture was allowed to stir at −78° C. for 90 minutes. Progress of reaction was monitored by TLC. After completion, reaction mixture was brought to 0° C., diluted with ammonium chloride solution (30 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash on silica gel using ethyl acetate-hexane as eluent to afford (E)-1-(3-(6,7-dihydro-[1,4]dioxino[2,3-d]pyrimidin-2-yl)acryloyl)-5,6-dihydropyridin-2(1H)-one (0.092 g, 20%).

LCMS: 288 [M+1]$^+$ $^1$HNMR (400 MHz, CDCl$_3$) δ 8.22 (s, 1H), 7.87 (d, 1H), 7.55 (d, 1H), 6.96-6.88 (m, 1H), 6.01 (d, 1H), 4.58-4.50 (m, 2H), 4.38-4.30 (m, 2H), 2.50-2.40 (m, 2H).

Example 80

Preparation of (E)-1-(3-(3,5-dimethyl-1H-pyrazol-4-yl)acryloyl)-5,6-dihydropyridin-2(1H)-one

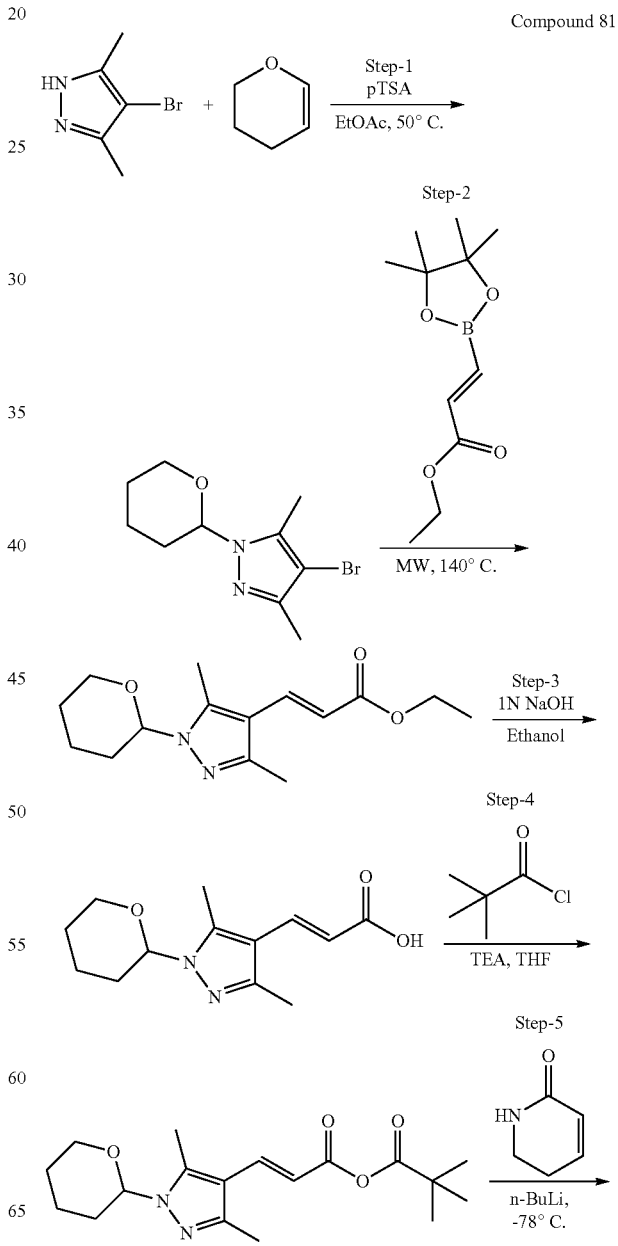

185

-continued

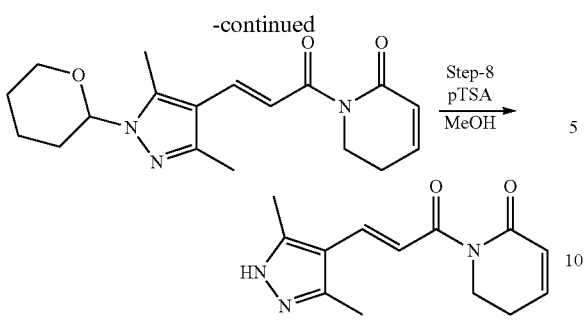

Step-8
pTSA
MeOH

Step-1

To a solution of 4-bromo-3,5-dimethyl-1H-pyrazole (3 g, 17.14 mmol, 1 eq) in ethyl acetate (40 mL) were added p-TSA (0.3 g, 1.71 mmol, 0.1 eq) and 3,4-dihydro-2H-pyran (4.7 mL, 51.42 mmol, 3 eq and the reaction mixture was allowed to stir at 50° C. for 3 h. Progress of reaction was monitored by TLC. After completion, reaction mixture was diluted with water and extracted with ethyl acetate (3×70 mL). Combined organic layer was washed with brine and dried over anhydrous sodium sulfate. Removal of solvent under reduce afforded crude 4-bromo-3,5-dimethyl-1-(tetrahydro-2H-pyran-2-yl)-1H-pyrazole which was purified by crystallization in ethyl acetate-pentane afford pure 4-bromo-3,5-dimethyl-1-(tetrahydro-2H-pyran-2-yl)-1H-pyrazole (2.5 g, 56.43%).

Step-2

To a solution of 4-bromo-3,5-dimethyl-1-(tetrahydro-2H-pyran-2-yl)-1H-pyrazole (0.5 g, 2.86 mmol) in dioxane (6 mL) was added ethyl (E)-3-(4,4,5,5-tetramethyl-1,3,2-dioxaborolan-2-yl)acrylate (0.77 g, 3.42 mmol, 1.2 eq) and tert-butoxide (0.481 g, 1.5 eq) in water (3 mL) and the reaction mixture was deoxygenated using nitrogen gas for 10 minutes. Tetrakis(triphenylphosphine)palladium(0) (0.165 g, 0.14 mmol, 0.05 eq) was added and the reaction mixture was again deoxygenated for 10 minutes. Reaction mixture was allowed to stir at 140° C. for 1 h in microwave. Reaction mixture was cooled to RT, diluted with water (50 mL) and extract using ethyl acetate (3×20 mL). Combined organic layer was washed with brine and dried over anhydrous sodium sulfate. Removal of solvent under reduced pressure afforded crude which was purified by Combi-Flash to afford ethyl (E)-3-(3,5-dimethyl-1-(tetrahydro-2H-pyran-2-yl)-1H-pyrazol-4-yl)acrylate (1.2 g).

Step-3

To a solution of ethyl (E)-3-(3,5-dimethyl-1-(tetrahydro-2H-pyran-2-yl)-1H-pyrazol-4-yl)acrylate (1.2 g, 5.47 mmol, 1 eq) in ethanol (20 mL) was added 1N NaOH (6 mL) dropwise and the mixture was allowed to stir at the RT for overnight. Progress of reaction was monitored by TLC. Reaction mixture was acidifying using 1N HCl upto pH 6 and extracted using mixture of ethanol and ethyl acetate (20:80) (3×50 mL). Combined organic layer was washed with brine and dried over anhydrous sodium sulfate. Removal of solvent afforded crude (E)-3-(3,5-dimethyl-1-(tetrahydro-2H-pyran-2-yl)-1H-pyrazol-4-yl)acrylic acid (0.520 g, 38.23%).

Step-4

To a solution of (E)-3-(3,5-dimethyl-1-(tetrahydro-2H-pyran-2-yl)-1H-pyrazol-4-yl)acrylic acid (0.5 g, 1.99 mmol, 1.0 eq.) in dry THF was added triethylamine (0.33 mL, 2.38 mmol, 1.2 eq.) and pivaloyl chloride (0.22 mL, 1.79 mmol, 0.9 eq.) the reaction mixture was stirred at 0° C. for 45 minutes. Progress of reaction was monitored by TLC. After completion, reaction mixture was filtered and the filtrate was used directly for the next step.

Step-5

To a stirred solution of 5,6-dihydropyridin-2(1H)-one (0.193 g, 1.99 mmol, 1 eq.) in dry THF at −78° C. was added n-butyl lithium (2.5 M in hexane, 0.79 mL, 1.99 mmol, 1 eq.) and the mixture was allowed to stir at the same temperature for 30 minutes. To this solution was added (E)-(E)-3-(3,5-dimethyl-1-(tetrahydro-2H-pyran-2-yl)-1H-pyrazol-4-yl)acrylic pivalic anhydride (0.665 g, 1.99 mmol, 1 eq.). Reaction mixture was allowed to stir at −78° C. for 90 min. Progress of reaction was monitored by TLC. Reaction mixture was brought to 0° C., diluted with ammonium chloride solution (30 mL) and extracted with ethyl acetate (3×50 mL). combined organic layer was washed with brine, dried over anhydrous $Na_2SO_4$ and evaporated to dryness under vacuum to afford crude which was purified by Combi-Flash to afford (E)-1-(3-(3,5-dimethyl-1-(tetrahydro-2H-pyran-2-yl)-1H-pyrazol-4-yl)acryloyl)-5,6-dihydropyridin-2(1H)-one (0.320 g, 48.92%).

Step-6

To a solution of (E)-1-(3-(3,5-dimethyl-1-(tetrahydro-2H-pyran-2-yl)-1H-pyrazol-4-yl)acryloyl)-5,6-dihydropyridin-2(1H)-one (0.3 g, 0.91 mmol, 1 eq) in methanol (15 mL) was added p-TSA (0.188 g, 1.09 mmol, 1.2 eq). Allow the reaction mixture to stir at Room temperature for 2 h. Progress of reaction was monitored by TLC. After completion pour water and extract using ethyl acetate (3×30 mL). Combined organic layer was washed with brine and dried over anhydrous sodium sulfate. Removal of solvent is done under reduce pressure. To afford crude (E)-1-(3-(3,5-dimethyl-1H-pyrazol-4-yl)acryloyl)-5,6-dihydropyridin-2(1H)-one which was purified by crystallization in ethyl acetate-pentane to afford pure (E)-1-(3-(3,5-dimethyl-1H-pyrazol-4-yl)acryloyl)-5,6-dihydropyridin-2(1H)-one (0.1 g, 44.84%).

LCMS: 246 [M+1]+

$^1$H NMR (400 MHz, $CDCl_3$) δ 7.75 (d, 1H), 7.25 (d, 1H), 6.97-6.87 (m, 1H), 6.02 (d, 1H), 4.05 (t, 2H), 2.46-2.41 (m, 2H), 2.39 (s, 6H).

Example 81

Preparation (E)-N-(4-fluorophenyl)-4-(2-((6-oxo-3,6-dihydropyridin-1(2H)-yl)sulfonyl)vinyl)piperidine-1-carboxamide Compound 82

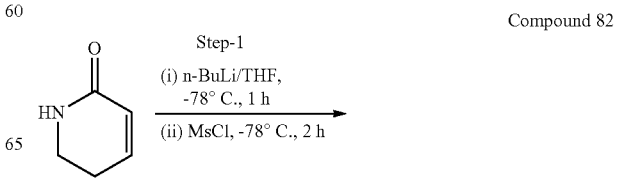

Step-1
(i) n-BuLi/THF, −78° C., 1 h
(ii) MsCl, −78° C., 2 h

187

-continued

Step-2

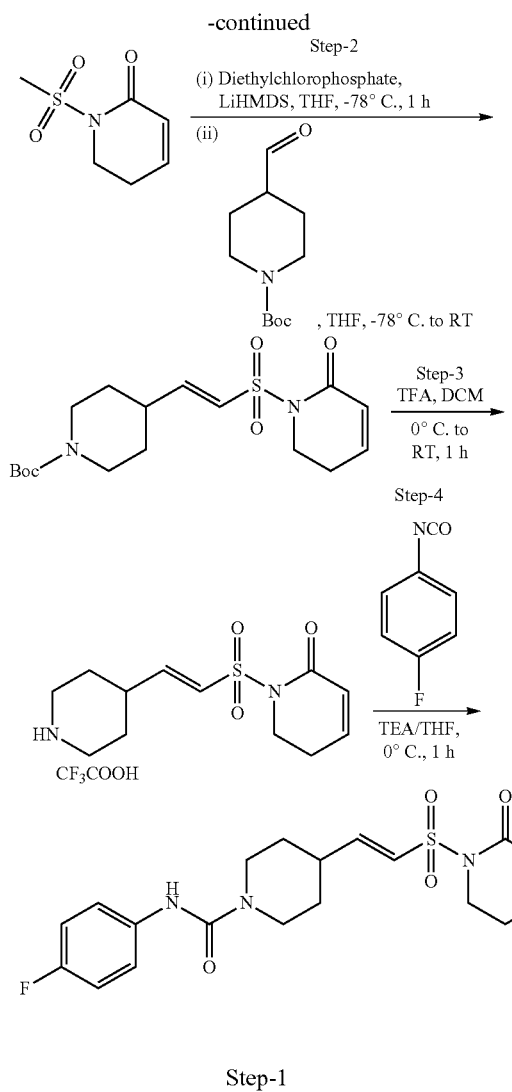

Step-1

To a stirred solution of 5,6-dihydropyridin-2(1H)-one (1 g, 10.3 mmol, 1.0 eq.) in dry THF at −78° C. was added n-butyllithium (2.5M in hexane, 4.2 ml, 10.30 mmol, 1 eq.) and the mixture was allowed to stir at the same temperature for 1 h. To this solution was added a solution of methane sulfonyl chloride (0.92 ml, 1.67 mmol, 1.1 eq.) in THF and the reaction mixture was allowed to stir at −78° C. for 1 h. Progress of reaction was monitored by TLC and LCMS. After completion, reaction mixture was quenched aq. NH$_4$Cl solution (50 mL) and extracted with ethyl acetate (3×30 mL). Combined organic layer was washed with brine (50 mL), dried over anhydrous Na$_2$SO$_4$ and evaporated to dryness under vacuum to afford crude which was purified silica gel chromatography using ethyl acetate-hexane system as eluent to afford 1-(methylsulfonyl)-5,6-dihydropyridin-2(1H)-one (700 mg, 38.88%).

LCMS: 176 [M+1]$^+$

Step-2

To a suspension of 1-(methylsulfonyl)-5,6-dihydropyridin-2(1H)-one (0.5 g, 2.857 mmol 1 eq) in THF (50 mL) and diethyl chloro phosphate (0.49 g, 2.857 mol, 1 eq) was added LiHMDS at −78° C. and the mixture was allowed to stir at the same temperature for 1 h. To this mixture was added a solution of tert-butyl 4-formylpiperidine-1-carboxylate (0.6 g, 2.857 mol, 1.0 eq) in THF (5 mL) and the resulting mixture was allowed to stir at room temperature for 1 h. Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash using ethyl acetate-hexane system as eluent to afford product tert-butyl (E)-4-(2-((6-oxo-3,6-dihydropyridin-1(2H)-yl)sulfonyl) vinyl) piperidine-1-carboxylate (80 mg, 7.5%).

LCMS: 371 [M+1]$^+$

Step-3

To a stirred solution (90 mg, 0.245 mmol, 1 eq) in DCM (5 mL) at 0° C. was added TFA (0.5 mL) dropwise and the resulting reaction mixture was stirred at RT for 1 h. Progress of reaction was monitored by TLC. After completion, reaction mixture was concentrate under reduced pressure to afford (E)-14(2-(piperidin-4-yl)vinyl)sulfonyl)-5,dihydropyridin-2(1H)-one which was used in the next step without purification (70 mg, 84%).

LCMS: 271[M+1]$^+$

Step-4

To a stirred solution of (E)-1-((2-(piperidin-4-yl)vinyl) sulfonyl)-5,dihydropyridin-2(1H)-one (80 mg, 0.295 mmol, 1 eq) in THF (5 mL) was cooled up to 0° C. and added TEA (76 µL, 0.590 mmol, 2 eq) and stirred for 10 minute then added 1-fluoro-4-isocyanatobenzene (8 mg, 0.762 mmol, 2 eq) already dissolved in THF (5 mL) and stirred for 20 minute. Reaction was monitored by TLC and LCMS, after completion of reaction, reaction mixture was diluted with ethyl acetate (40 mL) and washed with brine (3×20 mL). Organic layer was dried over sodium sulphate and concentrated under reduced pressure to yield crude which is purified by Combi-Flash on silica gel using ethyl acetate-hexane system as eluent to afford (E)-N-(4-fluorophenyl)-4-(2-((6-oxo-3,6-dihydropyridin-1(2H)-yl)sulfonyl)vinyl)piperidine-1-carboxamide (22 mg, 25%).

LCMS: 408 [M+1]$^+$ $^1$H NMR (400 MHz, DMSO-d$_6$) δ 8.50 (s, 1H), 7.46-7.40 (m, 2H), 7.10-6.95 (m, 3H), 6.90-6.80 (m, 1H), 6.76 (d, 1H), 5.86 (d, 1H), 4.17-4.03 (m, 2H), 3.80 (t, 2H), 2.89-2.79 (m, 2H), 2.60-2.40 (m, 2H), 1.60-1.50 (m, 2H), 1.40-1.20 (m, 3H).

Example 82

Preparation of 1-[(2E)-3-(1-methyl-1H-pyrazol-4-yl)-2-phenylprop-2-enoyl]-5,6-dihydropyridin-2(1H)-one Compound 83

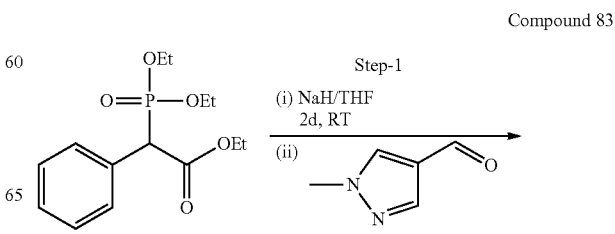

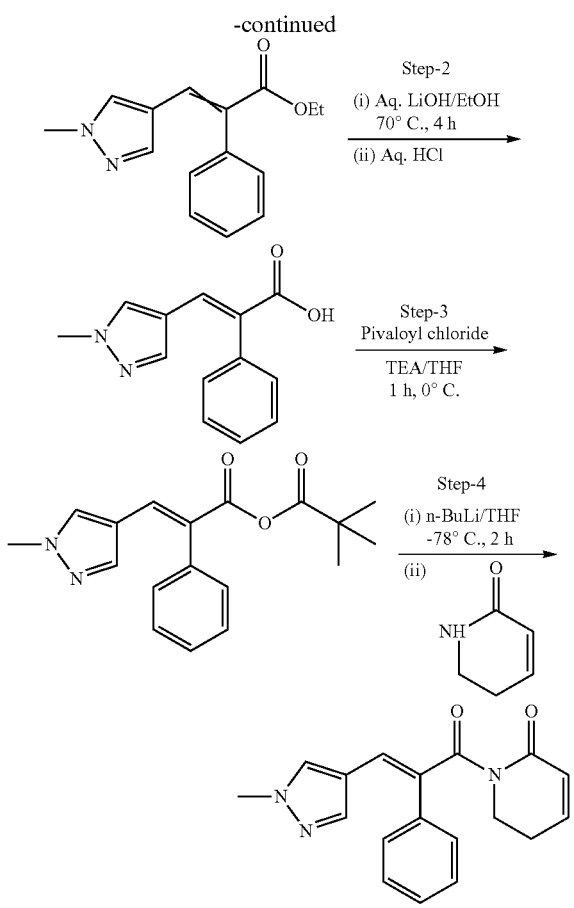

Step-1

To a suspension of sodium hydride (60% in mineral oil, 545 mg 13.63 mmol, 1.5 eq) in THF (50 mL) was added ethyl(diethoxyphosphoryl)(phenyl)acetate (3.37 g, 10.90 mmol, 1.2 eq) dropwise at 0° C. and the mixture was allowed to stir at the same temperature for 30 minutes. To this mixture was added a solution of 1-methyl-1H-pyrazole-4-carbaldehyde (1 g, 9.09 mmol, 1.0 eq) in THF (5 mL) and the resulting mixture was allowed to stir at room temperature for 2 days. Progress of reaction was monitored by TLC. After completion, reaction mixture was diluted with saturated aq. NH$_4$Cl (100 mL) and extracted with ethyl acetate (3×50 ml). Combined organic layer was washed with brine, dried over anhydrous Na$_2$SO$_4$ and evaporated to dryness under vacuum to afford crude which was purified by Combi-Flash ethyl acetate-hexane system as eluent to afford ethyl (2E)-3-(1-methyl-1H-pyrazol-4-yl)-2-phenylprop-2-enoate (0.5 g, 21.55%).

LCMS: 257 [M+1]$^+$

Step-2

To a solution of ethyl (2E)-3-(1-methyl-1H-pyrazol-4-yl)-2-phenylprop-2-enoate (90 mg, 0.351 mmol, 1.0 eq) in ethanol (20 mL) was added a solution of lithium hydroxide (42 mg, 1.76 mmol, 5 eq) in water (2 mL) and the reaction mixture was stirred at 70° C. for 4 h. Progress of reaction was monitored by TLC. After completion, reaction mixture was concentrated under vacuum and then acidified with 2N HCl make pH up to 3. The mixture was diluted saturated aq. NH$_4$Cl (30 mL) and extracted with dichloromethane (3×30 mL). Combined organic layer was washed with brine solution (50 mL) and dried over anhydrous Na$_2$SO$_4$. Removal of solvent under reduced pressure to obtain (2E)-3-(1-methyl-1H-pyrazol-4-yl)-2-phenylprop-2-enoic acid (70 mg, 87.50%).

LCMS: 229 [M+1]$^+$

Step-3

To a solution of (2E)-3-(1-methyl-1H-pyrazol-4-yl)-2-phenylprop-2-enoic acid (70 mg, 0.307 mmol, 1.0 eq.) in dry THF was added triethylamine (46 µl, 0.337 mmol, 1.1 eq.) followed by pivaloyl chloride (40 mg, 0.337 mmol, 1.1 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one 32 mg, 0.337 mmol, 1.1 eq.) in dry THF at −78° C. was added n-butyl lithium (2.5 M in hexane, 0.14 mL, 0.337 mmol, 1.1 eq.) and the mixture was allowed to stir at the same temperature for 30 minutes. To this solution was added a solution of 2,2-dimethylpropanoic (2E)-3-(1-methyl-1H-pyrazol-4-yl)-2-phenylprop-2-enoic anhydride (0.307 mmol, 1 eq.) in THF and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×30 mL). Combined organic layer was washed with brine, dried over anhydrous Na$_2$SO$_4$ and evaporated to dryness under vacuum to afford crude which was purified by reversed phase HPLC to afford 1-[(2E)-3-(1-methyl-1H-pyrazol-4-yl)-2-phenylprop-2-enoyl]-5,6-dihydropyridin-2(1H)-one (12 mg 12.76%).

LCMS: 308 [M+1]$^+$ $^1$H NMR (400 MHz, CDCl$_3$) δ 7.31-7.42 (m, 4H), 7.13 (s, 1H), 7.04 (s, 1H), 6.84 (s, 1H), 6.76-6.83 (m, 1H), 5.80 (d, 1H), 3.88 (t, 2H), 3.73 (s, 3H), 2.55-2.55 (d, 2H).

Example 83

Preparation of (Z)-1-(3-(1-methyl-1H-pyrazol-4-yl)-2-phenylacryloyl)-5,6-dihydropyridin-2(1H)-one Compound 84

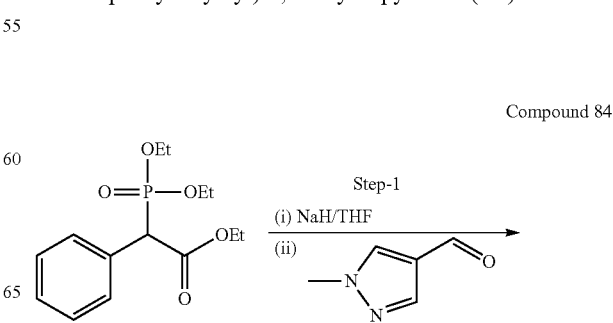

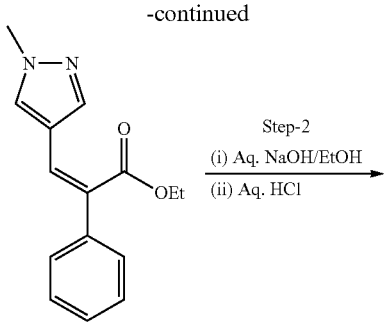

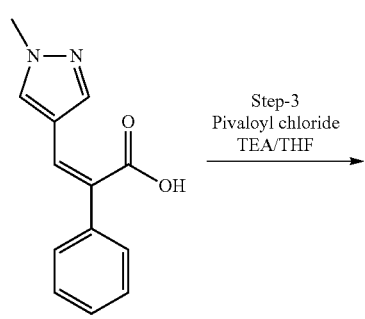

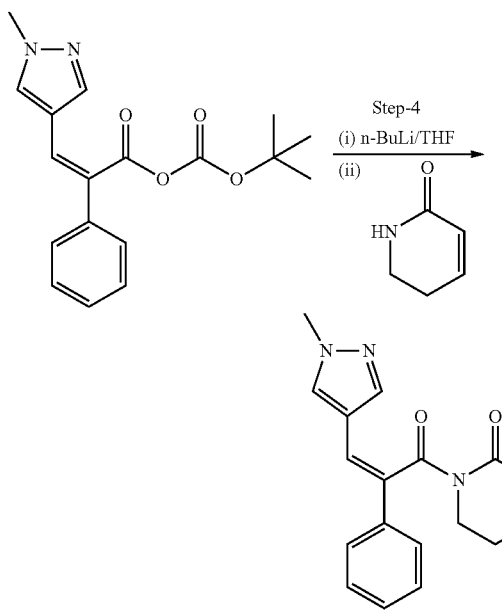

Step-1

To a suspension of sodium hydride (60% in mineral oil, 545 mg 13.63 mmol, 1.5 eq) in THF (50 mL) was added ethyl(diethoxyphosphoryl)(phenyl)acetate (3.37 g, 10.90 mmol, 1.2 eq) dropwise at 0° C. and the mixture was allowed to stir at the same temperature for 30 minutes. To this mixture was added a solution of 1-methyl-1H-pyrazole-4-carbaldehyde (1 g, 9.09 mmol, 1.0 eq) in THF (5 mL) and the resulting mixture was allowed to stir at room temperature for 2 days. Progress of reaction was monitored by TLC. After completion, reaction mixture was diluted with saturated aq. NH₄Cl (100 mL) and extracted with ethyl acetate (3×50 mL). Combined organic layer was washed with brine, dried over anhydrous Na₂SO₄ and evaporated to dryness under vacuum to afford crude which was purified by Combi-Flash using ethyl acetate-hexane system as eluent to afford (Z)-ethyl 3-(1-methyl-1H-pyrazol-4-yl)-2-phenylacrylate (0.5 g, 21.55%).

LCMS: 257 [M+1]⁺

Step-2

To a solution of ethyl (2E)-3-(1-methyl-1H-pyrazol-4-yl)-2-phenylprop-2-enoate (150 mg, 0.585 mmol, 1.0 eq) in ethanol (30 mL) was added a solution of lithium hydroxide (70 mg, 2.929 mmol, 5 eq) in water (3 mL) and the reaction mixture was stirred at 70° C. for 4 h. Progress of reaction was monitored by TLC. After completion, reaction mixture was concentrated under vacuum and then acidified with 2N HCl make pH up to 3. The mixture was diluted with saturated aq. NH₄Cl (30 mL) and extracted with dichloromethane (3×30 mL). The combined organic layer was washed with brine solution (50 mL) and dried over anhydrous Na₂SO₄. Removal of solvent under reduced pressure to obtain (Z)-3-(1-methyl-1H-pyrazol-4-yl)-2-phenylacrylic acid (120 mg, 90.22%).

LCMS: 229 [M+1]⁺

Step-3

To a solution of (2E)-3-(1-methyl-1H-pyrazol-4-yl)-2-phenylprop-2-enoic acid (120 mg, 0.526 mmol, 1.0 eq.) in dry THF was added triethylamine (81 µl 0.578 mmol, 1.1 eq.) followed by pivaloyl chloride (69 mg 0.578 mmol, 1.1 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (56 mg, 0.578 mmol, 1.1 eq.) in dry THF at −78° C. was added n-butyl lithium (2.5M in hexane, 0.23 mL, 0.578 mmol, 1.1 eq.) and the mixture was allowed to stir at the same temperature for 30 minutes. To this solution was added a solution of 2,2-dimethylpropanoic (2E)-3-(1-methyl-1H-pyrazol-4-yl)-2-phenylprop-2-enoic anhydride (0.526 mmol, 1 eq.) in THF and the reaction mixture was allowed to stir at −78° C. for 1 h. Progress of reaction was monitored by TLC and LCMS. After completion, reaction mixture was brought to 0° C., diluted with water (30 mL) and extracted with ethyl acetate (3×30 mL). Combined organic layer was washed with brine, dried over anhydrous Na₂SO₄ and evaporated to dryness under vacuum to afford crude which was purified by reversed phase HPLC to afford (Z)-1-(3-(1-methyl-1H-pyrazol-4-yl)-2-phenylacryloyl)-5,6-dihydropyridin-2(1H)-one (50 mg, 31.05%).

LCMS: 308 [M+1]⁺

¹H NMR (400 MHz CDCl₃) δ 7.47 (s, 1H), 7.37-7.44 (m, 3H), 7.33 (t, 2H), 7.24-7.29 (m, 1H), 6.76-6.87 (m, 1H), 6.66 (s, 1H), 5.80 (d, 1H), 4.16 (t, 2H) 3.86 (s, 3H) 2.50-2.35 (d, 2H).

Example 84

Preparation of (E)-5,5-dimethyl-1-(3-(1-methyl-1H-pyrazol-4-yl)acryloyl)-5,6-dihydropyridin-2(1H)-one Compound 85

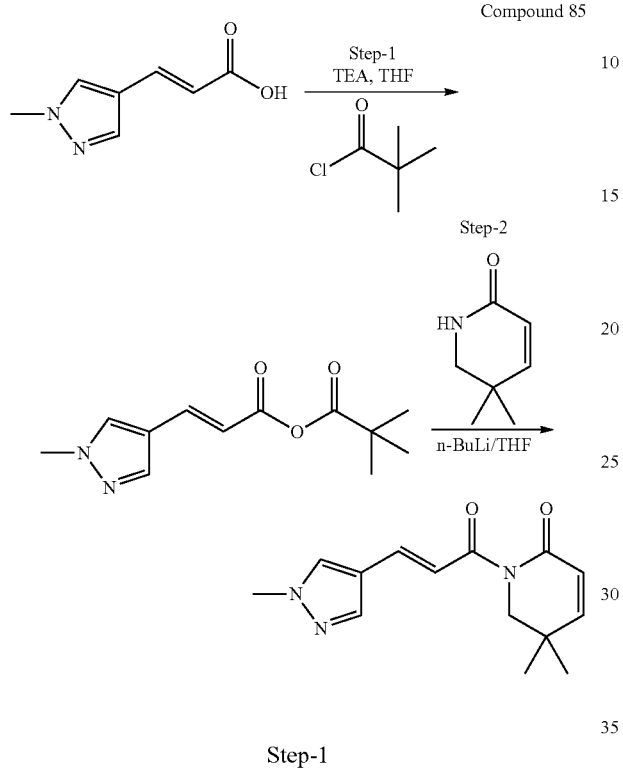

Step-1

To a solution of (E)-3-(1-methyl-1H-pyrazol-4-yl)acrylic acid (85 mg, 0.56 mmol, 1.0 eq.) in dry THF (10 mL) was added triethylamine (0.093 mL, 0.67 mmol, 1.2 eq.) followed by pivaloyl chloride (0.61 mL, 0.67 mmol, 1.2 eq.) and the reaction mixture was stirred at 0° C. for 45 minutes. Progress of reaction was monitored by TLC. After completion, reaction mixture was filtered and the filtrate was used directly for the next step.

Step-2

To a stirred solution of 5,5-dimethyl-5,6-dihydropyridin-2(1H)-one (70 mg, 0.56 mmol, 1.0 eq.) in dry THF at −78° C. was added n-BuLi (0.23 mL, 0.56 mmol, 1 eq.) and the mixture was allowed to stir at the same temperature for 30 minutes. To this solution was added a solution of (E)-(E)-3-(1-methyl-1H-pyrazol-4-yl)acrylic pivalic anhydride (0.56 mmol, 1.0 eq.) in THF and the reaction mixture was allowed to stir at room temperature for 1 h. Progress of reaction was monitored by TLC and LCMS. After completion, reaction mixture was diluted with saturated aq. ammonium chloride solution (50 mL) and extracted with ethyl acetate (3×50 mL). Combined organic layer was washed with brine (50 mL) and dried over anhydrous sodium sulfate. Removal of solvent gave crude which was purified by Combi-Flash on silica gel using ethyl acetate-hexane system as eluent to afford (E)-5,5-dimethyl-1-(3-(1-methyl-1H-pyrazol-4-yl)acryloyl)-5,6-dihydropyridin-2(1H)-one (9 mg, 6.3%).

LCMS: 260 [M+1]$^+$ $^1$H NMR (400 MHz, DMSO-d$_6$) δ 7.75 (s, 1H), 7.68 (d, 1H), 7.60 (d, 1H), 7.30 (d, 1H), 6.61 (d, 1H), 5.81 (d, 1H), 3.90 (s, 3H), 3.79 (s, 2H), 1.18 (s, 6H).

Example 85

Preparation of (E)-1-(3-(1-cyclopropyl-1H-pyrazol-4-yl)acryloyl)-5,6-dihydropyridin-2(1H)-one Compound 86

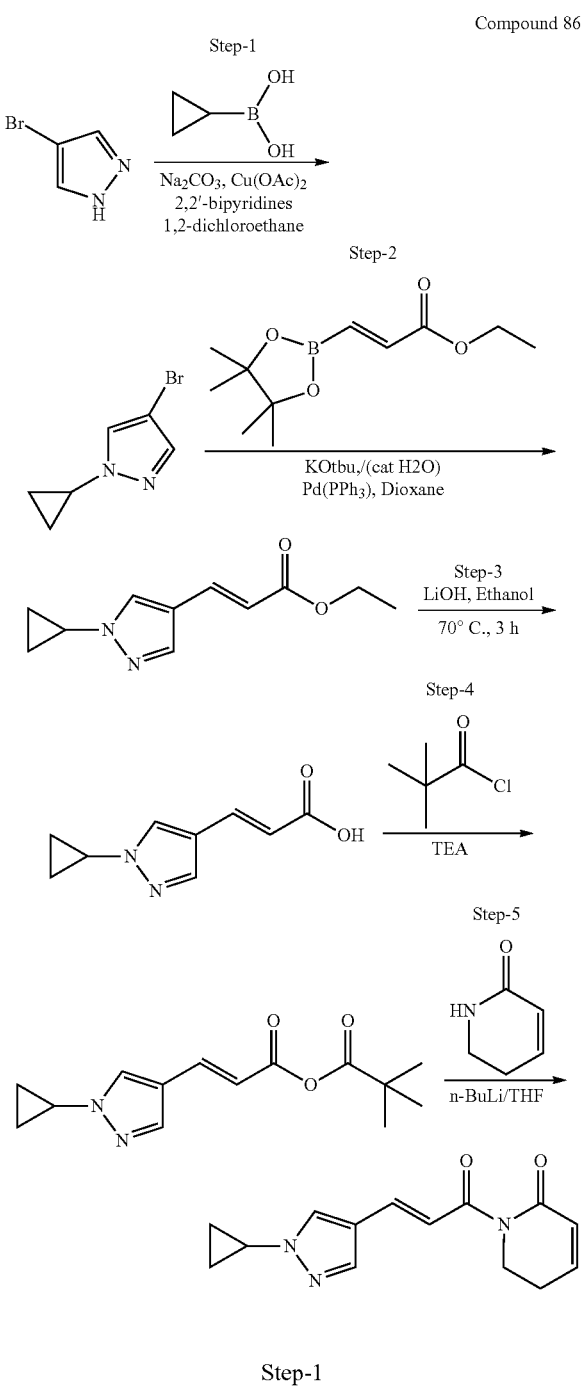

Step-1

A mixture of 4-bromo-1H-pyrazole (0.50 g), cyclopropylboronic acid (1.0 g, 6.80 mmol, 1.0 eq), copper (11) acetate (0.5 g, 7.48 mmol, 1.1 eq.), 2,2'-bipyridine (1.0 g, 7.48 mmol, 1.1 eq.), and sodium carbonate (0.5 g, 14.96 mmol, 2.2 eq) in 1,2-dichloroethane (15 mL) was stirred under reflux temperature for 4 h. To this mixture was again added cyclopropylboronic acid (0.5 g, 14.96 mmol, 2.2 eq.) and the mixture was further stirred under reflux overnight. Progress of reaction was monitored by TLC. Reaction mixture was cooled to RT, diluted with aqueous NH$_4$Cl solution (30 mL) and extracted with dichloromethane (3×30 mL). Combined organic layer was dried over Na$_2$SO$_4$ and concentrated under vacuum to afford crude which was purified by Combi-Flash on silica gel using ethyl acetate-hexane as eluent to afford 4-bromo-1-cyclopropyl-1H-pyrazole (0.7 g, 55.55%) as colorless oil.

Step-2

To a solution of 4-bromo-1-cyclopropyl-1H-pyrazole (0.5 g, 2.68 mmol) in dioxane (10 mL) was added ethyl (E)-3-(4,4,5,5-tetramethyl-1,3,2-dioxaborolan-2-yl)acrylate (0.73 g, 3.22 mmol, 1.2 eq) and potassium tert-butoxide (0.602 g, 5.37 mmol, 1.5 eq) in water (3 mL) and the reaction mixture was deoxygenated using nitrogen gas for 10 minutes. Tetrakis(triphenylphosphine)palladium(0) (0.154 g, 0.135 mmol, 0.05 eq) was added and the reaction mixture was again deoxygenated for 10 minutes. Reaction mixture was allowed to stir at 140° C. for 1 h in microwave. Reaction mixture was cooled to RT, diluted with water (50 mL) and extract using ethyl acetate (3×30 mL). Combined organic layer was washed with brine and dried over anhydrous sodium sulfate. Removal of solvent under reduced pressure afforded crude which was purified by Combi-Flash to afford ethyl (E)-3-(1-cyclopropyl-1H-pyrazol-4-yl) acrylate (0.370 g, 66.90%).
LCMS: 207 [M+1]$^+$ Step-3

To a solution of ethyl (E)-3-(1-cyclopropyl-1H-pyrazol-4-yl) acrylate (0.35 g, 1.699 mmol, 1.0 eq) in ethanol (100 mL) was added a solution of lithium hydroxide (0.122 g, 5.097 mmol, 3.0 eq) in water (10.0 mL) and the reaction mixture was stirred at 70° C. for 2 h. Reaction mixture was concentrated under vacuum and then acidified with 1N HCl (10 mL). The mixture was diluted with water (30 mL) and extracted with ethyl acetate (3×30 mL). Combined organic layer was washed with brine solution (50 mL) and dried over anhydrous Na$_2$SO$_4$. Removal of solvent under reduced pressure gave (E)-3-(1-cyclopropyl-1H-pyrazol-4-yl)acrylic acid (0.260 g, 86%) as crystalline solid.
LCMS: 179 [M+1]$^+$ Step-4

To a solution of (E)-3-(1-cyclopropyl-1H-pyrazol-4-yl) acrylic acid (0.25 g, 1.404 mmol, 1.0 eq.) in dry THF (20 mL) was added triethylamine (0.164 mL, 1.17 mmol, 1.2 eq.) followed by pivaloyl chloride (0.185 mL, 1.54 mmol, 1.1 eq.) and the reaction mixture was stirred at 0° C. for 45 minutes. Progress of reaction was monitored by TLC. After completion, reaction mixture was filtered and the filtrate was used directly for the next step.

Step-5

To a stirred solution of 5,6-dihydropyridin-2(1H)-one (0.100 g, 1.030 mmol, 1.0 eq.) in dry THF (15.0 mL) at −78° C. was added nBuLi (0.45 mL, 1.134 mmol, 1.1 eq.) and the mixture was allowed to stir at the same temperature for 30 minutes. To this solution was added a solution of (E)-(E)-3-(1-cyclopropyl-1H-pyrazol-4-yl)acrylic pivalic anhydride (0.297 g, 1.134 mmol, 1.1 eq.) in THF and the reaction mixture was allowed to stir at room temperature for 1 h. Progress of reaction was monitored by TLC and LCMS. After completion, reaction mixture was evaporated to dryness under vacuum to afford crude which was purified by reversed phase HPLC to afford (E)-1-(3-(1-cyclopropyl-1H-pyrazol-4-yl)acryloyl)-5,6-dihydropyridin-2(1H)-one (0.033 g, 12.45c %) was obtained as off white solid.
LCMS: 258 [M+1]$^+$
$^1$H NMR (400 MHz, CD$_3$OD) δ 8.00 (s, 1H) 7.75 (s, 1H) 7.58 (d, 1H) 7.22 (d, 1H) 7.01-7.12 (m, 1H) 5.99 (d, 1H) 3.96 (t, 2H) 3.61-3.72 (m, 1H) 2.48 (d, 2H) 1.00-1.14 (m, 4H).

Example 86

Preparation of (Z)-1-(2-methyl-3-(piperidin-4-yl)acryloyl)-5,6-dihydropyridin-2(1H)-one 2,2,2-trifluoroacetate

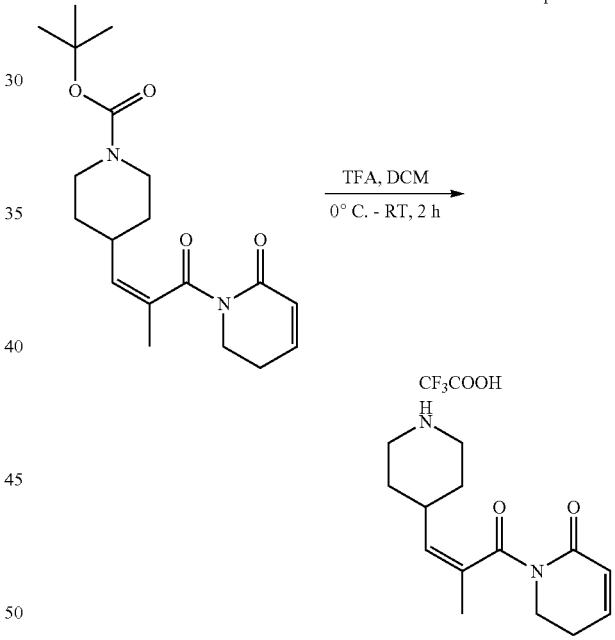

Compound 87

TFA, DCM
0° C. - RT, 2 h

CF$_3$COOH

To a solution of (Z)-tert-butyl 4-(2-methyl-3-oxo-3-(2-oxo-5,6-dihydropyridin-1(2H)-yl)prop-1-enyl)piperidine-1-carboxylate (0.38 g, 1.09 mmol, 1.0 eq) in DCM (10 mL) was added TFA (0.37 mL, 3.2 mmol, 3.0 eq) at 0° C. and then the reaction mixture was allowed to stir at RT for 2 h. Progress of reaction was monitored by TLC. After completion, removal of solvent under reduced pressure afforded (Z)-1-(2-methyl-3-(piperidin-4-yl)acryloyl)-5,6-dihydropyridin-2(1H)-one 2,2,2-trifluoroacetate (0.21 g, 53.16%) as a solid.
LCMS: 249 [M+1]$^+$
$^1$H NMR (400 MHz, DMSO-d$_6$) δ 8.55 (brs, 1H), 8.20 (brs, 1H), 7.10-7.00 (m, 1H), 5.86 (d, 1H), 5.60 (d, 1H), 3.82 (t, 2H), 3.30-3.20 (m, 2H), 3.00-2.82 (m, 2H), 2.60-2.40 (m, 3H), 1.80 (s, 3H), 1.70-1.62 (m, 2H), 1.50-1.35 (m, 2H).

Example 87

Preparation of (E)-1-(2-methyl-3-(piperidin-4-yl)acryloyl)-5,6-dihydropyridin-2(1H)-one 2,2,2-trifluoroacetate

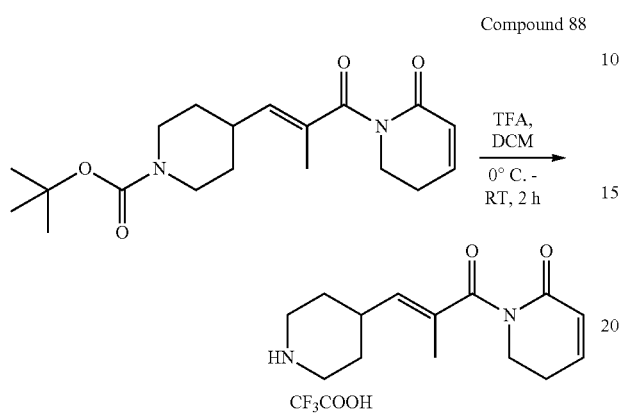

Compound 88

To a solution of (E)-tert-butyl 4-(2-methyl-3-oxo-3-(2-oxo-5,6-dihydropyridin-1(2H)-yl)prop-1-enyl)piperidine-1-carboxylate (0.19 g, 0.54 mmol, 1.0 eq) in DCM (10 mL) was added TFA (0.186 mL, 1.63 mmol, 3.0 eq) at 0° C. and reaction mixture was allowed to stir at RT for 3 h. Progress of reaction was monitored by TLC. After completion, removal of solvent under reduced pressure gave (E)-1-(2-methyl-3-(piperidin-4-yl)acryloyl)-5,6-dihydropyridin-2(1H)-one 2,2,2-trifluoroacetate (0.14 g, 71.06%) as solid.

LCMS: 249 [M+1]$^+$ $^1$H NMR (400 MHz, DMSO-d$_6$) δ 8.55 (brs, 1H), 8.20 (brs, 1H), 7.10-7.00 (m, 1H), 5.86 (d, 1H), 5.60 (d, 1H), 3.75 (t, 2H), 3.30-3.20 (m, 2H), 3.00-2.82 (m, 2H), 2.60-2.40 (m, 3H), 1.80 (s, 3H), 1.70-1.62 (m, 2H), 1.50-1.35 (m, 2H).

Example 88

Preparation of (E)-1-(3-(1H-pyrazol-4-yl)acryloyl)-5,6-dihydropyridin-2(1H)-one

Compound 89

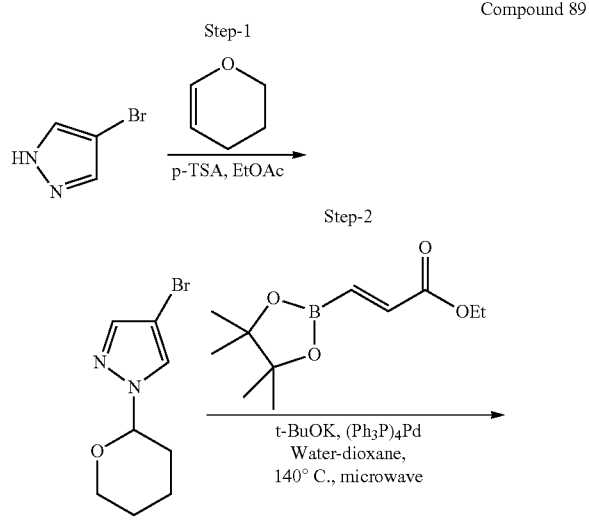

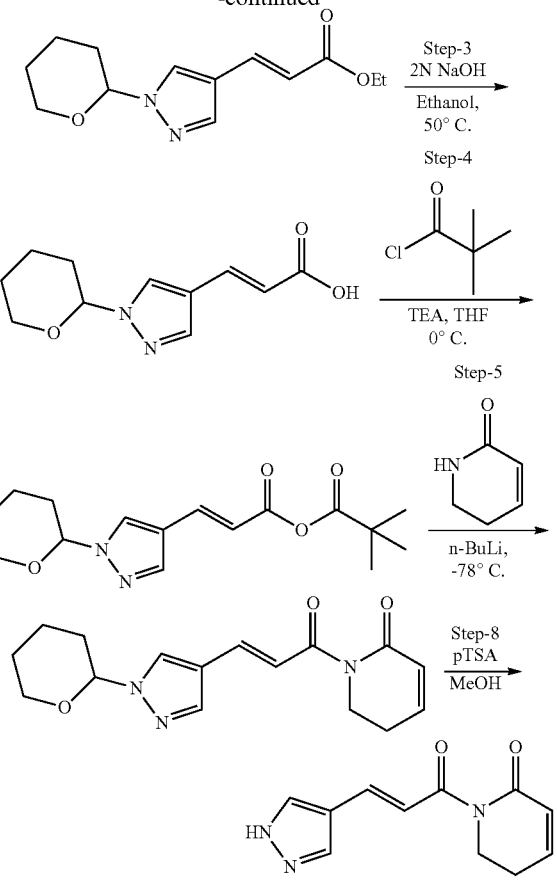

Step-1

To a solution of 4-bromo-1H-pyrazole (5 g, 34.01 mmol, 1 eq) in ethyl acetate (50 mL) were added p-TSA (0.585 g, 3.40 mmol, 0.1 eq) and 3,4-dihydro-2H-pyran (9.34 mL, 102.05 mmol, 3 eq) and the reaction mixture was allowed to stir at 50° C. for 4 h. Progress of reaction was monitored by TLC. After completion, reaction mixture was diluted with water (200 mL) and extract using ethyl acetate (3×70 mL). Combined organic layer was washed with brine (100 mL) and dried over anhydrous sodium sulfate. Removal of solvent under reduce pressure gave crude which was purified by Combi-Flash on silica gel using ethyl acetate-hexane system as eluent to afford 4-bromo-1-(tetrahydro-2H-pyran-2-yl)-1H-pyrazole (5 g, 63.21%).

Step-2

To a solution of 4-bromo-1-(tetrahydro-2H-pyran-2-yl)-1H-pyrazole (0.5 g, 2.16 mmol) in 1,4-dioxane (6 mL) was added ethyl (E)-3-(4,4,5,5-tetramethyl-1,3,2-dioxaborolan-2-yl)acrylate (0.587 g, 2.59 mmol, 1.2 eq) and tert-butoxide (0.363 g, 1.5 eq) in water (3 mL) and the reaction mixture was deoxygenated using nitrogen gas for 10 minutes. Tetrakis(triphenylphosphine)palladium(0) (0.124 g, 0.10 mmol, 0.05 eq) was added and the reaction mixture was again deoxygenated for 10 minutes. Reaction mixture was allowed to stir at 140° C. for 1 h in microwave. Reaction mixture was cooled to RT, diluted with water (100 mL) and extract with ethyl acetate (3×20 mL). Combined organic layer was washed with brine (100 mL) and dried over anhydrous sodium sulfate. Removal of solvent under reduced pressure afforded crude which was purified by Combi-Flash to afford ethyl (E)-3-(1-(tetrahydro-2H-pyran-2-yl)-1H-pyrazol-4-yl) acrylate (0.3 g, 55.45%)

Step-3

To a solution of ethyl (E)-3-(1-(tetrahydro-2H-pyran-2-yl)-1H-pyrazol-4-yl) acrylate (0.3 g, 1.19 mmol, 1 eq) in ethanol (10 mL) was added 2N NaOH (3 mL) dropwise and the mixture was allowed to stir at the RT for overnight. Progress of reaction was monitored by TLC. Reaction mixture was acidified using 1N HCl up to pH 6 and extracted using mixture of ethanol-ethyl acetate (20%) (3×50 mL). Combined organic layer was washed with brine and dried over anhydrous sodium sulfate. Removal of solvent afforded crude (E)-3-(1-(tetrahydro-2H-pyran-2-yl)-1H-pyrazol-4-yl)acrylic acid (0.160 g, 60.15%) which was used in the next step without further purification.

Step-4

To a solution of (E)-3-(1-(tetrahydro-2H-pyran-2-yl)-1H-pyrazol-4-yl)acrylic acid (0.160 g, 0.72 mmol, 1.0 eq.) in dry THF was added triethylamine (0.120 mL, 0.86 mmol, 1.2 eq.) and pivaloyl chloride (0.079 mL, 0.65 mmol, 0.9 eq.) the reaction mixture was stirred at 0° C. for 45 minutes. Progress of reaction was monitored by TLC. After completion, reaction mixture was filtered and the filtrate was used directly for the next step.

Step-5

To a stirred solution of 5,6-dihydropyridin-2(1H)-one (0.070 g, 0.72 mmol, 1 eq.) in dry THF at −78° C. was added n-butyl lithium (2.5M in hexane, 0.29 mL, 0.72 mmol, 1 eq.) and the mixture was allowed to stir at the same temperature for 30 minutes. To this solution was added (E)-(E)-3-(1-(tetrahydro-2H-pyran-2-yl)-1H-pyrazol-4-yl)acrylic pivalic anhydride (0.220 g, 0.72 mmol, 1 eq.). Reaction mixture was allowed to stir at −78° C. for 90 min. Progress of reaction was monitored by TLC. Reaction mixture was brought to 0° C., diluted with ammonium chloride solution (30 mL) and extracted with ethyl acetate (3×40 mL). Combined organic layer was washed with brine, dried over anhydrous Na$_2$SO$_4$ and evaporated to dryness under vacuum to afford crude which was purified by Combi-Flash to afford (E)-1-(3-(1-(tetrahydro-2H-pyran-2-yl)-1H-pyrazol-4-yl)acryloyl)-5,6-dihydropyridin-2(1H)-one (85 mg, 39.35%).

Step-6

To a solution of (E)-1-(3-(1-(tetrahydro-2H-pyran-2-yl)-1H-pyrazol-4-yl)acryloyl)-5,6-dihydropyridin-2(1H)-one (85 mg, 0.28 mmol, 1 eq.) in methanol (6 mL) was added p-TSA (58 mg, 0.33 mmol, 1.2 eq). The reaction mixture was allowed to stir at room temperature for 2 h. Progress of reaction was monitored by TLC. After completion, the mixture was poured into water and extracted using ethyl acetate (3×20 mL). Combined organic layer was washed with brine and dried over anhydrous sodium sulfate. Removal of solvent was done under reduce pressure to afford crude material, which was purified by Combi-Flash to afford (E)-1-(3-(1H-pyrazol-4-yl)acryloyl)-5,6-dihydropyridin-2(1H)-one (10 mg, 16.39%).
LCMS: 218 [M+1]$^+$ $^1$H NMR (400 MHz, CDCl$_3$) δ 7.85 (brs, 1H), 7.75 (d, 1H), 7.32 (d, 1H), 6.98-6.90 (m, 1H), 6.05 (d, 1H), 4.03 (t, 2H), 2.50-2.43 (m, 2H).

Example 89

Preparation of 1 11-{(2E)-3-[1-(2,2,2-trifluoro-ethyl)-1H-pyrazol-4-yl]prop-2-enoyl}-5,6-dihydro-pyridin-2(1H)-one Compound 90

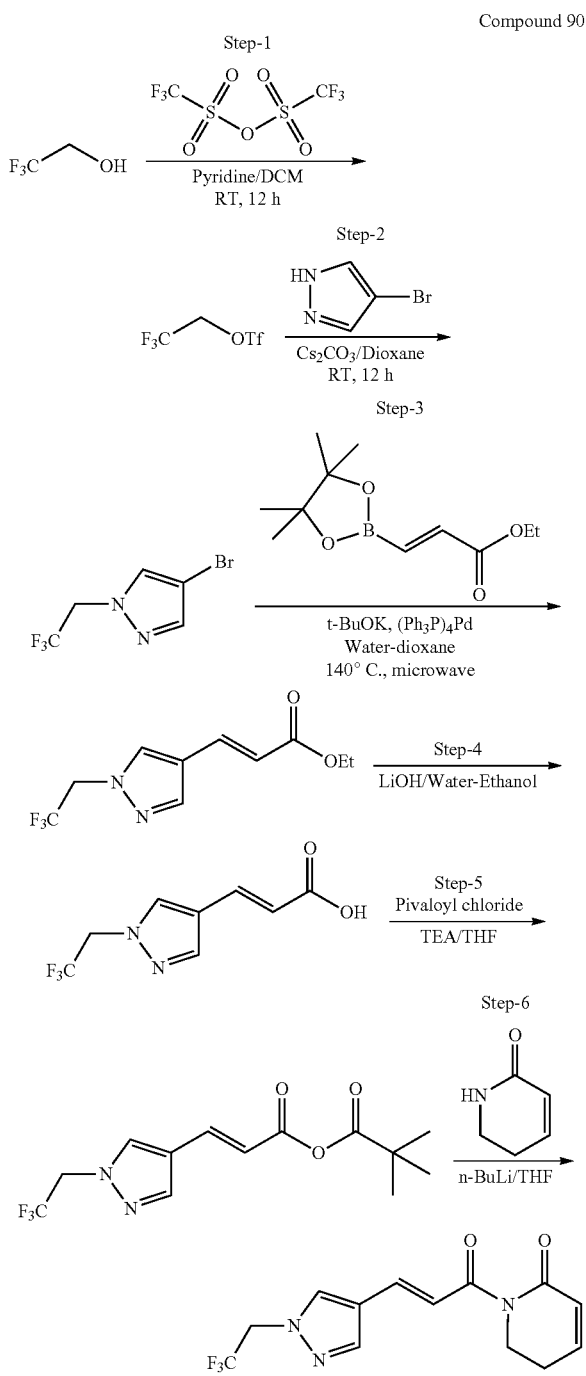

Step-1

To a solution of 2,2,2-trifluoroethanol (2 g, 20.00 mmol, 1.0 eq.) in dry DCM (50 mL) was added pyridine (1.6 ml, 20.00 mmol, 1.0 eq.) at 0° C. followed by addition of triflic anhydride (6.4 g, 23.00 mmol, 1.15 eq.) and the reaction mixture was stirred at 0° C. for 5 minutes then at RT for 12 h. Progress of reaction was monitored by TLC. After completion, reaction mixture was diluted with water (100 mL) and extracted with DCM (3×50 mL). Combined organic layer was washed with brine solution (50 mL) and dried over anhydrous $Na_2SO_4$. Removal of solvent under reduced pressure gave 2,2,2-trifluoroethyl trifluoromethanesulfonate (2 g, 43.10%) which was used in the next step without further purification.

Step-2

To a solution of 4-bromo-1H-pyrazole (500 mg, 3.40 mmol, 1.0 eq.) in dioxane (50 mL) was added cesium carbonate (2.2 g, 6.80 mmol, 2.0 eq.) and the reaction mixture was stirred at RT for 15 minutes. To this mixture was added 2,2,2-trifluoroethyl trifluoromethanesulfonate (986 mg, 4.25 mmol, 1.25 eq.) and the reaction mixture was stirred at RT for 12 h. Progress of reaction was monitored by TLC. After completion, reaction mixture was filtered and the filtrate was evaporated under reduced pressure to afford 4-bromo-1-(2,2,2-trifluoroethyl)-1H-pyrazole (600 mg, 77.14%). Which was used in the next step without purification.

Step-3

To a solution of 4-bromo-1-(2,2,2-trifluoroethyl)-1H-pyrazole (600 mg, 2.62 mmol) and ethyl (2E)-3-(4,4,5,5-tetramethyl-1,3,2-dioxaborolan-2-yl)acrylate (710 mg, 3.14 mmol, 1.2 eq) in 1,4-dioxane (10 mL) was added potassium tert butoxide (587 mg, 5.2 mmol, 2.0 eq) and the reaction mixture was deoxygenated by purging nitrogen for 10 minutes. To this mixture was added $(PPh_3)_4Pd$ (151 mg, 0.13 mmol, 0.15 eq) and mixture was again deoxygenated by purging nitrogen for 10 minutes. The reaction mixture was then allowed to stir under microwave at 140° C. for 1.5 h. Reaction mixture was cooled to RT, diluted with EtOAc (50 mL) and washed with brine (3×50 mL). Removal of solvent under reduced pressure gave crude which was purified by Combi-flash on silica gel using EtOAc-hexane as eluent to afford ethyl (2E)-3-[4-bromo-1-(2,2,2-trifluoroethyl)-1H-pyrazol-3-yl]prop-2-enoate (400 mg, 61.34%).

Step-4

To a solution of ethyl (2E)-3-[4-bromo-1-(2,2,2-trifluoroethyl)-1H-pyrazol-3-yl]prop-2-enoate (300 mg, 1.20 mmol, 1.0 eq) in ethanol (10 mL) was added a solution of lithium hydroxide (87 mg, 3.62 mmol, 3.0 eq) in water (2.0 mL) and the reaction mixture was stirred at 70° C. for 2 h. Reaction mixture was concentrated under vacuum and then acidified with 1N HCl (10 mL). The mixture was diluted with water (30 mL) and extracted with ethyl acetate (3×50 mL). Combined organic layer was washed with brine solution (50 mL) and dried over anhydrous $Na_2SO_4$. Removal of solvent under reduced pressure gave (2E)-3-[1-(2,2,2-trifluoroethyl)-1H-pyrazol-4-yl]prop-2-enoic acid (260 mg, 97.74%) as crystalline solid.

Step-5

To a solution of 2E)-3-[1-(2,2,2-trifluoroethyl)-1H-pyrazol-4-yl]prop-2-enoic acid (260 mg, 1.18 mmol, 1.0 eq.) in dry THF (10 mL) was added triethylamine (0.22 mL, 1.41 mmol, 1.2 eq.) followed by pivaloyl chloride (0.14 mL, 1.18 mmol, 1.0 eq.) and the reaction mixture was stirred at 0° C. for 45 minutes. Progress of reaction was monitored by TLC. After completion, reaction mixture was filtered and the filtrate was used directly for the next step.

Step-6

To a stirred solution of 5,6-dihydropyridin-2(1H)-one (114 mg, 1.17 mmol, 1.0 eq.) in dry THF (10 mL) at −78° C. was added nBuLi (0.50 mL, 1.17 mmol, 1.0 eq.) and the mixture was allowed to stir at the same temperature for 30 minutes. To this solution was added a solution of 22,2-dimethylpropanoic (2E)-3-[1-(2,2,2-trifluoroethyl)-1H-pyrazol-4-yl]prop-2-enoic anhydride (357 mg, 1.17 mmol, 1.0 eq) in THF and the reaction mixture was allowed to stir at room temperature for 1 h. Progress of reaction was monitored by TLC and LCMS. After completion, reaction mixture was evaporated to dryness under vacuum to afford crude which was purified Combi-Flash chromatography (0-50% EtOAc-Hexane) to afford 1 11-{(2E)-3-[1-(2,2,2-trifluoroethyl)-1H-pyrazol-4-yl]prop-2-enoyl}-5,6-dihydropyridin-2(1H)-one (120 mg, 34.18%). LCMS: 300 $[M+1]^+$ $^1H$ NMR (400 MHz, CHLOROFORM-d) d=7.82 (s, 1H), 7.72 (s, 1H), 7.63 (d, 1H), 7.33-7.25 (m, 1H), 6.96-6.91 (m, 1H), 6.03 (d, 1H), 4.70 (q, 2H), 4.02 (t, 2H), 2.47 (td, 2H).

Example 90

Preparation of (E)-tert-butyl 4-(3-oxo-3-(2-oxo-5,6-dihydropyridin-1(2H)-yl)-2-phenylprop-1-enyl)piperidine-1-carboxylate and (Z)-tert-butyl 4-(3-oxo-3-(2-oxo-5,6-dihydropyridin-1(2H)-yl)-2-phenylprop-1-enyl)piperidine-1-carboxylate

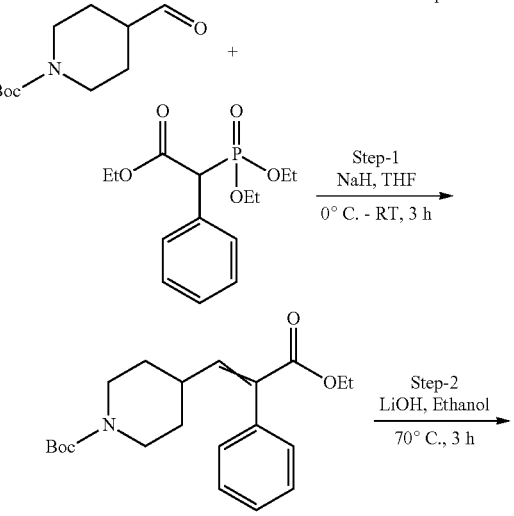

Compounds 91 and 92

Step-1

To a suspension of sodium hydride (60% in mineral oil) (450 mg, 11.26 mmol, 1.2 eq) in THF (50 mL) was added ethyl (diethoxyphosphoryl)(phenyl)acetate (3.57 g, 11.26 mmol, 1.2 eq) dropwise at 0° C. and the mixture was allowed to stir at the same temperature for 30 minutes. To this mixture was added a solution of tert-butyl 4-formylpiperidine-1-carboxylate (2.0 g, 9.38 mmol, 1.0 eq) in THF (5 mL) and the resulting mixture was allowed to stir at room temperature for 2 h. Progress of reaction was monitored by TLC. After completion, reaction mixture was diluted with saturated aq. NH$_4$Cl (100 mL) and extracted with ethyl acetate (3×50 mL). Combined organic layer was washed with brine, dried over anhydrous Na$_2$SO$_4$ and evaporated to dryness under vacuum to afford crude which was purified by Combi-Flash on silica gel using ethyl acetate-hexane system as eluent to afford a mixture of (E) and (Z)-tert-butyl 4-(3-ethoxy-3-oxo-2-phenylprop-1-enyl)piperidine-1-carboxylate (900 mg, 30.00%).

Step-2

To a solution of ((E) and (Z)-tert-butyl 4-(3-ethoxy-3-oxo-2-phenylprop-1-enyl)piperidine-1-carboxylate (900 mg, 2.50 mmol, 1.0 eq) in ethanol (50 mL) was added 2M NaOH solution (10 mL) and the reaction mixture was stirred at 70° C. for 0.5 h. Reaction mixture was concentrated under vacuum and then acidified with 1N HCl (10 mL). The mixture was diluted with water (30 mL) and extracted with ethyl acetate (3×50 mL). Combined organic layer was washed with brine solution (50 mL) and dried over anhydrous Na$_2$SO$_4$. Removal of solvent under reduced pressure gave (E) and (Z)-3-(1-(tert-butoxycarbonyl)piperidin-4-yl)-2-phenylacrylic acid (680 mg 82.02%) as crystalline solid

Step-3

To a solution of (E) and (Z)-3-(1-(tert-butoxycarbonyl)piperidin-4-yl)-2-phenylacrylic acid (680 mg, 2.05 mmol, 1.0 eq.) in dry THF (10 mL) was added triethylamine (0.32 mL, 2.25 mmol, 1.1 eq.) followed by pivaloyl chloride (1.0 mL, 2.05 mmol, 1.0 eq.) and the reaction mixture was stirred at 0° C. for 45 minutes. Progress of reaction was monitored by TLC. After completion, reaction mixture was filtered and the filtrate was used directly for the next step.

Step-4

To a stirred solution of 5,6-dihydropyridin-2(1H)-one (175 mg, 1.80 mmol, 1.0 eq.) in dry THF (10 mL) at −78° C. was added nBuLi (0.70 mL, 1.80 mmol, 1.0 eq.) and the mixture was allowed to stir at the same temperature for 30 minutes. To this solution was added a solution of (E)-3-(1-(tert-butoxycarbonyl)piperidin-4-yl)-2-phenylacrylic pivalic anhydride (748 mg, 1.80 mmol, 1.0 eq.) in THF and the reaction mixture was allowed to stir at room temperature for 1 h. Progress of reaction was monitored by TLC and LCMS. After completion, reaction mixture was evaporated to dryness under vacuum to afford crude which was purified HPLC column chromatography to afford (E)-tert-butyl 4-(3-oxo-3-(2-oxo-5,6-dihydropyridin-1(2H)-yl)-2-phenylprop-1-enyl) piperidine-1-carboxylate (50 mg, 20%) and (Z)-tert-butyl 4-(3-oxo-3-(2-oxo-5,6-dihydropyridin-1(2H)-yl)-2-phenyl-prop-1-enyl)piperidine-1-carboxylate (50 mg, 20%).

Analytical Data

Compound 91

LCMS: 411[M+1]$^+$
$^1$H NMR (400 MHz, CDCl$_3$) δ 7.40-7.20 (m, 5H), 6.85-6.75 (m, 1H), 5.90 (d, 1H), 5.80 (d, 1H), 4.10-3.95 (m, 2H), 3.90 (t, 2H), 2.70-2.52 (m, 2H), 2.45-2.36 (m, 2H), 1.55 (s, 9H), 1.70-1.20 (m, 5H).

Compound 92

LCMS: 411[M+1]$^+$
$^1$H NMR (400 MHz, CDCl$_3$) δ 7.32-7.20 (m, 5H), 6.87-6.75 (m, 1H), 5.80 (d, 1H), 5.67 (d, 1H), 4.19-3.95 (m, 4H), 2.70-2.52 (m, 2H), 2.45-2.36 (m, 2H), 1.55 (s, 9H), 1.70-1.20 (m, 5H).

Example 91

Preparation of (E)-3-methyl-1-(3-(1-methyl-1H-pyrazol-4-yl)acryloyl)-5,6-dihydropyridin-2(1H)-one

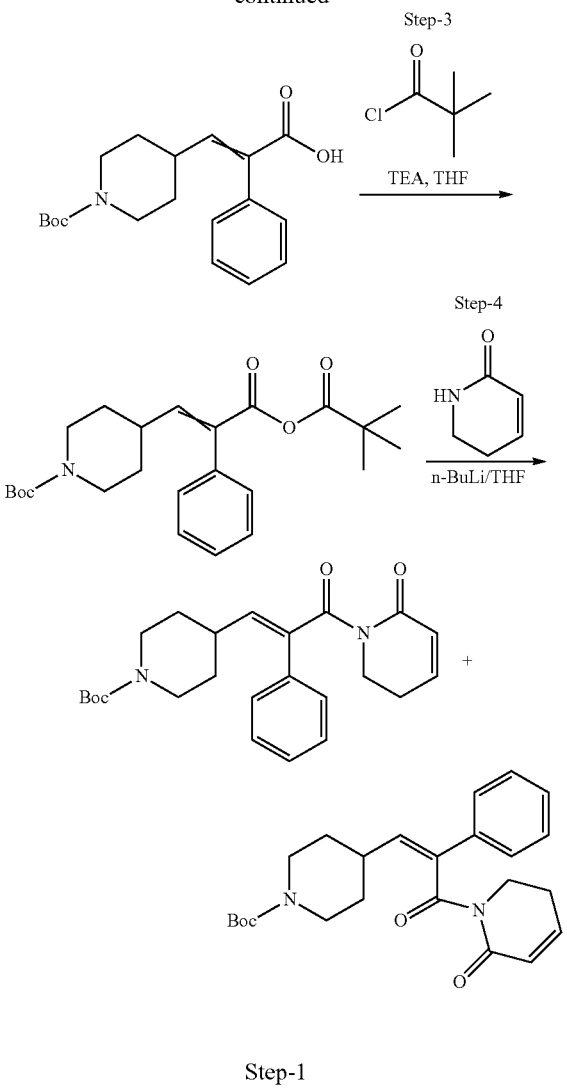

Compound 93

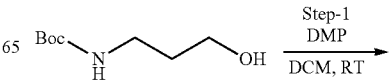

Step-1
DMP
DCM, RT

205
-continued

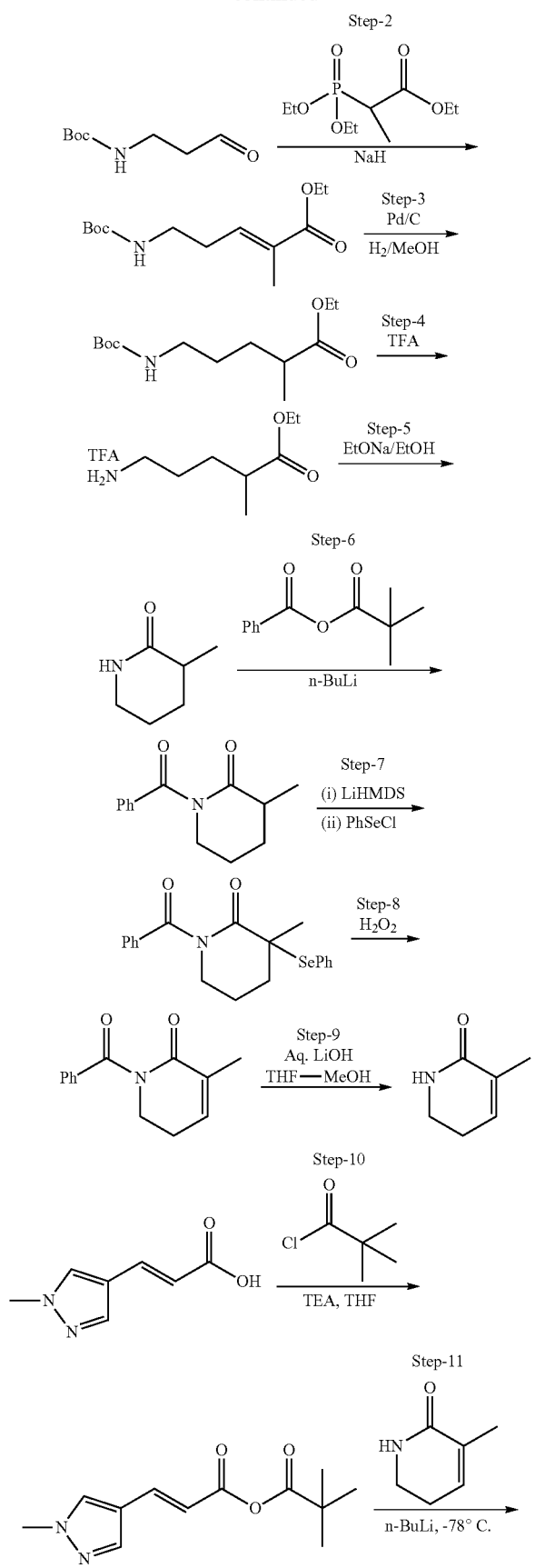

206
-continued

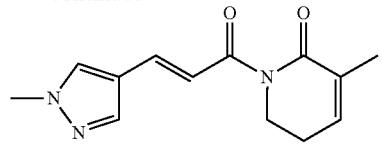

Step-1

To a solution of tert-butyl (3-hydroxypropyl)carbamate (5 g, 28.57 mmol, 1 eq) in DCM (50 mL) was added Dess-Martin periodinane (16 g, 37.14 mmol, 1.3 eq) and the reaction mixture was allowed to stir at room temperature for 2 h. Progress of reaction was monitored by proton NMR. After completion, reaction mixture was diluted with hexane (500 mL) and stirred for 15 minutes. Reaction mixture was filtered, organic layer was washed with sat. NaHCO₃ (2×100 mL). Organic layer was washed with brine (100 mL) and dried over anhydrous sodium sulfate. Removal of solvent afforded crude tert-butyl (3-oxopropyl)carbamate (4.1 g, 82.99%) which was used in the next step without further purification.

Step-2

To a solution of ethyl 2-(diethoxyphosphoryl)propanoate (2.9 g, 16.8 mmol, 1 eq) in THF (30 mL) was added NaH (0.8 g, 20 mmol, 1.3 eq) at 0° C. and the reaction mixture was allowed to stir at the same temperature for 10 minutes. To this solution was added tert-butyl (3-oxopropyl)carbamate (4.1 g, 16.8 mmol, 1 eq) and the reaction mixture was allowed to stir at room temperature for 30 minutes. Progress of reaction was monitored by proton NMR. After completion, reaction mixture was diluted with a Aq. ammonium chloride solution (50 mL) and extracted with ethyl acetate (3×100 mL). Combined organic layer was washed with brine (100 mL) and dried over anhydrous sodium sulfate. Removal of solvent afforded crude ethyl (E)-5-((tert-butoxycarbonyl)amino)-2-methylpent-2-enoate (3.9 g, 66.10%) which was used in the next step without further purification.

Step-3

To a solution of ethyl (E)-5-((tert-butoxycarbonyl)amino)-2-methylpent-2-enoate (5.15 g, 20 mmol, 1 eq) in MeOH (100 mL) was added Pd/C (0.6 g) and the reaction mixture was allowed to stir at room temperature under H₂ atmosphere for 16 h. Progress of reaction was monitored by proton NMR. After completion, reaction mixture was passed through celite bed. Removal of solvent afforded crude ethyl 5-((tert-butoxycarbonyl)amino)-2-methylpentanoate (4.64 g, 90.09%) which was used in the next step without further purification.

Step-4

To a solution of ethyl 5-((tert-butoxycarbonyl)amino)-2-methylpentanoate (4.64 g, 17.89 mmol, 1 eq) in DCM (10 mL) was added TFA (10 mL, 130 mmol, 7.3 eq) dropwise and the reaction mixture was allowed to stir at room temperature for 1 h. Progress of reaction was monitored by proton NMR. After completion, removal of solvent and azeotrope with toluene afforded crude ethyl 5-amino-2- methylpentanoate (6.3 g, crude) which was used in the next step without further purification.

Step-5

To a solution of ethyl 5-amino-2-methylpentanoate (5.8 g, 36.42 mmol, 1 eq) in ethanol (120 mL) was added NaH (1.74 g, 72.85 mmol, 2 eq) portion-wise at 0° C. and the reaction mixture was allowed to stir 0° C. for 10 minutes followed by stirring at 70° C. for 2 h. Progress of reaction was monitored by proton NMR. After completion, removal of solvent under reduced pressure afforded crude which was purified by CombiFlash on silica gel using ethyl acetate-hexane system as eluent to afford 3-methylpiperidin-2-one (1.46 g, 35.44%).

Step-6

To a stirred solution of 3-methylpiperidin-2-one (0.5 g, 4.41 mmol, 1 eq.) in dry THF at −78° C. was added n-butyl lithium (2.5 M in hexane, 1.94 mL, 4.85 mmol, 1.1 eq.) and the mixture was allowed to stir at the same temperature for 30 minutes. To this solution was added benzoic pivalic anhydride (0.592 g, 4.85 mmol, 1.1 eq.). Reaction mixture was allowed to stir at −78° C. for 90 min. Progress of reaction was monitored by TLC. Reaction mixture was brought to 0° C., diluted with ammonium chloride solution (30 mL) and extracted with ethyl acetate (3×30 mL). Combined organic layer was washed with brine, dried over anhydrous $Na_2SO_4$ and evaporated to dryness under vacuum to afford crude which was purified by CombiFlash to afford 1-benzoyl-3-methylpiperidin-2-one (0.480 g, 50%).

Step-7

To a stirred solution of 1-benzoyl-3-methylpiperidin-2-one (0.230 g, 1.06 mmol, 1 eq.) in dry THF at −78° C. was added LiHMDS (1 M in THF, 1.27 mL, 1.27 mmol, 1.2 eq.) and the mixture was allowed to stir at the same temperature for 30 minutes. To this solution was added phenyl hypochloroselenoite (0.241 g, 1.27 mmol, 1.2 eq.). Reaction mixture was allowed to stir at −78° C. for 90 min. Progress of reaction was monitored by TLC and LCMS. Reaction mixture was brought to 0° C., diluted with water (25 mL) and extracted with ethyl acetate (3×40 mL). Combined organic layer was washed with brine, dried over anhydrous $Na_2SO_4$ and evaporated to dryness under vacuum to afford crude which was purified by Combi-Flash to afford 1-benzoyl-3-methyl-3-(phenylselanyl)piperidin-2-one (0.330 g, 83.45%).

Step-8

To a stirred solution of 1-benzoyl-3-methyl-3-(phenylselanyl)piperidin-2-one (5 g, 13.42 mmol, 1 eq.) in dry THF (40 mL) at 0° C. was added $H_2O_2$ (30%) (15 mL) and the mixture was allowed to stir at the same temperature for 10 minutes followed by stirring at RT for 30 minutes.

Progress of reaction was monitored by TLC and LCMS. After completion, reaction mixture was diluted with water (100 mL) and extracted with ethyl acetate (3×50 mL). Combined organic layer was washed with brine (50 mL), dried over anhydrous $Na_2SO_4$ and evaporated to dryness under vacuum to afford crude 1-benzoyl-3-methyl-5,6-dihydropyridin-2(1H)-one (1.4 g, crude) which was used in next step without purification.

Step-9

To a stirred solution of 1-benzoyl-3-methyl-5,6-dihydropyridin-2(1H)-one (1.4 g, 6.50 mmol, 1 eq.) in mixture of MeOH (8 mL) and THF (8 mL) and the mixture was allowed to stir at room temperature for 10 minutes followed by addition of LiOH (0.8 g, 39.02 mmol, 8 eq.). The resulting reaction mixture was stirred at room temperature for 3 h. Progress of reaction was monitored by TLC. Reaction mixture was diluted with water and extracted with ethyl acetate (6×40 mL). Combined organic layer was washed with brine, dried over anhydrous $Na_2SO_4$ and evaporated to dryness under vacuum. Crude was purified by CombiFlash to afford 3-methyl-5,6-dihydropyridin-2(1H)-one (0.5 g, 69.25%).

Step-10

To a solution of (E)-3-(1-methyl-1H-pyrazol-4-yl)acrylic acid (0.273 g, 1.79 mmol, 1.0 eq.) in dry THF (12 mL) was added triethylamine (0.3 mL, 2.15 mmol, 1.2 eq.) and pivaloyl chloride (0.24 mL, 1.97 mmol, 1.1 eq.) the reaction mixture was stirred at 0° C. for 45 minutes.

Progress of reaction was monitored by TLC. After completion, reaction mixture was filtered and the filtrate was used directly for the next step.

Step-11

To a stirred solution of 3-methyl-5,6-dihydropyridin-2(1H)-one (0.2 g, 1.79 mmol, 1 eq.) in dry THF (15 mL) at −78° C. was added n-butyllithium (2.5 M in hexane, 0.71 mL, 1.79 mmol, 1 eq.) and the mixture was allowed to stir at the same temperature for 30 minutes. To this solution was added (E)-(E)-3-(1-methyl-1H-pyrazol-4-yl)acrylic pivalic anhydride (0.402 g, 1.79 mmol, 1 eq.). Reaction mixture was allowed to stir at −78° C. for 2 h. Progress of reaction was monitored by TLC and LCMS. Reaction mixture was brought to 0° C., diluted with sat. ammonium chloride solution and extracted with ethyl acetate (3×30 mL). Combine organic layer was washed with brine, dried over anhydrous $Na_2SO_4$ and evaporated to dryness under vacuum. To afford crude which was purified by Combi-Flash afford (E)-3-methyl-1-(3-(1-methyl-1H-pyrazol-4-yl)acryloyl)-5,6-dihydropyridin-2(1H)-one (3 mg, 0.72%).

LCMS: 246 [M+1]$^+$ $^1$H NMR (400 MHz, CDCl3) δ 7.75 (s, 1H), 7.61 (s, dH), 7.59 (s, 1H), 7.23 (d, 1H), 6.65 (s, 1H), 3.99 (t, 2H), 3.90 (s, 3H), 2.42-2.34 (m, 2H), 1.95 (s, 3H).

Example 92

Preparation of (E)-6,6-dimethyl-1-(3-(3,4,5-trimethoxyphenyl)acryloyl)-5,6-dihydropyridin-2(1H)-one

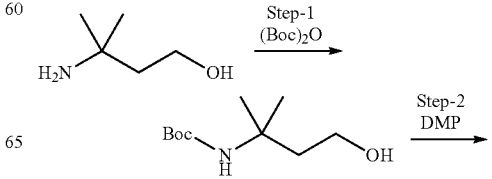

Compound 94

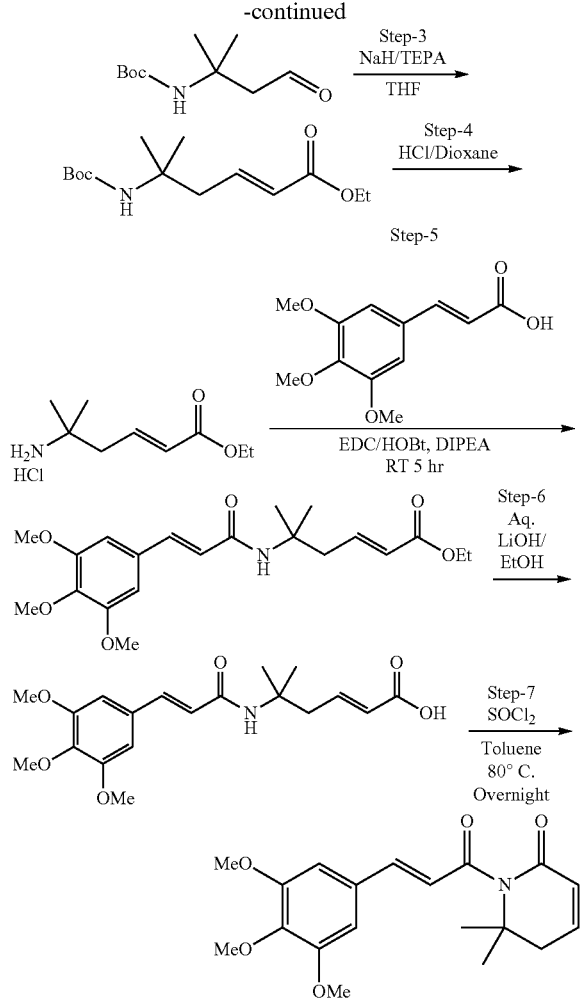

Step-1

To a solution of 3-amino-3-methyl-butan-1-ol (5.0 g, 48.54 mmol) in CH₂Cl₂ (150 mL) was added di-tert-butyl dicarbonate (13.22 g, 60.27 mmol) at RT and resulting mixture was stirred for 18 h. Progress of reaction was monitored by TLC. After completion, reaction mixture was concentrated under vacuum to afford tert-butyl (4-hydroxy-2-methylbutan-2-yl)carbamate as an amber oil (9.8 g) which was used in the next step without purification.

Step-2

To a solution of the tert-butyl (4-hydroxy-2-methylbutan-2-yl)carbamate (2 g, 9.8 mmol) in DCM (18 mL) at 0° C. was added Dess-Martin periodinane (7.2 g, 17.14 mmol). The reaction mixture was stirred at RT for 3 h. Progress of reaction was monitored TLC. After completion, reaction mixture was quenched with aq. NaHCO₃, and extracted with EtOAc (2×50 mL). Combined organic layer was washed with brine (2×20 mL), dried over sodium sulfate. Removal of solvent gave crude which was purified by silica gel column chromatography using ethyl acetate-hexane as eluent to afford tert-butyl (2-methyl-4-oxobutan-2-yl)carbamate as a yellow solid (1.8 g).

Step-3

To a suspension of sodium hydride (60% in mineral oil, 0.56 g 13.87 mmol, 1.2 eq) in THF (50 mL) was added triethylphosphonoacetate (2.58 g, 11.52 mmol, 1.2 eq) dropwise at 0° C. and the mixture was allowed to stir at the same temperature for 30 minutes. To this mixture was added a solution of tert-butyl (2-methyl-4-oxobutan-2-yl)carbamate (2 g, 11.52 mmol, 1.0 eq) in THF (5 mL) and the resulting mixture was allowed to stir at room temperature for 1 h. Progress of reaction was monitored by TLC. After completion, reaction mixture was diluted with saturated aq. NH₄Cl (100 mL) and extracted with ethyl acetate (3×50 ml). Combined organic layer was washed with brine, dried over anhydrous Na₂SO₄ and evaporated to dryness under vacuum to afford crude which was purified by Combi-Flash on silica gel using ethyl acetate-hexane system as eluent to afford ethyl (E)-5-((tert-butoxycarbonyl)amino)-5-methylhex-2-enoate (2 g).

Step-4

To a solution of ethyl (E)-5-((tert-butoxycarbonyl)amino)-5-methylhex-2-enoate (2 g) 1,4-dioxane (8 mL) at RT was added 20% HCl in dioxane (8 mL) and reaction mixture was allowed to stir at RT for 2 h. Progress of reaction was monitored by TLC. After completion, reaction mixture was removed under vacuum and the resulting yellow solid was triturated with EtOAc to afford ethyl (E)-5-amino-5-methylhex-2-enoate hydrochloride as a yellow solid (1.5 g).

Step-5

To a solution of (E)-ethyl 5-amino-5-methylhex-2-enoate hydrochloride (1 g, 4.83 mmol) in DCM (30 mL) was added DIPEA (1.38 ml, 8.40 mmol), EDC.HCL (960 mg, 5.04 mmol), HOBt (770 mg, 5.04 mmol) and ethyl (E)-5-amino-5-methylhex-2-enoate hydrochloride (870 mg, 4.20 mmol) at 0° C. and reaction mixture was stirred at RT for 5 h. Progress of reaction was monitored by TLC. After completion, reaction mixture was diluted with water (50 mL) and extracted with EtOAc (3×50 mL). Combined organic layer was over sodium sulfate and concentrated under vacuum to afford crude which was purified by Combi-Flash on silica gel using ethyl acetate-hexane system as eluent to afford ethyl (E)-5-methyl-5-((E)-3-(3,4,5-trimethoxyphenyl)acrylamido)hex-2-enoate (0.8 g).

Step-6

To a solution of ethyl (E)-5-methyl-5-((E)-3-(3,4,5-trimethoxyphenyl)acrylamido)hex-2-enoate (800 mg, 2.04 mmol, 1.0 eq) in ethanol (30 mL) was added a solution of lithium hydroxide (244 mg 10.20 mmol, 5 eq) in water (3 mL) and the reaction mixture was stirred at room temperature for 4 h. Reaction mixture was concentrated under vacuum and then acidified with 2N HCl make pH up to 3. The mixture was diluted saturated aq. NH₄Cl (30 mL) and extracted with dichloromethane (3×30 mL). The combined organic layer was washed with brine solution (50 mL) and dried over anhydrous Na₂SO₄. Removal of solvent under reduced vacuum gave product (E)-5-methyl-5-(3-(3,4,5-trimethoxyphenyl)acrylamido)hexanoic acid as crystalline solid (0.7 g).

Step-7

A mixture of (E)-5-methyl-5-((E)-3-(3,4,5-trimethoxyphenyl)acrylamido)hex-2-enoic acid (150 mg, 0.413 mmol 1 eq) and thionyl chloride (0.14 mL, 2.07 mmol, 5 eq) in toluene (10 mL) was stirred at 80° C. for 16 h. Reaction mixture was cooled to RT, diluted with EtOAc and washed with NaHCO$_3$ (3×50 ml). The combined organic layer was washed with brine solution (50 mL) and dried over anhydrous Na$_2$SO$_4$. Removal of solvent under reduced pressure gave crude which was purified by Combi-Flash on silica gel using ethyl acetate-hexane system as eluent to afford (E)-6,6-dimethyl-1-(3-(3,4,5-trimethoxyphenyl)acryloyl)-5,6-dihydropyridin-2(1H)-one (20 mg).

LCMS: 346 [M+1]$^+$ $^1$H NMR (400 MHz, CD$_3$OD) δ ppm 7.55 (d, 1H), 6.97 (s, 2H), 6.96-6.82 (m, 1H), 6.80 (d, 1H), 6.00 (d, 1H), 3.85 (s, 6H), 3.60 (s, 3H), 2.40-2.35 (m, 2H).

Example 93

In Vitro Cell Viability Assay

The present disclosure provides a method for inhibiting cell viability, as measured by ATP levels. The method for inhibiting cell viability is drawn to contacting various cancer cells with the compounds described herein at various concentrations. The cancer cell lines were maintained in culture conditions at at 37° C. in an atmosphere of 5% CO$_2$ in air. The cells growing in an exponential growth phase were harvested and counted for plating. Compounds were incubated in two cancer cell types representing multiple myeloma (MOLP-8) and triple negative breast cancer (DU4475). Cells were plated at an optimized cell numbers per well in 96-well plates and allowed to attach to the plates overnight at approximately 80% confluency.

After addition of compounds, plates were incubated for 7-day. At the end of incubation period on day 8, media was removed and replaced with a solution of CellTiter-Glo™ reagent (Promega®) according to protocol. Luminescence was read using an EnVision® multi-label plate reader (Perkin-Elmer®), and signal intensity was calculated relative to positive and negative control wells. Cisplatin was included as the positive control. A dose-response calculation was performed in a non-linear regression fit and by using the Hill equation to calculate a concentration-response curve and 50% inhibitory concentration (IC$_{50}$) values for each compound.

The average IC$_{50}$ values of piperlongumine in multiple myeloma (MOLP-8) and triple negative breast cancer (DU4475) cells were approximately 1.01 uM and 1.24 uM, respectively. The average IC$_{50}$ values of compounds 1-15 in multiple myeloma (MOLP-8) and triple negative breast cancer (DU4475) cells are shown in Table 1.

Example 94

Determination of Potency of Compounds in Cell Viability Assay Using Colorectal Cancer Cells The blue dye resazurin-based assay was performed to determine cell viability and used according to manufacture protocol (Sigma®). HCT116 (colorectal cancer) cells were seeded in the DMEM medium (10% FBS serum). Approximately 1,500 cells were plated per well in 96 well plates. Cells were allowed to grow at 37° C. for 24 hr in 5% CO$_2$ environment in a humidified incubator. Serially diluted compounds (100 μL) were added to the culture plate after 24 hr. After addition of compounds, plates were incubated for 72 hr. Experiment was terminated at the designated incubation time by replacing the medium with 100 μL of 1 mM of resazurin (Sigma®) prepared in culture medium (DMEM) and were further incubated in culture conditions for 4-6 hours. Fluorescence was recorded using a multimodal plate reader (Biotek Synergy Neo®) at an excitation wavelength of 535 nm and emission wavelength of 590 nm to obtain relative fluorescence units. Data analysis was done by subtracting the background fluorescence (medium blank) value from each reading and then normalizing with the vehicle control (DMSO treated cells) to obtain percent survival/proliferation. IC$_{50}$ was calculated from percent survival values using GraphPad Prism® (see Table 1).

Example 95

In Vivo Pharmacokinetic Analysis

Age 8 to 9 weeks Balb/C female mice were used for this study. The mice were maintained in a special pathogen-free environment and in disposable cages. Animal room was set to maintain temperature and relative humidity at 23° C.±3° C. and 55%±15%, respectively. Housing room was on a 12:12 light/dark cycle. Water was supplied ad libitum to each cage via water bottles. All mice were fed rodent diet with 18% protein. All animals were weighed before commencement of the study.

Compound 1 was stored at 4° C. protected from light. Dosing solutions were used within 2 hours of preparation. Compound 1 was formulated within 2 hours prior to dosing by adding the pre-calculated volume of PEG 400 (40% of total solution volume). Formulated compound 1 was vortexed and sonicated until a clear solution was formed. To this clear formulation, saline (60% of total solution volume) was added and vortexed until a clear solution was formed. The Compound 1 solution was filtered using a sterile syringe filter (0.2 μm corning filter). All Compound 1 solutions were mixed thoroughly prior to pulling up into syringes and prior to dosing. 12 mice were dosed intravenously at 5 mg/kg. 12 mice were dosed intraperitoneally at 10 mg/kg. 12 mice were dosed orally at 10 mg/kg. Animals were sacrificed for blood and organs sampling. Under isoflurane anesthesia, blood was collected via retro-orbital route. Blood samples were then centrifuged for 5 minutes at a minimum of 2,000×g. Plasma supernatant (a minimum of 50 μL or as much as feasible to collect) was collected. Plasma was stored at −80° C.

Bioanalytical analysis of plasma levels of Compound 1 was performed by mass spectrometry. Calibration standards were prepared by spiking the test compound into blank plasma. Calibrator concentrations were 5,000, 2,000, 1,000, 200, 100, 20, 10, 2 and 1 ng/mL. Calibration standard samples were processed along with the test samples.

Twenty μL aliquots of plasma test samples were treated with 100 μL of methanol: acetonitrile (5:95 v:v) containing internal standard (12.5 ng/mL verapamil). The mixtures were vortexed on a shaker for 15 minutes and subsequently centrifuged at 4,000 rpm for 15 minutes. An aliquot of 50 μL of the supernatant was mixed with 100 μL of water with 0.1% formic acid for injection to the LC/MS/MS (liquid chromatography/tandem-mass spectrometry).

The concentration of Compound 1 was determined by a UPLC-TIS-MS-MS method (ultra performance liquid chromatography-turbo ion spray-tandem mass spectrometry). The UPLC comprised a Shimadzu LC-30AD HPLC (high performance liquid chromatography). Chromatographic separation was achieved using a Waters UPLC column (Acquity UPLC BEH C18, 50×2.1 mm, 1.7 μM). Mobile phase A was water with 0.1% formic acid; mobile phase B was acetonitrile with 0.1% formic acid. The gradient program was as follows: 20% B (0-0.2 min), 20-95% B (0.2-1.2 min), 95% B (1.2-1.8 min), 95-20% B (1.81-2.2 min). The flow rate was 0.6 mL/minute. The column was maintained at 50° C.

Mass spectrometric analysis was performed using an AB Sciex API5000 with Turbo Ion Spray interface operating in a positive ionization mode. Quantification was performed using multiple reaction monitoring (MRM) method with the transitions of (m/z) 316.104→(m/z) 219.014 for Compound 1 and (m/z) 455.346→(m/z) 165 for verapamil (internal standard). Pharmacokinetics of Compound 1 ((E)-1-(3-(8-methoxy-2,3-dihydrobenzo[b][1,4]dioxin-6-yl)acryloyl)-5,6-dihydropyridin-2(1H)-one) in the plasma of the mice dosed intravenously (IV; 5 mg/kg), intraperitoneally (IP; 10 mg/kg) and orally (PO; 10 mg/kg) (n=3 per time point) is illustrated in FIG. 1. Plasma half-life ($t_{1/2}$) of Compound 1 and piperlongumine is shown in Table 2 below.

TABLE 2

| Route | Dose (mg/kg) | Compound 1 $t_{1/2}$ (hr) | Piperlongumine $t_{1/2}$ (hr) |
|---|---|---|---|
| IV | 5 | 1.66 | 1.26 |
| IP | 10 | 1.14 | 1.07 |
| PO | 10 | 2.16 | 1.31 |

As illustrated in FIG. 1 and Table 2, Compound 1 exhibited increased in vivo plasma half-life ($t_{1/2}$) as compared to piperlongumine. Consistent with these results, in vitro microsome stability analyses revealed that Compounds 1 and compounds in Table 1 having $R^1$ functional group according to Formula (I) demostrated potency and/or metabolic stability. Particularly, a subset of compounds containing heterocyclic $R^1$ exhibited a combined potency and microsomal stability that is at least 2-fold greater than piperlongumine. Enhanced in vivo cytotoxicity, bioavailability, and stability of the compounds disclosed herein allow for lower and less frequent dosing, thus promoting a better clinical outcome.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled. Such modifications are intended to fall within the scope of the appended claims.

All references, patent and non-patent, cited herein are incorporated herein by reference in their entireties and for all purposes to the same extent as if each individual publication or patent or patent application was specifically and individually indicated to be incorporated by reference in its entirety for all purposes.

What is claimed is:

1. A compound of Formula I:

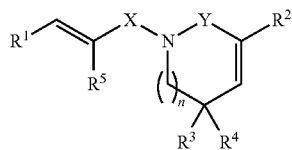

Formula I or a pharmaceutically acceptable salt thereof,
wherein n is an integer of 1,
X or Y is independently C(O) or S(O)$_2$;
  $R^1$ is selected from the group consisting of:
    i) a 3-9 member saturated cycloalkyl group having 0-5 heteroatom(s);
    ii) a 6 member monocyclic heteroaryl group having 1-3 heteroatom(s), wherein said 6 member monocyclic heteroaryl group has:
       a) 1-3 heteroatom(s), and X or Y is S(O)$_2$;
       b) two heteroatoms, and said 6 member monocyclic heteroaryl group is pyridazinyl or pyrimidyl; or
       c) three heteroatoms, and at least one of X or Y is independently C(O);
    iii) a 7-9 member monocyclic unsaturated cycloheteroalkyl group having 1-3 heteroatoms(s); and
    iv) a 7-13 member polycyclic heteroaryl group having 1-5 heteroatom(s), wherein said 7-13 member heteroaryl group has
  1-5 heteroatom(s), and at least one of X or Y is S(O)$_2$ and at least one of $R^2$, $R^3$ or $R^4$ is not hydrogen,
    wherein said heteroatom(s) contained in each cyclic group is independently selected from the group consisting of N, O, and S; and
    wherein each cyclic group is optionally substituted with halo, alkyl, alkenyl, alkynyl, alkoxy, acyl, acyloxy, carbocylic acid, ester, amine, amide, carbonate, carbamate, cyano, nitro, thioether, thioester, cycloalkyl, cycloheteroalkyl, heterocyclyl, aryl, or heteroaryl, any of which is unsubstituted or substituted with halo, hydroxyl, sulfhydryl, nitro, nitroso, cyano, azido, alkyl, alkenyl, cycloalkyl, cycloheteroalkyl, heterocyclyl, aryl or heteroaryl;
  $R^2$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl;
  each of $R^3$ and $R^4$ is independently selected from the group consisting of hydrogen, halo, hydroxyl, alkyl, alkenyl, and alkynyl, any of which is optionally substituted with halo, hydroxyl, alkyl, or cycloalkyl; or $R^3$ taken together with one or more atoms of $R^4$ forms a cycloalkyl or cycloheteroalkyl, each of which is optionally substituted with halo, hydroxyl, alkyl, alkenyl, alkynyl, or alkoxy; and
  $R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

2. The compound of claim 1, or a pharmaceutically acceptable salt thereof, wherein $R^1$ is a 3-9 member saturated cycloalkyl group having 0-5 heteroatom(s).

3. The compound of claim 2, or a pharmaceutically acceptable salt thereof, wherein $R^1$ is a 3-9 member saturated cycloalkyl group having no heteroatom.

4. The compound of claim 2, or a pharmaceutically acceptable salt thereof, wherein $R^1$ is a 3-9 member saturated cycloalkyl group having 1-5 heteroatom(s).

5. The composition compound of claim 1, or a pharmaceutically acceptable salt thereof, wherein $R^1$ is a 6 member monocyclic heteroaryl group having 1-3 heteroatom(s), and at least one of X or Y is $S(O)_2$.

6. The composition compound of claim 1, or a pharmaceutically acceptable salt thereof, wherein $R^1$ is a 6 member monocyclic heteroaryl group having 1-3 heteroatom(s) selected from N, O, or S, at least one of X or Y is $S(O)_2$ and at least one of $R^2$, $R^3$ or $R^4$ is not hydrogen.

7. The composition compound of claim 1, or a pharmaceutically acceptable salt thereof, wherein $R^1$ is a 6 member monocyclic heteroaryl group having three heteroatoms independently selected from N, O, or S, at least one of X or Y is independently C(O).

8. The composition compound of claim 1, or a pharmaceutically acceptable salt thereof, wherein $R^1$ is a 7-9 member monocyclic unsaturated cycloheteroalkyl group having 1-3 heteroatom(s) selected from the group consisting of azepinyl, diazepinyl, oxepinyl, thiepinyl, thiazepinyl, azocinyl, oxocinyl, thiocinyl, azoninyl, oxoninyl, and thioninyl.

9. The compound of claim 1, or a pharmaceutically acceptable salt thereof, wherein $R^1$ is a 7-13 member polycyclic heterocyclyl group having 1-5 heteroatom(s) independently selected from N, O, or S, w at least one of X or Y is $S(O)_2$ and at least one of $R^2$, $R^3$ or $R^4$ is not hydrogen.

10. The composition compound of claim 1, or a pharmaceutically acceptable salt thereof, wherein $R^2$ is hydrogen.

11. The composition compound of claim 1, or a pharmaceutically acceptable salt thereof, wherein $R^3$ is selected from the group consisting of hydrogen, halo, hydroxyl, alkyl, alkenyl, and alkynyl.

12. The composition compound of claim 1, or a pharmaceutically acceptable salt thereof, wherein $R^4$ is selected from the group consisting of hydrogen, halo, hydroxyl, alkyl, alkenyl, and alkynyl.

13. The composition compound of claim 1, or a pharmaceutically acceptable salt thereof, wherein $R^3$ taken together with one or more atoms of $R^4$ forms cycloalkyl or cycloheteroalkyl, each of which is optionally substituted with halo, hydroxyl, alkyl, alkenyl, alkynyl, or alkoxy.

14. A compound of Formula I:

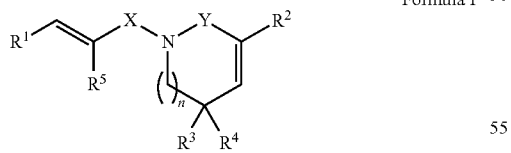

Formula I or a pharmaceutically acceptable salt thereof,
wherein n is an integer of 0 or 2;
   X or Y is independently C(O) or $S(O)_2$;
   $R^1$ is
      a) a branched $C_3$ alkyl group; or
      b) a saturated or partially unsaturated $C_3$-$C_9$ cycloalkyl group having no heteroatom;
      wherein each group is optionally substituted with halo, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, aryl, heteroaryl, or heterocyclyl, any of which is unsubstituted or substituted with halo, hydroxyl, sulfhydryl, nitro, nitroso, cyano, azido, alkyl, alkenyl, cycloalkyl, cycloheteroalkyl, aryl, heteroaryl, or heterocyclyl;

$R^2$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl;

each of $R^3$ and $R^4$ is independently selected from the group consisting of hydrogen, halo, hydroxyl, alkyl, alkenyl, alkynyl, alkoxy, cycloalkyl, and cycloheteroalkyl, any of which is optionally substituted with halo, hydroxyl, alkyl, or cycloalkyl; or $R^3$ taken together with one or more atoms of $R^4$ forms a cycloalkyl or cycloheteroalkyl, each of which is optionally substituted with halo, hydroxyl, alkyl, alkenyl, alkynyl, or alkoxy; and $R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

15. A compound of Formula I:

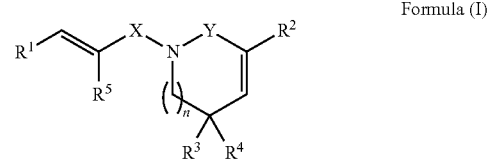

Formula (I)

or a pharmaceutically acceptable salt thereof,
   wherein n is an integer of 1, 2, or 3;
   wherein X or Y is independently C(O) or $S(O)_2$ and at least one of X or Y is $S(O)_2$ and at least one of $R^2$, $R^3$ or $R^4$ is not hydrogen; and wherein:

$R^1$ is a 3-13 member heterocyclyl group having 1-5 heteroatom(s) independently selected from the group consisting of N, O, and S, wherein the 3-13 member heterocyclyl group is optionally substituted halo, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, aryl, heteroaryl, or heterocyclyl, any of which is unsubstituted or substituted with halo, hydroxyl, sulfhydryl, nitro, nitroso, cyano, azido, alkyl, alkenyl, cycloalkyl, cycloheteroalkyl, aryl, heteroaryl, and heterocyclyl;

$R^2$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, aryl, heteroaryl, and heterocyclyl, each of which is optionally substituted with halo, hydroxyl, sulfhydryl, nitro, nitroso, cyano, azido, alkyl, alkenyl, cycloalkyl, cycloheteroalkyl, aryl, heteroaryl, or heterocyclyl;

each of $R^3$ and $R^4$ is independently selected from the group consisting of hydrogen, halo, hydroxyl, alkyl, alkenyl, alkynyl, alkoxy, cycloalkyl, and cycloheteroalkyl, any of which is optionally substituted with halo, hydroxyl, alkyl, or cycloalkyl; or $R^3$ taken together with one or more atoms of $R^4$ forms a cycloalkyl or cycloheteroalkyl, each of which is optionally substituted with halo, hydroxyl, alkyl, alkenyl, alkynyl, or alkoxy; and $R^5$ is selected from the group consisting of hydrogen, halo, hydroxyl, alkyl, alkenyl, alkynyl, alkoxy, acyl, acyloxy, carboxylic acid, ester, amine, amide, carbonate, carbamate, cyano, nitro, thioether, thioester, cycloalkyl, cycloheteroalkyl, heterocyclyl, aryl, and heteroaryl, each of which is optionally substituted with halo, hydroxyl, sulfhydryl, nitro, nitroso, cyano, azido, alkyl, alkenyl, cycloalkyl, cycloheteroalkyl, heterocyclyl, aryl or heteroaryl.

16. A pharmaceutical composition comprising a compound of claim 1, or a pharmaceutically acceptable salt thereof in combination with a pharmaceutically acceptable carrier, diluent or excipient.

17. The compound of claim 1, or a pharmaceutically acceptable salt thereof, wherein $R^1$ is pyridazinyl or pyrimidyl.

18. The compound of claim 1, or a pharmaceutically acceptable salt thereof, wherein $R^1$ is pyridazinyl.

19. The compound of claim 1, or a pharmaceutically acceptable salt thereof, wherein $R^1$ is pyrimidyl.

20. A compound selected from the group consisting of

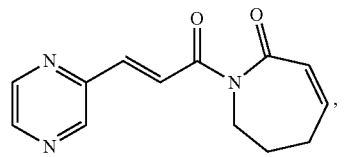

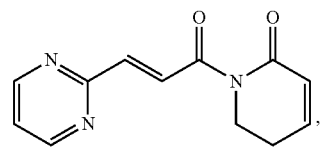

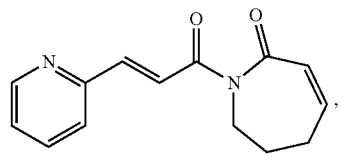

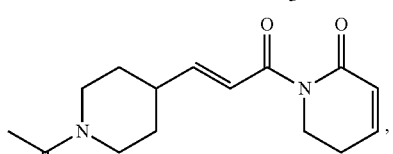

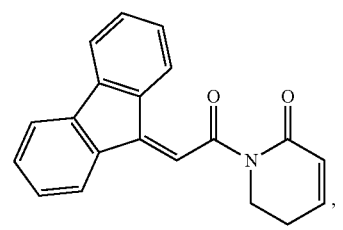

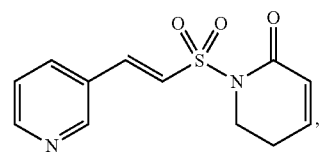

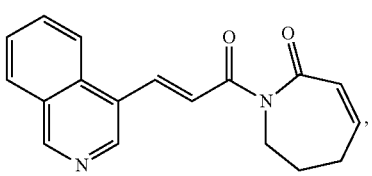

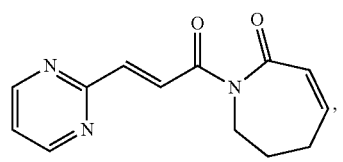

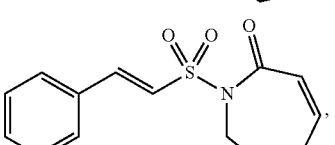

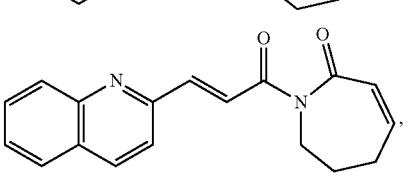

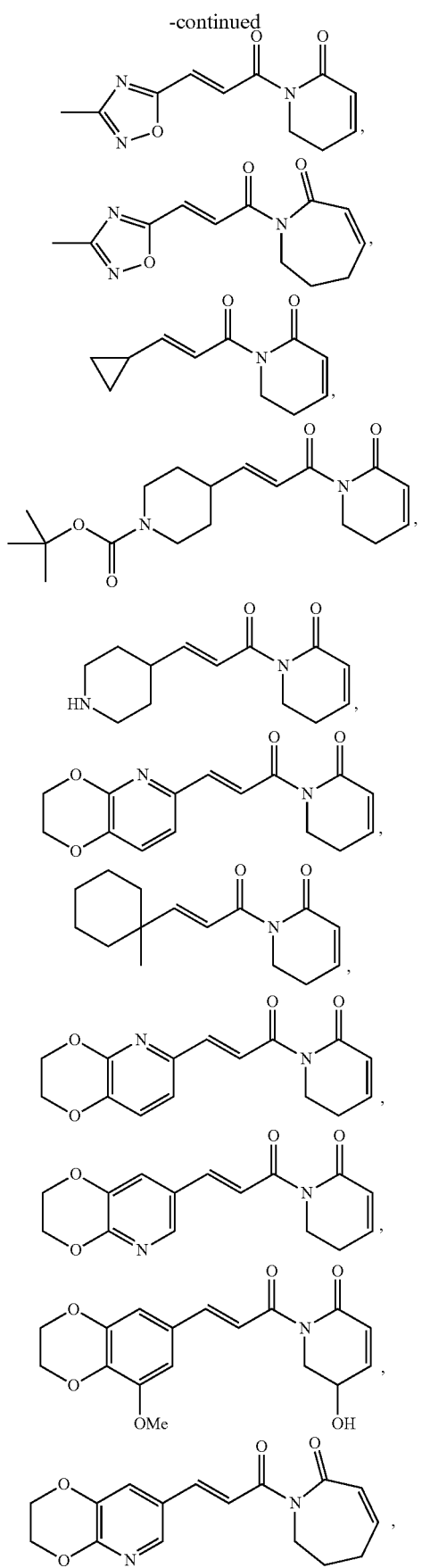
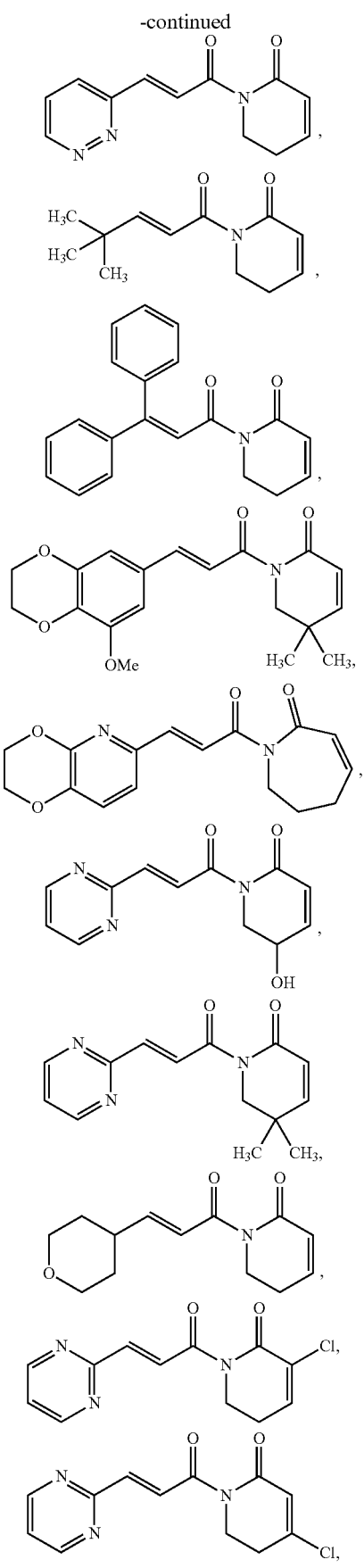

221
-continued
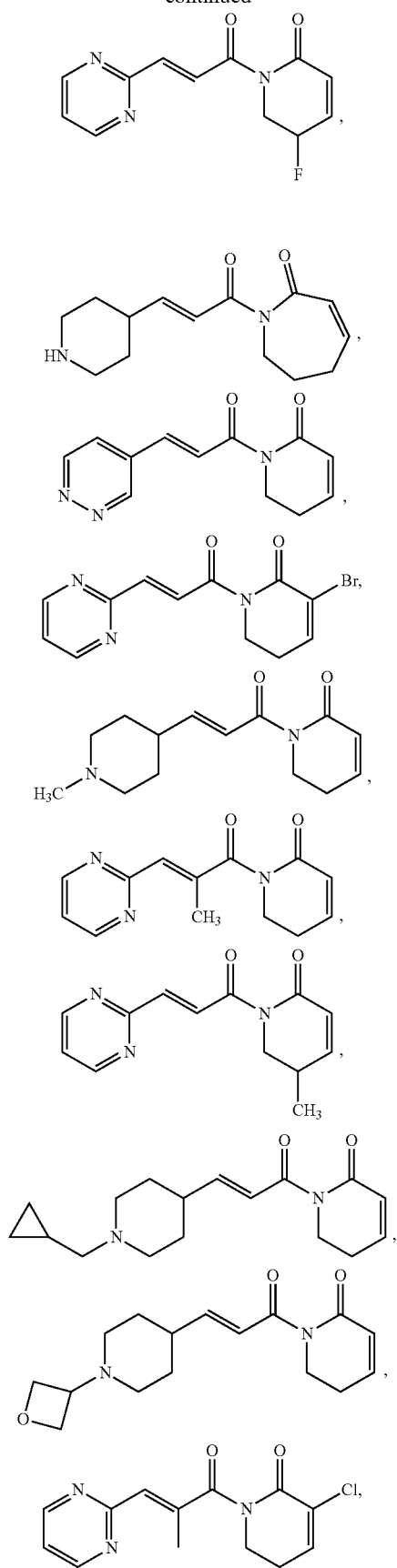
222
-continued
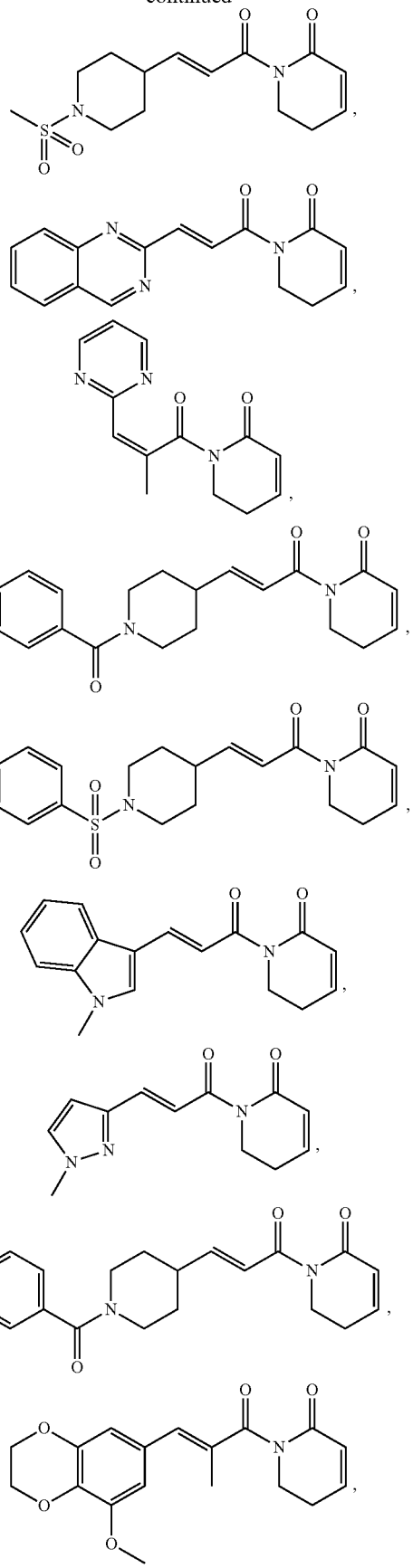

223
-continued
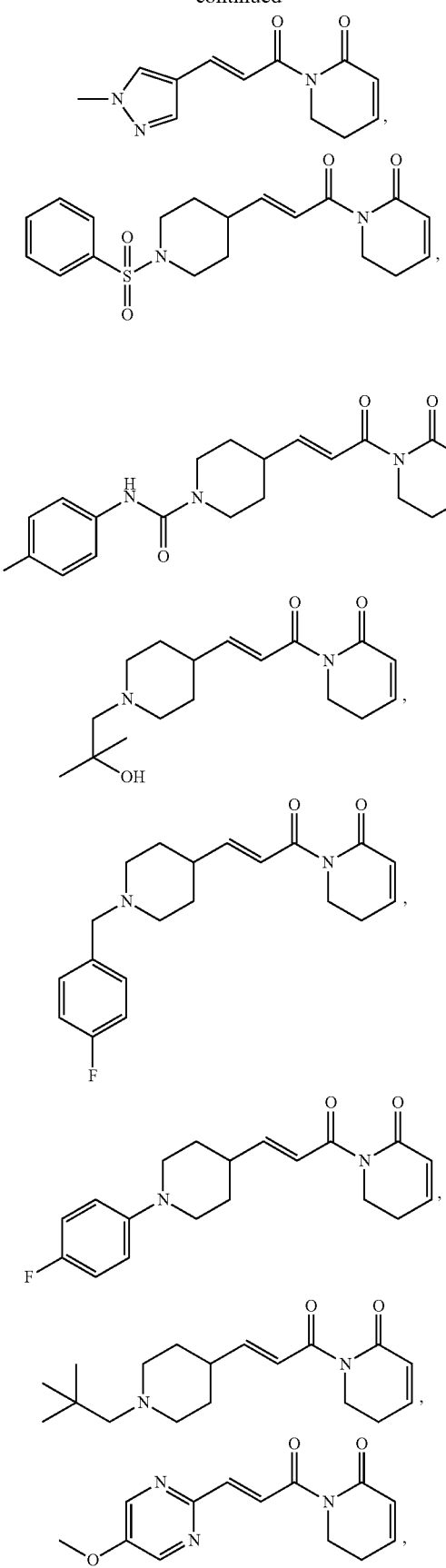
224
-continued
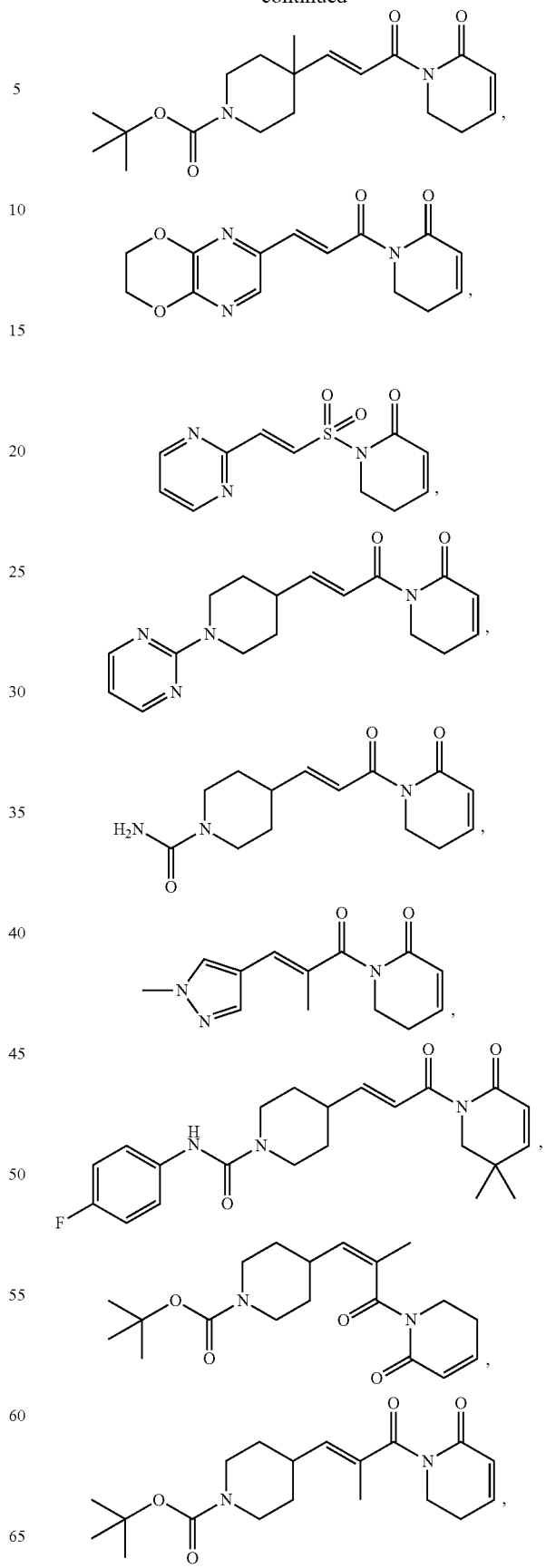

-continued
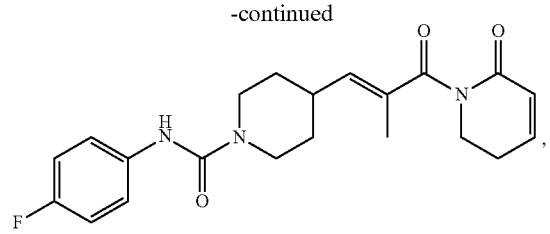
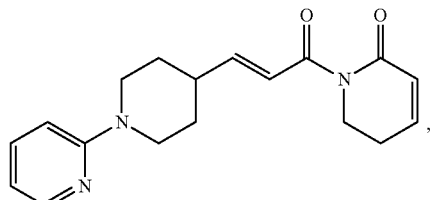
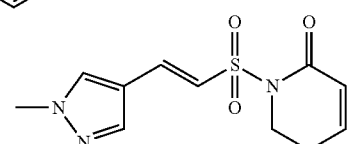
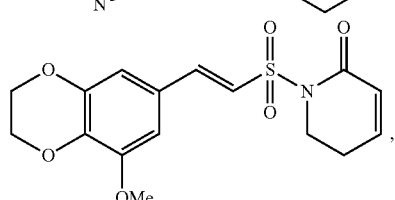
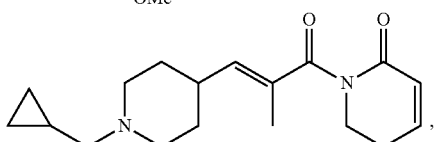
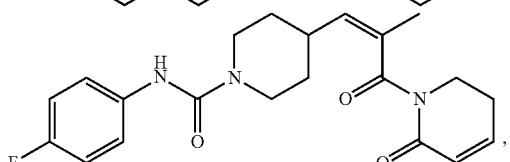
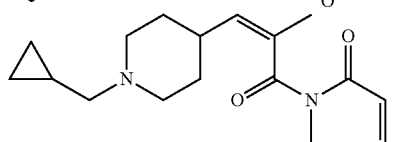
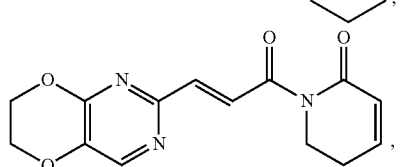
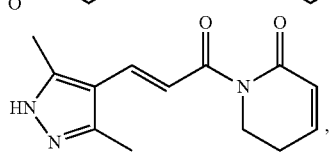
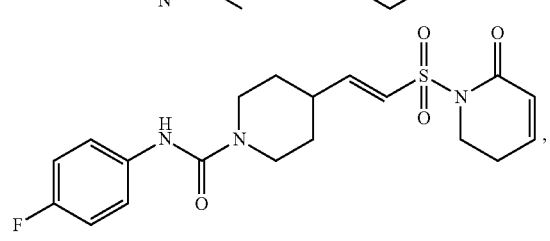
-continued
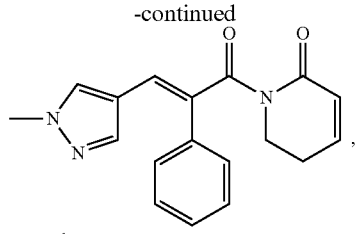
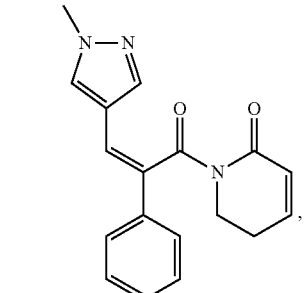
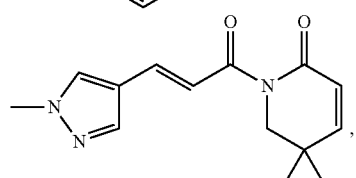
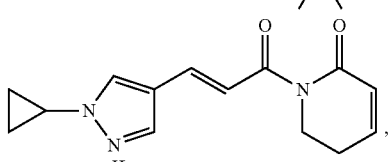
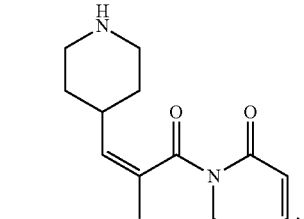
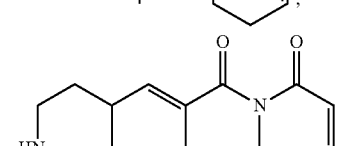
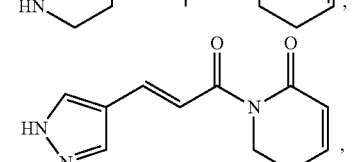
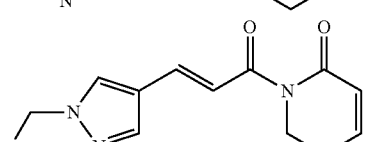
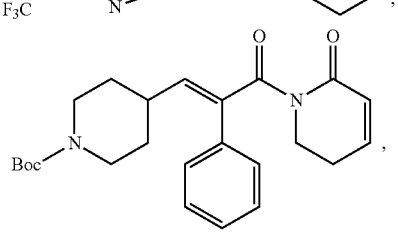

-continued

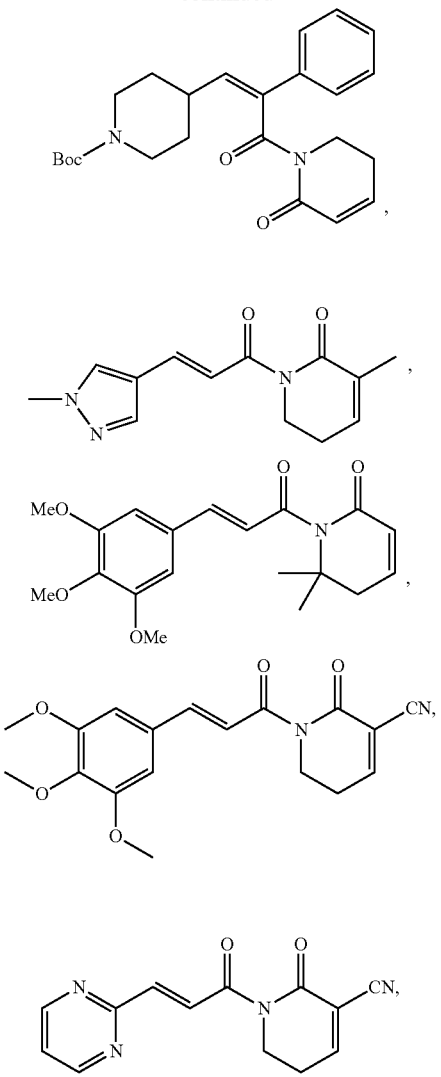

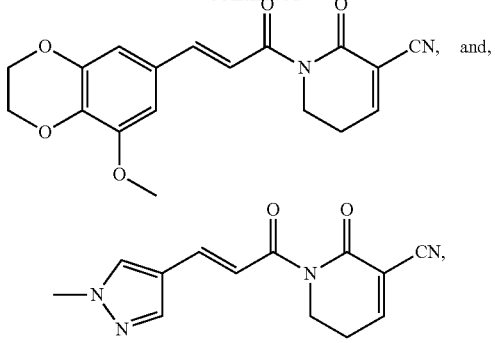

or a pharmaceutically acceptable salt thereof.

21. A method of treating a subject having cancer, the method comprising administering to said subject a therapeutically effective amount of a compound according to claim 1 or a pharmaceutically acceptable salt thereof, wherein said cancer is selected from the group of consisting of lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, and gastrointestinal cancer.

22. A method of treating a subject having cancer, the method comprising administering to said subject a therapeutically effective amount of a compound according to claim 14 or a pharmaceutically acceptable salt thereof, wherein said cancer is selected from the group of consisting of lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, and gastrointestinal cancer.

23. A method of treating a subject having cancer, the method comprising administering to said subject a therapeutically effective amount of a compound according to claim 15 or a pharmaceutically acceptable salt thereof, wherein said cancer is selected from the group of consisting of lymphoma, osteosarcoma, melanoma, breast cancer, renal cancer, prostate cancer, colorectal cancer, thyroid cancer, ovarian cancer, pancreatic cancer, neuronal cancer, lung cancer, uterine cancer, and gastrointestinal cancer.

* * * * *